United States Patent
Saphier et al.

(10) Patent No.: US 11,930,154 B2
(45) Date of Patent: *Mar. 12, 2024

(54) RAY TRACKING FOR INTRAORAL 3D SCANNER

(71) Applicant: Align Technology, Inc., San Jose, CA (US)

(72) Inventors: Ofer Saphier, Rechovot (IL); Tal Levy, Rehovot (IL); Gal Peleg, Kiryat-Ono (IL); Eliran Dafna, Beer-sheva (IL); Sergei Ozerov, Yerevan (AM); Tal Verker, Ofra (IL); Nir Makmel, Tel Aviv (IL); Yossef Atiya, Modiin-Maccabim-Reut (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/156,349

(22) Filed: Jan. 18, 2023

(65) Prior Publication Data

US 2023/0156173 A1 May 18, 2023

Related U.S. Application Data

(63) Continuation of application No. 16/910,042, filed on Jun. 23, 2020, now Pat. No. 11,563,929.
(Continued)

(51) Int. Cl.
*H04N 13/204* (2018.01)
*G01B 11/25* (2006.01)
(Continued)

(52) U.S. Cl.
CPC ........... *H04N 13/204* (2018.05); *G01B 11/25* (2013.01); *G06T 7/521* (2017.01); *H04N 1/00018* (2013.01)

(58) Field of Classification Search
CPC ........... G06T 2207/30036; G06T 7/521; G06T 17/00; G06T 2207/10028;
(Continued)

(56) References Cited

U.S. PATENT DOCUMENTS

| D925,739 S | 7/2021 | Shalev et al. |
| 11,563,929 B2 * | 1/2023 | Saphier .................. G01B 11/25 |

(Continued)

OTHER PUBLICATIONS

Co-pending U.S. Appl. No. 16/784,493, inventor Babayoff, Noam; filed Feb. 7, 2020.
(Continued)

*Primary Examiner* — Negussie Worku
(74) *Attorney, Agent, or Firm* — LOWENSTEIN SANDLER LLP

(57) ABSTRACT

An intraoral scanning system comprises and intraoral scanner and a processor. The intraoral scanner comprises one or more cameras and one or more structured light projectors, the intraoral scanner to generate a series of images using the one or more cameras, each image including at least a portion of a pattern projected by the one or more structured light projectors onto an intraoral three-dimensional surface. The processor runs a correspondence algorithm to compute respective three-dimensional positions of a plurality of features of the pattern on the intraoral three-dimensional surface, as captured in the series of images. The processor identifies the computed three-dimensional position of a detected feature of the pattern as corresponding to a particular projector ray r, in at least a subset of the series of images. The processor tracks the particular projector ray r across one or more additional images of the series of images.

27 Claims, 94 Drawing Sheets

Related U.S. Application Data

(60) Provisional application No. 62/953,060, filed on Dec. 23, 2019, provisional application No. 62/865,878, filed on Jun. 24, 2019.

(51) Int. Cl.
  *G06T 7/521* (2017.01)
  *H04N 1/00* (2006.01)

(58) Field of Classification Search
  CPC . G06T 2207/10024; G06T 2207/10052; G06T 7/586; G06T 7/80; G06T 7/85; G06T 2207/20081; G06T 2207/20084; G06T 19/20; G06T 2219/028; G06T 2219/2004; G06T 2219/2008; G06T 7/33; A61C 9/006; A61C 9/0066; A61C 9/0053; A61C 13/0004; A61C 8/0001; G01B 11/245; G01B 11/2513; G01B 11/2545; G01B 11/25; A61B 5/0088; A61B 1/00096; A61B 1/00172; A61B 1/00177; A61B 1/00193; A61B 1/0615; A61B 1/24; A61B 1/00009; A61B 5/1077; A61B 2034/102; A61B 1/00194; A61B 1/0625; A61B 1/0638; G02B 27/4222; G02B 27/4227; H04N 9/3161; H04N 1/00018; H04N 13/204; H04N 2013/0081; H04N 23/90; G16H 30/00; G16H 50/50; Y02A 90/10
  USPC .......................................................... 347/47
  See application file for complete search history.

(56) References Cited

U.S. PATENT DOCUMENTS

| | | | |
|---|---|---|---|
| 2014/0093835 A1* | 4/2014 | Levin | A61B 5/4547 433/29 |
| 2014/0302452 A1* | 10/2014 | Hack | A61B 1/00193 433/29 |
| 2018/0211404 A1* | 7/2018 | Zhu | G06T 7/579 |
| 2019/0388193 A1* | 12/2019 | Saphier | G06T 7/80 |
| 2019/0388194 A1* | 12/2019 | Atiya | A61B 1/00177 |
| 2020/0404243 A1* | 12/2020 | Saphier | A61C 9/006 |
| 2021/0121049 A1* | 4/2021 | Rudnitsky | A61B 1/063 |
| 2021/0128281 A1 | 5/2021 | Peleg | |
| 2021/0137653 A1* | 5/2021 | Saphier | A61B 5/1077 |
| 2021/0196152 A1 | 7/2021 | Saphier et al. | |
| 2022/0164955 A1* | 5/2022 | Sabina | G06T 7/30 |
| 2022/0280269 A1* | 9/2022 | Saphier | G06T 7/521 |
| 2023/0068727 A1* | 3/2023 | Saphier | A61C 9/006 |
| 2023/0156173 A1* | 5/2023 | Saphier | G01B 11/245 347/47 |

OTHER PUBLICATIONS

Co-pending U.S. Appl. No. 16/784,501, inventor Babayoff, Noam; filed Feb. 7, 2020.
Co-pending U.S. Appl. No. 16/784,515, inventor Babayoff, Noam; filed Feb. 7, 2020.
Co-pending U.S. Appl. No. 17/032,366, inventor Kopelman, Avi; filed Sep. 25, 2020.
Co-pending U.S. Appl. No. 29/768,525, inventors Zakhar; Ginzburg et al., filed Jan. 29, 2021.
Co-pending U.S. Appl. No. 29/768,563, inventors Zakhar; Ginzburg et al., filed Jan. 29, 2021.

* cited by examiner

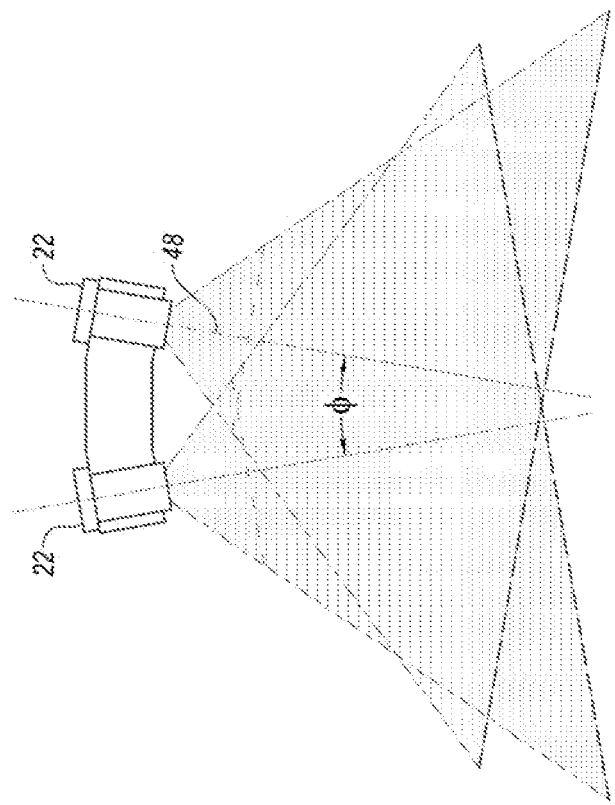
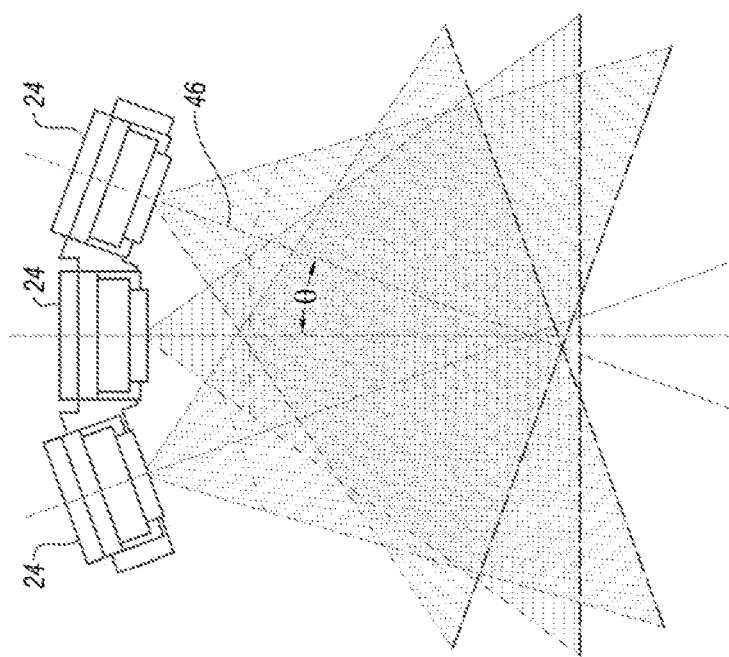
FIG. 2A
FIG. 2B

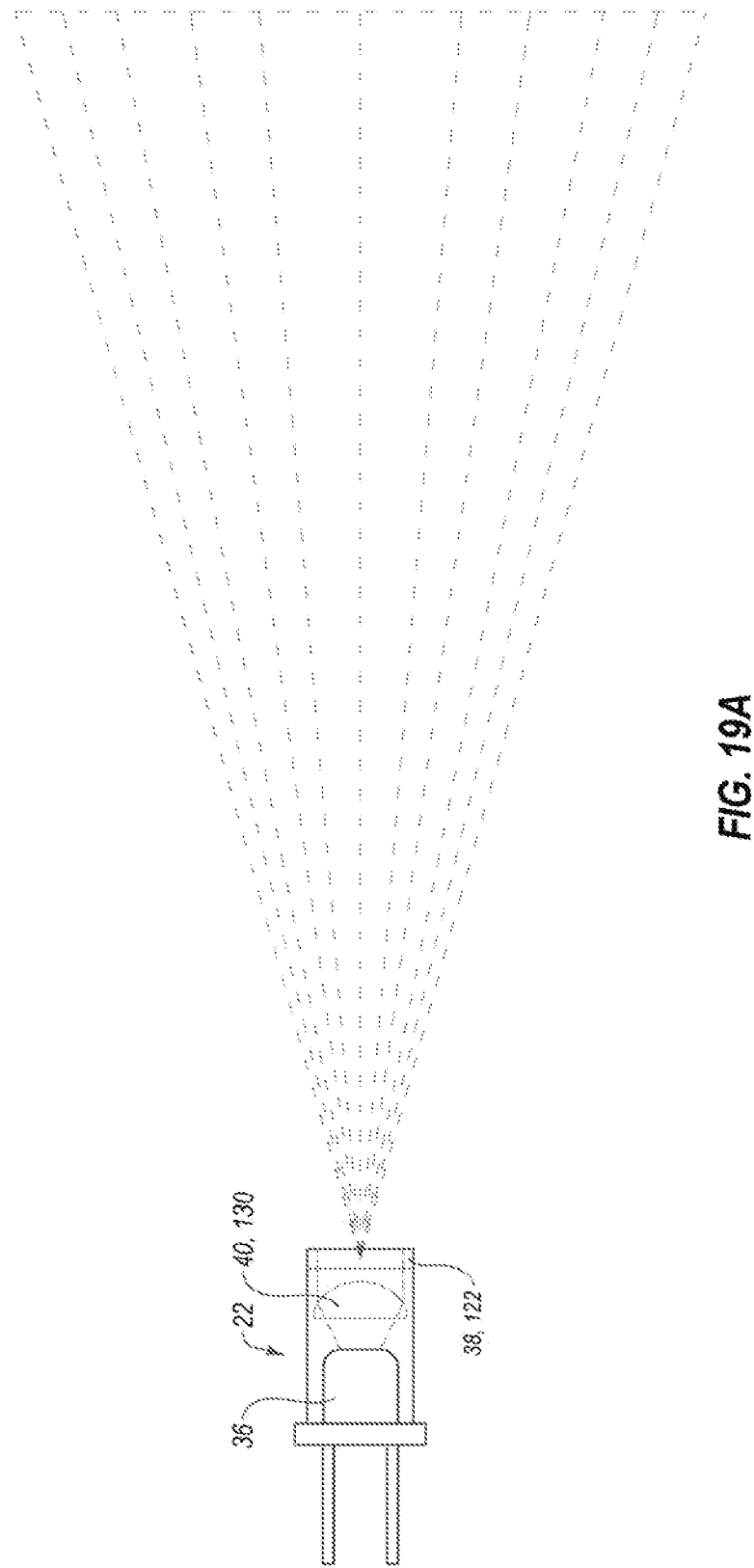

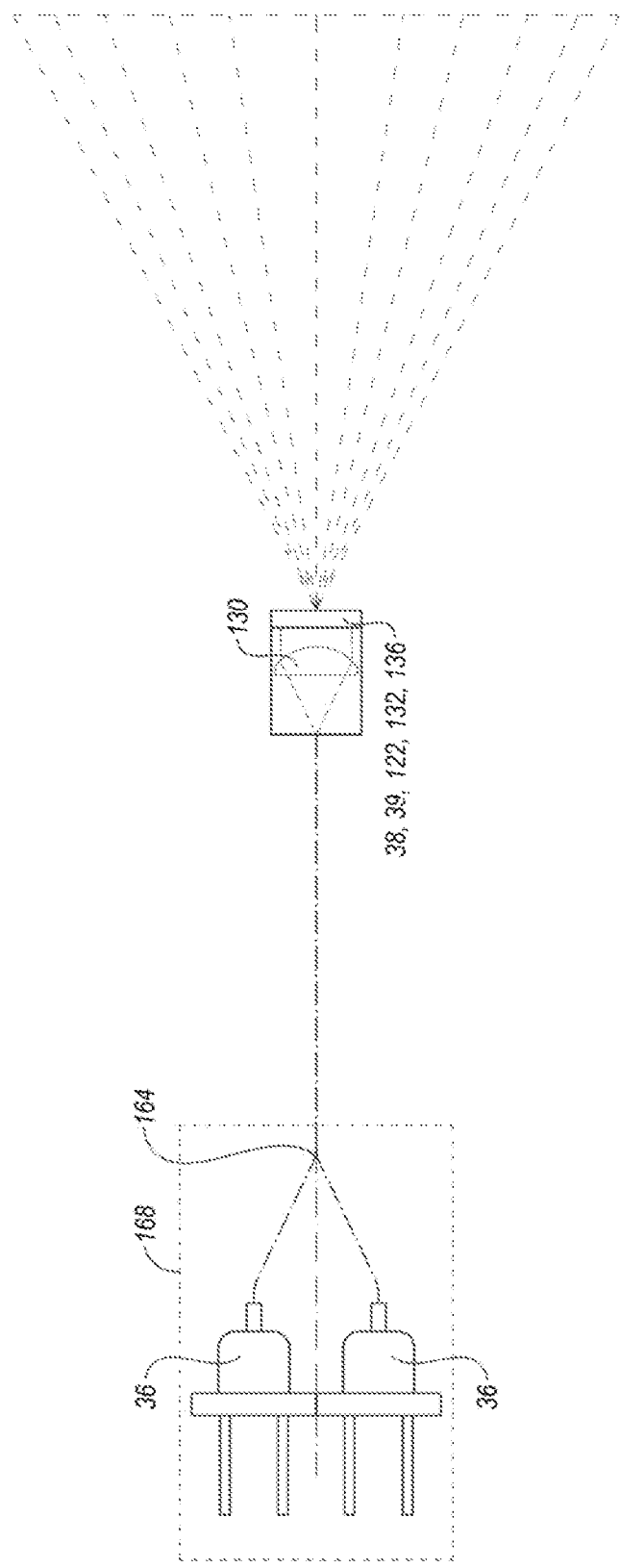

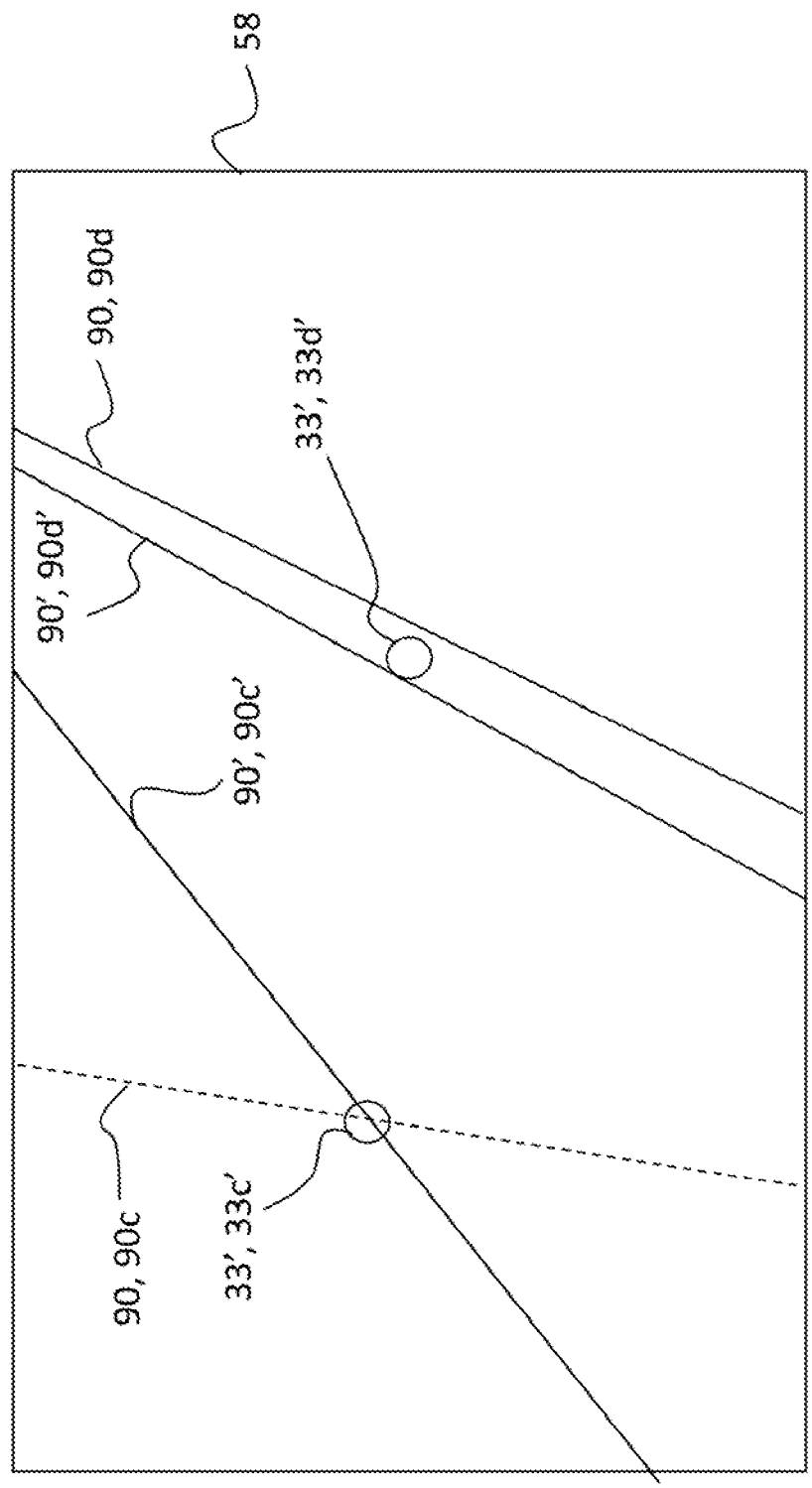

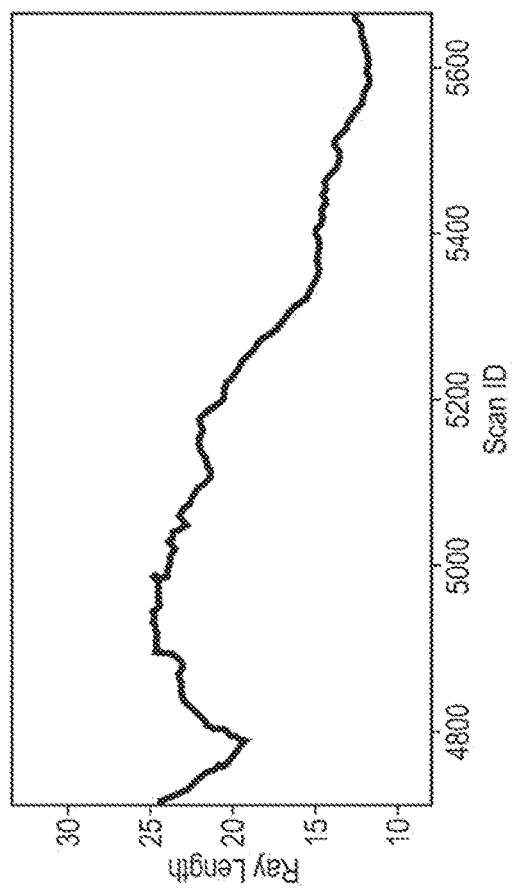
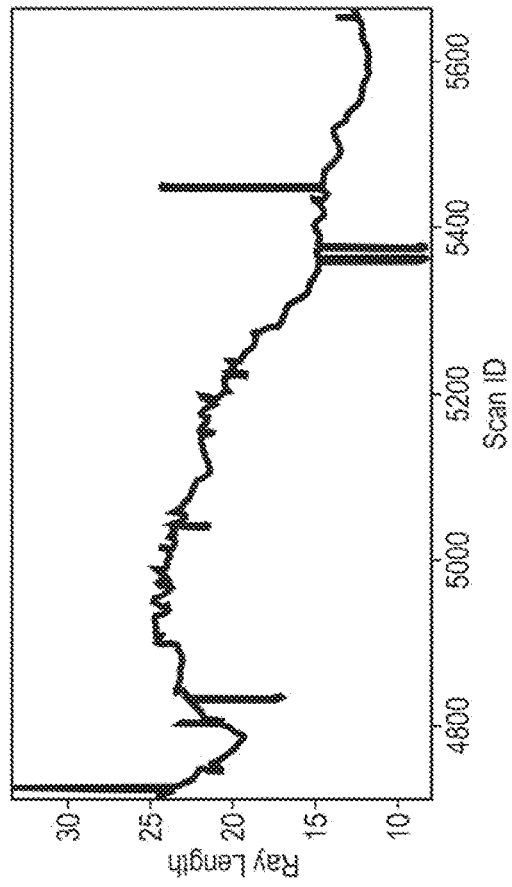
FIG. 40A
FIG. 40B

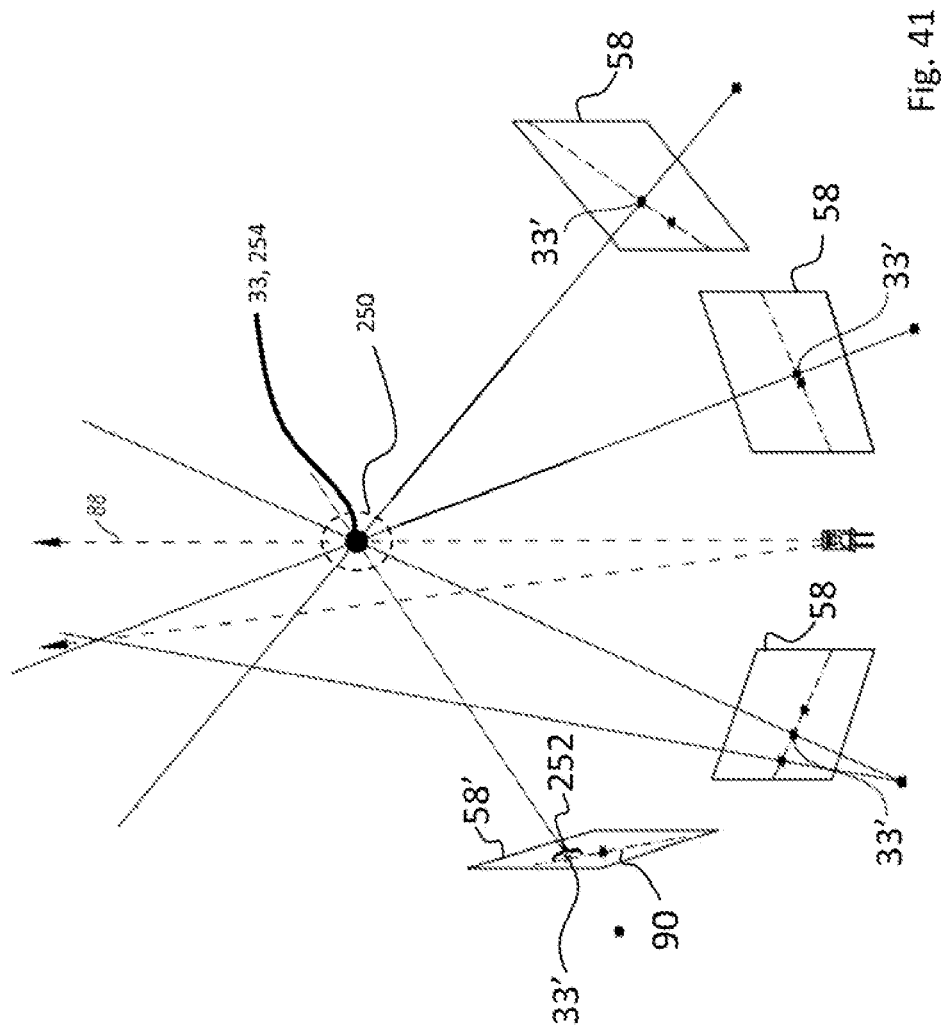

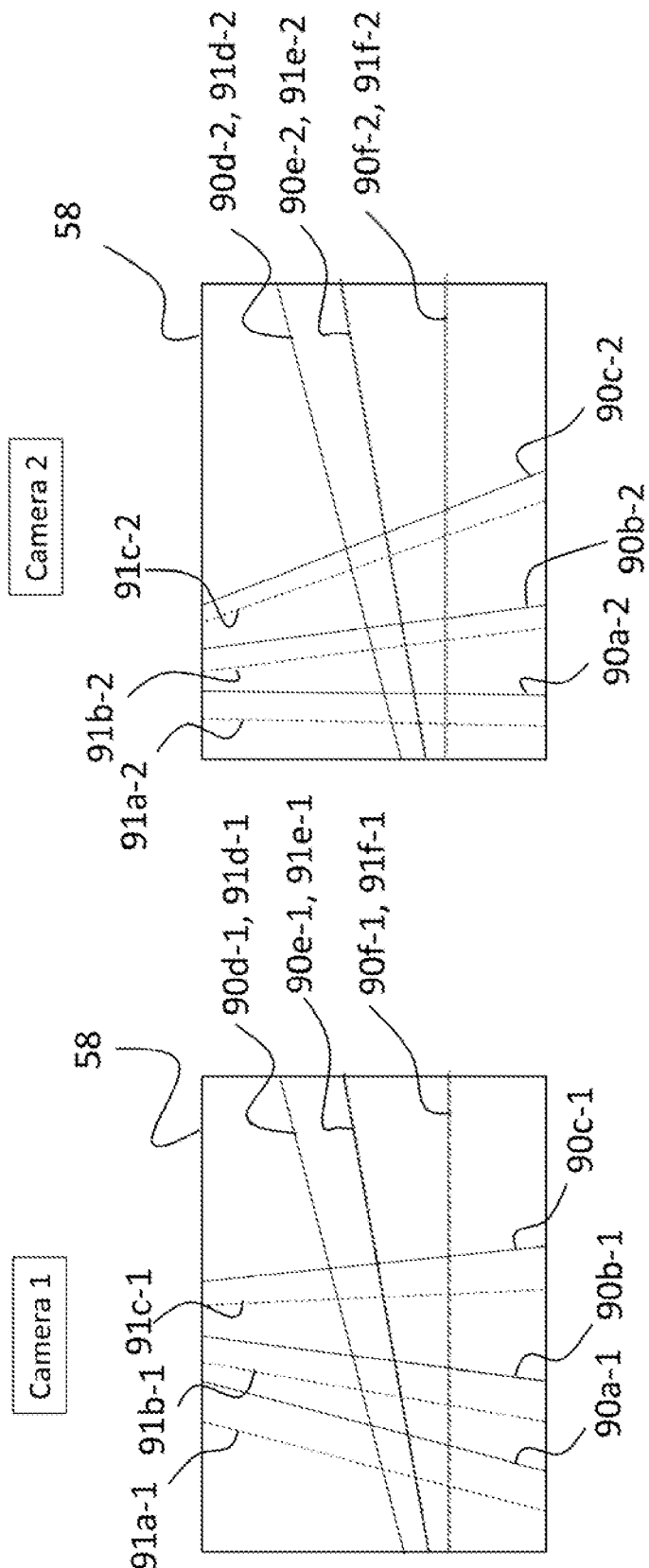

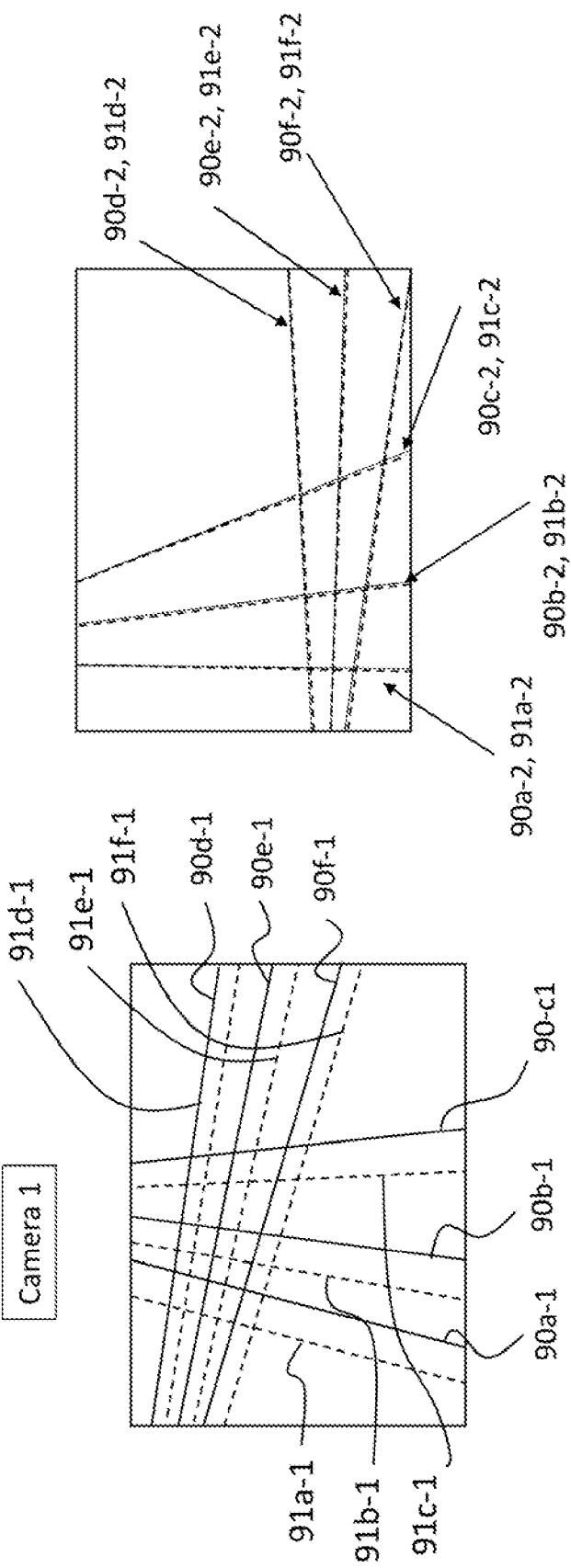

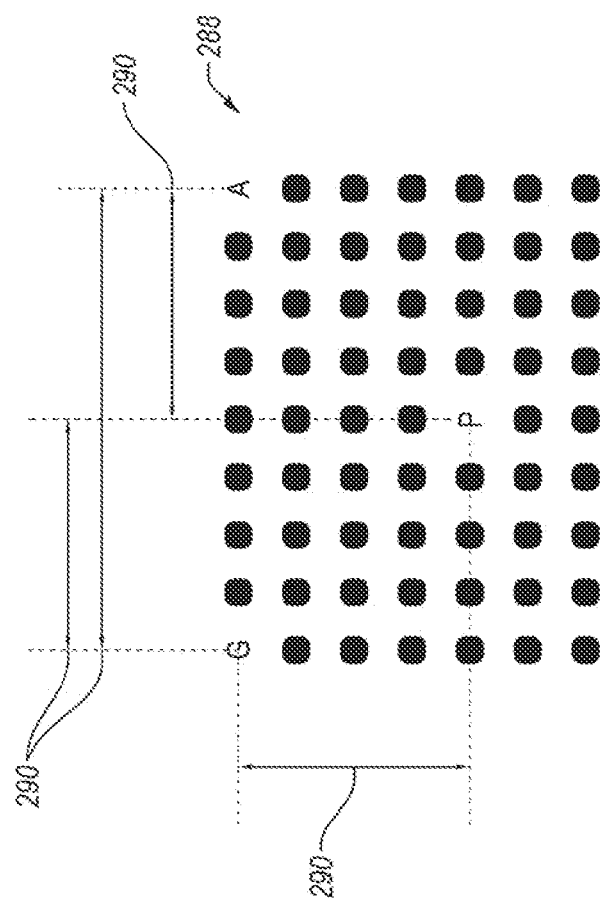
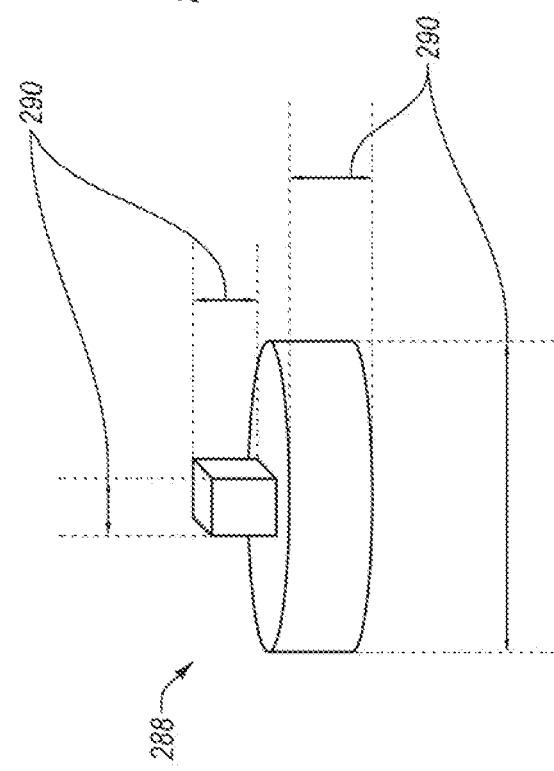
FIG. 49B
FIG. 49A

USING AT LEAST TWO CAMERAS THAT ARE RIGIDLY CONNECTED TO EACH OTHER, WITH NON-OVERLAPPING PORTIONS OF THEIR FIELDS OF VIEW, CAPTURE A PLURALITY OF IMAGES OF AN INTRAORAL 3D SURFACE 358

RUN A SLAM ALGORITHM USING THE PLURALITY OF IMAGES, THE LOCALIZATION OF THE CAMERAS BEING SOLVED BASED ON THE MOTION OF ALL THE CAMERAS BEING THE SAME 360

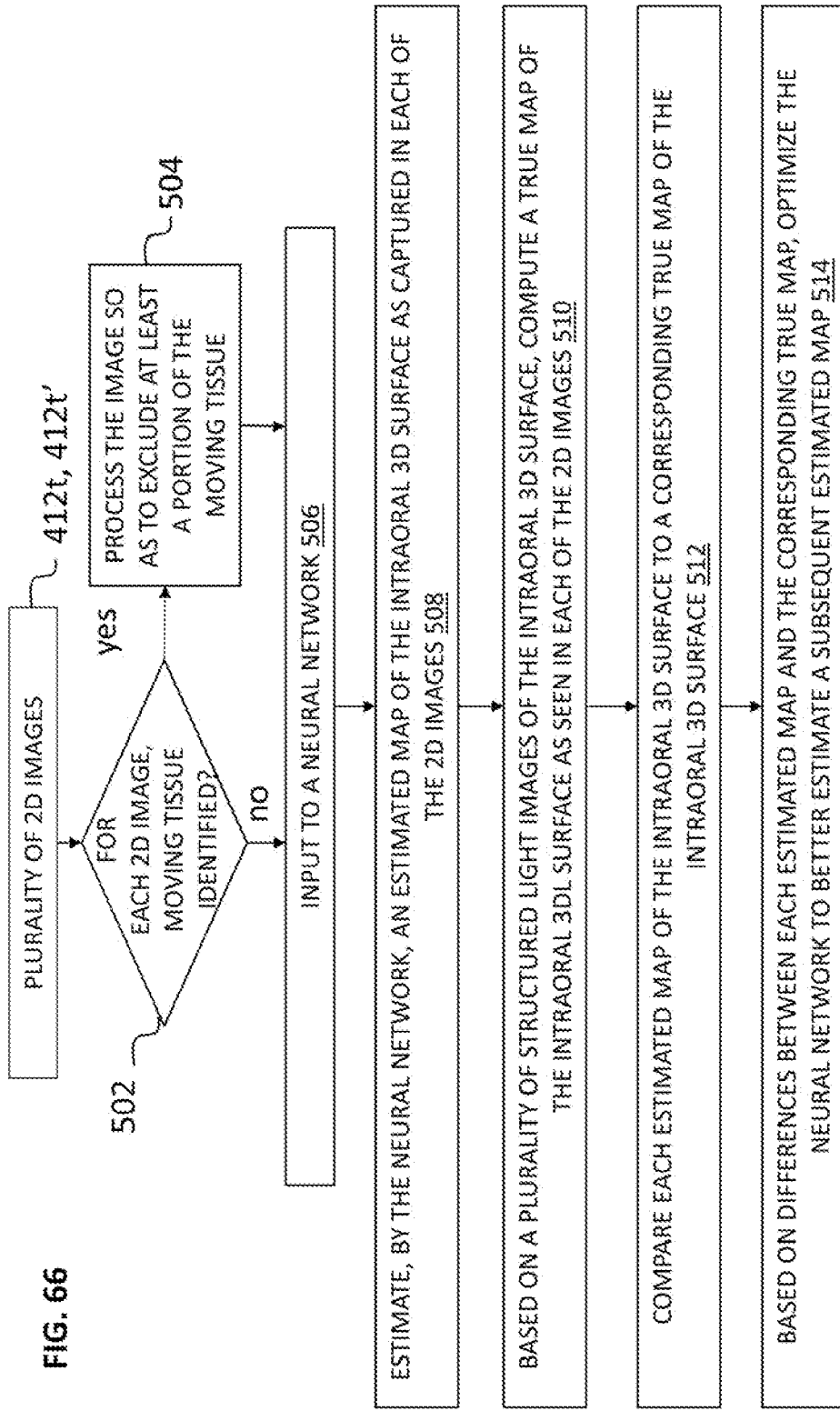

RAY TRACKING FOR INTRAORAL 3D SCANNER

CROSS REFERENCE TO RELATED APPLICATIONS

This patent application is a continuation application of U.S. application Ser. No. 16/910,042, filed Jun. 23, 2020, which claims the benefit under 35 U.S.C. § 119(e) of U.S. Provisional Application No. 62/865,878, filed Jun. 24, 2019, and of U.S. Provisional Application No. 62/953,060, filed Dec. 23, 2019, each of which is herein incorporated by reference.

FIELD OF THE INVENTION

The present invention relates generally to three-dimensional imaging, and more particularly to intraoral three-dimensional imaging using structured light illumination.

BACKGROUND

Dental impressions of a subject's intraoral three-dimensional surface, e.g., teeth and gingiva, are used for planning dental procedures. Traditional dental impressions are made using a dental impression tray filled with an impression material, e.g., PVS or alginate, into which the subject bites. The impression material then solidifies into a negative imprint of the teeth and gingiva, from which a three-dimensional model of the teeth and gingiva can be formed.

Digital dental impressions utilize intraoral scanning to generate three-dimensional digital models of an intraoral three-dimensional surface of a subject. Digital intraoral scanners often use structured light three-dimensional imaging. The surface of a subject's teeth may be highly reflective and somewhat translucent, which may reduce the contrast in the structured light pattern reflecting off the teeth. Therefore, in order to improve the capture of an intraoral scan, when using a digital intraoral scanner that utilizes structured light three-dimensional imaging, a subject's teeth are frequently coated with an opaque powder prior to scanning in order to facilitate a usable level of contrast of the structured light pattern, e.g., in order to turn the surface into a scattering surface. While intraoral scanners utilizing structured light three-dimensional imaging have made some progress, additional advantages may be had.

SUMMARY OF THE INVENTION

The use of structured light three-dimensional imaging may lead to a "correspondence problem," where a correspondence between points in the structured light pattern and points seen by a camera viewing the pattern needs to be determined. One technique to address this issue is based on projecting a "coded" light pattern and imaging the illuminated scene from one or more points of view. Encoding the emitted light pattern makes portions of the light pattern unique and distinguishable when captured by a camera system. Since the pattern is coded, correspondences between image points and points of the projected pattern may be more easily found. The decoded points can be triangulated and 3D information recovered.

Applications of the present invention include systems and methods related to a three-dimensional intraoral scanning device that includes one or more cameras, and one or more pattern projectors. For example, certain applications of the present invention may be related to an intraoral scanning device having a plurality of cameras and a plurality of pattern projectors.

Further applications of the present invention include methods and systems for decoding a structured light pattern.

Still further applications of the present invention may be related to systems and methods of three-dimensional intraoral scanning utilizing non-coded structured light patterns.

For example, in some particular applications of the present invention, an apparatus is provided for intraoral scanning, the apparatus including an elongate handheld wand with a probe at the distal end. During a scan, the probe may be configured to enter the intraoral cavity of a subject. One or more miniature structured light projectors as well as one or more miniature cameras are coupled to a rigid structure disposed within a distal end of the probe. Each of the structured light projectors transmits light using a light source, such as a laser diode. In some applications, the structured light projectors may have a field of illumination of at least 45 degrees. Optionally, the field of illumination may be less than 120 degrees. Each of the structured light projectors may further include a pattern generating optical element. The pattern generating optical element may utilize diffraction and/or refraction to generate a light pattern. In some applications, the light pattern may be a distribution of discrete unconnected spots of light. Optionally, the light pattern maintains the distribution of discrete unconnected spots at all planes located between 1 mm and 30 mm from the pattern generating optical element, when the light source (e.g., laser diode) is activated to transmit light through the pattern generating optical element. In some applications, the pattern generating optical element of each structured light projector may have a light throughput efficiency, i.e., the fraction of light falling on the pattern generator that goes into the pattern, of at least 80%, e.g., at least 90%. Each of the cameras includes a camera sensor and objective optics including one or more lenses.

A laser diode light source and diffractive and/or refractive pattern generating optical elements may provide certain advantages in some applications. For example, the use of laser diodes and diffractive and/or refractive pattern generating optical elements may help maintain an energy efficient structured light projector so as to prevent the probe from heating up during use. Further, such components may help reduce costs by not necessitating active cooling within the probe. For example, present-day laser diodes may use less than 0.6 Watts of power while continuously transmitting at a high brightness (in contrast, for example, to a present-day light emitting diode (LED)). When pulsed in accordance with some applications of the present invention, these present-day laser diodes may use even less power, e.g., when pulsed with a duty cycle of 10%, the laser diodes may use less than 0.06 Watts (but for some applications the laser diodes may use at least 0.2 Watts while continuously transmitting at high brightness, and when pulsed may use even less power, e.g., when pulsed with a duty cycle of 10%, the laser diodes may use at least 0.02 Watts). Further, a diffractive and/or refractive pattern generating optical element may be configured to utilize most, if not all, the transmitted light (in contrast, for example, to a mask which stops some of the rays from hitting the object).

In particular, the diffraction- and/or refraction-based pattern generating optical element generates the pattern by diffraction, refraction, or interference of light, or any combination of the above, rather than by modulation of the light as done by a transparency or a transmission mask. In some applications, this may be advantageous as the light throughput efficiency (the fraction of light that goes into the pattern out of the light that falls on the pattern generator) is nearly 100%, e.g., at least 80%, e.g., at least 90%, regardless of the pattern "area-based duty cycle." In contrast, the light throughput efficiency of a transparency mask or transmission mask pattern generating optical element is directly related to the "area-based duty cycle." For example, for a desired "area-based duty cycle" of 100:1, the throughput efficiency of a mask-based pattern generator would be 1% whereas the efficiency of the diffraction- and/or refraction-based pattern generating optical element remains nearly 100%. Moreover, the light collection efficiency of a laser is at least 10 times higher than an LED having the same total light output, due to a laser having an inherently smaller emitting area and divergence angle, resulting in a brighter output illumination per unit area. The high efficiency of the laser and diffractive and/or refractive pattern generator may help enable a thermally efficient configuration that limits the probe from heating up significantly during use, thus reducing cost by potentially eliminating or limiting the need for active cooling within the probe. While, laser diodes and DOEs may be particularly preferable in some applications, they are by no way essential individually or in combination. Other light sources, including LEDs, and pattern generating elements, including transparency and transmission masks, may be used in other applications with or without active cooling.

In some applications, in order to improve image capture of an intraoral scene under structured light illumination, without using contrast enhancement means such as coating the teeth with an opaque powder, the inventors have realized that a light pattern such as a distribution of discrete unconnected spots of light (as opposed to lines, for example) may provide an improved balance between increasing pattern contrast while maintaining a useful amount of information. Generally speaking, a denser structured light pattern may provide more sampling of the surface, higher resolution, and enable better stitching of the respective surfaces obtained from multiple image frames. However, too dense a structured light pattern may lead to a more complex correspondence problem due to there being a larger number of spots for which to solve the correspondence problem. Additionally, a denser structured light pattern may have lower pattern contrast resulting from more light in the system, which may be caused by a combination of (a) stray light that reflects off the somewhat glossy surface of the teeth and may be picked up by the cameras, and (b) percolation, i.e., some of the light entering the teeth, reflecting along multiple paths within the teeth, and then leaving the teeth in many different directions. As described further hereinbelow, methods and systems are provided for solving the correspondence problem presented by the distribution of discrete unconnected spots of light. In some applications, the discrete unconnected spots of light from each projector may be non-coded.

In some applications, the field of view of each of the cameras may be at least 45 degrees, e.g., at least 80 degrees, e.g., 85 degrees. Optionally, the field of view of each of the cameras may be less than 120 degrees, e.g., less than 90 degrees. For some applications, one or more of the cameras has a fisheye lens, or other optics that provide up to 180 degrees of viewing.

In any case, the field of view of the various cameras may be identical or non-identical. Similarly, the focal length of the various cameras may be identical or non-identical. The term "field of view" of each of the cameras, as used herein, refers to the diagonal field of view of each of the cameras.

Further, each camera may be configured to focus at an object focal plane that is located between 1 mm and 30 mm, e.g., at least 5 mm and/or less than 11 mm, e.g., 9 mm-10 mm, from the lens that is farthest from the respective camera sensor. Similarly, in some applications, the field of illumination of each of the structured light projectors may be at least 45 degrees and optionally less than 120 degrees. The inventors have realized that a large field of view achieved by combining the respective fields of view of all the cameras may improve accuracy due to reduced amount of image stitching errors, especially in edentulous regions, where the gum surface is smooth and there may be fewer clear high resolution 3-D features. Having a larger field of view enables large smooth features, such as the overall curve of the tooth, to appear in each image frame, which improves the accuracy of stitching respective surfaces obtained from multiple such image frames.

In some applications, a method is provided for generating a digital three-dimensional image of an intraoral surface. It is noted that a "three-dimensional image," as the phrase is used in the present application, is based on a three-dimensional model, e.g., a point cloud, from which an image of the three-dimensional intraoral surface is constructed. The resultant image, while generally displayed on a two-dimensional screen, contains data relating to the three-dimensional structure of the scanned object, and thus may typically be manipulated so as to show the scanned object from different views and perspectives. Additionally, a physical three-dimensional model of the scanned object may be made using the data from the three-dimensional image.

For example, one or more structured light projectors may be driven to project a light pattern such as a distribution of discrete unconnected spots of light, a pattern of intersecting lines (e.g., a grid), a checkerboard pattern, or some other pattern on an intraoral surface, and one or more cameras may be driven to capture an image of the projection. The image captured by each camera may include a portion of the projected pattern (e.g., at least one of the spots). In some implementations, the one or more structured light projectors project a pattern that is spatially fixed relative to the one or more cameras.

Each camera includes a camera sensor that has an array of pixels, for each of which there exists a corresponding ray in 3-D space originating from the pixel whose direction is towards an object being imaged; each point along a particular one of these rays, when imaged on the sensor, will fall on its corresponding respective pixel on the sensor. As used throughout this application, including in the claims, the term used for this is a "camera ray." Similarly, for each projected spot from each projector there exists a corresponding projector ray. Each projector ray corresponds to a respective path of pixels on at least one of the camera sensors, i.e., if a camera sees a feature or portion of a pattern (e.g., a spot) projected by a specific projector ray, that feature or portion of the pattern (e.g., the spot) will necessarily be detected by a pixel on the specific path of pixels that corresponds to that specific projector ray. Values for (a) the camera ray corresponding to each pixel on the camera sensor of each of the cameras, and (b) the projector ray corresponding to each of the projected features or portions of the pattern (e.g., spots of light) from each of the projectors, may be stored during a calibration process, as described hereinbelow.

With regard to the camera rays, for some applications, instead of storing individual values for each camera ray corresponding to each pixel on the camera sensor of each of the cameras, a smaller set of calibration values are stored that may be used to indicate each camera ray. For example, parameter values may be stored for a parametrized camera calibration function that takes a given three-dimensional position in space and translates it to a given pixel in the two-dimensional pixel array of the camera sensor, in order to define a camera ray.

With regard to the projector rays, (a) for some applications an indexed list which contains a value for each projector ray is stored, and (b) alternatively, for some applications, a smaller set of calibration values are stored that may be used to indicate each projector ray. For example, parameter values may be stored for a parametrized projector calibration model that defines each projector ray for a given projector.

Based on the stored calibration values a processor may be used to run a correspondence algorithm in order to identify a three-dimensional location for each portion of feature of a projected light pattern (e.g., for a projected spot) on the surface. For a given projector ray, the processor "looks" at the corresponding camera sensor path on one of the cameras. Each detected spot or other feature along that camera sensor path will have a camera ray that intersects the given projector ray. That intersection defines a three-dimensional point in space. The processor then searches among the camera sensor paths that correspond to that given projector ray on the other cameras and identifies how many other cameras, on their respective camera sensor paths corresponding to the given projector ray, also detected a feature of the pattern (e.g., a spot) whose camera ray intersects with that three-dimensional point in space. As used herein throughout the present application, if two or more cameras detect portions or features of a pattern (e.g., spots) whose respective camera rays intersect a given projector ray at the same three-dimensional point in space, the cameras are considered to "agree" on the portion or feature (e.g., spot) being located at that three-dimensional point. The process is repeated for the additional features (e.g., spots) along a camera sensor path, and the feature (e.g., spot) for which the highest number of cameras "agree" is identified as the feature (e.g., spot) that is being projected onto the surface from the given projector ray. A three-dimensional position on the surface is thus computed for that feature of the pattern (e.g., that spot).

In some embodiments, once a position on the surface is determined for a specific feature of the pattern (e.g., a specific spot), the projector ray that projected that feature (e.g., spot), as well as all camera rays corresponding to that feature (e.g., spot), may be removed from consideration and the correspondence algorithm is run again for a next projector ray.

Further applications of the present invention are directed to scanning an intraoral object by projecting a structured light pattern (e.g., parallel lines, grids, checkerboard, unconnected and/or uniform spots, random spot patterns, etc.) onto the intraoral object, capturing at least a portion of the structured light pattern projected onto the intraoral object, and tracking a portion of the captured structured light pattern across successive images. In some embodiments, tracking portions of the captured structured light pattern across successive images may help improve scanning speed and/or accuracy.

In a more specific example related to the structured light scanner using a projected pattern (e.g., of unconnected spots) described above, a processor may be used to compare a series of images (e.g., a plurality of consecutive images) captured by each camera to determine which features of the projected pattern (e.g., which of the projected spots) can be tracked across the series of images (e.g., across the plurality of consecutive images). The inventors have realized that movement of a particular detected feature or spot can be tracked in multiple images in a series of images (e.g., in consecutive image frames). Thus, correspondence that was solved for that particular spot in any of the images or frames across which the feature or spot was tracked provides the solution to correspondence for the feature or spot in all the images or frames across which the feature or spot was tracked. Since detected features or spots that can be tracked across multiple images are features or spots generated by the same specific projector ray, the trajectory of the tracked feature or spot will be along a specific camera sensor path that corresponds to that specific projector ray.

For some applications, alternatively or additionally to tracking detected features or spots within two-dimensional images, the length of each projector ray can be tracked in three-dimensional space. The length of a projector ray is defined as the distance between the origin of the projector ray, i.e., the light source, and the three-dimensional position at which the projector ray intersects the intraoral surface. As further described hereinbelow, tracking the length of a specific projector ray over time may help solve correspondence ambiguities. While the above concepts of spot and ray tracking are described in some instances herein with respect to a scanner projecting unconnected spots, it should be understood that this is exemplary and in no way limiting— the tracking techniques may be equally applicable to scanners projecting other patterns (e.g., parallel lines, grids, checkerboard, unconnected and/or uniform spots, random spot patterns, etc.) onto the intraoral object.

In some embodiments, for the purpose of object scanning, an estimation of the location of the scanner with respect to an object being scanned, i.e., the three-dimensional intraoral surface, may be desirable during a scan and in certain embodiments, the estimation is desirable at all times during the scan. In accordance with some applications of the present invention, the inventors have developed a method of combining visual tracking of a scanner's motion with inertial measurement of the scanner's motion to accommodate for times when sufficient visual tracking may not be available. Accumulated data of motion of the intraoral scanner with respect to intraoral surface (visual tracking) and motion of the intraoral scanner with respect to a fixed coordinate system (inertial measurement) may be used to build a predictive model of motion of the intraoral surface with respect to the fixed coordinate system (further described hereinbelow). When sufficient visual tracking is unavailable, the processor may calculate an estimated location of the intraoral scanner with respect to the intraoral surface by factoring in (e.g., subtracting, in some embodiments) the prediction of the motion of the intraoral surface with respect to the fixed coordinate system from the inertial measurement of motion of the intraoral scanner with respect to the fixed coordinate system (further described hereinbelow). It should be understood that the scanner location estimation concepts described herein may be used with intraoral scanners, no matter the scanning technology employed (e.g., parallel confocal scanning, focus scanning, wavefront scanning, stereovision, structured light, triangulation, light field, and/or combinations thereof). Accordingly, while discussed in relation to the structured light concepts described herein, this is exemplary and in no way limiting.

In some embodiments of structured light scanners described herein, the stored calibration values may indicate (a) a camera ray corresponding to each pixel on the camera sensor of each camera, and (b) a projector ray corresponding to each projected feature (e.g., spot of light) from each structured light projector, whereby each projector ray corresponds to a respective path of pixels on at least one of the camera sensors. However, it is possible that, over time, at least one of the cameras and/or at least one of the projectors may move (e.g., by rotation or translation), the optics of at least one of the cameras and/or at least one of the projectors may be altered, or the wavelengths of the lasers may be altered, resulting in the stored calibration values no longer accurately corresponding to camera ray and projector ray.

For any given projector ray, if the processor collects data including computed respective three-dimensional positions on the intraoral surface of a plurality of detected features (e.g., spots) from that projector ray that were detected at respective different points in time, and superimposes them on one image, the features (e.g., spots) should all fall on the camera sensor path of pixels that corresponds to that projector ray. If something has altered the calibration of either the camera or the projector, then it may appear as though the detected features (e.g., spots) from that particular projector ray do not fall on the expected camera sensor path of pixels as per the stored calibration values, but rather they fall on a new updated camera sensor path of pixels. In the event that the calibration of the camera(s) and/or the projector(s) has been altered, the processor may reduce the difference between the updated path of pixels and the original path of pixels from the calibration data by varying (i) the stored calibration values indicating a camera ray corresponding to each pixel on the camera sensor of each one of the one or more cameras (e.g., stored parameter values of the parametrized camera calibration model, e.g., function), and/or (ii) the stored calibration values indicating a projector ray r corresponding to each one of the projected features (e.g., spots of light) from each one of the one or more projectors (e.g., stored values in an indexed list of projector rays, or stored parameter values of a parametrized projector calibration model).

An assessment of a current calibration may automatically be performed on a periodic basis (e.g., every scan, every $10^{th}$ scan, every month, every few months, etc.) or in response to certain criteria being met (e.g., in response to a threshold number of scans having been made). As a result of the assessment, the system may determine whether a state of the calibration is accurate or inaccurate. In one embodiment, as a result of the assessment the system determines whether the calibration is drifting. For example, the previous calibration may still be accurate enough to produce high quality scans, but the system may have deviated such that in the future it will no longer be able to produce accurate scans if a detected trend continues. In one embodiment, the system determines a rate of drift, and projects that rate of drift into the future to determine a projected date/time at which the calibration will no longer be accurate. In one embodiment, automatic calibration or manual calibration may be scheduled for that future date/time. In an example, processing logic assesses a state of calibration through time (e.g., by comparing states of calibration at multiple different points in time), and from such a comparison determines a rate of drift. From the rate of drift, the processing logic can predict when calibration should be performed based on the trend data.

Conventional intraoral scanners are recalibrated manually by users according to a set schedule (e.g., every six months). Conventional intraoral scanners do not have an ability to monitor or assess the current state of calibration (e.g., to determine whether a recalibration should be performed). Moreover, calibration of conventional intraoral scanners is performed manually using special calibration targets. The calibration of conventional intraoral scanners is time consuming and inconvenient to users. Accordingly, the dynamic calibration performed in certain embodiments described herein provides increased convenience to users, and can be performed in less time, as compared to calibration of conventional intraoral scanners.

For some applications, in the event that the calibration of the camera(s) and/or the projector(s) has been altered, the processor may not perform a recalibration, but rather may only determine that at least some of the stored calibration values for the camera(s) and/or the projector(s) are incorrect. For example, based on the determination that the stored calibration values are incorrect, a user may be prompted to return the intraoral scanner to the manufacturer for maintenance and/or recalibration, or request a new scanner.

Visual tracking of the motion of the intraoral scanner with respect to an object being scanned may be obtained by stitching of the respective surfaces or point clouds obtained from adjacent image frames. As described herein, for some applications, illumination of the intraoral cavity under near-infrared (NIR) light may increase the number of visible features that can be used to stitch the respective surfaces or point clouds obtained from adjacent image frames. In particular, NIR light penetrates the teeth, such that images captured under NIR light include features that are inside the teeth, e.g., cracks within a tooth, as opposed to two-dimensional color images taken under broad spectrum illumination in which only features appearing on the surface of the teeth are visible. These additional sub-surface features may be used for stitching the respective surfaces or point clouds obtained from adjacent image frames.

For some applications the processor may use two-dimensional images (e.g., two-dimensional color images, and/or two-dimensional monochromatic NIR images) in a 2D-to-3D surface reconstruction of the intraoral three-dimensional surface. As described hereinbelow, using two-dimensional images (e.g., two-dimensional color images, and/or two-dimensional monochromatic NIR images) may significantly increase the resolution and speed of the three-dimensional reconstruction. Thus, as described herein, for some applications it is useful to augment the three-dimensional reconstruction of the intraoral three-dimensional surface with three-dimensional reconstruction from two-dimensional images (e.g., two-dimensional color images, and/or two-dimensional monochromatic NIR images). For some applications, the processor computes respective three-dimensional positions of a plurality of points on the intraoral three-dimensional surface, e.g., using the correspondence algorithm described herein, and computes a three-dimensional structure of the intraoral three-dimensional surface, based on a plurality of two-dimensional images (e.g., two-dimensional color images, and/or two-dimensional monochromatic NIR images) and the computed three-dimensional positions on the intraoral surface.

In accordance with some applications of the present invention, the computation of the three-dimensional structure is performed by a neural network. The processor inputs to the neural network (a) the plurality of two-dimensional images (e.g., two-dimensional color images) of the intraoral three-dimensional surface, and (b) the computed three-dimensional positions of the plurality of points on the intraoral three-dimensional surface, and the neural network determines and returns a respective estimated map (e.g., depth map, normal map, and/or curvature map) of the intraoral three-dimensional surface captured in each of the two-dimensional images (e.g., two-dimensional colored images and/or two-dimensional monochromatic NIR images).

The inventors have realized that when the intraoral scanners are commercially produced there may exist small manufacturing deviations that cause (a) the calibration of the camera(s) and/or projector(s) on each commercially-produced intraoral scanner to be slightly different than the calibration of the training-stage camera(s) and/or projector(s), and/or (b) the illumination relationships between the camera(s) and the projector(s) on each commercially-produced intraoral scanner to be slightly different than those of training-stage camera(s) and projector(s) that are used for training the neural network. Other manufacturing deviations in the cameras and/or projectors may exist as well. In accordance with some applications of the present invention, a method is provided in which the processor is used to overcome manufacturing deviations of the camera(s) and/or projector(s) of the intraoral scanner, to reduce a difference between the estimated maps and a true structure of the intraoral three-dimensional surface.

In accordance with some applications of the present invention, one way in which the manufacturing tolerances may be overcome is by modifying, e.g., cropping and morphing, the images from in-the-field intraoral scanners so as to obtain modified images that match the fields of view of a set of reference cameras that are used to train the neural network. The neural network is trained based on images received from the set of reference cameras and, subsequently, in-the-field images are modified such that it is as if the neural network is receiving those images as they would have been captured by the reference cameras. The three-dimensional structure of the intraoral three-dimensional surface is then computed based on the plurality of modified two-dimensional images of the intraoral three-dimensional surface, e.g., the neural network determines a respective estimated map of the intraoral three-dimensional surface as captured in each of the plurality of modified two-dimensional images.

In accordance with some applications of the present invention, the neural network determines a respective estimated depth map of the intraoral three-dimensional surface captured in each of the two-dimensional images, and the depth maps are stitched together in order to obtain the three-dimensional structure of the intraoral surface. However, there may sometimes be contradictions between the estimated depth maps. The inventors have realized that it would be advantageous if for every estimated depth map determined by the neural network, the neural network also determines an estimated confidence map, each confidence map indicating a confidence level per region of the respective estimated depth map. Thus, a method is provided herein for inputting a plurality of two-dimensional images of the intraoral three-dimensional surface to a first neural network module and to a second neural network module. The first neural network module determines a respective estimated depth map of the intraoral three-dimensional surface as captured in each of the two-dimensional images. The second neural network module determines a respective estimated confidence map corresponding to each estimated depth map. Each confidence map indicates a confidence level per region of the respective estimated depth map.

In accordance with some applications of the present invention, the neural network is trained using (a) two-dimensional images of training-stage three-dimensional surfaces, e.g., model surfaces and/or intraoral surfaces, and (b) corresponding true output maps of the training-stage three-dimensional surfaces, which are computed based on structured light images of the training-stage three-dimensional surfaces. The neural network estimates for each two-dimensional image an estimated map of the intraoral three-dimensional surface as captured in each of the two-dimensional images, and each estimated image is then compared to a corresponding true map of the intraoral three-dimensional surface. Based on differences between each estimated map and the corresponding true map, the neural network is optimized to better estimate a subsequent estimated map.

For some applications, when intraoral three-dimensional surfaces are used for training the neural network, moving tissue, e.g., a subject's tongue, lips, and/or cheek, may be blocking part of the intraoral three-dimensional surface from the view of one or more of the cameras. In order to avoid the neural network "learning" based on the images of moving tissue (as opposed to the fixed tissue of the intraoral three-dimensional surface being scanned), for a two-dimensional image in which moving tissue is identified, the image may be processed so as to exclude at least a portion of the moving tissue prior to inputting the two-dimensional image to the neural network.

For some applications, a disposable sleeve is placed over the distal end of the intraoral scanner, e.g. over the probe, prior to the probe being placed inside a patient's mouth, in order to prevent cross contamination between patients. Due to the relative positioning of the structured light projectors and neighboring cameras within the probe, as described further herein, a portion of the projected structured light pattern may be reflected off the sleeve and reach the camera sensor of a neighboring camera. As further described herein, due to the polarization of the laser light of the structured light projectors the laser may be rotated around its own optical axis such that a polarization angle of the laser light with respect to the sleeve is found so as to reduce the extent of the reflections.

In accordance with some applications of the present invention, a simultaneous localization and mapping (SLAM) algorithm is used to track motion of the handheld wand and to generate three-dimensional images. SLAM may be performed using two or more cameras seeing generally the same image, but from slightly different angles. However, due to the positioning of cameras 24 within probe 28, and the close positioning of probe 28 to the object being scanned, i.e., the intraoral three-dimensional surface, it is often not the case that two or more of the cameras in the probe see generally the same image. As described hereinbelow, additional challenges to utilizing a SLAM algorithm may be encountered when scanning an intraoral three-dimensional surface. The inventors have invented a number of ways to overcome these challenges in order to utilize SLAM to track the motion of the handheld wand and generate three-dimensional images of an intraoral three-dimensional surface, as further described herein.

In accordance with some applications of the present invention, when the handheld wand is being used to scan an intraoral three-dimensional surface, it is possible that as the structured light projectors are projecting their distributions of features (e.g., distributions of spots) on the intraoral surface, some of the features (e.g., spots) may land on moving tissue (e.g., the patient's tongue). For improvement of accuracy of the three-dimensional reconstruction algorithm, features (e.g., spots) that fall on moving tissue should generally not be relied upon for reconstruction of the intraoral three-dimensional surface. As described herein, whether a feature (e.g., spot) has been projected on moving or stable tissue within the intraoral cavity may be determined on image frames of unstructured light (e.g., which may be broad spectrum light) interspersed through image frames of structured light. A confidence grading system may be used to assign confidence grades based on the determination of whether the detected featured (e.g., spots) are projected on fixed or moving tissue. Based on the confidence grade for each of the plurality of features (e.g., spots), the processor may run a three-dimensional reconstruction algorithm using the detected features (e.g., spots).

In one method set forth herein for generating a digital three-dimensional image, the method includes driving each one of one or more structured light projectors to project a pattern on an intraoral three-dimensional surface. The method further includes driving each one of one or more cameras to capture a plurality of images, each image including at least a portion of the projected pattern. The method further includes using a processor to compare a series of images captured by the one or more cameras, determine which of portions of the projected pattern can be tracked across the series of images based on the comparison of the series of images, and construct a three-dimensional model of the intraoral three-dimensional surface based at least in part on the comparison of the series of images. In one implementation, the method further includes solving a correspondence algorithm for the tracked portions of the projected pattern in at least one of the series of images, and using the solved correspondence algorithm in the at least one of the series of images to address the tracked portions of the projected pattern, e.g., to solve the correspondence algorithm for the tracked portions of the projected pattern, in images of the series of images where the correspondence algorithm is not solved, wherein the solution to the correspondence algorithm is used to construct the three-dimensional model. In one implementation, the method further includes solving a correspondence algorithm for the tracked portions of the projected pattern based on portions of the tracked positions of the tracked portions in each image throughout the series of images, wherein the solution to the correspondence algorithm is used to construct the three-dimensional model.

In one implementation of the method, the projected pattern comprises a plurality of projected spots of light, and the portion of the projected pattern corresponds to a projected spot of the plurality of projected spots of light. In a further implementation, the processor is used to compare the series of images based on stored calibration values indicating (a) a camera ray corresponding to each pixel on a camera sensor of each one of the one or more cameras, and (b) a projector ray corresponding to each one of the projected spots of light from each one of the one or more structured light projectors, wherein each projector ray corresponds to a respective path of pixels on at least one of the camera sensors, wherein determining which portions of the projected pattern can be tracked comprises determining which of the projected spots s can be tracked across the series of images, and wherein each tracked spot s moves along a path of pixels corresponding to a respective projector ray r.

In a further implementation of the method, using the processor further comprises using the processor to determine, for each tracked spot s, a plurality of possible paths p of pixels on a given one of the cameras, paths p corresponding to a respective plurality of possible projector rays r. In a further implementation, using the processor further comprises using the processor to run the correspondence algorithm to, for each of the possible projector rays r, perform multiple operations. The multiple operations include identifying how many other cameras, on their respective paths p1 of pixels corresponding to projector ray r, detected respective spots q corresponding to respective camera rays that intersect projector ray r and the camera ray of the given one of the cameras corresponding to the tracked spot s. The operations further include identifying a given projector ray r1 for which the highest number of other cameras detected respective spots q. The operations further include identifying projector ray r1 as the particular projector ray r that produced the tracked spot s.

In a further implementation of the method, the method includes using the processor to (a) run the correspondence algorithm to compute respective three-dimensional positions of a plurality of detected spots on the intraoral three-dimensional surface, as captured in the series of images, and (b) in at least one of the series of images, identify a detected spot as being from a particular projector ray r by identifying the detected spot as being a tracked spot s moving along the path of pixels corresponding to the particular projector ray r.

In a further implementation of the method, the method includes using the processor to (a) run a correspondence algorithm to compute respective three-dimensional positions of a plurality of detected spots on the intraoral three-dimensional surface, as captured in the series of images, and (b) remove from being considered as a point on the intraoral three-dimensional surface a spot that (i) is identified as being from particular projector ray r based on the three-dimensional position computed by the correspondence algorithm, and (ii) is not identified as being a tracked spot s moving along the path of pixels corresponding to particular projector ray r.

In a further implementation of the method, the method includes using the processor to (a) run the correspondence algorithm to compute respective three-dimensional positions of a plurality of detected spots on the intraoral three-dimensional surface, as captured in the series of images, and (b) for a detected spot which is identified as being from two distinct projector rays r based on the three-dimensional position computed by the correspondence algorithm, identify the detected spot as being from one of the two distinct projector rays r by identifying the detected spot as a tracked spot s moving along the one of the two distinct projector rays r.

In a further implementation of the method, the method includes using the processor to (a) run the correspondence algorithm to compute respective three-dimensional positions of a plurality of detected spots on the intraoral three-dimensional surface, as captured in the series of images, and (b) identify a weak spot whose three-dimensional position was not computed by the correspondence algorithm as being a projected spot from a particular projector ray r, by identifying the weak spot as being a tracked spots moving along the path of pixels corresponding to particular projector ray r.

In a further implementation of the method, the method includes using the processor to compute respective three-dimensional positions on the intraoral three-dimensional surface at an intersection of the projector ray r and the respective camera rays corresponding to the tracked spot s in each of the series of images across which spot s was tracked.

In a further implementation of the method, the three-dimensional model is constructed using a correspondence algorithm, wherein the correspondence algorithm uses, at least in-part, the portions of the projected pattern that are determined the be trackable across the series of images.

In a further implementation of the method, the method includes using the processor to (a) determine a parameter of a tracked portion of the projected pattern in at least two adjacent images from the series of images, the parameter selected from the group consisting of: a size of the portion, a shape of the portion, an orientation of the portion, an intensity of the portion, and a signal-to-noise ratio (SNR) of the portion, and (b) based on the parameter of the tracked portion of the projected pattern in the at least two adjacent images, predict the parameter of the tracked portion of the projected pattern in a later image.

In a further implementation of the method, using the processor further comprises, based on the predicted parameter of the tracked portion of the projected pattern, using the processor to search for the portion of the projected pattern having substantially the predicted parameter in the later image.

In a further implementation of the method, the parameter is the shape of the portion of the projected pattern, and using the processor further comprises using the processor to, based on the predicted shape of the tracked portion of the projected pattern, determine a search space in a next image in which to search for the tracked portion of the projected pattern.

In a further implementation of the method, using the processor to determine the search space comprises using the processor to determine the search space in the next image in which to search for the tracked portion of the projected pattern, the search space having a size and aspect ratio based on a size and aspect ratio of the predicted shape of the tracked portion of the projected pattern.

In a further implementation of the method, the parameter is the shape of the portion of the projected pattern, and using the processor further comprises using the processor to (a) based on a direction and distance that the tracked portion of the projected pattern has moved between the at least two adjacent images from the series of images, determine a velocity vector of the tracked portion of the projected pattern, (b) in response to the shape of the tracked portion of the projected pattern in at least one of the at least two adjacent images, predict the shape of the tracked portion of the projected pattern in a later image, and (c) in response to (i) the determination of the velocity vector of the tracked portion of the projected pattern in combination with (ii) the predicted shape of the tracked portion of the projected pattern, determine a search space in the later image in which to search for the tracked portion of the projected pattern.

In a further implementation of the method, the parameter is the shape of the portion of the projected pattern, and using the processor further comprises using the processor to (a) based on a direction and distance that the tracked portion of the projected pattern has moved between the at least two adjacent images from the series of images, determine a velocity vector of the tracked portion of the projected pattern, (b) in response to the determination of the velocity vector of the tracked portion of the projected pattern, predict the shape of the tracked portion of the projected pattern in a later image, and (c) in response to (i) the determination of the velocity vector of the tracked portion of the projected pattern in combination with (ii) the predicted shape of the tracked portion of the projected pattern, determine a search space in the later image in which to search for the tracked portion of the projected pattern.

In a further implementation of the method, using the processor comprises using the processor to predict the shape of the tracked portion of the projected pattern in the later image in response to (i) the determination of the velocity vector of the tracked portion of the projected pattern in combination with (ii) the shape of the tracked portion of the projected pattern in at least one of the two adjacent images.

In a further implementation of the method, using the processor further comprises using the processor to (a) based on a direction and distance that a tracked portion of the projected pattern has moved between two consecutive images in the series of images, determine a velocity vector of the tracked portion of the projected pattern, and (b) in response to the determination of the velocity vector of the tracked portion of the projected pattern, determine a search space in a later image in which to search for the tracked portion of the projected pattern.

In one implementation of a second method set forth herein for generating a digital three-dimensional image, the method includes, driving each one of one or more structured light projectors to project a pattern of light on an intraoral three-dimensional surface along a plurality of projector rays, and driving each one of one or more cameras to capture a plurality of images, each image including at least a portion of the projected pattern, each one of the one or more cameras comprising a camera sensor comprising an array of pixels. The second method further includes using a processor to: run a correspondence algorithm to compute respective three-dimensional positions on the intraoral three-dimensional surface of a plurality of detected features of the projected pattern for each of the plurality of images; using data corresponding to the respective three-dimensional positions of at least three features, each feature corresponding to a respective projector ray r of the plurality of projector rays, estimate a three-dimensional surface based on the at least three features; for a projector ray r1 of the plurality of projector rays for which a three-dimensional position of a feature corresponding to that projector ray r1 was not computed, estimate a three-dimensional position in space of an intersection of projector ray r1 and the estimated three-dimensional surface; and using the estimated three-dimensional position in space, identify a search space in the pixel array of at least one camera in which to search for a feature corresponding to projector ray r1.

In a further implementation of the second method, the correspondence algorithm is run based on stored calibration values indicating (a) a camera ray corresponding to each pixel on the camera sensor of each one of the one or more cameras, and (b) a projector ray corresponding to each feature of the projected pattern from each one of the one or more structured light projectors, whereby each projector ray corresponds to a respective path of pixels on at least one of the camera sensors. Additionally, the search space in the data comprises a search space defined by one or more thresholds.

In a further implementation of the second method, the processor sets a threshold, such that a detected feature that is below the threshold is not considered by the correspondence algorithm, and to search for the feature corresponding to projector ray r1 in the identified search space, the processor lowers the threshold in order to consider features that were not considered by the correspondence algorithm. For some implementations, the threshold is an intensity threshold.

In a further implementation of the second method, the pattern of light comprises a distribution of discrete spots, and each of the features comprises a spot from the distribution of discrete spots.

In a further implementation of the second method, the data corresponding to the respective three-dimensional positions of at least three features comprises using data corresponding to the respective three-dimensional positions of at least three features that were all captured in one of the plurality of images.

In a further implementation of the second method, the second method further comprises refining the estimation of the three-dimensional surface using data corresponding to a three-dimensional position of at least one additional feature of the projected pattern, the at least one additional feature having a three-dimensional position that was computed based on another one of plurality of images. In a further implementation of the second method, refining the estimation of the three-dimensional surface comprises refining the estimation of the three-dimensional surface such that all of the at least three features and the at least one additional feature lie on the estimated three-dimensional surface.

In a further implementation of the second method, using data corresponding to the respective three-dimensional positions of at least three features comprises using data corresponding to at least three features, each captured in a respective one of the plurality of images.

In one implementation of a third method for generating a digital three-dimensional image, the third method includes driving each one of one or more structured light projectors to project a pattern of light on an intraoral three-dimensional surface and driving each of a plurality of cameras to capture an image, the image including at least a portion of the projected pattern, each one of the plurality of cameras comprising a camera sensor comprising an array of pixels. The third method further includes using a processor to: run a correspondence algorithm to compute respective three-dimensional positions on the intraoral three-dimensional surface of a plurality of features of the projected pattern; using data from a first camera of the plurality of cameras, identify a candidate three-dimensional position of a given feature of the projected pattern corresponding to or otherwise associated with one or more particular projector ray(s) r, wherein data from a second camera of the plurality of cameras is not used to identify that candidate three-dimensional position; using the candidate three-dimensional position as seen by the first camera, identify a search space on the second camera's pixel array in which to search for a feature of the projected pattern from projector ray(s) r; and if a feature of the projected pattern from projector ray r is identified within the search space, then, using the data from the second camera, refine the candidate three-dimensional position of the feature of the projected pattern.

In a further implementation of the third method, to identify the candidate three-dimensional position of a given spot corresponding to a particular projector ray r, the processor uses data from at least two of the cameras, wherein data from another one of the cameras that is not one of the at least two cameras is not used to identify that candidate three-dimensional position, and to identify the search space, the processor uses the candidate three-dimensional position as seen by at least one of the at least two cameras.

In a further implementation of the third method, the pattern of light comprises a distribution of discrete unconnected spots of light, and wherein the feature of the projected pattern comprises a projected spot from the unconnected spots of light.

In a further implementation of the third method, the processor uses stored calibration values indicating (a) a camera ray corresponding to each pixel on the camera sensor of each one of the plurality of cameras, and (b) a projector ray corresponding to each one of the features of the projected pattern of light from each one of the one or more structured light projectors, whereby each projector ray corresponds to a respective path of pixels on at least one of the camera sensors.

In a fourth method set forth herein for generating a digital three-dimensional image, the fourth method includes driving each of one or more structured light projectors to project a pattern of light on an intraoral three-dimensional surface, and driving each of one or more cameras to capture an image, the image including at least a portion of the pattern. The fourth method further includes using a processor to run a correspondence algorithm to compute respective three-dimensional positions of a plurality of features of the pattern on the intraoral three-dimensional surface as captured in the series of images, identify the computed three-dimensional position of a detected feature of the imaged pattern as associated with one or more particular projector ray r in at least a subset of the series of images, and based on the three-dimensional position of the detected feature corresponding to the one or more projector ray r in the subset of images, assess a length associated with the one or more projector ray r in each image of the subset of images.

In the fourth method the processor may further be used to compute an estimated length of the one or more projector ray r in at least one of the series of images in which a three-dimensional position of the projected feature from the one or more projector ray was not identified.

In one implementation of the fourth method, each of the one or more cameras comprises a camera sensor comprising an array of pixels, wherein the computation of the respective three-dimensional positions of the plurality of features of the pattern on the intraoral three-dimensional surface and identification of the computed three-dimensional position of a detected feature of the pattern as corresponding to a particular projector ray r is performed based on stored calibration values indicating (i) a camera ray corresponding to each pixel on the camera sensor of each one of the one or more camera sensors, and (ii) a projector ray corresponding to each one of the features of the projected pattern of light from each one of the one or more projectors, whereby each projector ray corresponds to a respective path of pixels on at least one of the camera sensors.

In a further implementation of the fourth method, using the processor further comprises using the processor to compute an estimated length of the projector ray r in at least one of the series of images in which a three-dimensional position of the projected feature from the projector ray r was not identified, and based on the estimated length of projector ray r in the at least one of the series of images, determine a one-dimensional search space in the at least one of the series of images in which to search for a projected feature from projector ray r, the one-dimensional search space being along the respective path of pixels corresponding to projector ray r.

In a further implementation of the fourth method, using the processor further comprises using the processor to compute an estimated length of the projector ray r in at least one of the series of images in which a three-dimensional position of the projected feature from the projector ray r was not identified, and based on the estimated length of projector ray r in the at least one of the series of images, determine a one-dimensional search space in respective pixel arrays of a plurality of the cameras in which to search for a projected spot from projector ray r, for each of the respective pixel arrays, the one-dimensional search space being along the respective path of pixels corresponding to ray r.

In a further implementation of the fourth method, using the processor to determine the one-dimensional search space in respective pixel arrays of a plurality of the cameras comprises using the processor to determine a one-dimensional search space in respective pixel arrays of all of the cameras, in which to search for a projected feature from projector ray r.

In a further implementation of the fourth method, using the processor further comprises using the processor to, based on the correspondence algorithm, in each of at least one of the series of images that is not in the subset of images, identify more than one candidate three-dimensional position of the projected feature from the projector ray r, and compute an estimated length of projector ray r in at least one of the series of images in which more than one candidate three-dimensional position of the projected feature from projector ray r was identified.

In a further implementation of the fourth method, using the processor further comprises using the processor to determine which of the more than one candidate three-dimensional positions is a correct three-dimensional position of the projected feature by determining which of the more than one candidate three-dimensional positions corresponds to the estimated length of projector ray r in the at least one of the series of images.

In a further implementation of the fourth method, using the processor further comprises using the processor to, based on the estimated length of projector ray r in the at least one of the series of images: determine a one-dimensional search space in the at least one of the series of images in which to search for a projected feature from projector ray r; and determine which of the more than one candidate three-dimensional positions of the projected feature is a correct three-dimensional position of the projected feature produced by projector ray r by determining which of the more than one candidate three-dimensional positions corresponds to a feature produced by projector ray r found within the one-dimensional search space.

In a further implementation of the fourth method, using the processor further comprises using the processor to: define a curve based on the assessed length of projector ray r in each image of the subset of images; and remove from being considered as a point on the intraoral three-dimensional surface a detected feature which was identified as being from projector ray r if the three-dimensional position of the projected feature corresponds to a length of projector ray r that is at least a threshold distance away from the defined curve.

In a further implementation of the fourth method, the pattern comprises a plurality of spots, and each of the plurality of features of the pattern comprises a spot of the plurality of spots.

In a fifth method set forth herein for generating a digital three-dimensional image, the method includes driving each one of one or more structured light projectors to project a pattern of light on an intraoral three-dimensional surface along a plurality of projector rays, and driving each one of one or more cameras to capture a plurality of images, each image including at least a portion of the projected pattern, each one of the one or more cameras comprising a camera sensor comprising an array of pixels. The method further includes: using a processor to run a correspondence algorithm to compute respective three-dimensional positions on the intraoral three-dimensional surface of a plurality of detected features of the projected pattern for each of the plurality of images; using data corresponding to the respective three-dimensional positions of at least three of the detected features, estimate a three-dimensional surface based on the at least three features, each feature corresponding to a respective projector ray r of the plurality of projector rays; for a projector ray r1 of the plurality of projector rays for which more than one candidate three-dimensional position of a feature corresponding to that projector ray r1 was computed, estimate a three-dimensional position in space of an intersection of projector ray r1 and the estimated three-dimensional surface; and using the estimated three-dimensional position in space of the intersection of projector ray r1, select which of the more than one candidate three-dimensional positions is the correct three-dimensional position of the feature corresponding to that projector r1.

In a further implementation of the fifth method, the correspondence algorithm is run based on stored calibration values indicating (a) a camera ray corresponding to each pixel on the camera sensor of each one of the one or more cameras, and (b) a projector ray corresponding to each feature of the projected pattern from each one of the one or more structured light projectors, whereby each projector ray corresponds to a respective path of pixels on at least one of the camera sensors. Additionally, the search space in the data comprises a search space defined by one or more thresholds.

In a further implementation of the fifth method, the pattern of light comprises a distribution of discrete spots, and each of the features comprises a spot from the distribution of discrete spots.

In a further implementation of the fifth method, the data corresponding to the respective three-dimensional positions of at least three features comprises using data corresponding to the respective three-dimensional positions of at least three features that were all captured in one of the plurality of images.

In a further implementation of the fifth method, the fifth method further comprises refining the estimation of the three-dimensional surface using data corresponding to a three-dimensional position of at least one additional feature of the projected pattern, the at least one additional feature having a three-dimensional position that was computed based on another one of plurality of images. In a further implementation of the fifth method, refining the estimation of the three-dimensional surface comprises refining the estimation of the three-dimensional surface such that all of the at least three features and the at least one additional feature lie on the estimated three-dimensional surface.

In a further implementation of the fifth method, using data corresponding to the respective three-dimensional positions of at least three features comprises using data corresponding to at least three features, each captured in a respective one of the plurality of images.

In one method set forth herein for tracking motion of an intraoral scanner, the method includes using at least one camera coupled to the intraoral scanner to measure motion of the intraoral scanner with respect to an intraoral surface being scanned and using at least one inertial measurement unit (IMU) coupled to the intraoral scanner to measure motion of the intraoral scanner with respect to an intraoral surface being scanned with respect to a fixed coordinate system. The method further includes using a processor to calculate motion of the intraoral surface with respect to the fixed coordinate system based on (a) motion of the intraoral scanner with respect to the intraoral surface and (b) motion of the intraoral scanner with respect to the fixed coordinate system, build a predictive model of motion of the intraoral surface with respect to the fixed coordinate system based on accumulated data of motion of the intraoral surface with respect to the fixed coordinate system, and calculate an estimated location of the intraoral scanner with respect to the intraoral surface based on (a) a prediction of the motion of the intraoral surface with respect to the fixed coordinate system (derived based on the predictive model of motion) and (b) motion of the intraoral scanner with respect to the fixed coordinate system (measured by the IMU). In a further implementation of the method for tracking motion, the method further includes determining whether measuring motion of the intraoral scanner with respect to the intraoral surface using the at least one camera is inhibited, and in response to determining that the measuring of the motion is inhibited, calculating the estimated location of the intraoral scanner with respect to the intraoral surface. In a further implementation of the method for tracking motion, calculating of the motion is performed by calculating a difference between (a) the motion of the intraoral scanner with respect to the intraoral surface and (b) the motion of the intraoral scanner with respect to the fixed coordinate system.

One method of determining if calibration data of the intraoral scanner is incorrect set forth herein includes driving each one of one or more light sources to project light on an intraoral three-dimensional surface, and driving each one of one or more cameras to capture a plurality of images of the intraoral three-dimensional surface. The method further includes, based on stored calibration data for the one or more light sources and for the one or more cameras, using a processor: running a correspondence algorithm to compute respective three-dimensional positions on the intraoral three-dimensional surface of a plurality of features of the projected light; collecting data at a plurality of points in time, the data including the computed respective three-dimensional positions on the intraoral three-dimensional surface of the plurality of features; and based on the collected data, determining that at least some of the stored calibration data is incorrect.

In a further implementation of the method, the one or more light sources are one or more structured light projectors, and the method includes driving each one of the one or more structured light projectors to project a pattern of light on the intraoral three-dimensional surface, driving each one of the one or more cameras to capture a plurality of images of the intraoral three-dimensional surface, each image including at least a portion of the projected pattern, wherein each one of the one or more cameras comprises a camera sensor comprising an array of pixels, and the stored calibration data comprises stored calibration values indicating (a) a camera ray corresponding to each pixel on the camera sensor of each one of the one or more cameras, and (b) a projector ray corresponding to each feature of the projected pattern of light from each one of the one or more structured light projectors, whereby each projector ray corresponds to a respective path p of pixels on at least one of the camera sensors.

In a further implementation of the method, determining that at least some of the stored calibration data is incorrect comprises, using the processor: for each projector ray r, based on the collected data, defining an updated path p' of pixels on each of the camera sensors, such that all of the computed three-dimensional positions corresponding to features produced by projector ray r correspond to locations along the respective updated path p' of pixels for each of the camera sensors; comparing each updated path p' of pixels to the path p of pixels corresponding to that projector ray r on each camera sensor from the stored calibration values; and in response to the updated path p' for at least one camera sensor s differing from the path p of pixels corresponding to that projector ray r from the stored calibration values, determining that at least some of the stored calibration values are incorrect.

One method of recalibration set forth herein includes driving each one of one or more light sources to project light on an intraoral three-dimensional surface and driving each one of one or more cameras to capture a plurality of images of the intraoral three-dimensional surface. The method includes, based on stored calibration data for the one or more light sources and for the one or more cameras, using a processor: running a correspondence algorithm to compute respective three-dimensional positions on the intraoral three-dimensional surface of a plurality of features of the projected light; collecting data at a plurality of points in time, the data including the computed respective three-dimensional positions on the intraoral three-dimensional surface of the plurality of features; and using the collected data to recalibrate the stored calibration data.

In a further implementation of the method of recalibration, the one or more light sources are one or more structured light projectors, and the method includes driving each one of the one or more structured light projectors to project a pattern of light on the intraoral three-dimensional surface, driving each one of the one or more cameras to capture a plurality of images of the intraoral three-dimensional surface, each image including at least a portion of the projected pattern, wherein each one of the one or more cameras comprises a camera sensor comprising an array of pixels. The processor uses the stored calibration data to perform multiple operations, the stored calibration data comprising stored calibration values indicating the stored calibration data comprises stored calibration values indicating (a) a camera ray corresponding to each pixel on the camera sensor of each one of the one or more cameras, and (b) a projector ray corresponding to each feature of the projected pattern of light from each one of the one or more structured light projectors, whereby each projector ray corresponds to a respective path p of pixels on at least one of the camera sensors. The operations include running a correspondence algorithm to compute respective three-dimensional positions on the intraoral three-dimensional surface of a plurality of features of the projected pattern. The operations further include collecting the data at a plurality of points in time, the data including the computed respective three-dimensional positions on the intraoral three-dimensional surface of the plurality of features. The operations further include, for each projector ray r, based on the collected data, defining an updated path p' of pixels on each of the camera sensors, such that all of the computed three-dimensional positions corresponding to features produced by projector ray r correspond to locations along the respective updated path p' of pixels for each of the camera sensors. The operations further include using the updated paths p' to recalibrate the stored calibration values.

In a further implementation of the method of recalibration, to recalibrate the stored calibration values, the processor performs additional operations. The additional operations include comparing each updated path p' of pixels to the path p of pixels corresponding to that projector ray r on each camera sensor from the stored calibration values. The additional operations further include, if for at least one camera sensor s, the updated path p' of pixels corresponding to projector ray r differs from the path p of pixels corresponding to projector ray r from the stored calibration values, reducing the difference between the updated path p' of pixels corresponding to each projector ray r and the respective path p of pixels corresponding to each projector ray r from the stored calibration values, by varying stored calibration data selected from the group consisting of: (i) the stored calibration values indicating a camera ray corresponding to each pixel on the camera sensor s of each one of the one or more cameras, and (ii) the stored calibration values indicating a projector ray r corresponding to each one of the projected features from each one of the one or more structured light projectors.

In a further implementation of the method of recalibration, the stored calibration data that is varied comprises the stored calibration values indicating a camera ray corresponding to each pixel on the camera sensor of each one of the one or more cameras. Additionally, varying the stored calibration data comprises varying one or more parameters of a parametrized camera calibration function that defines the camera rays corresponding to each pixel on at least one camera sensor s, in order to reduce the difference between: (i) the computed respective three-dimensional positions on the intraoral three-dimensional surface of the plurality of features of the projected pattern; and (ii) the stored calibration values indicating respective camera rays corresponding to each pixel on the camera sensor where a respective one of the plurality of features should have been detected.

In a further implementation of the method of recalibration, the stored calibration data that is varied comprises the stored calibration values indicating a projector ray corresponding to each one of the plurality of features from each one of the one or more structured light projectors, and varying the stored calibration data comprises varying: (i) an indexed list assigning each projector ray r to a path p of pixels, or (ii) one or more parameters of a parametrized projector calibration model that defines each projector ray r.

In a further implementation of the method of recalibration, varying the stored calibration data comprises varying the indexed list by re-assigning each projector ray r based on the respective updated paths p' of pixels corresponding to each projector ray r.

In a further implementation of the method of recalibration, varying the stored calibration data comprises varying: (i) the stored calibration values indicating a camera ray corresponding to each pixel on the camera sensor s of each one of the one or more cameras, and (ii) the stored calibration values indicating a projector ray r corresponding to each one of the plurality of features from each one of the one or more structured light projectors.

In a further implementation of the method of recalibration, varying the stored calibration values comprises iteratively varying the stored calibration values.

In a further implementation of the method of recalibration, the method further includes driving each one of the one or more cameras to capture a plurality of images of a calibration object having predetermined parameters. The method of recalibration further includes using a processor: running a triangulation algorithm to compute the respective parameters of the calibration object based on the captured images; and running an optimization algorithm: (a) to reduce a difference between (i) updated path p' of pixels corresponding to projector ray r and (ii) the path p of pixels corresponding to projector ray r from the stored calibration values, using (b) the computed respective parameters of the calibration object based on the captured images.

In a further implementation of the method of recalibration, the calibration object is a three-dimensional calibration object of known shape, and wherein driving each one of the one or more cameras to capture a plurality of images of the calibration object comprises driving each one of the one or more cameras to capture images of the three-dimensional calibration object, and wherein the predetermined parameters of the calibration object are dimensions of the three-dimensional calibration object. In a further implementation, with regard to the processor using the computed respective parameters of the calibration object to run the optimization algorithm, the processor further uses the collected data including the computed respective three-dimensional positions on the intraoral three-dimensional surface of the plurality of features.

In a further implementation of the method of recalibration, the calibration object is a two-dimensional calibration object having visually-distinguishable features, wherein driving each one of the one or more cameras to capture a plurality of images of the calibration object comprises driving each one of the one or more cameras to capture images of the two-dimensional calibration object, and wherein the predetermined parameters of the two-dimensional calibration object are respective distances between respective visually-distinguishable features. In a further implementation, with regard to the processor using the computed respective parameters of the calibration object to run the optimization algorithm, the processor further uses the collected data including the computed respective three-dimensional positions on the intraoral three-dimensional surface of the plurality of features.

In a further implementation of the method of recalibration, driving each one of the one or more cameras to capture images of the two-dimensional calibration object comprises driving each one of the one or more cameras to capture a plurality of images of the two-dimensional calibration object from a plurality of different viewpoints with respect to the two-dimensional calibration object.

In one implementation of an apparatus for intraoral scanning, the apparatus includes an elongate handheld wand comprising a probe at a distal end of the elongate handheld wand, one or more illumination sources coupled to the probe, one or more near infrared (NIR) light sources coupled to the probe, and one or more cameras coupled to the probe, and configured to (a) capture images using light from the one or more illumination sources, and (b) capture images using NIR light from the NIR light source. The apparatus further includes a processor configured to run a navigation algorithm to determine a location of the elongate handheld wand as the elongate handheld wand moves in space, inputs to the navigation algorithm being (a) the images captured using the light from the one or more illumination sources, and (b) the images captured using the NIR light.

In a further implementation of the apparatus for intraoral scanning, the one or more illumination sources comprise one or more structured light sources.

In a further implementation of the apparatus for intraoral scanning, the one or more illumination sources comprise one or more non-coherent light sources.

A method for tracking motion of an intraoral scanner includes illuminating an intraoral three-dimensional surface using one or more illumination sources coupled to the intraoral scanner, driving each one of one or more NIR light sources coupled to the intraoral scanner to emit NIR light onto the intraoral three-dimensional surface, and using one or more cameras coupled to the intraoral scanner, (a) capturing a first plurality of images using light from the one or more illumination sources, and (b) capturing a second plurality of images using the NIR light. The method further includes using a processor to run a navigation algorithm to track motion of the intraoral scanner with respect to the intraoral three-dimensional surface using (a) the first plurality of images captured using light from the one or more illumination sources, and (b) the second plurality of images captured using the NIR light.

In one implementation of the method for tracking motion, using the one or more illumination sources comprises illuminating the intraoral three-dimensional surface.

In one implementation of the method for tracking motion, using the one or more illumination sources comprises using one or more non-coherent light sources.

One implementation of a sixth method for computing a three-dimensional structure of an intraoral three-dimensional surface includes driving one or more structured light projectors to project a structured light pattern on the intraoral three-dimensional surface, driving one or more cameras to capture a plurality of structured light images, each structured light image including at least a portion of the structured light pattern, driving one or more unstructured light projectors to project unstructured light on the intraoral three-dimensional surface, and driving the one or more cameras to capture a plurality of two-dimensional images of the intraoral three-dimensional surface. The sixth method further includes using a processor to compute respective three-dimensional positions of a plurality of points on the intraoral three-dimensional surface, as captured in the plurality of structured light images, and compute a three-dimensional structure of the intraoral three-dimensional surface, based on the plurality of two-dimensional images of the intraoral three-dimensional surface, constrained by some or all of the computed three-dimensional positions of the plurality of points.

In some implementations of the sixth method, the unstructured light is non-coherent light, and the plurality of two-dimensional images comprise a plurality of color two-dimensional images.

In some implementations of the sixth method, the unstructured light is near infrared (NIR) light, and the plurality of two-dimensional images comprise a plurality of monochromatic NIR images.

In a further implementation of the sixth method, driving the one or more structured light projectors comprises driving the one or more structured light projectors to each project a distribution of discrete unconnected spots of light.

In a further implementation of the sixth method, computing the three-dimensional structure comprises: inputting to a neural network the plurality of two-dimensional images of the intraoral three-dimensional surface; and determining, by the neural network, a respective estimated map of the intraoral three-dimensional surface as captured in each of the two-dimensional images.

In a further implementation of the sixth method, the sixth method further includes inputting to the neural network the computed three-dimensional positions of the plurality of points on the intraoral three-dimensional surface.

In a further implementation of the sixth method, the sixth method further includes using the processor to stich the respective maps together to obtain the three-dimensional structure of the intraoral three-dimensional surface.

In a further implementation of the sixth method, the sixth method further includes regulating the capturing of the structured light images and the capturing of the two-dimensional images to produce an alternating sequence of one or more image frames of structured light interspersed with one or more image frames of unstructured light.

In a further implementation of the sixth method, determining comprises determining, by the neural network, a respective estimated depth map of the intraoral three-dimensional surface as captured in each of the two-dimensional images. In one implementation, the processor is used to stitch the respective estimated depth maps together to obtain the three-dimensional structure of the intraoral three-dimensional surface.

In one implementation (a) the processor generates a respective point cloud corresponding to the computed respective three-dimensional positions of the plurality of points on the intraoral three-dimensional surface, as captured in each of the structured light images, and the method further includes using the processor to stitch the respective estimated depth maps to the respective point clouds. In one implementation, the method further includes determining, by the neural network, a respective estimated normal map of the intraoral three-dimensional surface as captured in each of the two-dimensional images.

In a further implementation of the sixth method, determining comprises determining, by the neural network, a respective estimated normal map of the intraoral three-dimensional surface as captured in each of the two-dimensional images. In one implementation, the processor is used to stitch the respective estimated normal maps together to obtain the three-dimensional structure of the intraoral three-dimensional surface.

In one implementation, the method further includes, based on the respective estimated normal maps of the intraoral three-dimensional surface as captured in each of the two-dimensional images, interpolating three-dimensional positions on the intraoral three-dimensional surface between the computed respective three-dimensional positions of the plurality of points on the intraoral three-dimensional surface, as captured in the plurality of structured light images.

In one implementation, the method further includes regulating the capturing of the structured light images and the capturing of the two-dimensional images to produce an alternating sequence of one or more image frames of structured light interspersed with one or more image frames of unstructured light. The method includes using the processor to further: (a) generate a respective point cloud corresponding to the computed respective three-dimensional positions of the plurality of points on the intraoral three-dimensional surface, as captured in each image frame of structured light; and (b) stitch the respective point clouds together using, as an input to the stitching, for a least a subset of the plurality of points for each point cloud, the normal to the surface at each point of the subset of points, wherein for a given point cloud the normal to the surface at at least one point of the subset of points is obtained from the respective estimated normal map of the intraoral three-dimensional surface as captured in an adjacent image frame of unstructured light.

In one implementation, the method further includes using the processor to compensate for motion of the intraoral scanner between an image frame of structured light and an adjacent image frame of unstructured light by estimating the motion of the intraoral scanner based on previous image frames.

In a further implementation of the sixth method, determining comprises determining, by the neural network, curvature of the intraoral three-dimensional surface as captured in each of the two-dimensional images. In one implementation, determining comprises determining, by the neural network, a respective estimated curvature map of the intraoral three-dimensional surface as captured in each of the two-dimensional images.

In one implementation, the method further includes, using the processor: assessing the curvature of the intraoral three-dimensional surface as captured in each of the two-dimensional images; and based on the assessed curvature of the intraoral three-dimensional surface as captured in each of the two-dimensional images, interpolating three-dimensional positions on the intraoral three-dimensional surface between the computed respective three-dimensional positions of the plurality of points on the intraoral three-dimensional surface, as captured in the plurality of structured light images.

In a further implementation of the sixth method, the sixth method further includes regulating the capturing of the structured light images and the capturing of the two-dimensional images to produce an alternating sequence of one or more image frames of structured light interspersed with one or more image frames of unstructured light.

In a further implementation of the sixth method, the sixth method includes driving the one or more cameras to capture the plurality of structured light images comprises driving each one of two or more cameras to capture a respective plurality of structured light images; and driving the one or more cameras to capture the plurality of two-dimensional images comprises driving each one of the two or more cameras to capture a respective plurality of two-dimensional images.

In one implementation, driving the two or more cameras comprises, in a given image frame, driving each one of the two or more cameras to simultaneously capture a respective two-dimensional image of a respective portion of the intraoral three-dimensional surface. Inputting to the neural network comprises, for the given image frame, inputting all of the respective two-dimensional images to the neural network as a single input, wherein each one of the respective two-dimensional images has an overlapping field of view with at least one other of the respective two-dimensional images. Determining by the neural network comprises, for the given image frame, determining an estimated depth map of the intraoral three-dimensional surface that combines the respective portions of intraoral three-dimensional surface.

In one implementation, driving the two or more cameras to capture the plurality of structured light images comprises driving each one of three or more cameras to capture a respective plurality of structured light images, driving the two or more cameras to capture the plurality of two-dimensional images comprises driving each one of the three or more cameras to capture a respective plurality of two-dimensional images. In a given image frame, each one of the three or more cameras is driven to simultaneously capture a respective two-dimensional image of a respective portion of the intraoral three-dimensional surface. Inputting to the neural network comprises, for a given image frame, inputting a subset of the respective two-dimensional images to the neural network as a single input, wherein the subset comprises at least two of the respective two-dimensional images, and each one of the subset of respective two-dimensional images has an overlapping field of view with at least one other of the subset of respective two-dimensional images. Determining by the neural network comprises, for the given image frame, determining an estimated depth map of the intraoral three-dimensional surface that combines the respective portions of the intraoral three-dimensional surface as captured in the subset of the respective two-dimensional images.

In one implementation, driving the two or more cameras comprises, in a given image frame, driving each one of the two or more cameras to simultaneously capture a respective two-dimensional image of a respective portion of the intraoral three-dimensional surface, and inputting to the neural network comprises, for a given image frame, inputting each one of the respective two-dimensional images to the neural network as a separate input. Determining, by the neural network, comprises, for the given image frame, determining a respective estimated depth map of each of the respective portions of the intraoral three-dimensional surface as captured in each of the respective two-dimensional images captured in the given image frame.

In one implementation, the method further includes, using the processor, merging the respective depth maps together to obtain a combined estimated depth map of the intraoral three-dimensional surface as captured in the given image frame. In one implementation, the method further includes training the neural network, wherein each input to the neural network during the training comprises an image captured by only one camera.

In one implementation, the method further includes determining, by the neural network, a respective estimated confidence map corresponding to each estimated depth map, each confidence map indicating a confidence level per region of the respective estimated depth map. In a further implementation, merging the respective estimated depth maps together comprises, using the processor, in response to determining a contradiction between corresponding respective regions in at least two of the estimated depth maps, merging the at least two estimated depth maps based on the confidence level of each of the corresponding respective regions as indicated by the respective confidence maps for each of the at least two estimated depth maps.

In a further implementation of the sixth method, driving the one or more cameras comprises driving one or more cameras of an intraoral scanner, and the method further includes training the neural network using training-stage images as captured by a plurality of training-stage handheld wands. Each of the training-stage handheld wands comprises one or more reference cameras, and each of the one or more cameras of the intraoral scanner corresponds to a respective one of the one or more reference cameras on each of the training-stage handheld wands.

In a further implementation of the sixth method, driving the one or more structured light projectors comprises driving one or more structured light projectors of an intraoral scanner, driving the one or more unstructured light projectors comprises driving one or more unstructured light projectors of the intraoral scanner, and driving the one or more cameras comprises driving one or more cameras of the intraoral scanner. The neural network is initially trained using training-stage images as captured by one or more training-stage cameras of a training-stage handheld wand, each of the one or more cameras of the intraoral scanner corresponding to a respective one of the one or more training-stage cameras. Subsequently, the method includes driving (i) the one or more structured light projectors of the intraoral scanner and (ii) the one or more unstructured light projectors of the intraoral scanner during a plurality of refining-stage scans; driving the one or more cameras of the intraoral scanner to capture (a) a plurality of refining-stage structured light images and (b) a plurality of refining-stage two-dimensional images, during the refining-stage scans; computing the three-dimensional structure of the intraoral three-dimensional surface based on the plurality of refining-stage structured light images; and refining the training of the neural network for the intraoral scanner using (a) the plurality of refining-stage two-dimensional images captured during the refining-stage scans and (b) the computed three-dimensional structure of the intraoral three-dimensional surface as computed based on the plurality of refining-stage structured light images.

In one implementation, the neural network comprises a plurality of layers and refining the training of the neural network comprises constraining a subset of the layers.

In one implementation, the method further includes selecting, from a plurality of scans, which of the plurality of scans to use as the refining-stage scans based on a quality level of each scan.

In one implementation, the method further includes, during the refining-stage scans, using the computed three-dimensional structure of the intraoral three-dimensional surface as computed based on the plurality of refining-stage structured light images as an end-result three-dimensional structure of the intraoral three-dimensional surface for a user of the intraoral scanner.

In a further implementation of the sixth method, driving the one or more cameras comprises driving one or more cameras of an intraoral scanner, each one of the one or more cameras of the intraoral scanner corresponding to a respective one of one or more reference cameras. The method further includes, using the processor: for each camera c of the one or more cameras of the intraoral scanner, cropping and morphing at least one of the two-dimensional images of the intraoral three-dimensional surface from camera c to obtain a plurality of cropped and morphed two-dimensional images, each cropped and morphed image corresponding to a cropped and morphed field of view of camera c, the cropped and morphed field of view of camera c matching a cropped field of view of the corresponding reference camera; inputting to the neural network the plurality of two-dimensional images comprises inputting to the neural network the plurality of cropped and morphed two-dimensional images of the intraoral three-dimensional surface; and determining comprises determining, by the neural network, a respective estimated map of the intraoral three-dimensional surface as captured in each of the cropped and morphed two-dimensional images, the neural network having been trained using training-stage images corresponding to the cropped fields of view of each of the one or more reference cameras.

In a further implementation, the step of cropping and morphing comprises the processor using (a) stored calibration values indicating a camera ray corresponding to each pixel on the camera sensor of each one of the one or more cameras, and (b) reference calibration values indicating (i) a camera ray corresponding to each pixel on a reference camera sensor of each one of one or more reference cameras, and (ii) a cropped field of view for each one of the one or more reference cameras.

In a further implementation the cropped fields of view of each of the one or more reference cameras is 85-97% of a respective full field of view of each of the one or more reference cameras.

In a further implementation, using the processor further comprises, for each camera c, performing a reverse of the morphing for each of the respective estimated maps of the intraoral three-dimensional surface as captured in each of the cropped and morphed two-dimensional images to obtain a respective non-morphed estimated map of the intraoral surface as seen in each of the at least one two-dimensional images from camera c prior to the morphing.

In a further implementation, the unstructured light is non-coherent light, and the plurality of two-dimensional images comprise a plurality of two-dimensional color images.

In a further implementation, the unstructured light is near infrared (NIR) light, and the plurality of two-dimensional images comprise a plurality of monochromatic NIR images.

In a further implementation, using the processor further includes, for each camera c, performing a reverse of the morphing for each of the respective estimated maps of the intraoral three-dimensional surface as captured in each of the cropped and morphed two-dimensional images to obtain a respective non-morphed estimated map of the intraoral surface as seen in each of the at least one two-dimensional images from camera c prior to the morphing.

It is noted that all of the above-described implementations of the sixth method relating to depth maps, normal maps, curvature maps, and the uses thereof, may be performed based on the cropped and morphed run-time images in the field, mutatis mutandis.

In one implementation, driving the one or more structured light projectors comprises driving one or more structured light projectors of the intraoral scanner, and driving the one or more unstructured light projectors comprises driving one or more unstructured light projectors of the intraoral scanner. The method further includes, subsequently to the neural network having been trained using the training-stage images corresponding to the cropped fields of view of each of the one or more reference cameras: driving the one or more structured light projectors of the intraoral scanner and the one or more unstructured light projectors of the intraoral scanner during a plurality of refining-stage scans. The one or more cameras of the intraoral scanner are driven to capture (a) a plurality of refining-stage structured light images and (b) a plurality of refining-stage two-dimensional images, during the plurality of refining-stage structured light scans. The three-dimensional structure of the intraoral three-dimensional surface is computed based on the plurality of refining-stage structured light images, and the training of the neural network is refined for the intraoral scanner using (a) the plurality of refining-stage two-dimensional images captured during the refining-stage scans and (b) the computed three-dimensional structure of the intraoral three-dimensional surface as computed based on the plurality of refining-stage structured light images. In a further implementation, the neural network comprises a plurality of layers and refining the training of the neural network comprises constraining a subset of the layers.

In one implementation, driving the one or more structured light projectors comprises driving one or more structured light projectors of the intraoral scanner, driving the one or more unstructured light projectors comprises driving one or more unstructured light projectors of the intraoral scanner, and determining comprises determining, by the neural network, a respective estimated depth map of the intraoral three-dimensional surface as captured in each of the cropped and morphed two-dimensional images. The method further includes: (a) computing the three-dimensional structure of the intraoral three-dimensional surface based on the computed respective three-dimensional positions of the plurality of points on the intraoral three-dimensional surface, as captured in the plurality of structured light images; (b) computing the three-dimensional structure of the intraoral three-dimensional surface based on the respective estimated depth maps of the intraoral three-dimensional surface, as captured in each of the cropped and morphed two-dimensional images; and (c) comparing (i) the three-dimensional structure of the intraoral three-dimensional surface as computed based on the computed respective three-dimensional positions of the plurality of points on the intraoral three-dimensional surface and (ii) the three-dimensional structure of the intraoral three-dimensional surface as computed based on the respective estimated depth maps of the intraoral three-dimensional surface. In response to determining a discrepancy between (i) and (ii), the method includes: driving (A) the one or more structured light projectors of the intraoral scanner and (B) the one or more unstructured light projectors of the intraoral scanner, during a plurality of refining-stage scans, driving the one or more cameras of the intraoral scanner to capture (a) a plurality of refining-stage structured light images and (b) a plurality of refining-stage two-dimensional images, during the plurality of refining-stage scans, computing the three-dimensional structure of the intraoral three-dimensional surface based on the plurality of refining-stage structured light images, and refining the training of the neural network for the intraoral scanner using (a) the plurality of two-dimensional images captured during the refining-stage scans and (b) the computed three-dimensional structure of the intraoral three-dimensional surface as computed based on the plurality of refining-stage structured light images. In a further implementation, the neural network comprises a plurality of layers and refining the training of the neural network comprises constraining a subset of the layers In a further implementation of the sixth method, the sixth method further comprises training the neural network, the training comprising: driving one or more training-stage structured light projectors to project a training-stage structured light pattern on a training-stage three-dimensional surface; driving one or more training-stage cameras to capture a plurality of structured light images, each image including at least a portion of the training-stage structured light pattern; driving one or more training-stage unstructured light projectors to project unstructured light onto the training-stage three-dimensional surface; driving the one or more training-stage cameras to capture a plurality of two-dimensional images of the training-stage three-dimensional surface using illumination from the training-stage unstructured light projectors; regulating the capturing of the structured light images and the capturing of the two-dimensional images to produce an alternating sequence of one or more image frames of structured light images interspersed with one or more image frames of two-dimensional images; inputting to the neural network the plurality of two-dimensional images; estimating, by the neural network, an estimated map of the training-stage three-dimensional surface as captured in each of the two-dimensional images; inputting to the neural network a respective plurality of three-dimensional reconstructions of the training-stage three-dimensional surface, based on structured light images of the training-stage three-dimensional surface, the three-dimensional reconstructions including computed three-dimensional positions of a plurality of points on the training-stage three-dimensional surface; interpolating a position of the one or more training-stage cameras with respect to the training-stage three-dimensional surface for each two-dimensional image frame based on the computed three-dimensional positions of the plurality of points on the training-stage three-dimensional surface as computed based on respective structured light image frames before and after each two-dimensional image frame; projecting the three-dimensional reconstructions on respective fields of view of each of the one or more training-stage cameras and, based on the projections, calculating a true map of the training-stage three-dimensional surface as seen in each two-dimensional image, constrained by the computed three-dimensional positions of the plurality of points; comparing each estimated depth map of the training-stage three-dimensional surface to a corresponding true map of the training-stage three-dimensional surface; and based on differences between each estimated map and the corresponding true map, optimizing the neural network to better estimate a subsequent estimated map.

In a further implementation, the training comprises an initial training of the neural network, driving the one or more structured light projectors comprises driving one or more structured light projectors of an intraoral scanner, driving the one or more unstructured light projectors comprises driving one or more unstructured light projectors of the intraoral scanner, and driving the one or more cameras comprises driving one or more cameras of the intraoral scanner. The method further includes, subsequently to the initial training of the neural network: driving (i) the one or more structured light projectors of the intraoral scanner and (ii) the one or more unstructured light projectors of the intraoral scanner during a plurality of refining-stage structured light scans; driving the one or more cameras of the intraoral scanner to capture (a) a plurality of refining-stage structured light images and (b) a plurality of refining-stage two-dimensional images, during the refining-stage structured light scans; computing the three-dimensional structure of the intraoral three-dimensional surface based on the plurality of refining-stage structured light images; and refining the training of the neural network for the intraoral scanner using (a) the plurality of two-dimensional images captured during the refining-stage scans and (b) the computed three-dimensional structure of the intraoral three-dimensional surface as computed based on the plurality of refining-stage structured light images. In a further implementation, the neural network comprises a plurality of layers, and refining the training of the neural network comprises constraining a subset of the layers.

In a further implementation of the sixth method, driving the one or more structured light projectors to project the training-stage structured light pattern comprises driving the one or more structured light projectors to each project a distribution of discrete unconnected spots of light on the training-stage three-dimensional surface.

In a further implementation of the sixth method, driving one or more training-stage cameras comprises driving at least two training-stage cameras.

In a further implementation of the sixth method, the unstructured light comprises broad spectrum light.

In one implementation of an apparatus for intraoral scanning, the apparatus includes an elongate handheld wand comprising a probe at a distal end of the elongate handheld wand that is configured for being removably disposed in a sleeve. The apparatus further includes at least one structured light projector coupled to the probe, the at least one structured light projector (a) comprising a laser configured to emit polarized laser light, and (b) comprising a pattern generating optical element configured to generate a pattern of light when the laser is activated to transmit light through the pattern generating optical element. The apparatus further includes a camera coupled to the probe, the camera comprising a camera sensor. The probe is configured such that light exits and enters the probe through the sleeve. Additionally, the laser is positioned at a distance with respect to the camera, such that when the probe is disposed in the sleeve, a portion of the pattern of light is reflected off of the sleeve and reaches the camera sensor. Additionally, the laser is positioned at a rotational angle, with respect to its own optical axis, such that, due to polarization of the pattern of light, an extent of reflection by the sleeve of the portion of the pattern of light is less than a threshold reflection for all possible rotational angles of the laser with respect to its optical axis.

In a further implementation of the apparatus for intraoral scanning, the threshold is 70% of a maximum reflection for all the possible rotational angles of the laser with respect to its optical axis.

In a further implementation of the apparatus for intraoral scanning, the laser is positioned at the rotational angle, with respect to its own optical axis, such that due to the polarization of the pattern of light, the extent of reflection by the sleeve of the portion of the pattern of light is less than 60% of the maximum reflection for all possible rotational angles of the laser with respect to its optical axis.

In a further implementation of the apparatus for intraoral scanning, the laser is positioned at the rotational angle, with respect to its own optical axis, such that due to the polarization of the pattern of light, the extent of reflection by the sleeve of the portion of the pattern of light is 15%-60% of the maximum reflection for all possible rotational angles of the laser with respect to its optical axis.

In a further implementation of the apparatus for intraoral scanning, a distance between the structured light projector and the camera is 1-6 times a distance between the structured light projector and the sleeve, when the elongate handheld wand is disposed in the sleeve.

In a further implementation of the apparatus for intraoral scanning, the at least one structured light projector has a field of illumination of at least 30 degrees, and wherein the camera has a field of view of at least 30 degrees.

In a seventh method for generating a three-dimensional image using an intraoral scanner, the seventh method comprises using at least two cameras that are rigidly connected to the intraoral scanner, such that respective fields of view of each of the cameras have non-overlapping portions, capturing a plurality of images of an intraoral three-dimensional surface. The seventh method further includes using a processor, running a simultaneous localization and mapping (SLAM) algorithm using captured images from each of the cameras for the non-overlapping portions of the respective fields of view, the localization of each of the cameras being solved based on motion of each of the cameras being the same as motion of every other one of the cameras.

In a further implementation of the seventh method, the respective fields of view of a first one of the cameras and a second one of the cameras also have overlapping portion. Additionally, the capturing comprises capturing the plurality of images of the intraoral three-dimensional surface such that a feature of the intraoral three-dimensional surface that is in the overlapping portions of the respective fields of view appears in the images captured by the first and second cameras. Additionally, using the processor comprises running the SLAM algorithm using features of the intraoral three-dimensional surface that appear in the images of at least two of the cameras.

In an eighth method for generating a three-dimensional image using an intraoral scanner, the eighth method comprises driving one or more structured light projectors to project a pattern of structured light on an intraoral three-dimensional surface, driving one or more cameras to capture a plurality of structured light images, each structured light image including at least a portion of the structured light pattern, driving one or more unstructured light projectors to project unstructured light onto the intraoral three-dimensional surface, driving at least one camera to capture two-dimensional images of the intraoral three-dimensional surface using illumination from the unstructured light projectors, and regulating capturing of the structured light and capturing of the unstructured light to produce an alternating sequence of one or more image frames of structured light interspersed with one or more image frames of unstructured light. The eighth method further includes using a processor to compute respective three-dimensional positions of a plurality of points on the intraoral three-dimensional surface, as captured in the one or more image frames of structured light. The eighth method further includes using the processor to interpolate motion of the at least one camera between a first image frame of unstructured light and a second image frame of unstructured light based on the computed three-dimensional positions of the plurality of points in respective structured light image frames before and after the image frames of unstructured light. The eighth method further includes running a simultaneous localization and mapping (SLAM) algorithm (a) using features of the intraoral three-dimensional surface as captured by the at least one camera in the first and second image frames of unstructured light, and (b) constrained by the interpolated motion of the camera between the first image frame of unstructured light and the second image frame of unstructured light.

In one implementation of the eighth method, driving the one or more structured light projectors to project the structured light pattern comprises driving the one or more structured light projectors to each project a distribution of discrete unconnected spots of light on the intraoral three-dimensional surface. In one implementation, the unstructured light comprises broad spectrum light, and the two-dimensional images comprise two-dimensional color images. In one implementation, the unstructured light comprises near infrared (NIR) light, and the two-dimensional images comprise two-dimensional monochromatic NIR images.

In one implementation of a ninth method for generating a three-dimensional image using an intraoral scanner, the ninth method comprises driving one or more structured light projectors to project a pattern of structured light on an intraoral three-dimensional surface, driving one or more cameras to capture a plurality of structured light images, each structured light image including at least a portion of the structured light pattern, driving one or more unstructured light projectors to project unstructured light onto the intraoral three-dimensional surface, driving the one or more cameras to capture two-dimensional images of the intraoral three-dimensional surface using illumination from the unstructured light projectors, and regulating capturing of the structured light and capturing of the unstructured light to produce an alternating sequence of one or more image frames of structured light interspersed with one or more image frames of unstructured light. The ninth method further includes using a processor to compute a three-dimensional position of a feature on the intraoral three-dimensional surface, based on the image frames of structured light, the feature also being captured in a first image frame of unstructured light and a second image frame of unstructured light; calculate motion of the one or more cameras between the first image frame of unstructured light and the second image frame of unstructured light based on the computed three-dimensional position of the feature; and run a simultaneous localization and mapping (SLAM) algorithm using (i) a feature of the intraoral three-dimensional surface for which the three-dimensional position was not computed based on the image frames of structured light, as captured by the one or more cameras in the first and second image frames of unstructured light, and (ii) the calculated motion of the camera between the first and second image frames of unstructured light. In one implementation, driving the one or more structured light projectors to project the structured light pattern comprises driving the one or more structured light projectors to each project a distribution of discrete unconnected spots of light on the intraoral three-dimensional surface. In one implementation, the unstructured light comprises broad spectrum light, and the two-dimensional images comprise two-dimensional color images. In one implementation, the unstructured light comprises near infrared (NIR) light, and the two-dimensional images comprise two-dimensional monochromatic NIR images.

In one method for computing a three-dimensional structure of an intraoral three-dimensional surface within an intraoral cavity of a subject, the method includes (a) driving one or more structured light projectors to project a pattern of structured light on the intraoral three-dimensional surface, the pattern comprising a plurality of features, (b) driving one or more cameras to capture a plurality of structured light images, each structured light image including at least one of the features of the structured light pattern, (c) driving one or more unstructured light projectors to project unstructured light onto the intraoral three-dimensional surface, (d) driving at least one camera to capture two-dimensional images of the intraoral three-dimensional surface using illumination from the one or more unstructured light projectors, and (e) regulating capturing of the structured light and capturing of the unstructured light to produce an alternating sequence of one or more image frames of structured light interspersed with one or more image frames of unstructured light. The method further includes using a processor to (a) determine for one or more features of the plurality of features of the structured light pattern whether the feature is being projected on moving or stable tissue within the intraoral cavity, based on the two-dimensional images, (b) based on the determination, assign a respective confidence grade for each of the one or more features, high confidence being for fixed tissue and low confidence being for moving tissue, and (c) based on the confidence grade for each of the one or more features, running a three-dimensional reconstruction algorithm using the one or more features. In one implementation, the unstructured light comprises broad spectrum light, and the two-dimensional images are two-dimensional color images. In one implementation, the unstructured light comprises near infrared (NIR) light, and the two-dimensional images are two-dimensional monochromatic NIR images. In one implementation the plurality of features comprise a plurality of spots, and driving the one or more structured light projectors to project the structured light pattern comprises driving the one or more structured light projectors to each project a distribution of discrete unconnected spots of light on the intraoral three-dimensional surface. In one implementation, running the three-dimensional reconstruction algorithm is performed using only a subset of the plurality of features, the subset consisting of features that were assigned a confidence grade above a fixed-tissue threshold value. In one implementation, running the three-dimensional reconstruction algorithm comprises, (a) for each feature, assigning a weight to that feature based on the respective confidence grade assigned to that feature, and (b) using the respective weights for each feature in the three-dimensional reconstruction algorithm.

In one implementation of a tenth method for computing a three-dimensional structure of an intraoral three-dimensional surface, the tenth method includes driving one or more light sources of an intraoral scanner to project light on the intraoral three-dimensional surface, and driving two or more cameras of the intraoral scanner to each capture a plurality of two-dimensional images of the intraoral three-dimensional surface, each of the two or more cameras of the intraoral scanner corresponding to a respective one of two or more reference cameras. The method includes, using a processor, for each camera c of the two or more cameras of the intraoral scanner, modifying at least one of the two-dimensional images from camera c to obtain a plurality of modified two-dimensional images, each modified image corresponding to a modified field of view of camera c, the modified field of view of camera c matching a modified field of view of a corresponding one of the reference cameras; and computing a three-dimensional structure of the intraoral three-dimensional surface, based on the plurality of modified two-dimensional images of the intraoral three-dimensional surface.

In one implementation of an eleventh method for computing a three-dimensional structure of an intraoral three-dimensional surface, the eleventh method includes driving one or more light sources of an intraoral scanner to project light on the intraoral three-dimensional surface, and driving two or more cameras of the intraoral scanner to each capture a plurality of two-dimensional images of the intraoral three-dimensional surface, each of the one or more cameras of the intraoral scanner corresponding to a respective one of two or more reference cameras. The method includes, using a processor, for each camera c of the two or more cameras of the intraoral scanner, cropping and morphing at least one of the two-dimensional images from camera c to obtain a plurality of cropped and morphed two-dimensional images, each cropped and morphed image corresponding to a cropped and morphed field of view of camera c, the cropped and morphed field of view of camera c matching a cropped field of view of a corresponding one of the reference cameras. A three-dimensional structure of the intraoral three-dimensional surface is computed, based on the plurality of cropped and morphed two-dimensional images of the intraoral three-dimensional surface by: inputting to a neural network the plurality of cropped and morphed two-dimensional images of the intraoral three-dimensional surface, and determining, by the neural network, a respective estimated map of the intraoral three-dimensional surface as captured in each of the plurality of cropped and morphed two-dimensional images, the neural network having been trained using training-stage images corresponding to the cropped fields of view of each of the one or more reference cameras.

In a further implementation of the eleventh method, the light is non-coherent light, and the plurality of two-dimensional images comprise a plurality of two-dimensional color images.

In a further implementation of the eleventh method, the light is near infrared (NIR) light, and the plurality of two-dimensional images comprise a plurality of monochromatic NIR images.

In a further implementation of the eleventh method, the light is broad spectrum light, and the plurality of two-dimensional images comprise a plurality of two-dimensional color images.

In a further implementation of the eleventh method, the step of cropping and morphing comprises the processor using (a) stored calibration values indicating a camera ray corresponding to each pixel on the camera sensor of each one of the one or more cameras c, and (b) reference calibration values indicating (i) a camera ray corresponding to each pixel on a reference camera sensor of each one of one or more reference cameras, and (ii) a cropped field of view for each one of the one or more reference cameras.

In a further implementation of the eleventh method, the cropped fields of view of each of the one or more reference cameras is 85-97% of a respective full field of view of each of the one or more reference cameras.

In a further implementation, using the processor further includes, for each camera c, performing a reverse of the morphing for each of the respective estimated maps of the intraoral three-dimensional surface as captured in each of the cropped and morphed two-dimensional images to obtain a respective non-morphed estimated map of the intraoral surface as seen in each of the at least one two-dimensional images from camera c prior to the morphing.

It is noted that all of the above-described implementations of the sixth method relating to depth maps, normal maps, curvature maps, and the uses thereof, may be performed based on the cropped and morphed run-time images in the field from the eleventh method, mutatis mutandis.

It is also noted that all of the above described implementations of the sixth method relating to structured light may be performed in the context of the eleventh method and the cropped and morphed run-time two-dimensional images, mutatis mutandis.

In one implementation of a twelfth method for computing a three-dimensional structure of an intraoral three-dimensional surface, the twelfth method includes driving one or more light projectors to project light on the intraoral three-dimensional surface, and driving one or more cameras to capture a plurality of two-dimensional images of the intraoral three-dimensional surface. The method includes, using a processor, inputting the plurality of two-dimensional images of the intraoral three-dimensional surface to a first neural network module and to a second neural network module; determining, by the first neural network module, a respective estimated depth map of the intraoral three-dimensional surface as captured in each of the two-dimensional images; and determining, by the second neural network module, a respective estimated confidence map corresponding to each estimated depth map, each confidence map indicating a confidence level per region of the respective estimated depth map.

In one implementation of the twelfth method, the first neural network module and the second neural network module are separate modules of a same neural network.

In one implementation of the twelfth method, each of the first and second neural network modules are not separate modules of a same neural network.

In a further implementation of the twelfth method, the method further includes training the second neural network module to determine the respective estimated confidence map corresponding to each estimated depth map as determined by the first neural network module, by initially training the first neural network module to determine the respective estimated depth maps using a plurality of depth-training-stage two-dimensional images, and subsequently: (i) inputting to the first neural network module a plurality of confidence-training-stage two-dimensional images of a training-stage three-dimensional surface, (ii) determining, by the first neural network module, a respective estimated depth map of the training-stage three-dimensional surface as captured in each of the confidence-training-stage two-dimensional images, (iii) computing a difference between each estimated depth map and a corresponding respective true depth map to obtain a respective target confidence map corresponding to each estimated depth map as determined by the first neural network module, (iv) inputting to the second neural network module the plurality of confidence-training-stage two-dimensional images, (v) estimating, by the second neural network module, a respective estimated confidence map indicating a confidence level per region of each respective estimated depth map, and (vi) comparing each estimated confidence map to the corresponding target confidence map, and based on the comparison, optimizing the second neural network module to better estimate a subsequent estimated confidence map.

In one implementation, the plurality of confidence-training-stage two-dimensional images are not the same as the plurality of depth-training-stage two-dimensional images.

In one implementation, the plurality of confidence-training-stage two-dimensional images are the same as the plurality of depth-training-stage two-dimensional images.

In a further implementation of the twelfth method, (a) driving the one or more cameras to capture the plurality of two-dimensional images comprises driving each one of two or more cameras, in a given image frame, to simultaneously capture a respective two-dimensional image of a respective portion of the intraoral three-dimensional surface, (b) inputting the plurality of two-dimensional images of the intraoral three-dimensional surface to the first neural network module and to the second neural network module comprises, for a given image frame, inputting each one of the respective two-dimensional images as a separate input to the first neural network module and to the second neural network module, (c) determining by the first neural network module comprises, for the given image frame, determining a respective estimated depth map of each of the respective portions of the intraoral three-dimensional surface as captured in each of the respective two-dimensional images captured in the given image frame, and (d) determining by the second neural network module comprises, for the given image frame, determining a respective estimated confidence map corresponding to each respective estimated depth map of each of the respective portions of the intraoral three-dimensional surface as captured in each of the respective two-dimensional images captured in the given image frame. The method further includes, using the processor, merging the respective estimated depth maps together to obtain a combined estimated depth map of the intraoral three-dimensional surface as captured in the given image frame. In response to determining a contradiction between corresponding respective regions in at least two of the estimated depth maps, the processor merges the at least two estimated depth maps based on the confidence level of each of the corresponding respective regions as indicated by the respective confidence maps for each of the at least two estimated depth maps.

In one implementation of a thirteenth method for computing a three-dimensional structure of an intraoral three-dimensional surface, the thirteenth method includes driving one or more light sources of the intraoral scanner to project light on the intraoral three-dimensional surface, and driving one or more cameras of the intraoral scanner to capture a plurality of two-dimensional images of the intraoral three-dimensional surface. The method includes, (a) using a processor, determining, by a neural network, a respective estimated map of the intraoral three-dimensional surface as captured in each of the two-dimensional images, and (b) using the processor, overcoming manufacturing deviations of the one or more cameras of the intraoral scanner, to reduce a difference between the estimated maps and a true structure of the intraoral three-dimensional surface.

In one implementation of the thirteenth method, overcoming manufacturing deviations of the one or more cameras comprises overcoming manufacturing deviations of the one or more cameras from a reference set of one or more cameras.

In one implementation of the thirteenth method, the intraoral scanner is one of a plurality of manufactured intraoral scanners, each manufactured intraoral scanner comprising a set of one or more cameras, and overcoming manufacturing deviations of the one or more cameras of the intraoral scanner comprises overcoming manufacturing deviations of the one or more cameras from the set of one or more cameras of at least one other of the plurality of manufactured intraoral scanners.

In a further implementation of the thirteenth method, driving one or more cameras comprises driving two or more cameras of the intraoral scanner to each capture a plurality of two-dimensional images of the intraoral three-dimensional surface, each of the two or more cameras of the intraoral scanner corresponding to a respective one of two or more reference cameras, the neural network having been trained using training-stage images captured by the two or more reference cameras. Overcoming the manufacturing deviations comprises overcoming manufacturing deviations of the two or more cameras of the intraoral scanner by, using the processor: (a) for each camera c of the two or more cameras of the intraoral scanner, modifying at least one of the two-dimensional images from camera c to obtain a plurality of modified two-dimensional images, each modified image corresponding to a modified field of view of camera c, the modified field of view of camera c matching a modified field of view of a corresponding one of the reference cameras, and (b) determining by the neural network the respective estimated maps of the intraoral three-dimensional surface based on the plurality of modified two-dimensional images of the intraoral three-dimensional surface.

In a further implementation, the light is non-coherent light, and the plurality of two-dimensional images comprise a plurality of two-dimensional color images.

In a further implementation, the light is near infrared (NIR) light, and the plurality of two-dimensional images comprise a plurality of monochromatic NIR images.

In a further implementation, the light is broad spectrum light, and wherein the plurality of two-dimensional images comprise a plurality of two-dimensional color images.

In a further implementation, the step of modifying comprises cropping and morphing the at least one of the two-dimensional images from camera c to obtain a plurality of cropped and morphed two-dimensional images, each cropped and morphed image corresponding to a cropped and morphed field of view of camera c, the cropped and morphed field of view of camera c matching a cropped field of view of a corresponding one of the reference cameras In a further implementation, the step of cropping and morphing comprises the processor using (a) stored calibration values indicating a camera ray corresponding to each pixel on the camera sensor of each one of the one or more cameras c, and (b) reference calibration values indicating (i) a camera ray corresponding to each pixel on a reference camera sensor of each one of one or more reference cameras, and (ii) a cropped field of view for each one of the one or more reference cameras.

In a further implementation, the cropped fields of view of each of the one or more reference cameras is 85-97% of a respective full field of view of each of the one or more reference cameras.

In a further implementation, the processor further comprises, for each camera c, performing a reverse of the morphing for each of the respective estimated maps of the intraoral three-dimensional surface as captured in each of the cropped and morphed two-dimensional images to obtain a respective non-morphed estimated map of the intraoral surface as seen in each of the at least one two-dimensional images from camera c prior to the morphing.

In a further implementation of the thirteenth method, overcoming the manufacturing deviations of the one or more cameras of the intraoral scanner comprises training the neural network using training-stage images as captured by a plurality of training-stage intraoral scanners. Each of the training-stage intraoral scanners includes one or more reference cameras, each of the one or more cameras of the intraoral scanner corresponds to a respective one of the one or more reference cameras on each of the training-stage intraoral scanners, and the manufacturing deviations of the one or more cameras are manufacturing deviations of the one or more cameras from the corresponding one or more reference cameras.

In a further implementation of the thirteenth method, driving one or more cameras comprises driving two or more cameras of the intraoral scanner to each capture a plurality of two-dimensional images of the intraoral three-dimensional surface. Overcoming the manufacturing deviations comprises overcoming manufacturing deviations of the two or more cameras of the intraoral scanner by: training the neural network using training-stage images that are each captured by only one camera; driving the two or more cameras of the intraoral scanner to, in a given image frame, simultaneously capture a respective two-dimensional image of a respective portion of the intraoral three-dimensional surface; inputting to the neural network, for a given image frame, each one of the respective two-dimensional images to the neural network as a separate input; determining, by the neural network, a respective estimated depth map of each of the respective portions of the intraoral three-dimensional surface as captured in each of the respective two-dimensional images captured in the given image frame; and, using the processor, merging the respective estimated depth maps together to obtain a combined estimated depth map of the intraoral three-dimensional surface as captured in the given image frame.

In a further implementation, determining further comprises determining, by the neural network, a respective estimated confidence map corresponding to each estimated depth map, each confidence map indicating a confidence level per region of the respective estimated depth map.

In a further implementation, merging the respective estimated depth maps together comprises, using the processor, in response to determining a contradiction between corresponding respective regions in at least two of the estimated depth maps, merging the at least two estimated depth maps based on the confidence level of each of the corresponding respective regions as indicated by the respective confidence maps for each of the at least two estimated depth maps.

In a further implementation of the thirteenth method, overcoming the manufacturing deviations of the one or more cameras of the intraoral scanner comprises: (a) initially training the neural network using training-stage images as captured by one or more training-stage cameras of a one or more training-stage handheld wand, each of the one or more cameras of the intraoral scanner corresponding to a respective one of the one or more training-stage cameras on each of the one or more training-stage handheld wands, and (b) subsequently, driving the intraoral scanner to perform a plurality of refining-stage scans of the intraoral three-dimensional surface, and refining the training of the neural network for the intraoral scanner using the refining-stage scans of the intraoral three-dimensional surface.

In a further implementation, the neural network comprises a plurality of layers, and wherein refining the training of the neural network comprises constraining a subset of the layers.

In a further implementation, the method further includes selecting, from a plurality of scans, which of the plurality of scans to use as the refining-stage scans based on a quality level of each scan.

In a further implementation, driving the intraoral scanner to perform the plurality of refining-stage scans comprises:

during the plurality of refining-stage scans, driving (i) one or more structured light projectors of the intraoral scanner to project a pattern of structured light on the intraoral three-dimensional surface and (ii) one or more unstructured light projectors of the intraoral scanner to project unstructured light on the intraoral three-dimensional surface; driving one or more cameras of the intraoral scanner to capture (a) a plurality of refining-stage structured light images using illumination from the structured light projectors and (b) a plurality of refining-stage two-dimensional images using illumination from the unstructured light projectors, during the refining-stage scans; and computing the three-dimensional structure of the intraoral three-dimensional surface based on the plurality of refining-stage structured light images.

In a further implementation, refining the training of the neural network comprises refining the training of the neural network for the intraoral scanner using (a) the plurality of refining-stage two-dimensional images captured during the refining-stage scans and (b) the computed three-dimensional structure of the intraoral three-dimensional surface as computed based on the plurality of refining-stage structured light images.

In a further implementation, the method further includes, during the refining-stage scans, using the computed three-dimensional structure of the intraoral three-dimensional surface as computed based on the plurality of refining-stage structured light images as an end-result three-dimensional structure of the intraoral three-dimensional surface for a user of the intraoral scanner.

In one implementation of a fourteenth method for training a neural network for use with an intraoral scanner, the fourteenth method includes inputting to the neural network a plurality of two-dimensional images of an intraoral three-dimensional surface; estimating, by the neural network, an estimated map of the intraoral three-dimensional surface as captured in each of the two-dimensional images; based on a plurality of structured light images of the intraoral three-dimensional surface, computing a true map of the intraoral three-dimensional surface as seen in each of the two-dimensional images; comparing each estimated map of the intraoral three-dimensional surface to a corresponding true map of the intraoral three-dimensional surface; and based on differences between each estimated map and the corresponding true map, optimizing the neural network to better estimate a subsequent estimated map, wherein, for a two-dimensional image in which moving tissue is identified, processing the image so as to exclude at least a portion of the moving tissue prior to inputting the two-dimensional image to the neural network.

In a further implementation of the fourteenth method, the method further includes: driving one or more structured light projectors to project a structured light pattern on the intraoral three-dimensional surface; driving one or more cameras to capture the plurality of structured light images, each image including at least a portion of the structured light pattern; driving one or more unstructured light projectors to project unstructured light onto the intraoral three-dimensional surface; driving the one or more cameras to capture the plurality of two-dimensional images of the intraoral three-dimensional surface using illumination from the unstructured light projectors; and regulating the capturing of the structured light images and the capturing of the two-dimensional images to produce an alternating sequence of one or more image frames of structured light images interspersed with one or more image frames of two-dimensional images. Additionally, computing the true map of the intraoral three-dimensional surface as seen in each of the two-dimensional images includes: inputting to the neural network a respective plurality of three-dimensional reconstructions of the intraoral three-dimensional surface, based on structured light images of the intraoral three-dimensional surface, the three-dimensional reconstructions including computed three-dimensional positions of a plurality of points on the intraoral three-dimensional surface; interpolating a position of the one or more cameras with respect to the intraoral three-dimensional surface for each two-dimensional image frame based on the computed three-dimensional positions of the plurality of points on the intraoral three-dimensional surface as computed based on respective structured light image frames before and after each two-dimensional image frame; and projecting the three-dimensional reconstructions on respective fields of view of each of the one or more cameras and, based on the projections, calculating a true map of the intraoral three-dimensional surface as seen in each two-dimensional image, constrained by the computed three-dimensional positions of the plurality of points.

There is additionally provided, in accordance with some applications of the present invention, a method for generating a digital three-dimensional image, the method including:
  driving each one of one or more structured light projectors to project a pattern of light (e.g., a distribution of discrete unconnected spots of light) on an intraoral three-dimensional surface;
  driving each one of one or more cameras to capture a plurality of images, each image including at least a portion of the projected pattern, each one of the one or more cameras including a camera sensor including an array of pixels; and
  using a processor to compare a plurality of consecutive images captured by each camera and determine portions of the captured projected pattern (e.g., projected spots s) that can be tracked across the plurality of images.

For some applications, the projected pattern is a distribution of unconnected spots of light and the processor may make the determination based on stored calibration values indicating (a) a camera ray corresponding to each pixel on the camera sensor of each one of the one or more cameras, and (b) a projector ray corresponding to each one of the projected spots of light from each one of the one or more projectors. In some embodiments, each projector ray corresponds to a respective path of pixels on at least one of the camera sensors. Further, in some embodiments, the processor may determine which projected spots s can be tracked across the plurality of images, each tracked spot s moving along a path of pixels corresponding to a respective projector ray r.

For some applications, using the processor further includes using the processor to compute respective three-dimensional positions on the intraoral three-dimensional surface at the intersection of the projector ray r and the respective camera rays corresponding to the tracked spot s in each of the plurality of consecutive images across which spot s was tracked.

For some applications, using the processor further includes using the processor to:
  (a) determine a parameter of a tracked spot in at least two adjacent images from the consecutive images, the parameter including one or more of the size of the spot, the shape of the spot, the orientation of the spot, intensity of the spot, and a signal-to-noise ratio (SNR) of the spot, and (b) based on the parameter of the tracked spot in the at least two adjacent images, predict the parameter of the tracked spot in a later image.

For some applications, using the processor further includes, based on the predicted parameter of the tracked spot, using the processor to search for a spot having substantially the predicted parameter in the later image.

For some applications, the selected parameter is the shape of the spot, and wherein using the processor further includes using the processor to, based on the predicted shape of the tracked spot, determine a search space in the next image in which to search for the tracked spot.

For some applications, using the processor to determine the search space includes using the processor to determine a search space in the next image in which to search for the tracked spot, the search space having a size and aspect ratio based on a size and/or aspect ratio of the predicted shape of the tracked spot.

For some applications, the selected parameter is the shape of the spot, and wherein using the processor further includes using the processor to:
(a) based on the direction and distance the tracked spot has moved between the two adjacent images from the consecutive images, determine a velocity vector of the tracked spot,
(b) in response to the shape of the tracked spot in at least one of the two adjacent images, predict the shape of the tracked spot in a later image, and
(c) in response to (i) the determination of the velocity vector of the tracked spot in combination with (ii) the predicted shape of the tracked spot, determine a search space in the later image in which to search for the tracked spot.

For some applications, the selected parameter is the shape of the spot, and wherein using the processor further includes using the processor to:
(a) based on the direction and distance the tracked spot has moved between the two adjacent images from the consecutive images, determine a velocity vector of the tracked spot,
(b) in response to the determination of the velocity vector of the tracked spot, predict the shape of the tracked spot in a later image, and
(c) in response to (i) the determination of the velocity vector of the tracked spot in combination with (ii) the predicted shape of the tracked spot, determine a search space in the later image in which to search for the tracked spot.

For some applications, using the processor includes using the processor to predict the shape of the tracked spot in the later image in response to (i) the determination of the velocity vector of the tracked spot in combination with (ii) the shape of the tracked spot in at least one of the two adjacent images.

For some applications, using the processor further includes using the processor to:
(a) based on the direction and distance a tracked spot has moved between two consecutive images, determine a velocity vector of the tracked spot, and
(b) in response to the determination of the velocity vector of the tracked spot, determine a search space in a later image in which to search for the tracked spot.

For some applications, using the processor further includes using the processor to determine, for each tracked spot s, a plurality of possible paths p of pixels on a given one of the cameras, paths p corresponding to a respective plurality of possible projector rays r.

For some applications, using the processor further includes using the processor to run a correspondence algorithm to:
(a) for each of the possible projector rays r:
identify how many other cameras, on their respective paths p1 of pixels corresponding to projector ray r, detected respective spots q corresponding to respective camera rays that intersect projector ray r and the camera ray of the given one of the cameras corresponding to the tracked spot s;
(b) identify a given projector ray r1 for which the highest number of other cameras detected respective spots q; and
(c) identify projector ray r1 as the particular projector ray r that produced the tracked spot s.

For some applications, using the processor further includes using the processor to:
(a) run a correspondence algorithm to compute respective three-dimensional positions of a plurality of detected spots on the intraoral three-dimensional surface, as captured in the plurality of consecutive images,
(b) in at least one of the plurality of consecutive images, identify a detected spot as being from a particular projector ray r by identifying the detected spot as being a tracked spot s moving along the path of pixels corresponding to the particular projector ray r.

For some applications, using the processor further includes using the processor to:
(a) run a correspondence algorithm to compute respective three-dimensional positions of a plurality of detected spots on the intraoral three-dimensional surface, as captured in the plurality of consecutive images, and
(b) remove from being considered as a point on the intraoral surface a spot which (i) is identified as being from particular projector ray r based on the three-dimensional position computed by the correspondence algorithm, and (ii) is not identified as being a tracked spot s moving along the path of pixels corresponding to particular projector ray r.

For some applications, using the processor further includes using the processor to:
(a) run a correspondence algorithm to compute respective three-dimensional positions of a plurality of detected spots on the intraoral three-dimensional surface, as captured in the plurality of consecutive images, and
(b) for a detected spot which is identified as being from two distinct projector rays r based on the three-dimensional position computed by the correspondence algorithm, identify the detected spot as being from one of the two distinct projector rays r by identifying the detected spot as a tracked spots moving along the one of the two distinct projector rays r.

For some applications, using the processor further includes using the processor to:
(a) run a correspondence algorithm to compute respective three-dimensional positions of a plurality of detected spots on the intraoral three-dimensional surface, as captured in the plurality of consecutive images, and
(b) identifying a weak spot whose three-dimensional position was not computed by the correspondence algorithm as being a projected spot from a particular projector ray r, by identifying the weak spot as being a tracked spot s moving along the path of pixels corresponding to particular projector ray r.

There is further provided, in accordance with some applications of the present invention, a method for generating a digital three-dimensional image, the method including:

driving each one of one or more structured light projectors to project a pattern of light (e.g., a distribution of discrete unconnected spots of light) on an intraoral three-dimensional surface;

driving each one of one or more cameras to capture an image, the image including at least a portion of the projected pattern, each one of the one or more cameras including a camera sensor including an array of pixels;

using a processor to:
- (a) run a correspondence algorithm to compute respective three-dimensional positions of portions of the detected pattern on the intraoral three-dimensional surface, as captured in a plurality of consecutive images,
- (b) identify the computed three-dimensional position of a portion of the detected pattern as corresponding to particular projector ray r, in at least a subset of the plurality of consecutive images, and
- (c) based on the three-dimensional position of the detected portion of the pattern corresponding to projector ray r in the subset of images, compute a length of projector ray r in each image of the subset of images.

In some embodiments, the pattern of light may be a distribution of unconnected spots. In some embodiments, a processor may perform steps (a)-(c) based on stored calibration values indicating (i) a camera ray corresponding to each pixel on the camera sensor of each one of the one or more cameras, and (ii) a projector ray corresponding to each one of the projected spots of light from each one of the one or more projectors. In some embodiments, each projector ray corresponds to a respective path of pixels on at least one of the camera sensors.

For some applications, using the processor further includes using the processor to compute an estimated length of projector ray r in at least one of the plurality of consecutive images in which a three-dimensional position of the projected spot from projector ray r was not identified in step (b).

For some applications, using the processor further includes using the processor to, based on the estimated length of projector ray r in the at least one of the plurality of images, determine a one-dimensional search space in the at least one of the plurality of images in which to search for a projected spot from projector ray r, the one-dimensional search space being along the respective path of pixels corresponding to projector ray r.

For some applications, using the processor further includes using the processor to, based on the estimated length of projector ray r in the at least one of the plurality of images, determine a one-dimensional search space in respective pixel arrays of a plurality of the cameras, in which to search for a projected spot from projector ray r, for each of the respective pixel arrays, the one-dimensional search space being along the respective path of pixels corresponding to ray r.

For some applications, using the processor to determine the one-dimensional search space in respective pixel arrays of a plurality of the cameras includes using the processor to determine a one-dimensional search space in respective pixel arrays of all of the cameras, in which to search for a projected spot from projector ray r.

For some applications, using the processor further includes using the processor to compute an estimated length of projector ray r in at least one of the plurality of consecutive images in which more than one candidate three-dimensional position of the projected spot from projector ray r was identified in step (b).

For some applications, using the processor further includes using the processor to determine which of the more than one candidate three-dimensional positions is the correct three-dimensional position of the projected spot by determining which of the more than one candidate three-dimensional positions corresponds to the estimated length of projector ray r in the at least one of the plurality of images.

For some applications, using the processor further includes using the processor to, based on the estimated length of projector ray r in the at least one of the plurality of images:
- (a) determine a one-dimensional search space in the at least one of the plurality of images in which to search for a projected spot from projector ray r, and
- (b) determine which of the more than one candidate three-dimensional positions of the projected spot is the correct three-dimensional position of the projected spot produced by projector ray r by determining which of the more than one candidate three-dimensional positions corresponds to a spot produced by projector ray r found within the one-dimensional search space.

For some applications, using the processor further includes using the processor to:
- (i) define a curve based on the length of projector ray r in each image of the subset of images, and
- (ii) remove from being considered as a point on the intraoral surface a detected spot which was identified as being from projector ray r in step (b) if the three-dimensional position of the projected spot corresponds to a length of projector ray r that is at least a threshold distance away from the defined curve.

There is further provided, in accordance with some applications of the present invention, a method for generating a digital three-dimensional image, the method including:

driving each one of one or more structured light projectors to project a distribution of discrete unconnected spots of light on an intraoral three-dimensional surface;

driving each one of one or more cameras to capture an image, the image including at least one of the spots, each one of the one or more cameras including a camera sensor including an array of pixels;

based on stored calibration values indicating (a) a camera ray corresponding to each pixel on the camera sensor of each one of the one or more cameras, and (b) a projector ray corresponding to each one of the projected spots of light from each one of the one or more projectors, whereby each projector ray corresponds to a respective path of pixels on at least one of the camera sensors:

using a processor to:
- (a) run a correspondence algorithm to compute respective three-dimensional positions on the intraoral three-dimensional surface of a plurality of the projected spots,
- (b) using data from at least two of the cameras, identify a candidate three-dimensional position of a given spot corresponding to a particular projector ray r, and substantially not using data from another one of the cameras to identify that candidate three-dimensional position,
- (c) using the candidate three-dimensional position as seen by at least one of the two cameras, identify a search space on the another one of the camera's pixel array in which to search for a spot from projector ray r, and (d) if a spot from projector ray r is identified within the search space, then, using the data from the another one of the cameras, refine the candidate three-dimensional position of the spot.

There is further provided, in accordance with some applications of the present invention, a method for generating a digital three-dimensional image, the method including:

driving each one of one or more structured light projectors to project a distribution of discrete unconnected spots of light on an intraoral three-dimensional surface;

driving each one of one or more cameras to capture a plurality of images, each image including at least one of the spots, each one of the one or more cameras including a camera sensor including an array of pixels;

based on stored calibration values indicating (a) a camera ray corresponding to each pixel on the camera sensor of each one of the one or more cameras, and (b) a projector ray corresponding to each one of the projected spots of light from each one of the one or more projectors, whereby each projector ray corresponds to a respective path of pixels on at least one of the camera sensors:

using a processor to:
(a) run a correspondence algorithm to compute respective three-dimensional positions on the intraoral three-dimensional surface of a plurality of detected spots for each of the plurality of images,
(b) using data corresponding to the respective three-dimensional positions of at least three spots, each spot corresponding to a respective projector ray r, estimate a three-dimensional surface on which all of the at least three spots lie,
(c) for a projector ray r1 for which a three-dimensional position of a spot corresponding to that projector ray r1 was not computed in step (a), estimate a three-dimensional position in space of the intersection of projector ray r1 and the estimated surface, and
(d) using the estimated three-dimensional position in space, identify a search space in the pixel array of at least one camera in which to search for a spot corresponding to projector ray r1.

For some applications, using data corresponding to the respective three-dimensional positions of at least three spots, includes using data corresponding to the respective three-dimensional positions of at least three spots that were all captured in one of the plurality of images.

For some applications, the method further includes refining the estimation of the three-dimensional surface using data corresponding to the three-dimensional position of at least one additional spot, the at least one additional spot having a three-dimensional position that was computed based on another one of plurality of images, such that all of the at least three spots and the at least one additional spot lie on the three-dimensional surface.

For some applications, using data corresponding to the respective three-dimensional positions of at least three spots includes using data corresponding to at least three spots, each spot captured in a respective one of the plurality of images.

There is further provided, in accordance with some applications of the present invention, a method for tracking motion of an intraoral scanner, the method including:

(A) using at least one camera coupled to the intraoral scanner, measuring motion of the intraoral scanner with respect to an intraoral surface being scanned;

(B) using at least one inertial measurement unit (IMU) coupled to the intraoral scanner, measuring motion of the intraoral scanner with respect to a fixed coordinate system; and (C) using a processor:
(i) calculating motion of the intraoral surface with respect to the fixed coordinate system by subtracting (a) motion of the intraoral scanner with respect to the intraoral surface from (b) motion of the intraoral scanner with respect to the fixed coordinate system,
(ii) based on accumulated data of motion of the intraoral surface with respect to the coordinate system, building a predictive model of motion of the intraoral surface with respect to the fixed coordinate system, and
(iii) calculating an estimated location of the intraoral scanner with respect to the intraoral surface by subtracting (a) a prediction of the motion of the intraoral surface with respect to the coordinate system, derived based on the predictive model, from (b) motion of the intraoral scanner with respect to the coordinate system, measured by the IMU.

For some applications, the method further includes determining whether measuring motion of the intraoral scanner with respect to an intraoral surface using the at least one camera is inhibited, and in response to determining that the measuring of the motion is inhibited, calculating the estimated location of the intraoral scanner with respect to the intraoral surface.

There is further provided, in accordance with some applications of the present invention, a method including:

driving each one of one or more structured light projectors to project a distribution of discrete unconnected spots of light on an intraoral three-dimensional surface;

driving each one of one or more cameras to capture a plurality of images, each image including at least one of the spots, each one of the one or more cameras including a camera sensor including an array of pixels;

based on stored calibration values indicating (a) a camera ray corresponding to each pixel on the camera sensor of each one of the one or more cameras, and (b) a projector ray corresponding to each one of the projected spots of light from each one of the one or more projectors, whereby each projector ray corresponds to a respective path p of pixels on at least one of the camera sensors:

using a processor:
(a) running a correspondence algorithm to compute respective three-dimensional positions on the intraoral three-dimensional surface of a plurality of the projected spots,
(b) collecting data at a plurality of points in time, the data including the computed respective three-dimensional positions on the intraoral surface of the plurality of detected spots,
(c) for each projector ray r, based on the collected data, defining an updated path p' of pixels on each of the camera sensors, such that all of the computed three-dimensional positions corresponding to spots produced by projector ray r correspond to locations along the respective updated path p' of pixels for each of the camera sensors, (d) comparing each updated path p' of pixels to the path p of pixels corresponding to that projector ray r on each camera sensor from the stored calibration values, and
(e) if for at least one camera sensor s, the updated path p' of pixels corresponding to projector ray r differs from the path p of pixels corresponding to projector ray r from the stored calibration values:
reducing the difference between the updated path p' of pixels corresponding to each projector ray r and the respective path p of pixels corresponding to each projector ray r from the stored calibration values, by varying stored calibration data selected from the group consisting of:
(i) the stored calibration values indicating a camera ray corresponding to each pixel on the camera sensor s of each one of the one or more cameras, and
(ii) the stored calibration values indicating a projector ray r corresponding to each one of the projected spots of light from each one of the one or more projectors.

For some applications:
the selected stored calibration data includes the stored calibration values indicating a camera ray corresponding to each pixel on the camera sensor of each one of the one or more cameras, and
varying the stored calibration data includes varying one or more parameters of a parametrized camera calibration function that defines the camera rays corresponding to each pixel on at least one camera sensor s, in order to reduce the difference between:
(i) the computed respective three-dimensional positions on the intraoral surface of the plurality of detected spots, and
(ii) the stored calibration values indicating respective camera rays corresponding to each pixel on the camera sensor where a respective one of the plurality of detected spots should have been detected.

For some applications, the selected stored calibration data includes the stored calibration values indicating a projector ray corresponding to each one of the projected spots of light from each one of the one or more projectors, and wherein varying the stored calibration data includes varying:
(i) an indexed list assigning each projector ray r to a path p of pixels, or
(ii) one or more parameters of a parametrized projector calibration model that defines each projector ray r.

For some applications, varying the stored calibration data includes varying the indexed list by re-assigning each projector ray r based on the respective updated paths p' of pixels corresponding to each projector ray r.

For some applications, varying the stored calibration data includes varying:
(i) the stored calibration values indicating a camera ray corresponding to each pixel on the camera sensor s of each one of the one or more cameras, and
(ii) the stored calibration values indicating a projector ray r corresponding to each one of the projected spots of light from each one of the one or more projectors.

For some applications, varying the stored calibration values includes iteratively varying the stored calibration values.

For some applications, the method further includes:
driving each one of the one or more cameras to capture a plurality of images of a calibration object having predetermined parameters;
using a processor:
running a triangulation algorithm to compute the respective parameters of the calibration object based on the captured images; and
running an optimization algorithm:
(a) to reduce the difference between (i) updated path p' of pixels corresponding to projector ray r and (ii) the path p of pixels corresponding to projector ray r from the stored calibration values, using
(b) the computed respective parameters of the calibration object based on the captured images.

For some applications, the calibration object is a three-dimensional calibration object of known shape, and wherein driving each one of the one or more cameras to capture a plurality of images of the calibration object includes driving each one of the one or more cameras to capture images of the three-dimensional calibration object, and the predetermined parameters of the calibration object are dimensions of the three-dimensional calibration object.

For some applications, the calibration object is a two-dimensional calibration object having visually-distinguishable features, driving each one of the one or more cameras to capture a plurality of images of the calibration object includes driving each one of the one or more cameras to capture images of the two-dimensional calibration object, and the predetermined parameters of the two-dimensional calibration object are respective distances between respective visually-distinguishable features.

There is further provided, in accordance with some applications of the present invention, a method for computing the three-dimensional structure of an intraoral three-dimensional surface, the method including:
scanning the intraoral surface;
driving one or more uniform light projectors to project broad spectrum light on the intraoral three-dimensional surface;
driving a camera to capture a plurality of two-dimensional color images of the intraoral three-dimensional surface; and
using a processor:
computing three-dimensional positions of a plurality of points on the intraoral three-dimensional surface based on the intraoral surface scan;
computing a three-dimensional structure of the intraoral three-dimensional surface, based on the plurality of two-dimensional color images of the intraoral three-dimensional surface, constrained by the three-dimensional positions of the plurality of points.

In some embodiments, the intraoral surface is scanned by driving one or more structured light projectors to project a structured light pattern on the intraoral three-dimensional surface and
driving one or more cameras to capture a plurality of structured light images, each image including at least a portion of the structured light pattern.

For some applications, driving one or more structured light projectors includes driving the one or more structured light projectors to each project a distribution of discrete unconnected spots of light.

For some applications, computing the three-dimensional structure includes:
inputting to a neural network (a) the plurality of two-dimensional color images of the intraoral three-dimensional surface, and (b) the computed three-dimensional positions of the plurality of points on the intraoral three-dimensional surface; and determining, by the neural network, a respective predicted depth map of the intraoral three-dimensional surface as captured in each of the two-dimensional color images.

For some applications, the method further includes using the processor to stich the respective depth maps together to obtain the three-dimensional structure of the intraoral three-dimensional surface.

For some applications, the method further includes regulating the capturing of the structured light images and the capturing of the two-dimensional color images to produce an alternating sequence of one or more image frames of structured light interspersed with one or more image frames of broad spectrum light.

For some applications:
driving one or more cameras to capture the plurality of structured light images includes driving each one of two or more cameras to capture a plurality of structured light images, and
driving the cameras to capture the plurality of two-dimensional color images includes driving each one of the two or more cameras to capture a plurality of two-dimensional color images.

For some applications:
determining, by the neural network, includes, for a given image frame, determining a respective predicted depth map of a portion of the intraoral three-dimensional surface as captured in the two-dimensional color image by each one of the two or more cameras, and
the method further includes, using the processor, stitching the respective depth maps together to obtain the predicted depth map of the intraoral three-dimensional surface as captured in the given image frame.

For some applications, the method further includes training the neural network, the training including:
(a) driving one or more structured light projectors to project a training-stage structured light pattern on a training-stage three-dimensional surface;
(b) driving one or more training-stage cameras to capture a plurality of structured light images, each image including at least a portion of the training-stage structured light pattern;
(c) driving one or more training-stage uniform light projectors to project broad spectrum light onto the training-stage three-dimensional surface;
(d) driving the one or more training-stage cameras to capture a plurality of two-dimensional color images of the training-stage three-dimensional surface using illumination from the training-stage uniform light projectors;
(e) regulating the capturing of the structured light images and the capturing of the two-dimensional colored images to produce an alternating sequence of one or more image frames of structured light images interspersed with one or more image frames of two-dimensional color images;
(f) inputting to the neural network the plurality of two-dimensional color images;
(g) inputting to the neural network a respective plurality of three-dimensional reconstructions of the training-stage three-dimensional surface, based on structured light images of the training-stage three-dimensional surface, the three-dimensional reconstructions including computed three-dimensional positions of a plurality of points on the training-stage three-dimensional surface;
(h) interpolating the position of the one or more training-stage cameras with respect to the training-stage three-dimensional surface for each two-dimensional color image frame based on the computed three-dimensional positions of the plurality of points on the training-stage surface as computed based on respective structured light image frames before and after each two-dimensional color image frame;
(i) projecting the three-dimensional reconstructions on respective fields of view of each of the one or more training-stage cameras and, based on the projections, estimating a predicted depth map of the training-stage three-dimensional surface as seen in each two-dimensional color image, constrained by the computed three-dimensional positions of the plurality of points;
(j) comparing each predicted depth map of the training-stage three-dimensional surface to a corresponding true depth map of the training-stage three-dimensional surface; and
(k) based on differences between each predicted depth map and the corresponding true depth map, optimizing the neural network to better estimate a subsequent predicted depth map.

For some applications, driving the one or more structured light projectors to project the training-stage structured light pattern includes driving the one or more structured light projectors to each project a distribution of discrete unconnected spots of light on the training-stage three-dimensional surface.

For some applications, driving one or more training-stage cameras includes driving at least two training-stage cameras.

There is further provided, in accordance with some applications of the present invention, apparatus for intraoral scanning, the apparatus including:
an elongate handheld wand including a probe at a distal end of the handheld wand;
one or more illumination sources coupled to the probe;
one or more near infrared (NIR) light sources coupled to the probe;
one or more cameras coupled to the probe, and configured to (a) capture images using light from the one or more illumination sources, and (b) capture images using NIR light from the NIR light source; and
a processor configured to run a navigation algorithm to determine the location of the handheld wand as the handheld wand moves in space, inputs to the navigation algorithm being (a) the images captured using the light from the one or more illumination light sources, and (b) the images captured using the NIR light.

For some applications, the one or more illumination sources are one or more structured light sources.

For some applications, the one or more illumination sources are one or more uniform light sources.

There is further provided, in accordance with some applications of the present invention, a method for tracking motion of an intraoral scanner, the method including:
using one or more illumination sources coupled to the intraoral scanner, illuminating an intraoral three-dimensional surface;
using one or more near infrared (NIR) light sources coupled to the intraoral scanner, driving each one of one or more NIR light sources to emit NIR light onto the intraoral three-dimensional surface;
using one or more cameras coupled to the intraoral scanner, (a) capturing a plurality of images using light from the one or more illumination sources, and (b) capturing a plurality of images using the NIR light;

using a processor:
  run a navigation algorithm to track the motion of the intraoral scanner with respect to the intraoral three-dimensional surface using (a) the images captured using light from the one or more illumination light sources, and (b) the images captured using the NIR light.

For some applications, using one or more illumination sources includes using one or more structured light sources, illuminating the intraoral three-dimensional surface.

For some applications, using one or more illumination sources includes using one or more uniform light sources.

There is further provided in accordance with some applications of the present invention, apparatus for intraoral scanning for use with a sleeve, the apparatus including:
  an elongate handheld wand including a probe at a distal end of the handheld wand that is configured for being removably disposed in the sleeve;
  at least one structured light projector coupled to the probe, the structured light projector (a) having a field of illumination of at least 30 degrees, (b) including a laser configured to emit polarized laser light, and (c) including a pattern generating optical element configured to generate a pattern of light when the laser diode is activated to transmit light through the pattern generating optical element; and
  at least one camera coupled to the probe, the camera including a camera sensor,
    the probe configured such that light exits and enters the probe through the sleeve,
    the laser being positioned at a distance with respect to the camera, such that when the probe is disposed in the sleeve, a portion of the pattern of light is reflected off of the sleeve and reaches the camera sensor, and
    the laser being positioned at a rotational angle, with respect to its own optical axis, such that, due to the polarization of the pattern of light, the extent of reflection by the sleeve of the portion of the pattern of light is less than 70% of a maximum reflection for all possible rotational angles of the laser with respect to its optical axis.

For some applications, a distance between the structured light projector and the camera is 1-6 times a distance between the structured light projector and the sleeve, when the handheld wand is disposed in the sleeve.

For some applications, each one of the at least one camera has a field of view of at least 30 degrees.

For some applications, the laser is positioned at the rotational angle, with respect to its own optical axis, such that due to the polarization of the pattern of light, the extent of reflection by the sleeve of the portion of the pattern of light is less than 60% of the maximum reflection for all possible rotational angles of the laser with respect to its optical axis.

For some applications, the laser is positioned at the rotational angle, with respect to its own optical axis, such that due to the polarization of the pattern of light, the extent of reflection by the sleeve of the portion of the pattern of light is 15%-60% of the maximum reflection for all possible rotational angles of the laser with respect to its optical axis.

There is further provided, in accordance with some applications of the present invention, a method for generating a three-dimensional image using an intraoral scanner, the method including:

(A) using at least two cameras that are rigidly connected to the intraoral scanner, such that respective fields of view of each of the cameras have non-overlapping portions:
  capturing a plurality of images of an intraoral three-dimensional surface; and
(B) using a processor:
  running a simultaneous localization and mapping (SLAM) algorithm using captured images from each of the cameras for the non-overlapping portions of the respective fields of view, the localization of each of the cameras being solved based on the motion of each of the cameras being the same as the motion of every other one of the cameras.

For some applications:
the respective fields of view of a first one of the cameras and a second one of the cameras also have overlapping portions,
capturing includes capturing a plurality of images of the intraoral three-dimensional surface such that a feature of the intraoral three-dimensional surface that is in the overlapping portion of the respective fields of view appears in the images captured by the first and second cameras, and
using the processor includes running a SLAM algorithm using features of the intraoral three-dimensional surface that appear in the images of at least two of the cameras.

There is further provided, in accordance with some applications of the present invention, a method for generating a three-dimensional image using an intraoral scanner, the method including:
  driving one or more structured light projectors to project a structured light pattern on an intraoral three-dimensional surface;
  driving one or more cameras to capture a plurality of structured light images, each image including at least a portion of the structured light pattern;
  driving one or more uniform light projectors to project broad spectrum light onto the intraoral three-dimensional surface;
  driving at least one camera to capture two-dimensional color images of the intraoral three-dimensional surface using illumination from the uniform light projectors;
  regulating the capturing of the structured light and the capturing of the broad spectrum light to produce an alternating sequence of one or more image frames of structured light interspersed with one or more image frames of broad spectrum light; and
  using a processor:
    computing respective three-dimensional positions of a plurality of points on the intraoral three-dimensional surface, as captured in the plurality of image frames of structured light,
    interpolating the motion of the at least one camera between a first image frame of broad spectrum light and a second image frame of broad spectrum light based on the computed three-dimensional positions of the plurality of points in respective structured light image frames before and after the image frames of broad spectrum light, and
    running a simultaneous localization and mapping (SLAM) algorithm (a) using features of the intraoral three-dimensional surface as captured by the at least one camera in the first and second image frames of broad spectrum light, and (b) constrained by the interpolated motion of the camera between the first image frame of broad spectrum light and the second image frame of broad spectrum light.

For some applications, driving the one or more structured light projectors to project the structured light pattern includes driving the one or more structured light projectors to each project a distribution of discrete unconnected spots of light on the intraoral three-dimensional surface.

There is further provided, in accordance with some applications of the present invention, a method for generating a three-dimensional image using an intraoral scanner, the method including:
  driving one or more structured light projectors to project a structured light pattern on an intraoral three-dimensional surface;
  driving one or more cameras to capture a plurality of structured light images, each image including at least a portion of the structured light pattern;
  driving one or more uniform light projectors to project broad spectrum light onto the intraoral three-dimensional surface;
  driving the one or more cameras to capture two-dimensional color images of the intraoral three-dimensional surface using illumination from the uniform light projectors,
  regulating the capturing of the structured light and the capturing of the broad spectrum light to produce an alternating sequence of one or more image frames of structured light interspersed with one or more image frames of broad spectrum light; and
  using a processor:
    (a) computing the three-dimensional position of a feature on the intraoral three-dimensional surface, based on the image frames of structured light, the feature also being captured in a first image frame of broad spectrum light and a second image frame of broad spectrum light,
    (b) calculating the motion of the at least one camera between the first image frame of broad spectrum light and the second image frame of broad spectrum light based on the computed three-dimensional position of the feature, and
    (c) running a simultaneous localization and mapping (SLAM) algorithm using (i) a feature of the intraoral three-dimensional surface for which the three-dimensional position was not computed based on the image frames of structured light, as captured by the at least one camera in the first and second image frames of broad spectrum light, and (ii) the calculated motion of the camera between the first and second image frames of broad spectrum light.

For some applications, driving the one or more structured light projectors to project the structured light pattern includes driving the one or more structured light projectors to each project a distribution of discrete unconnected spots of light on the intraoral three-dimensional surface.

There is further provided, in accordance with some applications of the present invention, a method for computing the three-dimensional structure of an intraoral three-dimensional surface within an intraoral cavity of a subject, the method including:
  driving one or more structured light projectors to project a structured light pattern of spots on the intraoral three-dimensional surface;
  driving one or more cameras to capture a plurality of structured light images, each image including at least one of the spots;
  driving one or more uniform light projectors to project broad spectrum light onto the intraoral three-dimensional surface;
  driving at least one camera to capture two-dimensional color images of the intraoral three-dimensional surface using illumination from the uniform light projectors;
  regulating the capturing of the structured light and the capturing of the broad spectrum light to produce an alternating sequence of one or more image frames of structured light interspersed with one or more image frames of broad spectrum light; and
  using a processor:
    determining for each of a plurality of the spots whether the spot is being projected on moving or stable tissue within the intraoral cavity, based on the two-dimensional color images,
    based on the determination, assigning a respective confidence grade for each of the plurality of detected spots, high confidence being for fixed tissue and low confidence being for moving tissue,
    based on the confidence grade for each of the plurality of detected spots, running a three-dimensional reconstruction algorithm using the detected spots.

For some applications, driving the one or more structured light projectors to project the structured light pattern includes driving the one or more structured light projectors to each project a distribution of discrete unconnected spots of light on the intraoral three-dimensional surface.

For some applications, running the three-dimensional reconstruction algorithm includes running the three-dimensional reconstruction algorithm using only a subset of the detected spots, the subset consisting of spots that were assigned a confidence grade above a fixed-tissue threshold value.

For some applications, running the three-dimensional reconstruction algorithm includes, (a) for each spot, assigning a weight to that spot based on the respective confidence grade assigned to that spot, and (b) using the respective weights for each spot in the three-dimensional reconstruction algorithm.

BRIEF DESCRIPTION OF THE DRAWINGS

The present invention will be more fully understood from the following detailed description of applications thereof, taken together with the drawings, in which:

FIGS. 2A-B are schematic illustrations of positioning configurations for the cameras and structured light projectors respectively, in accordance with some applications of the present invention;

FIGS. 19A-B are schematic illustrations of a structured light projector and a cross-section of a beam of light transmitted by a laser diode, with a pattern generating optical element shown disposed in the light path of the beam, in accordance with some applications of the present invention;

FIGS. 27A-B are schematic illustrations of different ways to combine laser diodes of different wavelengths, in accordance with some applications of the present invention;

FIGS. 34A-B are simplified schematic illustrations of a camera sensor showing two detected spots, in accordance with some applications of the present invention;

FIGS. 40A-B are graphs showing an experimental set of data before and after ray tracking, in accordance with some applications of the present invention;

FIG. 41 is a schematic illustration of a plurality of camera sensors and a projector projecting a spot, in accordance with some applications of the present invention;

FIGS. 46A-D show a simplified scenario in which the processor identifies that a projector should be recalibrated (and not any of the cameras), in accordance with some applications of the present invention;

FIGS. 47A-B show a simplified scenario in which the processor identifies that a camera that should be recalibrated (and not any of the projectors), in accordance with some applications of the present invention;

FIGS. 49A-B are schematic illustrations, respectively, of a three-dimensional and a two-dimensional calibration object, in accordance with some applications of the present invention;

FIGS. 51G-I are schematic illustrations graphically depicting different combinations of inputs to a neural network, in accordance with some applications of the present invention;

FIG. 66 is a flowchart depicting a method for training a neural network, in accordance with some applications of the present invention.

DETAILED DESCRIPTION

Figure 1:
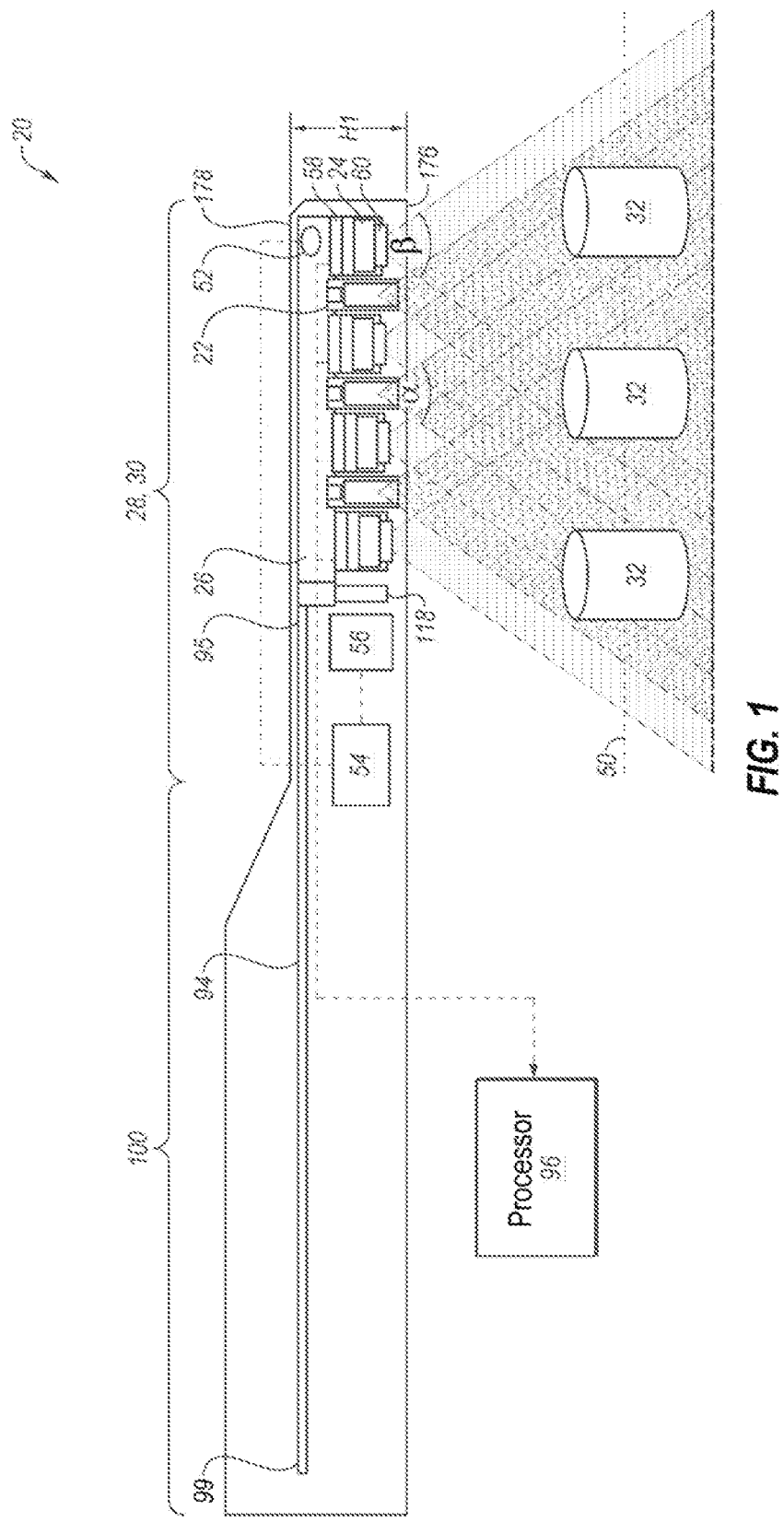
FIG. 1 is a schematic illustration of a handheld wand with a plurality of structured light projectors and cameras disposed within a probe at a distal end of the handheld wand, in accordance with some applications of the present invention.

Reference is now made to FIG. 1, which is a schematic illustration of an elongate handheld wand 20 for intraoral scanning, in accordance with some applications of the present invention. A plurality of structured light projectors 22 and a plurality of cameras 24 are coupled to a rigid structure 26 disposed within a probe 28 at a distal end 30 of the handheld wand. In some applications, during an intraoral scan, probe 28 enters the oral cavity of a subject.

For some applications, structured light projectors 22 are positioned within probe 28 such that each structured light projector 22 faces an object 32 outside of handheld wand 20 that is placed in its field of illumination, as opposed to positioning the structured light projectors in a proximal end of the handheld wand and illuminating the object by reflection of light off a mirror and subsequently onto the object. Similarly, for some applications, cameras 24 are positioned within probe 28 such that each camera 24 faces an object 32 outside of handheld wand 20 that is placed in its field of view, as opposed to positioning the cameras in a proximal end of the handheld wand and viewing the object by reflection of light off a mirror and into the camera. This positioning of the projectors and the cameras within probe 28 enables the scanner to have an overall large field of view while maintaining a low profile probe.

In some applications, a height H1 of probe 28 is less than 15 mm, height H1 of probe 28 being measured from a lower surface 176 (sensing surface), through which reflected light from object 32 being scanned enters probe 28, to an upper surface 178 opposite lower surface 176. In some applications, the height H1 is between 10-15 mm.

In some applications, cameras 24 each have a large field of view β (beta) of at least 45 degrees, e.g., at least 70 degrees, e.g., at least 80 degrees, e.g., 85 degrees. In some applications, the field of view may be less than 120 degrees, e.g., less than 100 degrees, e.g., less than 90 degrees. In experiments performed by the inventors, field of view β (beta) for each camera being between 80 and 90 degrees was found to be particularly useful because it provided a good balance among pixel size, field of view and camera overlap, optical quality, and cost. Cameras 24 may include a camera sensor 58 and objective optics 60 including one or more lenses. To enable close focus imaging cameras 24 may focus at an object focal plane 50 that is located between 1 mm and 30 mm, e.g., between 4 mm and 24 mm, e.g., between 5 mm and 11 mm, e.g., 9 mm-10 mm, from the lens that is farthest from the camera sensor. In experiments performed by the inventors, object focal plane 50 being located between 5 mm and 11 mm from the lens that is farthest from the camera sensor was found to be particularly useful because it was easy to scan the teeth at this distance, and because most of the tooth surface was in good focus. In some applications, cameras 24 may capture images at a frame rate of at least 30 frames per second, e.g., at a frame of at least 75 frames per second, e.g., at least 100 frames per second. In some applications, the frame rate may be less than 200 frames per second.

As described hereinabove, a large field of view achieved by combining the respective fields of view of all the cameras may improve accuracy due to reduced amount of image stitching errors, especially in edentulous regions, where the gum surface is smooth and there may be fewer clear high resolution 3-D features. Having a larger field of view enables large smooth features, such as the overall curve of the tooth, to appear in each image frame, which improves the accuracy of stitching respective surfaces obtained from multiple such image frames.

Similarly, structured light projectors 22 may each have a large field of illumination $\alpha$ (alpha) of at least 45 degrees, e.g., at least 70 degrees. In some applications, field of illumination $\alpha$ (alpha) may be less than 120 degrees, e.g., than 100 degrees. Further features of structured light projectors 22 are described hereinbelow.

For some applications, in order to improve image capture, each camera 24 has a plurality of discrete preset focus positions, in each focus position the camera focusing at a respective object focal plane 50. Each of cameras 24 may include an autofocus actuator that selects a focus position from the discrete preset focus positions in order to improve a given image capture. Additionally or alternatively, each camera 24 includes an optical aperture phase mask that extends a depth of focus of the camera, such that images formed by each camera are maintained focused over all object distances located between 1 mm and 30 mm, e.g., between 4 mm and 24 mm, e.g., between 5 mm and 11 mm, e.g., 9 mm-10 mm, from the lens that is farthest from the camera sensor.

In some applications, structured light projectors 22 and cameras 24 are coupled to rigid structure 26 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected pattern of light are in the field of view of at least one of the cameras at an object focal plane 50 that is located at least 4 mm from the lens that is farthest from the camera sensor. Due to different possible configurations of the projectors and cameras, some of the projected pattern may never be seen in the field of view of any of the cameras, and some of the projected pattern may be blocked from view by object 32 as the scanner is moved around during a scan.

Rigid structure 26 may be a non-flexible structure to which structured light projectors 22 and cameras 24 are coupled so as to provide structural stability to the optics within probe 28. Coupling all the projectors and all the cameras to a common rigid structure helps maintain geometric integrity of the optics of each structured light projector 22 and each camera 24 under varying ambient conditions, e.g., under mechanical stress as may be induced by the subject's mouth. Additionally, rigid structure 26 helps maintain stable structural integrity and positioning of structured light projectors 22 and cameras 24 with respect to each other. As further described hereinbelow, controlling the temperature of rigid structure 26 may help enable maintaining geometrical integrity of the optics through a large range of ambient temperatures as probe 28 enters and exits a subject's oral cavity or as the subject breathes during a scan.

Reference is now made to FIGS. 2A-B, which are schematic illustration of a positioning configuration for cameras 24 and structured light projectors 22 respectively, in accordance with some applications of the present invention. For some applications, in order to improve the overall field of view and field of illumination of the intraoral scanner, cameras 24 and structured light projectors 22 are positioned such that they do not all face the same direction. For some applications, such as is shown in FIG. 2A, a plurality of cameras 24 are coupled to rigid structure 26 such that an angle $\theta$ (theta) between two respective optical axes 46 of at least two cameras 24 is 90 degrees or less, e.g., 35 degrees or less. Similarly, for some applications, such as is shown in FIG. 2B, a plurality of structured light projectors 22 are coupled to rigid structure 26 such that an angle $\varphi$ (phi) between two respective optical axes 48 of at least two structured light projectors 22 is 90 degrees or less, e.g., 35 degrees or less.

Figure 2C:
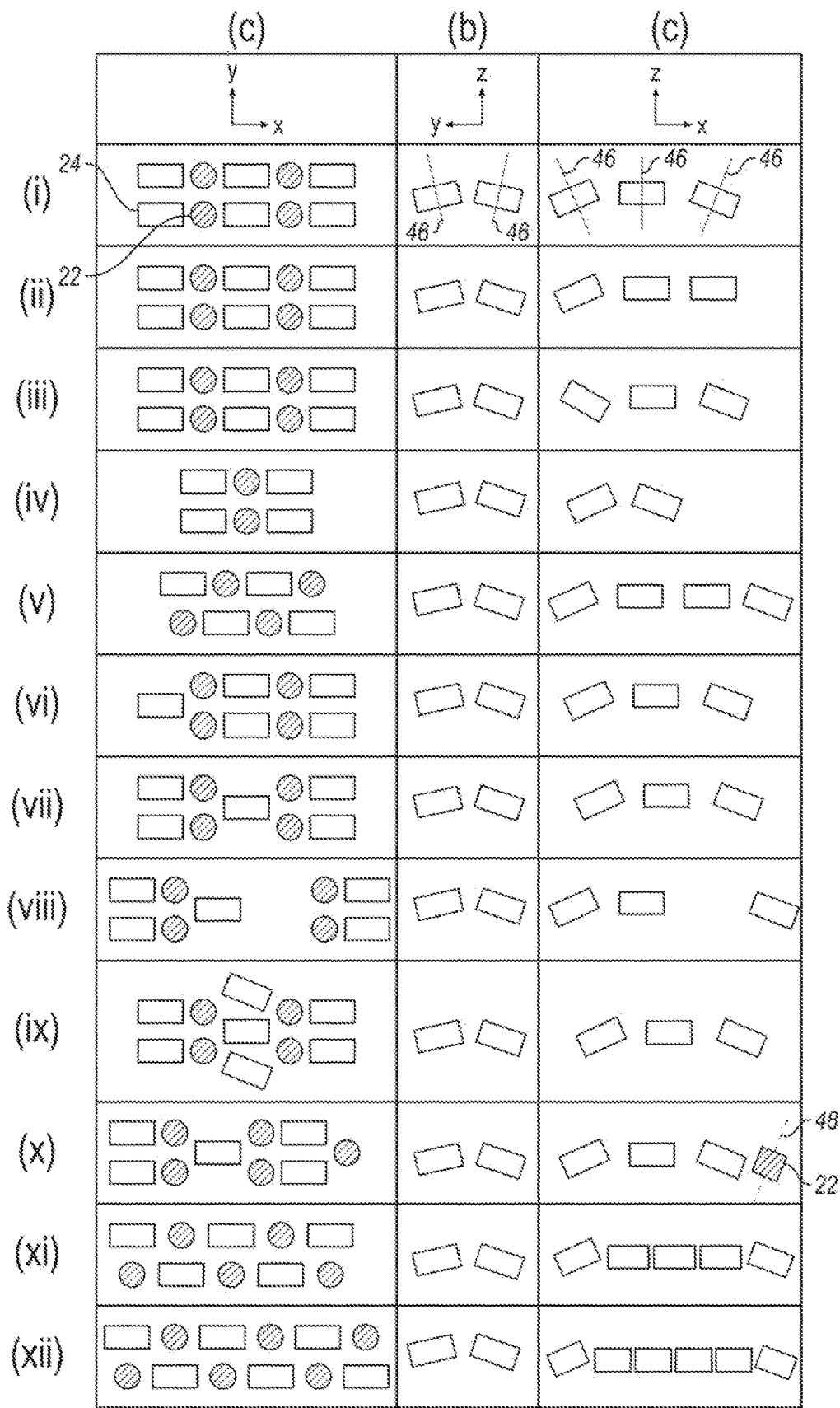
FIG. 2C is a chart depicting a plurality of different configurations for the position of the structured light projectors and the cameras in the probe, in accordance with some applications of the present invention.

Reference is now made to FIG. 2C, which is a chart depicting a plurality of different configurations for the position of structured light projectors 22 and cameras 24 in probe 28, in accordance with some applications of the present invention. Structured light projectors 22 are represented in FIG. 2C by circles and cameras 24 are represented in FIG. 2C by rectangles. It is noted that rectangles are used to represent the cameras, since typically, each camera sensor 58 and the field of view $\beta$ (beta) of each camera 24 have aspect ratios of 1:2. Column (a) of FIG. 2C shows a bird's eye view of the various configurations of structured light projectors 22 and cameras 24. The x-axis as labeled in the first row of column (a) corresponds to a central longitudinal axis of probe 28. Column (b) shows a side view of cameras 24 from the various configurations as viewed from a line of sight that is coaxial with the central longitudinal axis of probe 28. Similarly to as shown in FIG. 2A, column (b) of FIG. 2C shows cameras 24 positioned so as to have optical axes 46 at an angle of 90 degrees or less, e.g., 35 degrees or less, with respect to each other. Column (c) shows a side view of cameras 24 of the various configurations as viewed from a line of sight that is perpendicular to the central longitudinal axis of probe 28.

Typically, the distal-most (toward the positive x-direction in FIG. 2C) and proximal-most (toward the negative x-direction in FIG. 2C) cameras 24 are positioned such that their optical axes 46 are slightly turned inwards, e.g., at an angle of 90 degrees or less, e.g., 35 degrees or less, with respect to the next closest camera 24. The camera(s) 24 that are more centrally positioned, i.e., not the distal-most camera 24 nor proximal-most camera 24, are positioned so as to face directly out of the probe, their optical axes 46 being substantially perpendicular to the central longitudinal axis of probe 28. It is noted that in row (xi) a projector 22 is positioned in the distal-most position of probe 28, and as such the optical axis 48 of that projector 22 points inwards, allowing a larger number of spots 33 projected from that particular projector 22 to be seen by more cameras 24.

Typically, the number of structured light projectors 22 in probe 28 may range from two, e.g., as shown in row (iv) of FIG. 2C, to six, e.g., as shown in row (xii). Typically, the number of cameras 24 in probe 28 may range from four, e.g., as shown in rows (iv) and (v), to seven, e.g., as shown in row (ix). It is noted that the various configurations shown in FIG. 2C are by way of example and not limitation, and that the scope of the present invention includes additional configurations not shown. For example, the scope of the present invention includes more than five projectors 22 positioned in probe 28 and more than seven cameras positioned in probe 28.

Figure 2D:
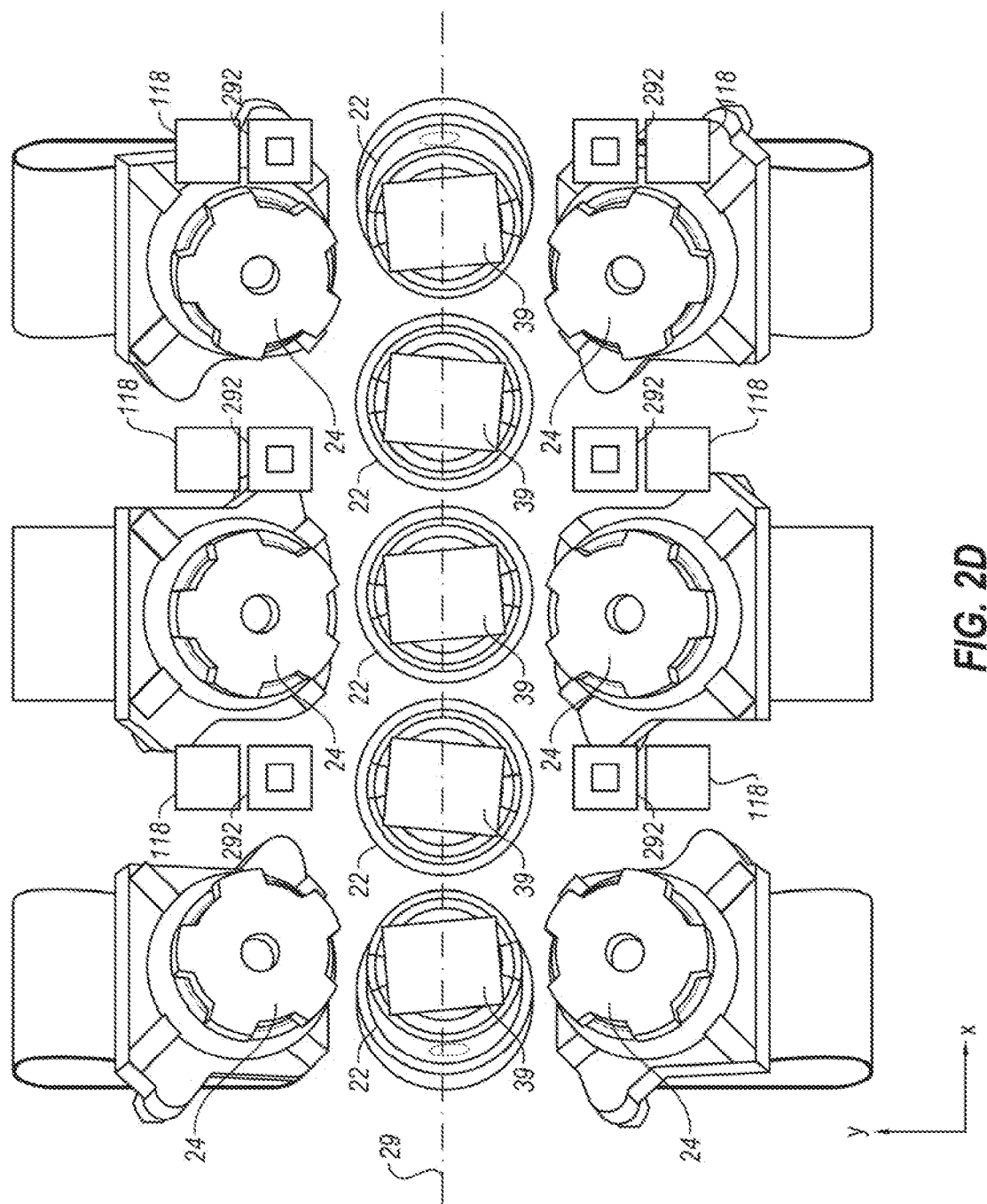
FIGS. 2D-E are isometric illustrations of a particular configuration for the position of the structured light projectors and the cameras in the probe, shown from two different respective perspectives, in accordance with some applications of the present invention.
Figure 2E:
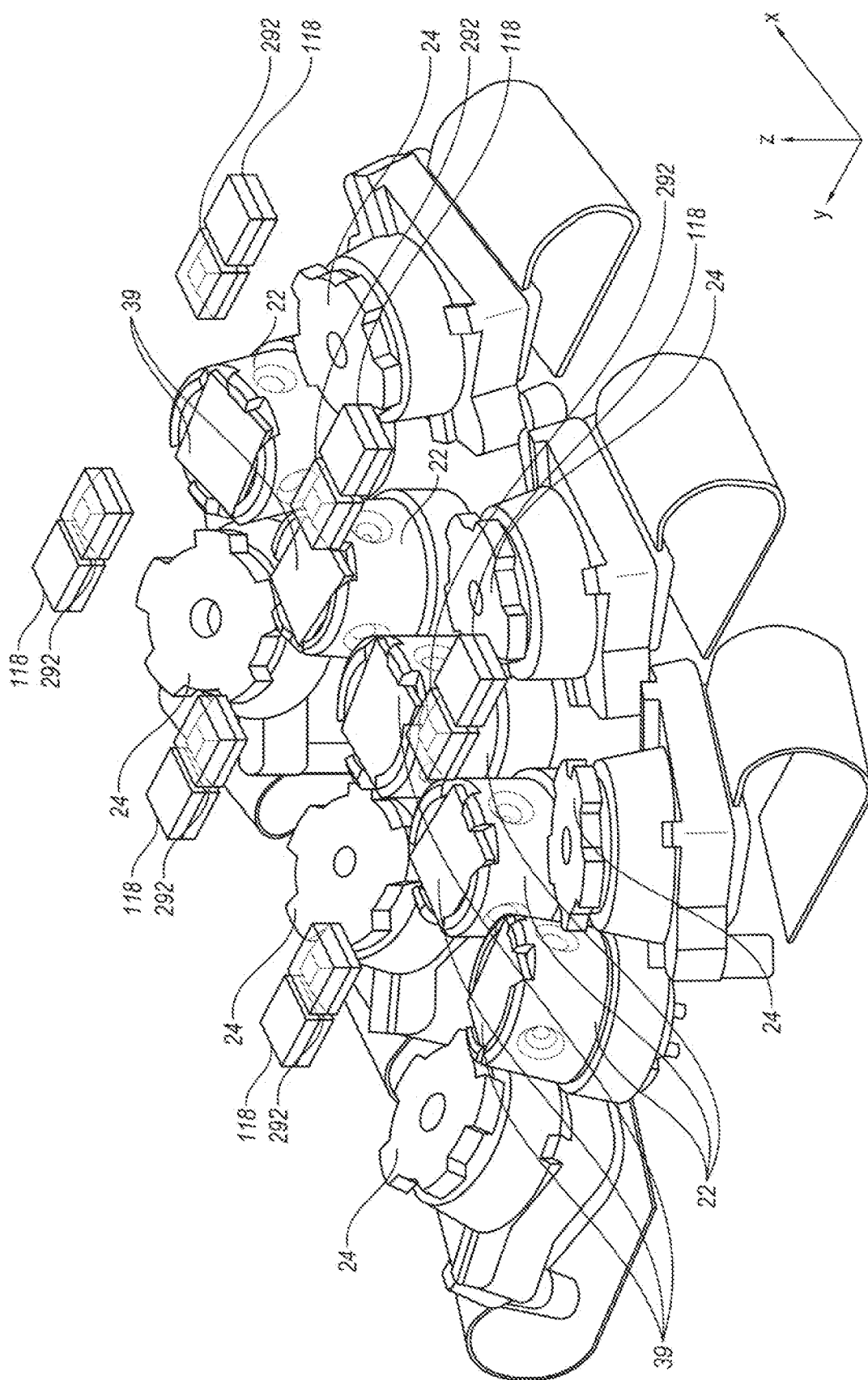

Reference is now made to FIGS. 2D-E, which are isometric illustrations of a particular configuration for the position of structured light projectors 22 and cameras 24 in probe 28, shown from two different respective perspectives, in accordance with some applications of the present invention. FIG. 2D is shown from the perspective of the same bird's eye view as that of column (a) in FIG. 2C. For some applications, there are six cameras 24 evenly spaced within probe 28, with three cameras on either side of probe 28, and five structured light projectors 22 disposed within probe 28 in the center along the central longitudinal axis of probe 28 (illustrated by dashed line 29).

For some applications, cameras 24 and structured light projectors 22 are all coupled to a flexible printed circuit board (PCB) so as to accommodate angular positioning of cameras 24 and structured light projectors 22 within probe 28. This angular positioning of cameras 24 and structured light projectors 22 is shown in FIG. 2E. The distal-most (i.e., toward the positive x-direction) cameras 24 and structured light projectors 22 are positioned such that their respective optical axes are tilted back toward handheld wand 20, e.g., at an angle of 45 degrees or less, e.g., 35 degrees or less. This allows, for example, the distal-most cameras to be able to capture the posterior wall of the rear molars in the intraoral cavity. The proximal-most (i.e., toward the negative x-direction) cameras 24 and structured light projectors 22 are positioned such that their respective optical axes tilt forward toward the distal end of probe 28, in order to obtain an improved overlap of the respective fields of view of cameras 24, e.g., at an angle of 45 degrees or less, e.g., 35 degrees or less. Additionally, all of the structured light projectors 22 are positioned such that their respective optical axes are tilted toward the center of probe 28, which improves overlap of the respective fields of illumination of the structured light projectors 22. The inventors have realized that positioning structured light projectors 22 generally all in a line allows them to more easily all be connected to the same flexible PCB.

Additionally shown in FIGS. 2D-E and further described hereinbelow are a plurality of uniform light projectors 118, a plurality of near infrared (NIR) light projectors 292, and a diffractive optical element (DOE) 39 disposed over each structured light projector 22.

Figure 3:
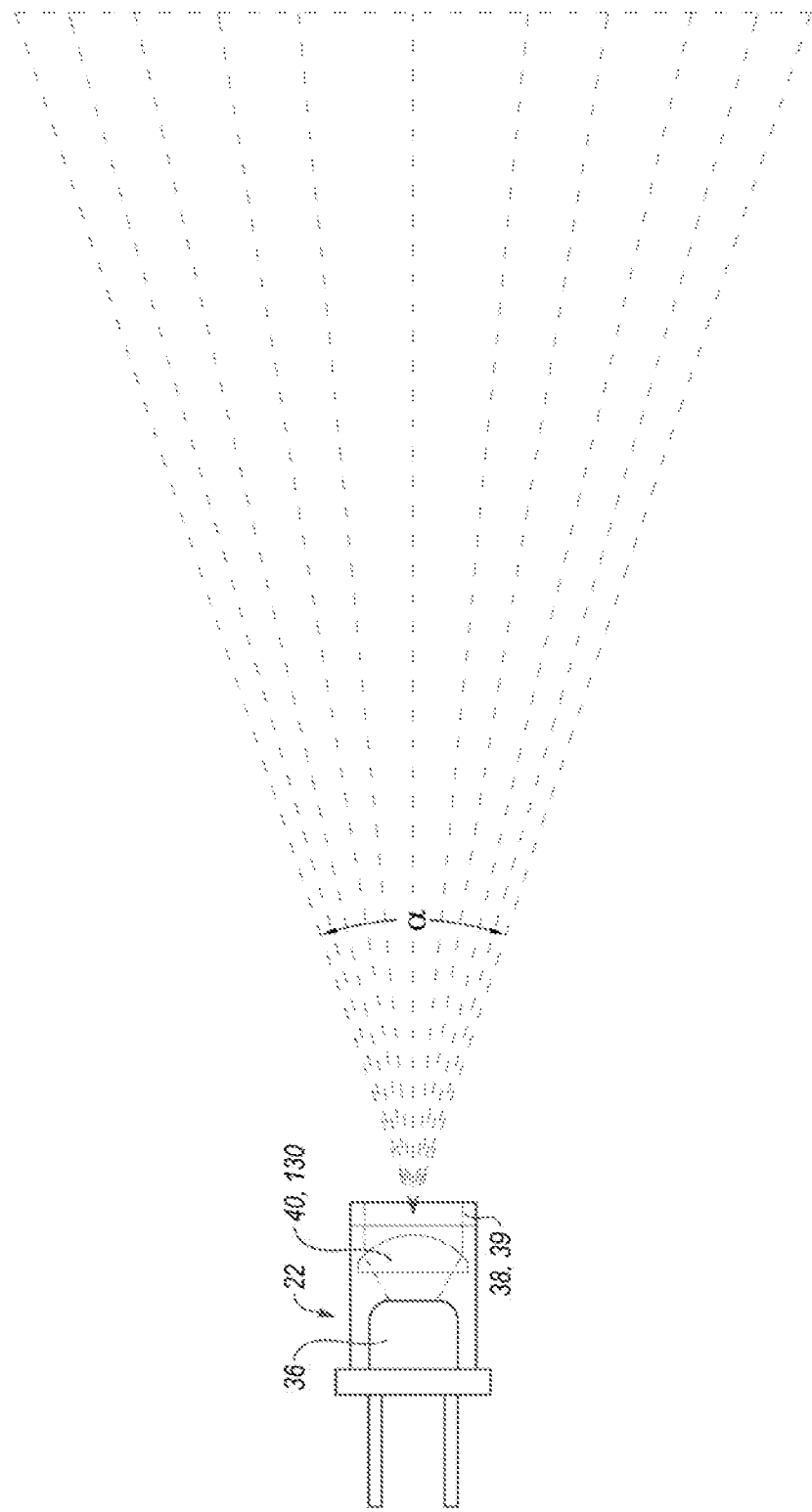
FIG. 3 is a schematic illustration of a structured light projector, in accordance with some applications of the present invention.

Reference is now made to FIG. 3, which is a schematic illustration of a structured light projector 22, in accordance with some applications of the present invention. In some applications, structured light projectors 22 include a laser diode 36, a beam shaping optical element 40, and a pattern generating optical element 38 that generates a distribution 34 of discrete unconnected spots of light (further discussed hereinbelow with reference to FIG. 4). In some applications, the structured light projectors 22 may be configured to generate a distribution 34 of discrete unconnected spots of light at all planes located between 1 mm and 30 mm, e.g., between 4 mm and 24 mm, from pattern generating optical element 38 when laser diode 36 transmits light through pattern generating optical element 38. For some applications, distribution 34 of discrete unconnected spots of light is in focus at one plane located between 1 mm and 30 mm, e.g., between 4 mm and 24 mm, yet all other planes located between 1 mm and 30 mm, e.g., between 4 mm and 24 mm, still contain discrete unconnected spots of light. While described above as using laser diodes, it should be understood that this is an exemplary and non-limiting application. Other light sources may be used in other applications. Further, while described as projecting a pattern of discrete unconnected spots of light, it should be understood that this is an exemplary and non-limiting application. Other patterns or arrays of lights may be used in other applications, including but not limited to, lines, grids, checkerboards, and other arrays. In some applications, the light pattern projected by the structured light projectors is spatially fixed relative to the one or more cameras.

Embodiments are described herein with reference to discrete spots of light, and to performing operations using or based on spots. Examples of such operations includes solving a correspondence algorithm to determine positions of spots of light, tracking spots of light, mapping projector rays to spots of light, identifying weak spots of light, and generating a three-dimensional model based on positions of spots. It should be understood that such operations and other operations that are described with reference to spots also work for other features of other projected patterns of light. Accordingly, discussions herein with reference to spots also apply to any other features of projected patterns of light.

Pattern generating optical element 38 may be configured to have a light throughput efficiency (i.e., the fraction of light that goes into the pattern out of the total light falling on pattern generating optical element 38) of at least 80%, e.g., at least 90%.

For some applications, respective laser diodes 36 of respective structured light projectors 22 transmit light at different wavelengths, i.e., respective laser diodes 36 of at least two structured light projectors 22 transmit light at two distinct wavelengths, respectively. For some applications, respective laser diodes 36 of at least three structured light projectors 22 transmit light at three distinct wavelengths respectively. For example, red, blue, and green laser diodes may be used. For some applications, respective laser diodes 36 of at least two structured light projectors 22 transmit light at two distinct wavelengths respectively. For example, in some applications there are six structured light projectors 22 disposed within probe 28, three of which contain blue laser diodes and three of which contain green laser diodes.

Figure 4:
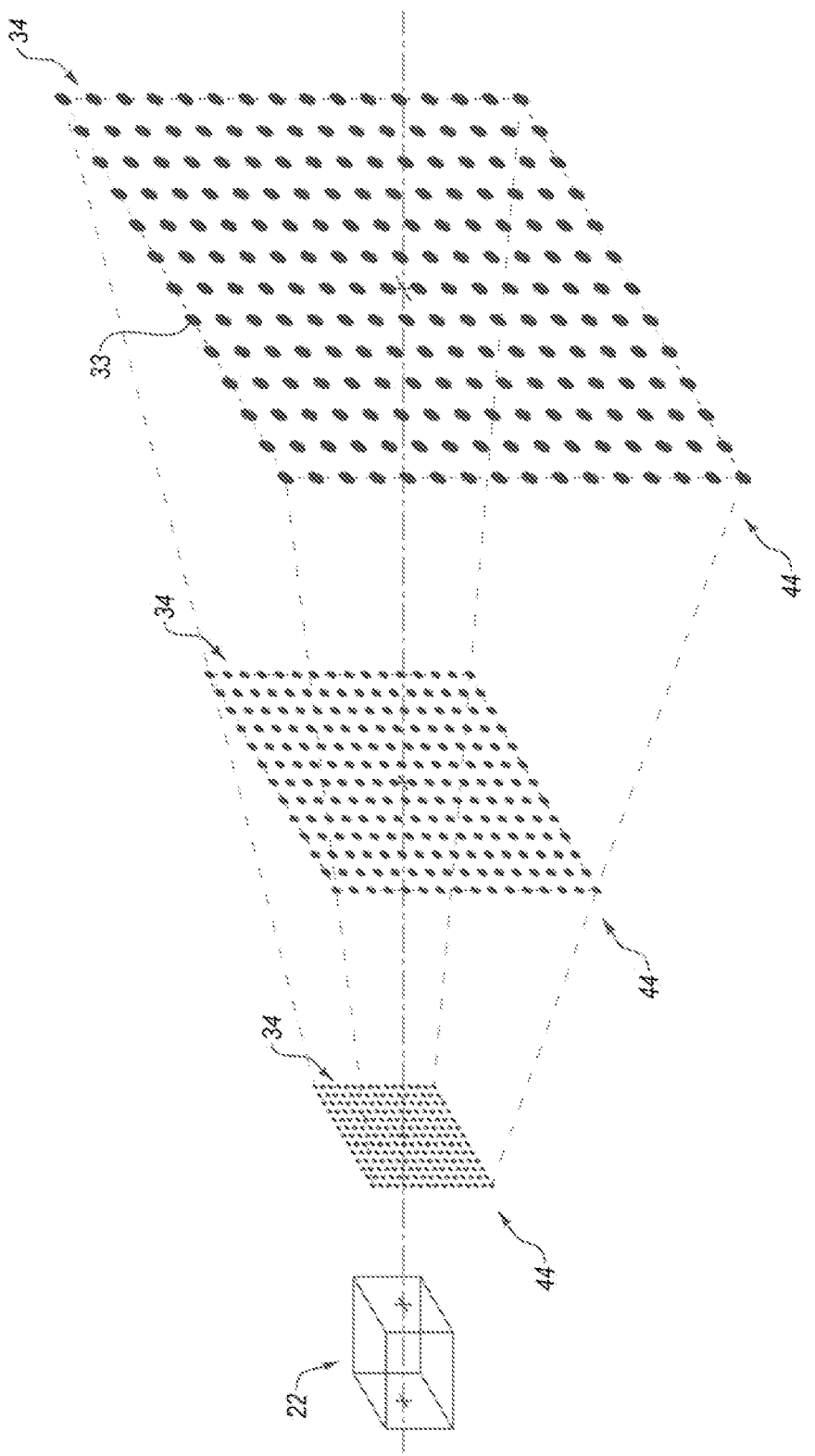
FIG. 4 is a schematic illustration of a structured light projector projecting a distribution of discrete unconnected spots of light onto a plurality of object focal planes, in accordance with some applications of the present invention.

Reference is now made to FIG. 4, which is a schematic illustration of a structured light projector 22 projecting a distribution of discrete unconnected spots of light onto a plurality of object focal planes, in accordance with some applications of the present invention. Object 32 being scanned may be one or more teeth or other intraoral object/tissue inside a subject's mouth. The somewhat translucent and glossy properties of teeth may affect the contrast of the structured light pattern being projected. For example, (a) some of the light hitting the teeth may scatter to other regions within the intraoral scene, causing an amount of stray light, and (b) some of the light may penetrate the tooth and subsequently come out of the tooth at any other point. Thus, in order to improve image capture of an intraoral scene under structured light illumination, without using contrast enhancement means such as coating the teeth with an opaque powder, the inventors have realized that a sparse distribution 34 of discrete unconnected spots of light may provide an improved balance between reducing the amount of projected light while maintaining a useful amount of information. The sparseness of distribution 34 may be characterized by a ratio of:

(a) illuminated area on an orthogonal plane 44 in field of illumination α (alpha), i.e., the sum of the area of all projected spots 33 on the orthogonal plane 44 in field of illumination α (alpha), to (b) non-illuminated area on orthogonal plane 44 in field of illumination α (alpha). In some applications, sparseness ratio may be at least 1:150 and/or less than 1:16 (e.g., at least 1:64 and/or less than 1:36).

In some applications, each structured light projector 22 projects at least 400 discrete unconnected spots 33 onto an intraoral three-dimensional surface during a scan. In some applications, each structured light projector 22 projects less than 3000 discrete unconnected spots 33 onto an intraoral surface during a scan. In order to reconstruct the three-dimensional surface from projected sparse distribution 34, correspondence between respective projected spots 33 (or other features of a projected pattern) and the spots (or other features) detected by cameras 24 must be determined, as further described hereinbelow with reference to FIGS. 7-19.

For some applications, pattern generating optical element 38 is a diffractive optical element (DOE) 39 (FIG. 3) that generates distribution 34 of discrete unconnected spots 33 of light when laser diode 36 transmits light through DOE 39 onto object 32. As used herein throughout the present application, including in the claims, a spot of light is defined as a small area of light having any shape. For some applications, respective DOE's 39 of different structured light projectors 22 generate spots having different respective shapes, i.e., every spot 33 generated by a specific DOE 39 has the same shape, and the shape of spots 33 generated by at least one DOE 39 is different from the shape of spots 33 generated by at least one other DOE 39. By way of example, some of DOE's 39 may generate circular spots 33 (such as is shown in FIG. 4), some of DOE's 39 may generate square spots, and some of the DOE's 39 may generate elliptical spots. Optionally, some DOE's 39 may generate line patterns, connected or unconnected.

Figure 5A:
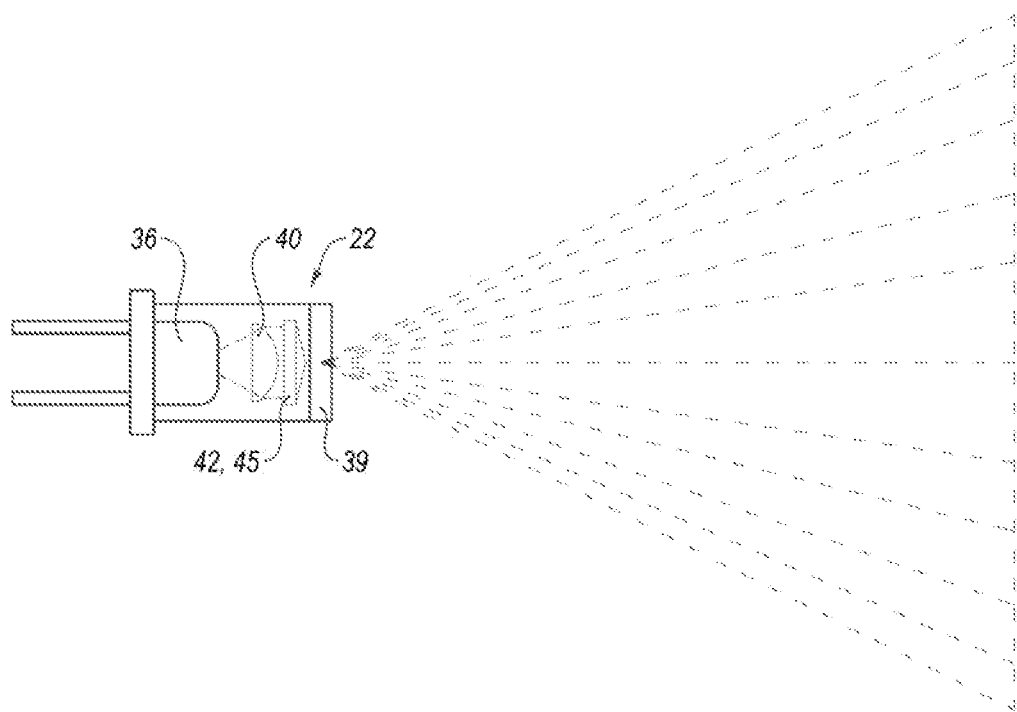
FIGS. 5A-B are schematic illustrations of a structured light projector, including a beam shaping optical element and an additional optical element disposed between the beam shaping optical element and a pattern generating optical element, in accordance with some applications of the present invention.
Figure 5B:
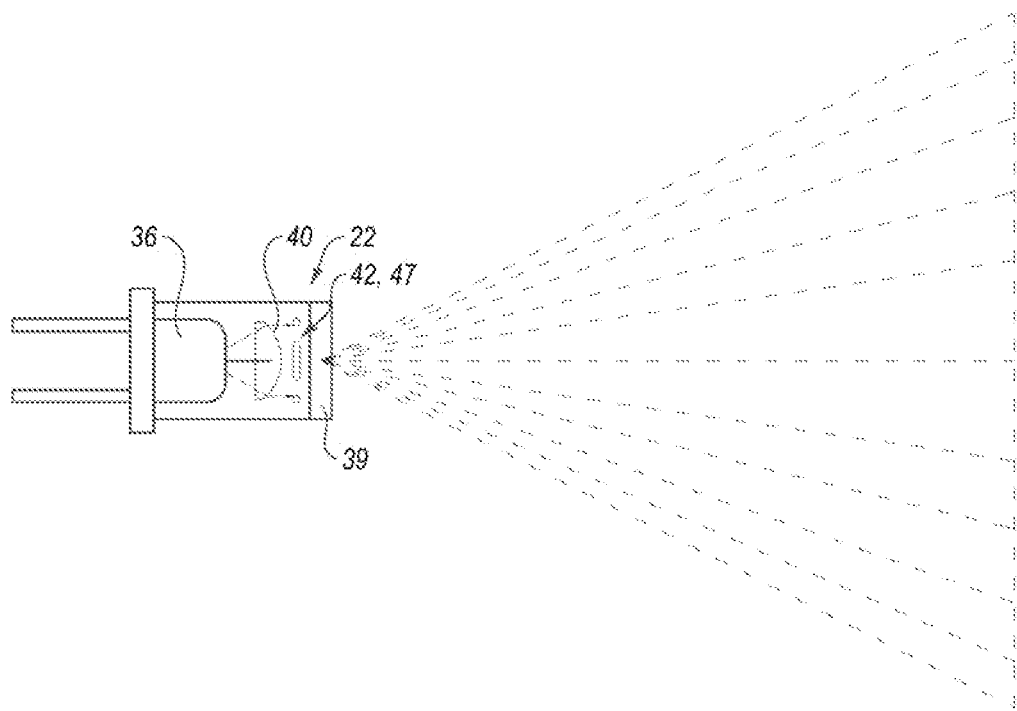

Reference is now made to FIGS. 5A-B, which are schematic illustrations of a structured light projector 22, including beam shaping optical element 40 and an additional optical element disposed between beam shaping optical element 40 and pattern generating optical element 38, e.g., DOE 39, in accordance with some applications of the present invention. Optionally, beam shaping optical element 40 is a collimating lens 130. Collimating lens 130 may be configured to have a focal length of less than 2 mm. Optionally, the focal length may be at least at least 1.2 mm. For some applications, an additional optical element 42, disposed between beam shaping optical element 40 and pattern generating optical element 38, e.g., DOE 39, generates a Bessel beam when laser diode 36 transmits light through optical element 42. In some applications, the Bessel beam is transmitted through DOE 39 such that all discrete unconnected spots 33 of light maintain a small diameter (e.g., less than 0.06 mm, e.g., less than 0.04 mm, e.g., less than 0.02 mm), through a range of orthogonal planes 44 (e.g., each orthogonal plane located between 1 mm and 30 mm from DOE 39, e.g., between 4 mm and 24 mm from DOE 39, etc.). The diameter of spots 33 is defined, in the context of the present patent application, by the full width at half maximum (FWHM) of the intensity of the spot.

Notwithstanding the above description of all spots being smaller than 0.06 mm, some spots that have a diameter near the upper end of these ranges (e.g., only somewhat smaller than 0.06 mm, or 0.02 mm) that are also near the edge of the field of illumination of a projector 22 may be elongated when they intersect a geometric plane that is orthogonal to DOE 39. For such cases, it is useful to measure their diameter as they intersect the inner surface of a geometric sphere that is centered at DOE 39 and that has a radius between 1 mm and 30 mm, corresponding to the distance of the respective orthogonal plane that is located between 1 mm and 30 mm from DOE 39. As used throughout the present application, including in the claims, the word "geometric" is taken to relate to a theoretical geometric construct (such as a plane or a sphere), and is not part of any physical apparatus.

For some applications, when the Bessel beam is transmitted through DOE 39, spots 33 having diameters larger than 0.06 mm are generated in addition to the spots having diameters less than 0.06 mm.

For some applications, optical element 42 is an axicon lens 45, such as is shown in FIG. 5A and further described hereinbelow with reference to FIGS. 23A-B. Alternatively, optical element 42 may be an annular aperture ring 47, such as is shown in FIG. 5B. Maintaining a small diameter of the spots improves 3D resolution and precision throughout the depth of focus. Without optical element 42, e.g., axicon lens 45 or annular aperture ring 47, the spot of spots 33 size may vary, e.g., becomes bigger, as you move farther away from a best focus plane due to diffraction and defocus.

Figure 6A:
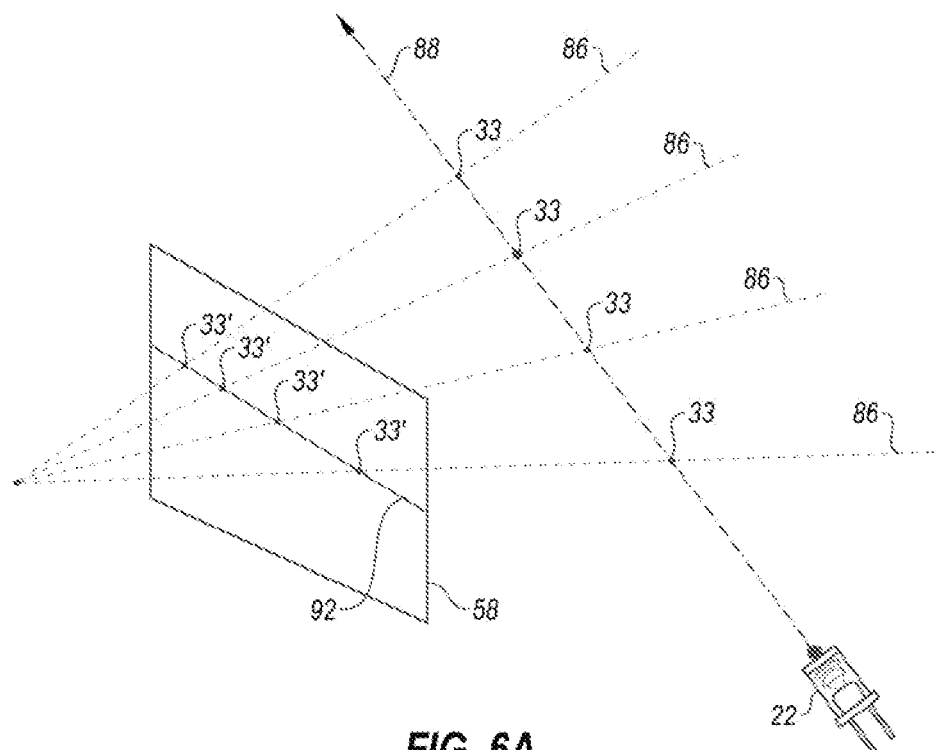
FIGS. 6A-B are schematic illustrations of a structured light projector projecting discrete unconnected spots and a camera sensor detecting spots, in accordance with some applications of the present invention.
Figure 6B:
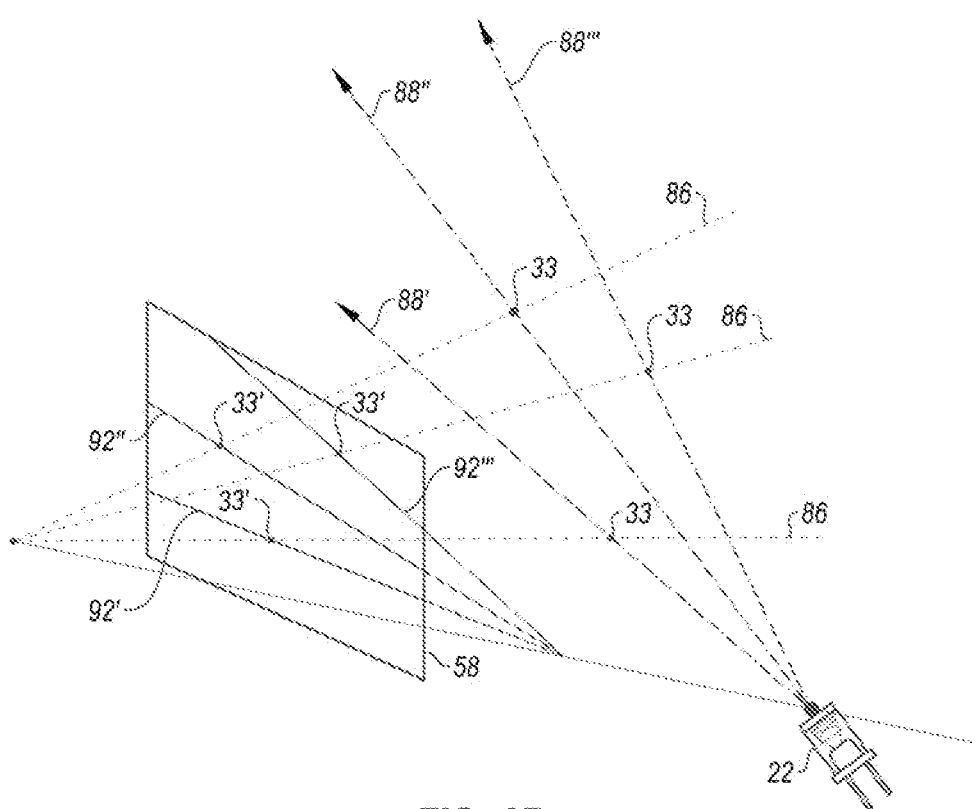

Reference is now made to FIGS. 6A-B, which are schematic illustrations of a structured light projector 22 projecting discrete unconnected spots 33 and a camera sensor 58 detecting spots 33', in accordance with some applications of the present invention. For some applications, a method is provided for determining correspondence between the projected spots 33 on the intraoral surface and detected spots 33' on respective camera sensors 58. As mentioned previously, the method also applies to determining correspondence between other projected features on the intraoral surface and detected features on respective camera sensors. Once the correspondence is determined, a three-dimensional image of the surface is reconstructed. Each camera sensor 58 has an array of pixels, for each of which there exists a corresponding camera ray 86. Similarly, for each projected spot 33 from each projector 22 there exists a corresponding projector ray 88. Each projector ray 88 corresponds to a respective path 92 of pixels on at least one of camera sensors 58. Thus, if a camera sees a spot 33' projected by a specific projector ray 88, that spot 33' will necessarily be detected by a pixel on the specific path 92 of pixels that corresponds to that specific projector ray 88. With specific reference to FIG. 6B, the correspondence between respective projector rays 88 and respective camera sensor paths 92 is shown. Projector ray 88' corresponds to camera sensor path 92', projector ray 88" corresponds to camera sensor path 92", and projector ray 88''' corresponds to camera sensor path 92'''. For example, if a specific projector ray 88 were to project a spot into a dust-filled space, a line of dust in the air would be illuminated. The line of dust as detected by camera sensor 58 would follow the same path on camera sensor 58 as the camera sensor path 92 that corresponds to the specific projector ray 88.

During a calibration process, calibration values are stored based on camera rays 86 corresponding to pixels on camera sensor 58 of each one of cameras 24, and projector rays 88 corresponding to projected spots 33 of light (or other features) from each structured light projector 22. For example, calibration values may be stored for (a) a plurality of camera rays 86 corresponding to a respective plurality of pixels on camera sensor 58 of each one of cameras 24, and (b) a plurality of projector rays 88 corresponding to a respective plurality of projected spots 33 of light from each structured light projector 22. As used throughout the present application, including in the claims, stored calibration values indicating a camera ray corresponding to each pixel on the camera sensor of each camera refers to (a) a value given to each camera ray, or (b) parameter values of a parametrized camera calibration model, e.g., function. As used throughout the present application, including in the claims, stored calibration values indicating a projector ray corresponding to each projected spot of light (or other projected feature) from each structured light projector refers to (a) a value given to each projector ray, e.g., in an indexed list, or (b) parameter values of a parametrized projector calibration model, e.g., function.

By way of example, the following calibration process may be used. A high accuracy dot target, e.g., black dots on a white background, is illuminated from below and an image is taken of the target with all the cameras. The dot target is then moved perpendicularly toward the cameras, i.e., along the z-axis, to a target plane. The dot-centers are calculated for all the dots in all respective z-axis positions to create a three-dimensional grid of dots in space. A distortion and camera pinhole model is then used to find the pixel coordinate for each three-dimensional position of a respective dot-center, and thus a camera ray is defined for each pixel as a ray originating from the pixel whose direction is towards a corresponding dot-center in the three-dimensional grid. The camera rays corresponding to pixels in between the grid points can be interpolated. The above-described camera calibration procedure is repeated for all respective wavelengths of respective laser diodes 36, such that included in the stored calibration values are camera rays 86 corresponding to each pixel on each camera sensor 58 for each of the wavelengths. Alternatively, the stored calibration values are parameter values of the distortion and camera pinhole model, which indicate a value of a camera ray 86 corresponding to each pixel on each camera sensor 58 for each of the wavelengths.

After cameras 24 have been calibrated and all camera ray 86 values stored, structured light projectors 22 may be calibrated as follows. A flat featureless target is used and structured light projectors 22 are turned on one at a time. Each spot (or other feature) is located on at least one camera sensor 58. Since cameras 24 are now calibrated, the three-dimensional spot location of each spot (or other feature) is computed by triangulation based on images of the spot (or other feature) in multiple different cameras. The above-described process is repeated with the featureless target located at multiple different z-axis positions. Each projected spot (or other feature) on the featureless target will define a projector ray in space originating from the projector.

Figure 7:
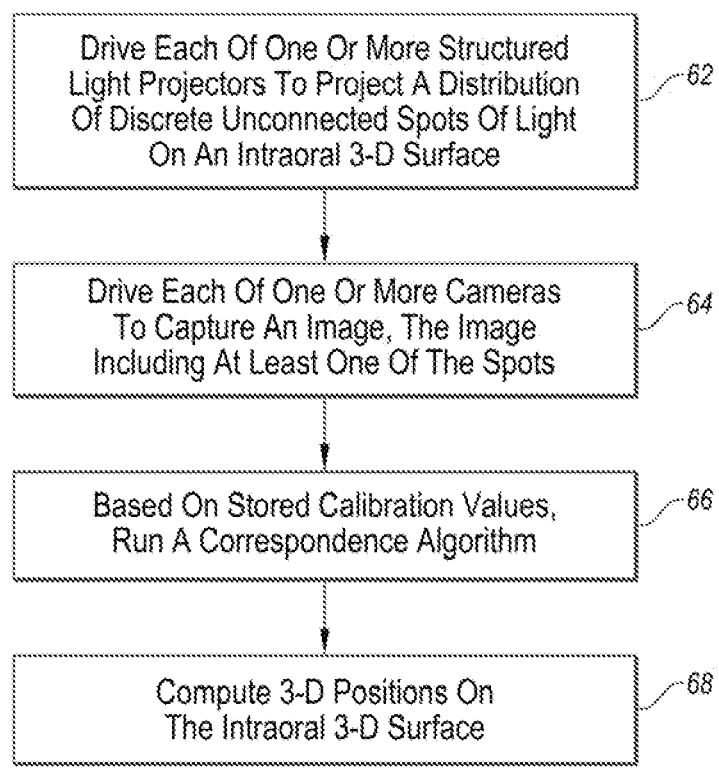
FIG. 7 is a flow chart outlining a method for generating a digital three-dimensional image, in accordance with some applications of the present invention.

Reference is now made to FIG. 7, which is a flow chart outlining a method for generating a digital three-dimensional image, in accordance with some applications of the present invention. In steps 62 and 64, respectively, of the method outlined by FIG. 7 each structured light projector 22 is driven to project a pattern of light (e.g., a distribution 34 of discrete unconnected spots 33 of light) on an intraoral three-dimensional surface, and each camera 24 is driven to capture an image that includes at least a portion of the pattern (e.g., one of spots 33). Based on the stored calibration values indicating (a) a camera ray 86 corresponding to each pixel on camera sensor 58 of each camera 24, and (b) a projector ray 88 corresponding to each projected spot 33 of light from each structured light projector 22, a correspondence algorithm is run in step 66 using a processor 96 (FIG. 1), further described hereinbelow with reference to FIGS. 8-12. In some embodiments, the processor 96 is a processor disposed in the elongate handheld wand 20. In some embodiments, the processor 96 is disposed in a computing device, such as described below with reference to FIGS. 60-61, which may be operatively connected to the elongate handheld wand 20 (e.g., via a wired or wireless connection). In some embodiments, multiple processors are used, where one or more processors may be disposed in the elongate handheld wand and/or one or more processors may be disposed in a computing device. Once the correspondence is solved, three-dimensional positions on the intraoral surface are computed in step 68 and used to generate a digital three-dimensional image of the intraoral surface. Furthermore, capturing the intraoral scene using multiple cameras 24 provides a signal to noise improvement in the capture by a factor of the square root of the number of cameras.

Figure 8:
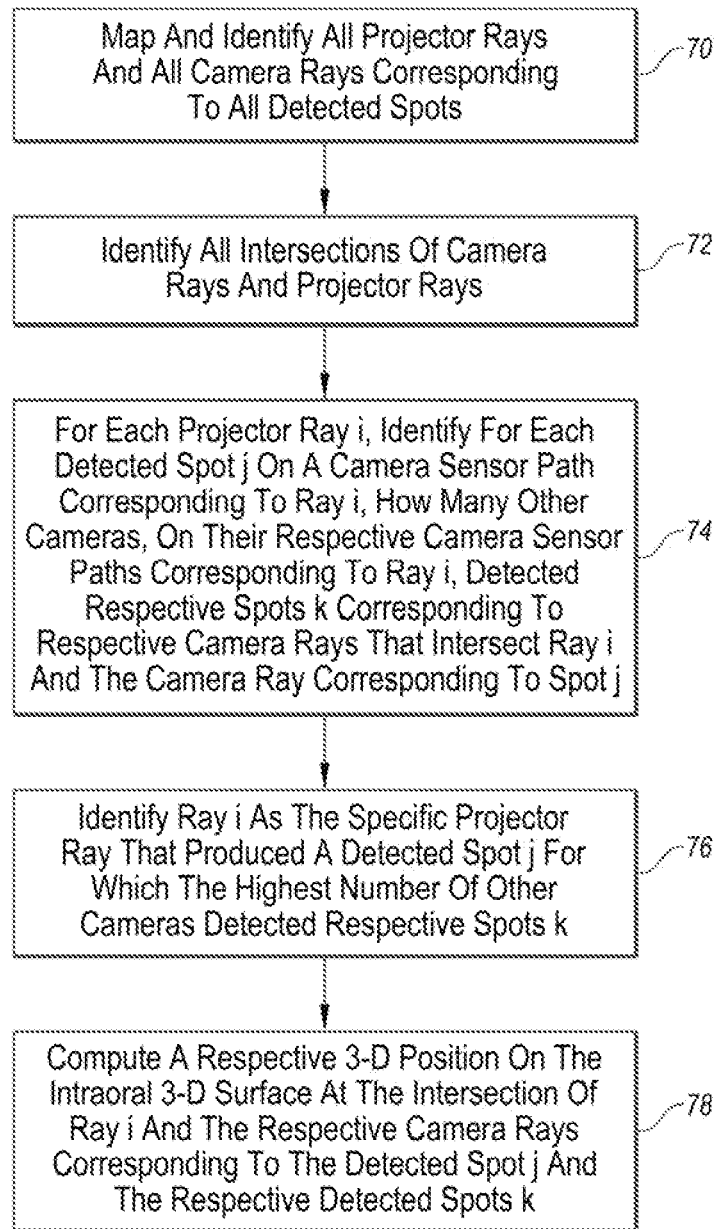
FIG. 8 is a flowchart outlining a method for carrying out a specific step in the method of FIG. 7, in accordance with some applications of the present invention.
Figure 9:
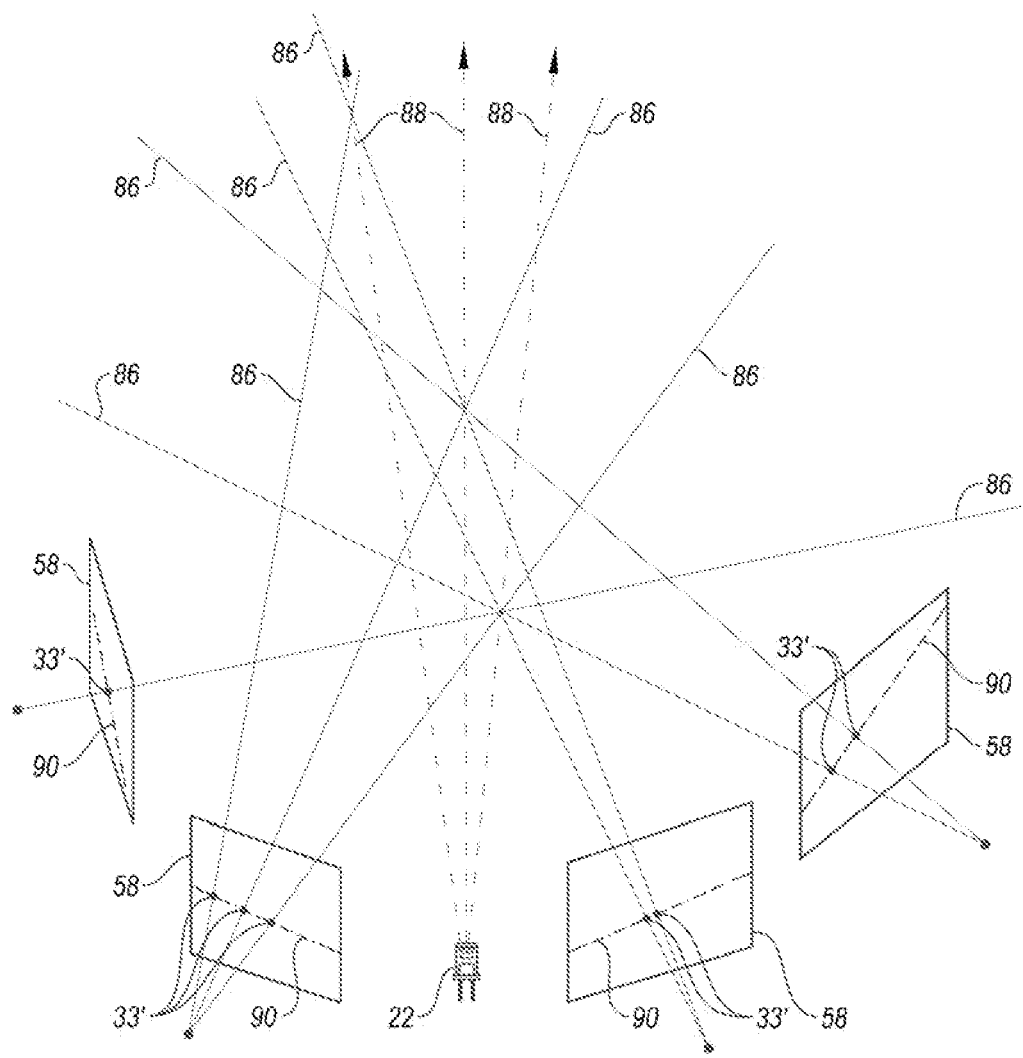
FIGS. 9, 10, 11, and 12 are schematic illustrations depicting a simplified example of the steps of FIG. 8, in accordance with some applications of the present invention.
Figure 10:
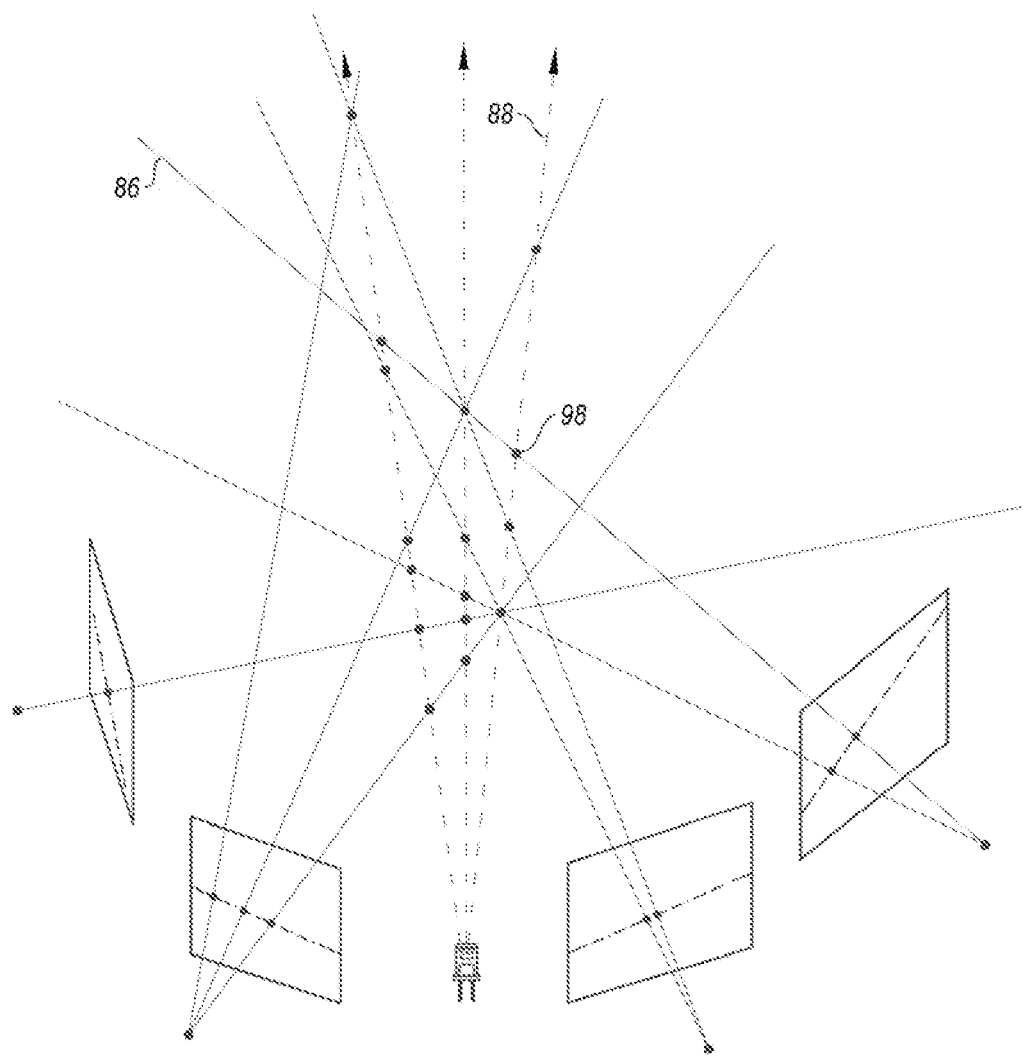

Reference is now made to FIG. 8, which is a flowchart outlining the correspondence algorithm of step 66 in FIG. 7, in accordance with some applications of the present invention. Based on the stored calibration values, all projector rays 88 and all camera rays 86 corresponding to all detected spots 33' are mapped (step 70), and all intersections 98 (FIG. 10) of at least one camera ray 86 and at least one projector ray 88 are identified (step 72). FIGS. 9 and 10 are schematic illustrations of a simplified example of steps 70 and 72 of FIG. 8, respectively. As shown in FIG. 9, three projector rays 88 are mapped along with eight camera rays 86 corresponding to a total of eight detected spots 33' on camera sensors 58 of cameras 24. As shown in FIG. 10, sixteen intersections 98 are identified.

Figure 11:
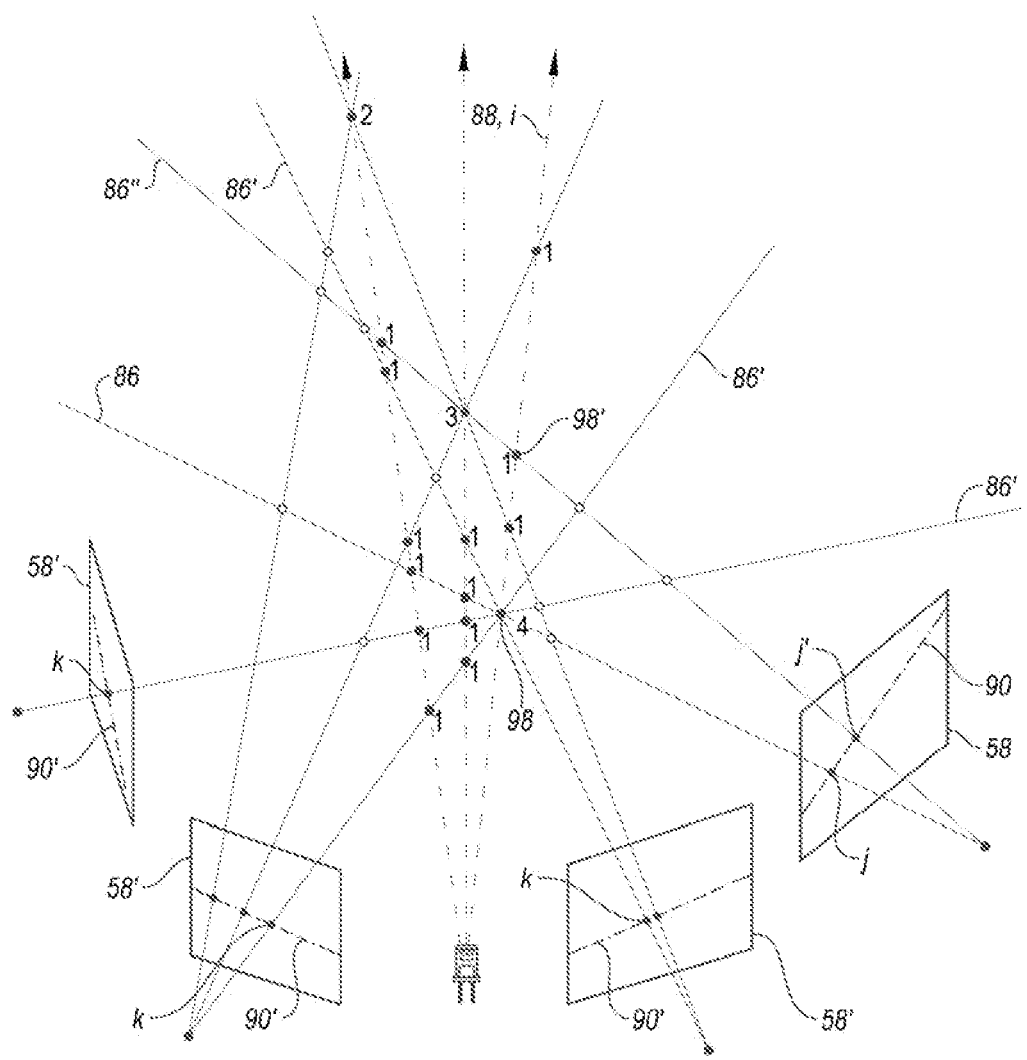

In steps 74 and 76 of FIG. 7, processor 96 determines a correspondence between projected spots 33 and detected spots 33' so as to identify a three-dimensional location for each projected spot 33 on the surface. FIG. 11 is a schematic illustration depicting steps 74 and 76 of FIG. 8 using the simplified example described hereinabove in the immediately preceding paragraph. For a given projector ray i, processor 96 "looks" at the corresponding camera sensor path 90 on camera sensor 58 of one of cameras 24. Each detected spot j along camera sensor path 90 will have a camera ray 86 that intersects given projector ray i, at an intersection 98. Intersection 98 defines a three-dimensional point in space. Processor 96 then "looks" at camera sensor paths 90' that correspond to given projector ray i on respective camera sensors 58' of other cameras 24, and identifies how many other cameras 24, on their respective camera sensor paths 90' corresponding to given projector ray i, also detected respective spots k whose camera rays 86' intersect with that same three-dimensional point in space defined by intersection 98. The process is repeated for all detected spots j along camera sensor path 90, and the spot j for which the highest number of cameras 24 "agree," is identified as the spot 33 (FIG. 12) that is being projected onto the surface from given projector ray i. That is, projector ray i is identified as the specific projector ray 88 that produced a detected spot j for which the highest number of other cameras detected respective spots k. A three-dimensional position on the surface is thus computed for that spot 33. The same process may be performed for computing three-dimensional positions on the surface of other features of a projected pattern.

Figure 12:
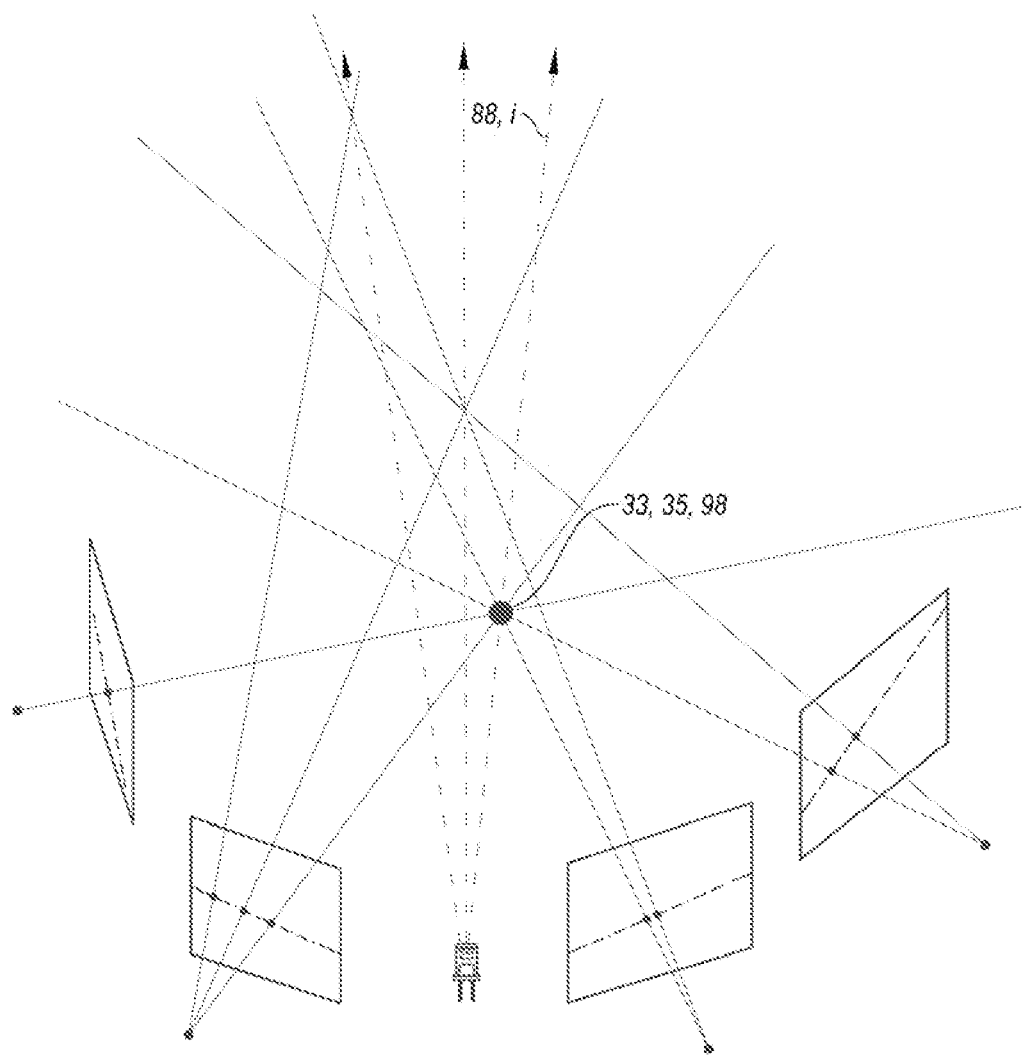

In an example, as shown in FIG. 11, all four of the cameras detect respective spots, on their respective camera sensor paths corresponding to projector ray i, whose respective camera rays intersect projector ray i at intersection 98, intersection 98 being defined as the intersection of camera ray 86 corresponding to detected spot j and projector ray i. Hence, all four cameras are said to "agree" on there being a spot 33 projected by projector ray i at intersection 98. When the process is repeated for a next spot j', however, none of the other cameras detect respective spots, on their respective camera sensor paths corresponding to projector ray i, whose respective camera rays intersect projector ray i at intersection 98', intersection 98' being defined as the intersection of camera ray 86" (corresponding to detected spot j') and projector ray i. Thus, only one camera is said to "agree" on there being a spot 33 (or other feature) projected by projector ray i at intersection 98', while four cameras "agree" on there being a spot 33 (or other feature) projected by projector ray i at intersection 98. Projector ray i is therefore identified as being the specific projector ray 88 that produced detected spot j, by projecting a spot 33 (or other feature) onto the surface at intersection 98 (FIG. 12). As per step 78 of FIG. 8, and as shown in FIG. 12, a three-dimensional position 35 on the intraoral surface is computed at intersection 98.

Figure 13:
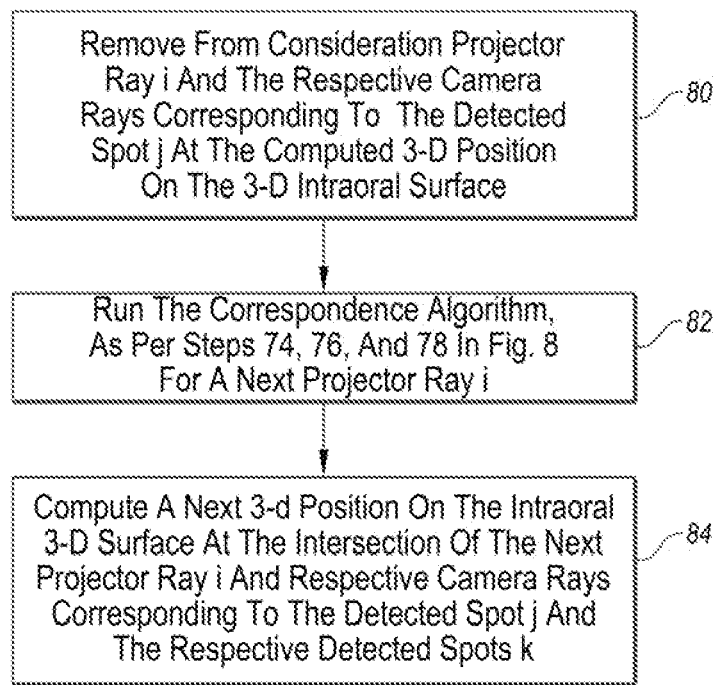
FIG. 13 is a flow chart outlining further steps in the method for generating a digital three-dimensional image, in accordance with some applications of the present invention.
Figure 14:
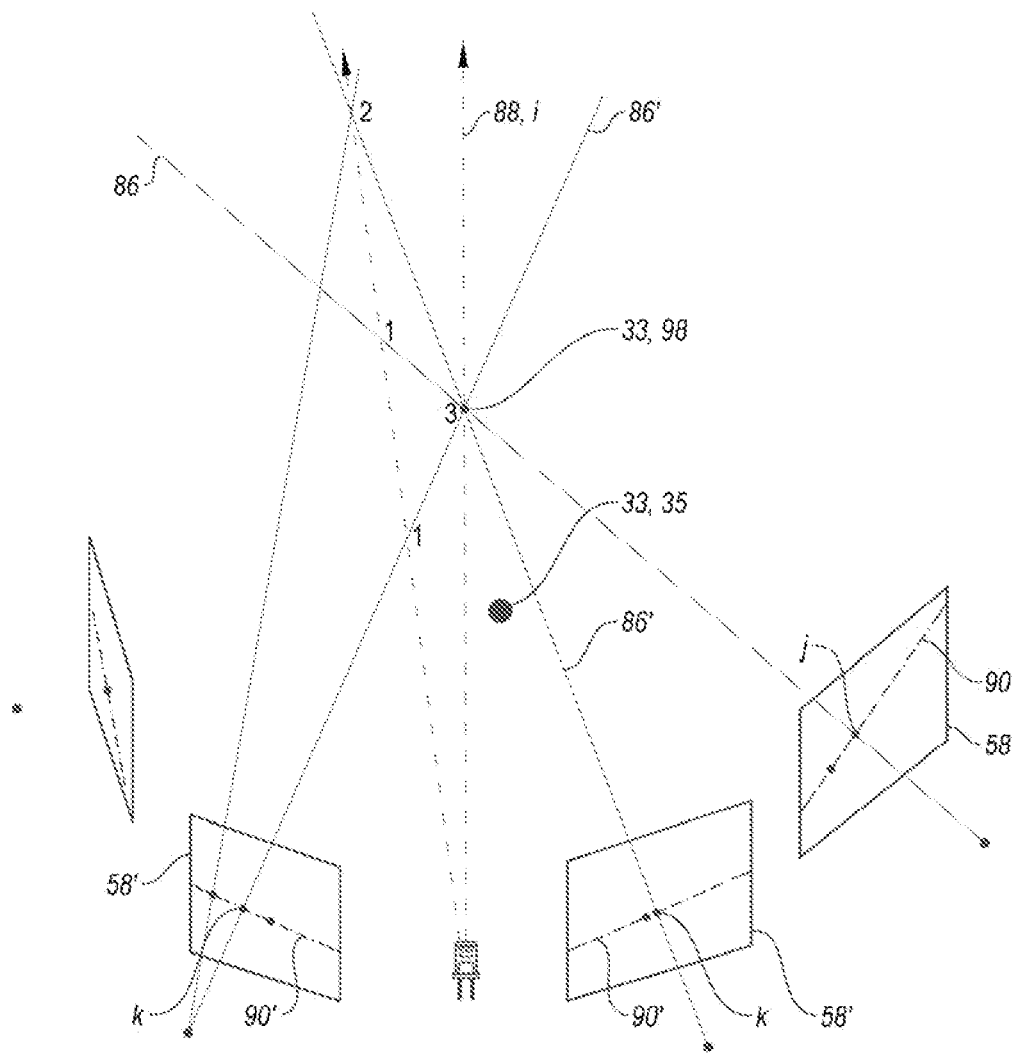
FIGS. 14, 15, 16, and 17 are schematic illustrations depicting a simplified example of the steps of FIG. 13, in accordance with some applications of the present invention.
Figure 15:
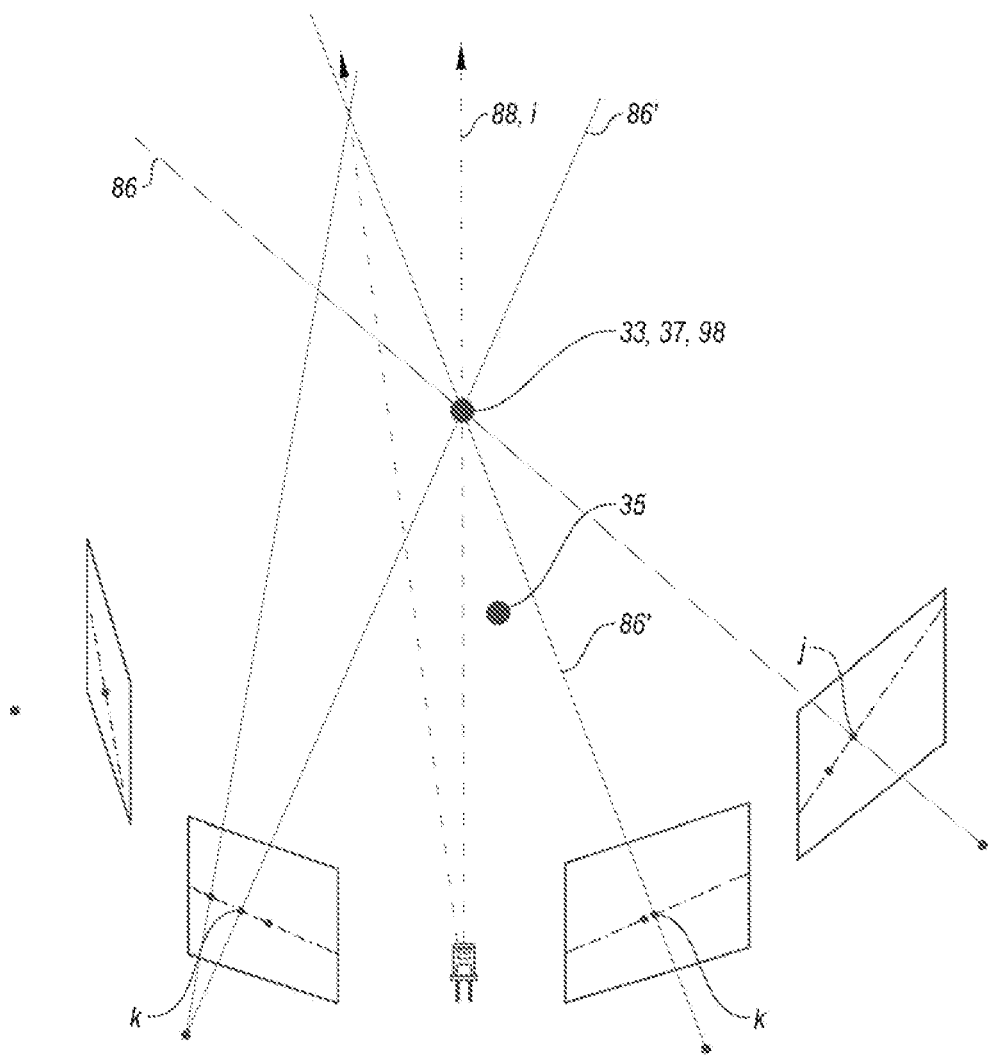

Reference is now made to FIG. 13, which is a flow chart outlining further steps in the correspondence algorithm, in accordance with some applications of the present invention. Once position 35 on the surface is determined, projector ray i that projected spot j, as well as all camera rays 86 and 86' corresponding to spot j and respective spots k are removed from consideration (step 80) and the correspondence algorithm is run again for a next projector ray i (step 82). FIG. 14 depicts the simplified example described hereinabove after the removal of the specific projector ray i that projected spot 33 at position 35. As per step 82 in the flow chart of FIG. 13, the correspondence algorithm is then run again for a next projector ray i. As shown in FIG. 14, the remaining data show that three of the cameras "agree" on there being a spot 33 at intersection 98, intersection 98 being defined by the intersection of camera ray 86 corresponding to detected spot j and projector ray i. Thus, as shown in FIG. 15, a three-dimensional position 37 is computed at intersection 98.

Figure 16:
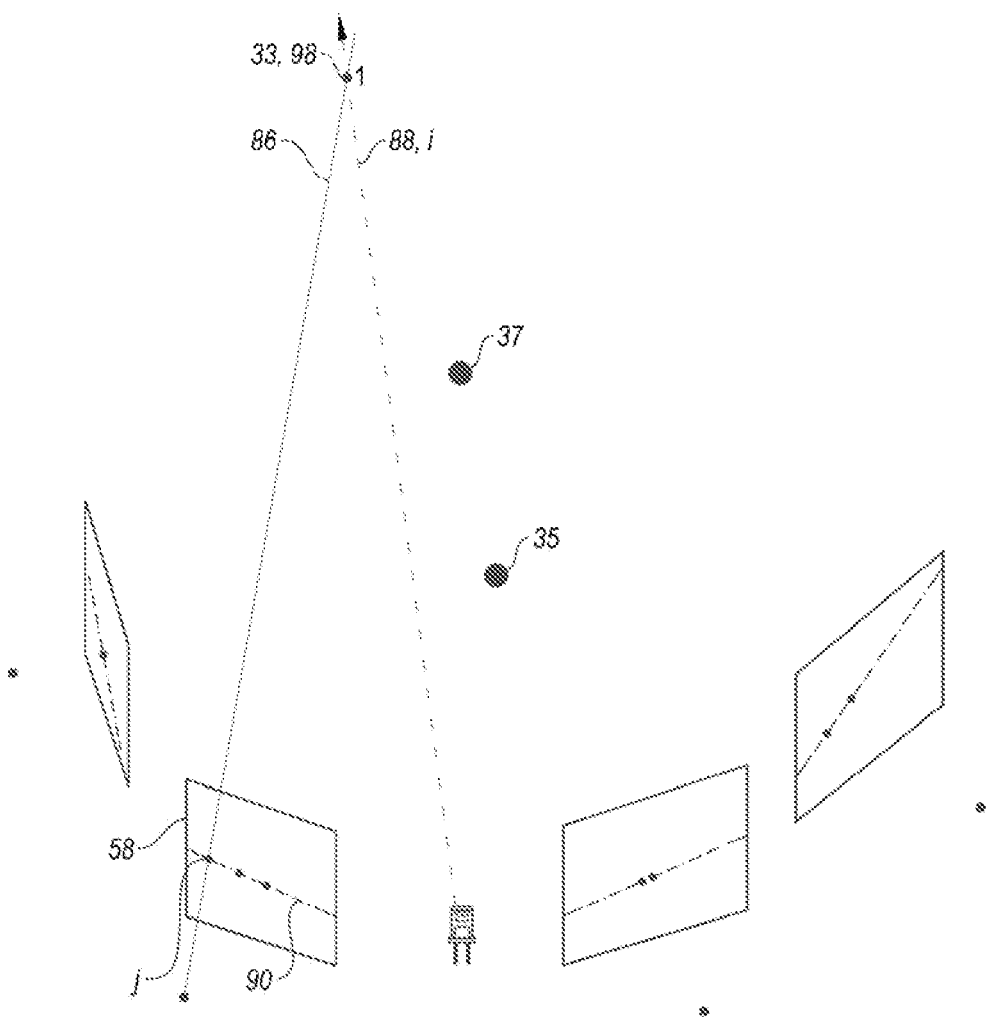
Figure 17:
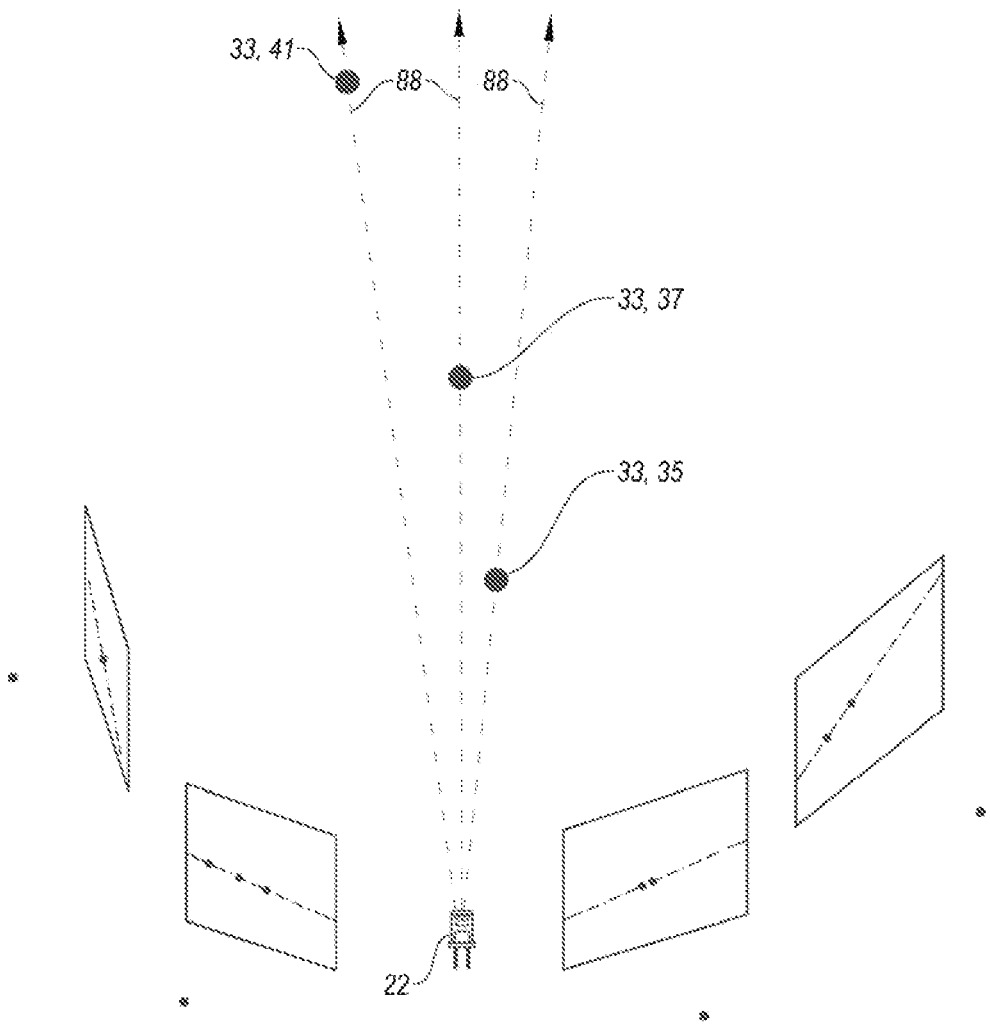

As shown in FIG. 16, once three-dimensional position 37 on the surface is determined, again projector ray i that projected spot j, as well as all camera rays 86 and 86' corresponding to spot j and respective spots k are removed from consideration. The remaining data show a spot 33 projected by projector ray i at intersection 98, and a three-dimensional position 41 on the surface is computed at intersection 98. As shown in FIG. 17, according to the simplified example, the three projected spots 33 of the three projector rays 88 of structured light projector 22 have now been located on the surface at three-dimensional positions 35, 37, and 41. In some applications, each structured light projector 22 projects 400-3000 spots 33. Once correspondence is solved for all projector rays 88, a reconstruction algorithm may be used to reconstruct a digital image of the surface using the computed three-dimensional positions of the projected spots 33.

Figure 28:
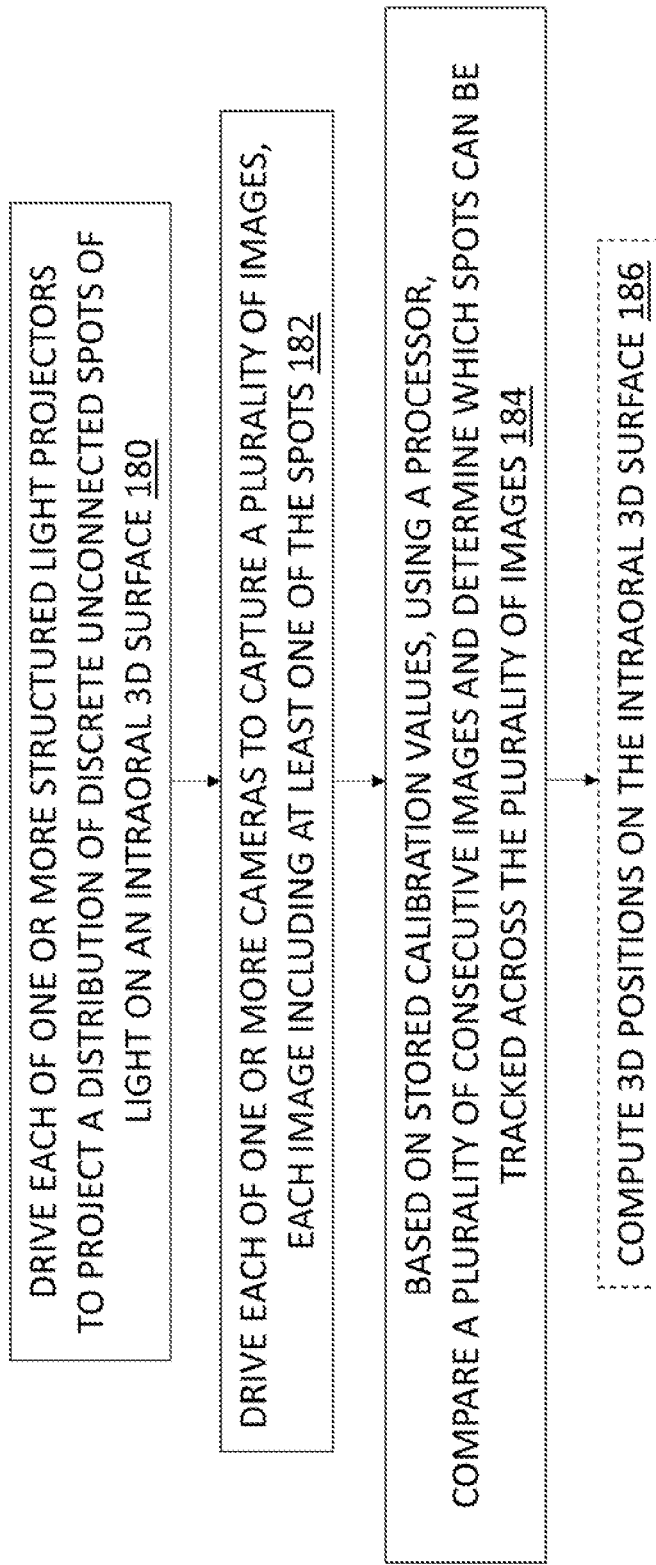
FIG. 28 is a flow chart outlining steps of a "spot tracking" method, in accordance with some applications of the present invention.

Reference is now made to FIG. 28, which is a flow chart outlining steps of a method for generating a digital three-dimensional image, and referred to hereinbelow as "spot-tracking," in accordance with some applications of the present invention. Though the method is referred to as "spot tracking", the method may equally be applied to track other types of features of a projected pattern. Due to motion of the handheld intraoral scanner with respect to the intraoral surface during a scan, the projected points move across the intraoral surface. The inventors have realized that if the movement of a particular detected spot (or other feature) can be tracked in consecutive image frames, then correspondence that was solved for that particular spot (or other feature) in any of the frames across which the spot (or other feature) was tracked provides the solution to correspondence for the spot (or other feature) in all the frames across which the spot (or other feature) was tracked. That is, if in one frame processor 96 solved that a given detected spot 33' was projected by a given projector ray 88, and due to spot-tracking processor 96 has determined that a detected spot 33' in a next image is the same spot, then automatically processor 96 determines that in the next image the same projector ray 88 produced the detected tracked spot.

Since detected spots 33' that can be tracked across consecutive images are generated by the same specific projector ray, the trajectory of the tracked spot will be along a specific camera sensor path 90 corresponding to that specific projector ray 88. If correspondence is solved for a detected spot 33' at one point along a specific camera sensor path 90, then three-dimensional positions can be computed on the surface for all the points along camera sensor path 90 at which that spot 33' was detected, i.e., the processor can compute respective three-dimensional positions on the intraoral three-dimensional surface at the intersection of the particular projector ray 88 that produced the detected spot 33' and the respective camera rays 86 corresponding to the tracked spot in each of the plurality of consecutive images across which spot 33' was tracked. This may be particularly useful for situations where a specific detected spot is only seen by one camera (or by a small number of cameras) in a particular image frame. If that specific detected spot was seen by other cameras 24 in previous consecutive image frames, and correspondence was solved for the specific detected spot in those previous image frames, then even in the image frame where the specific detected spot was seen by only one camera 24, the processor knows which projector ray 88 produced the spot, and can determine the three-dimensional position on the intraoral three-dimensional surface of the spot.

For example, a hard to reach region in the intraoral cavity may be imaged by only a single camera 24. In this case, if a detected spot 33' on the camera sensor 58 of the single camera 24 can be tracked through a plurality of previous consecutive images, then a three-dimensional position on the surface can be computed for the spot (even though it was only seen by a single camera 24), based on information obtained from the tracking, i.e., (a) which camera sensor path the spot is moving along and (b) which projector ray produced the tracked spot 33'.

In step 180 of the method outlined in FIG. 28, each structured light projector 22 is driven to project a pattern of light, which in one embodiment is a distribution 34 of discrete unconnected spots 33 of light, on an intraoral three-dimensional surface, and in step 182 each camera 24 is driven to capture an image that includes at least a portion of the projected pattern (e.g., at least one of spots 33). In one embodiment, based on the stored calibration values indicating (a) a camera ray 86 corresponding to each pixel on camera sensor 58 of each camera 24, and (b) a projector ray 88 corresponding to each projected spot 33 of light from each structured light projector 22, processor 96 is used in step 184 to compare a series of image (e.g., a plurality of consecutive images) captured by each camera 24 and determine which features of the projected pattern (e.g., which of the projected spots 33) can be tracked across the plurality of images, each tracked feature (e.g., spot 33s') moving along a path p of pixels corresponding to a respective projector ray, e.g., a particular camera sensor path 90 corresponding to a projector ray 88. For some applications, in step 186, processor 96 computes respective three-dimensional positions on the intraoral three-dimensional surface of the tracked features (e.g., spots 33s') in the series of images (e.g., in each of the consecutive images).

In one embodiment, each one of one or more structured light projectors is driven to project a pattern on an intraoral three-dimensional surface. Additionally, each one of one or more cameras is driven to capture a plurality of images, each image including at least a portion of the projected pattern. The projected pattern may comprise a plurality of projected spots of light, and the portion of the projected pattern may correspond to a projected spot of the plurality of projected spots of light. Processor 96 then compares a series of images captured by the one or more cameras, determines which of portions of the projected pattern can be tracked across the series of images based on the comparison of the series of images, and constructs a three dimensional model of the intraoral three-dimensional surface based at least in part on the comparison of the series of images. In one embodiment, the processor solves a correspondence algorithm for the tracked portions of the projected pattern in at least one of the series of images, and uses the solved correspondence algorithm in the at least one of the series of images to address the tracked portions of the projected pattern e.g., to solve the correspondence algorithm for the tracked portions of the projected pattern, in images of the series of images where the correspondence algorithm is not solved, wherein the solution to the correspondence algorithm is used to construct the three dimensional model. In one embodiment, the processor solves a correspondence algorithm for the tracked portions of the projected pattern based on positions of the tracked portions in each image throughout the series of images, wherein the solution to the correspondence algorithm is used to construct the three-dimensional model. In one embodiment, the processor compares the series of images based on stored calibration values indicating (a) a camera ray corresponding to each pixel on a camera sensor of each one of the one or more cameras, and (b) a projector ray corresponding to each one of the projected spots of light from each one of the one or more structured light projectors, wherein each projector ray corresponds to a respective path of pixels on at least one of the camera sensors, and wherein each tracked spots moves along a path of pixels corresponding to a respective projector ray r.

Figure 29:
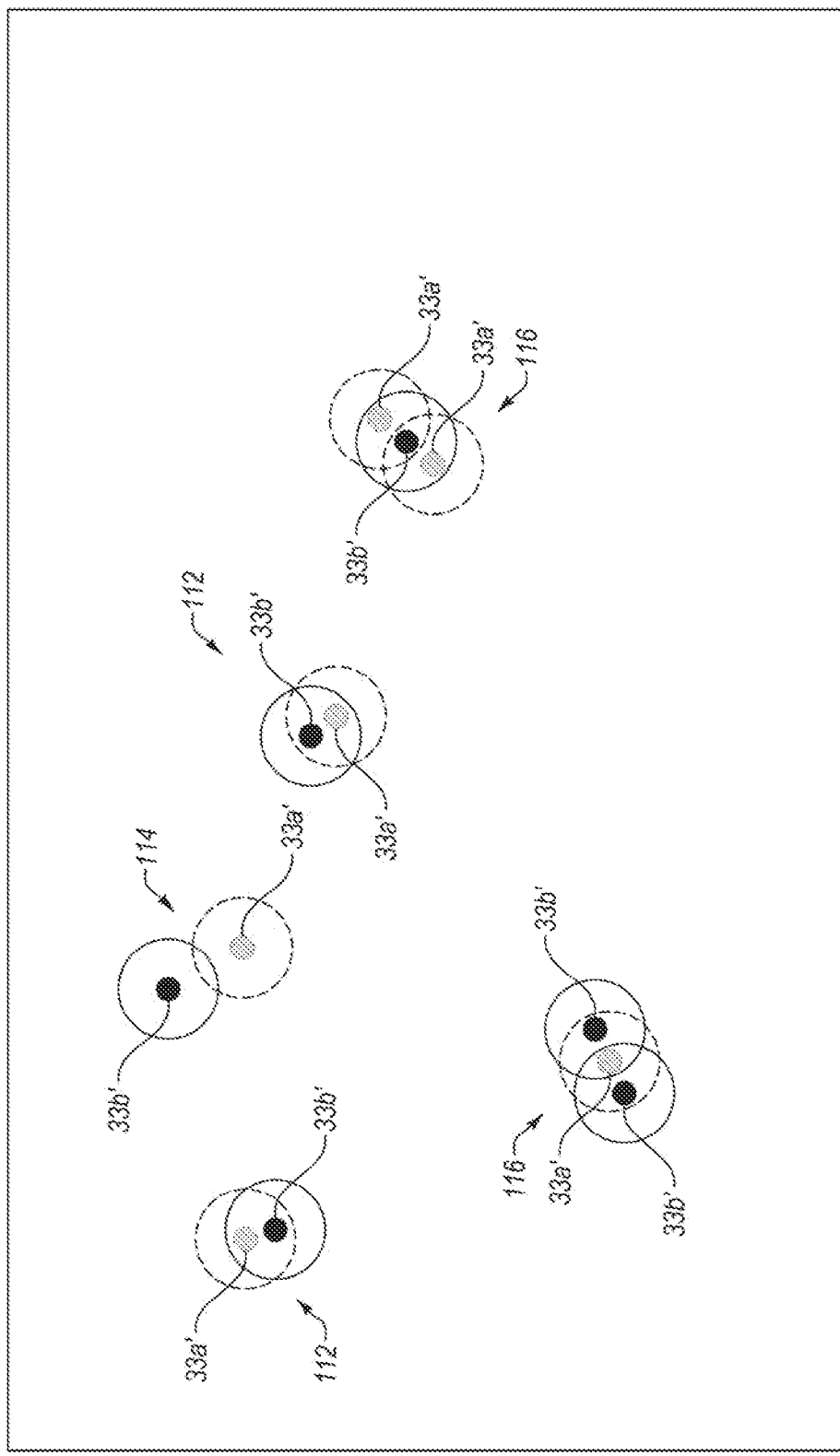
FIG. 29 is a schematic illustration depicting a simplified example of some detected spots, and how the processor may determine which sets of detected spots can be considered tracked, in accordance with some applications of the present invention.

Reference is now made to FIG. 29, which is a schematic illustration depicting a simplified example of some detected spots 33' (specifically, 33a' and 33b'), and how processor 96 may determine which sets of detected spots 33' can be considered tracked (step 184 of FIG. 28), in accordance with some applications of the present invention. Spots 33a' are spots 33' detected in a previous image, and spots 33b' are spots 33' detected in a current image. Processor 96 searches within a search radius to find possible matches for a spot 33a' and a spot 33b' to be considered the same spot 33' that was tracked between the two images.

The inventors have identified that there are typically three factors that may affect how far a spot has moved in between frames:

1. How far a spot has moved between frames is, typically, inversely proportional to the frame-rate of the cameras. That is, if the frame-rate of the cameras is very fast, the spots will appear to move only a relatively small distance between pairs of consecutive frames, and if the frame-rate of the cameras is slow, the spots will appear to move a farther distance between pairs of consecutive frames. How fast the wand is moving with respect to the intraoral surface will also have an effect on how far the spots move between frames, i.e., when the wand is moving quicker, the spots will appear to move a farther distance between pairs of consecutive frames.
2. How far a spot has moved between frames typically varies with the degree of incline of the intraoral surface being scanned, the degree of incline being with respect to projectors 22 and/or cameras 24. If a spot is being projected onto a sloped surface, and the spot is moving in the direction of the slope, the corresponding detected spot on the camera sensors will move faster, and thus the tracked spot will move a farther distance between pairs of consecutive frames.
3. How far a spot has moved between frames, from a camera's perspective, typically varies with the distance between the scanned surface and the projector. When the surface is closer to the projector, even small movements of the projector cause large movements of the tracked spot on a sensor 58 of a camera 24 between pairs of consecutive frames. In contrast, when the surface is farther away, the same movement of the projector will cause less of a movement of a tracked spot on a sensor 58 of a camera 24 between pairs of consecutive frames. For the sake of example, if the surface were approaching an infinite distance from the projector, movement of the projector would cause almost zero movement of a tracked spot on a sensor 58 of a camera 24.

For some applications, processor 96 searches within a fixed search radius of at least three pixels and/or less than ten pixels (e.g., five pixels). For some applications, processor 96 calculates a search radius taking into account parameters such as a level of spot location error, which may be determined during calibration. For example, the search radius may be defined as 2*(spot location error) or 3*(spot location error).

In the simplified example shown in FIG. 29, spots 33a' and 33b' in respective sets 112 are considered to be sufficiently close to each other such that they are considered to be the same projected spot 33 moving through the two images. That is, for each set 112, the two detected spots 33a' and 33b' are considered to be the same tracked spot 33s'. Spots 33a' and 33b' in set 114, by contrast, are too far away from each other to be considered tracked. Spots 33a' and 33b' in sets 116 are sufficiently close, but more than one match is found, so they are not considered to be tracked. As further described hereinbelow, it may be that in sets 116 there is a pair of tracked spots and that continuing to analyze more images may help determine which spot is indeed the tracked spot.

In one embodiment, to generate a digital three-dimensional image, an intraoral scanner drives each one of one or more structured light projectors to project a pattern of light on an intraoral three-dimensional surface. The intraoral scanner further drives each of a plurality of cameras to capture an image, the image including at least a portion of the projected pattern, each one of the plurality of cameras comprising a camera sensor comprising an array of pixels. The intraoral scanner further uses a processor to run a correspondence algorithm to compute respective three-dimensional positions on the intraoral three-dimensional surface of a plurality of features of the projected pattern. The processor uses data from a first camera, e.g., data from at least two of the cameras, of the plurality of cameras to identify a candidate three-dimensional position of a given feature of the projected pattern corresponding to a particular projector ray r, wherein data from a second camera, e.g., another camera that is not one of the at least two cameras, of the plurality of cameras is not used to identify that candidate three-dimensional position. The processor further uses the candidate three-dimensional position as seen by the first camera, identify a search space on the second camera's pixel array in which to search for a feature of the projected pattern from projector ray r. If a feature of the projected pattern from projector ray r is identified within the search space, then, using the data from the second camera, the processor refines the candidate three-dimensional position of the feature of the projected pattern. In one embodiment, the pattern of light comprises a distribution of discrete unconnected spots of light, and wherein the feature of the projected pattern comprises a projected spot from the unconnected spots of light. In one embodiment, the processor uses stored calibration values indicating (a) a camera ray corresponding to each pixel on the camera sensor of each one of the plurality of cameras, and (b) a projector ray corresponding to each one of the features of the projected pattern of light from each one of the one or more structured light projectors, whereby each projector ray corresponds to a respective path of pixels on at least one of the camera sensors.

Figure 30:
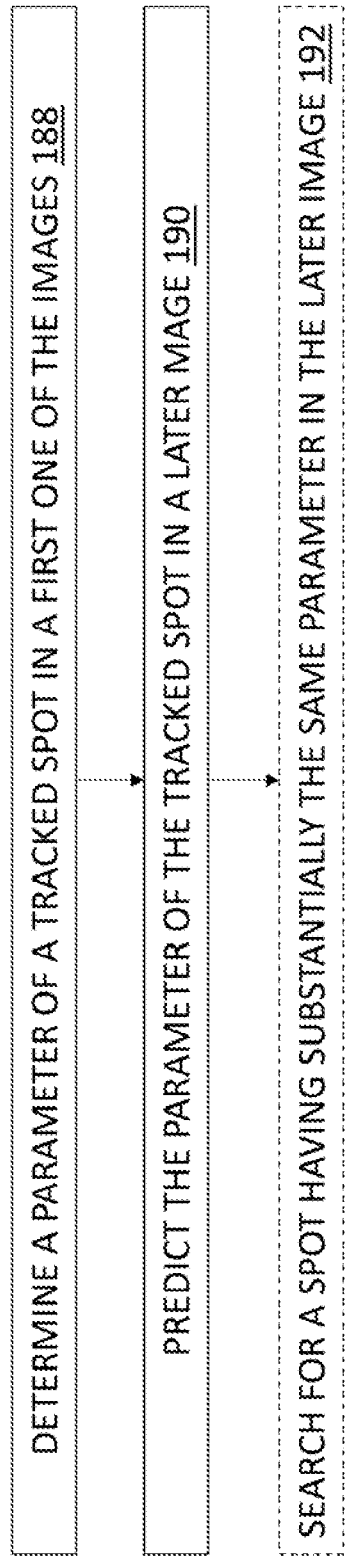
FIG. 30 is a flow chart outlining a method for determining tracked spots, in accordance with some applications of the present invention.

Reference is now made to FIG. 30, which is a flow chart outlining a method for determining tracked features (e.g., such as tracked spots 33s'), in accordance with some applications of the present invention. FIG. 30 is discussed with reference to tracked spots, but applies equally to other types of tracked features. For some applications, additionally to searching for tracked spots by monitoring the proximity of spots in consecutive images, processor 96 may search for tracked spots 33s' based on parameter(s) of a detected spot 33', referred to hereinbelow as "parametric tracking." Processor 96 determines a parameter of detected spot 33' in a first one of the consecutive images (step 188) and in an adjacent image. Processor 96 then uses the determined parameter of a detected spot 33' in the two adjacent images to predict the same parameter of the spot in a later image (step 190), e.g., in the next image (and in subsequent images). Processor 96 searches for a spot having substantially the predicted parameter in the later image (step 192), e.g., in the next image. For example, two particular detected spots 33a' and 33b' may be determined to both be from the same projector ray in the two adjacent frames, either via the correspondence algorithm as described hereinabove, or via proximity tracking as described in the immediately preceding two paragraphs. Once processor 96 knows that detected spots 33a' and 33b' in two adjacent frames were produced by the same projector ray 88, then processor 96 can determine a parameter of the spot, and based on the parameter of the spot in the two adjacent images, predict the parameter of the spot in a later image, e.g., in a next image.

For some applications, the parameter of a spot is the size of the spot, the shape of the spot, e.g., the aspect ratio of the spot, the orientation of the spot, the intensity of the spot, and/or a signal-to-noise ratio (SNR) of the spot. For example, if the determined parameter is the shape of the tracked spot 33s', then processor 96 predicts the shape of the tracked spot 33s' in a later image, e.g., in the next image, and based on the predicted shape of tracked spot 33s' in the later image, determines a search space, e.g., a search space having a size and aspect ratio based on (e.g., within a factor of two of) a size and aspect ratio of the predicted shape of the tracked spot 33s', in the later image in which to search for tracked spot 33s'. For some applications, the shape of the spot may refer to the aspect ratio of an elliptical spot.

Reference is again made to FIG. 29. For some applications, parametric tracking may help resolve ambiguities such as shown in sets 116 of spots in FIG. 29. As described hereinabove, spots 33a' and 33b' in sets 116 are sufficiently close to be considered tracked spots, but more than one match is found. Based on parametric tracking, processor 96 may now be able to determine which spots in sets 116 are indeed tracked spots.

Figure 31:
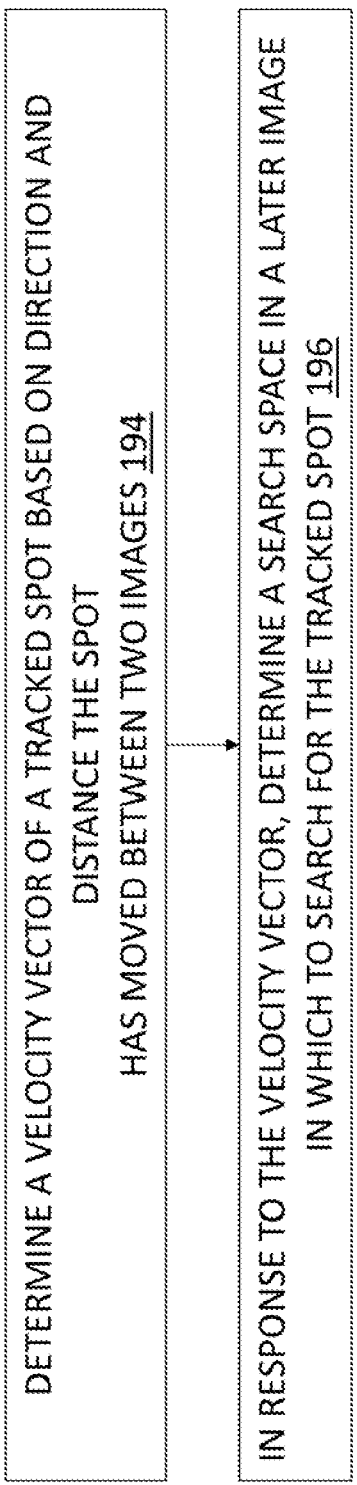
FIGS. 31-32 are flow charts outlining respective methods for finding a tracked spot in a later image, in accordance with some applications of the present invention.

Reference is now made to FIG. 31, which is a flow chart outlining a method for finding a tracked spot 33s' in a later image, in accordance with some applications of the present invention. FIG. 31 also applies to finding other tracked features in a later image. For some applications, based on the direction and distance a tracked spot 33s' has moved between two images (e.g., between two consecutive images), processor 96 determines a velocity vector of the tracked spot 33s' (step 194). Processor 96 then uses the velocity vector to determine a search space in a later image, e.g., in the next image, in which to search for the tracked spot 33s' (step 196).

For some applications, the search space in the later image may be determined by using a predictive filter, e.g., a Kalman filter, to estimate the new location of the tracked spot 33s'.

Figure 32:
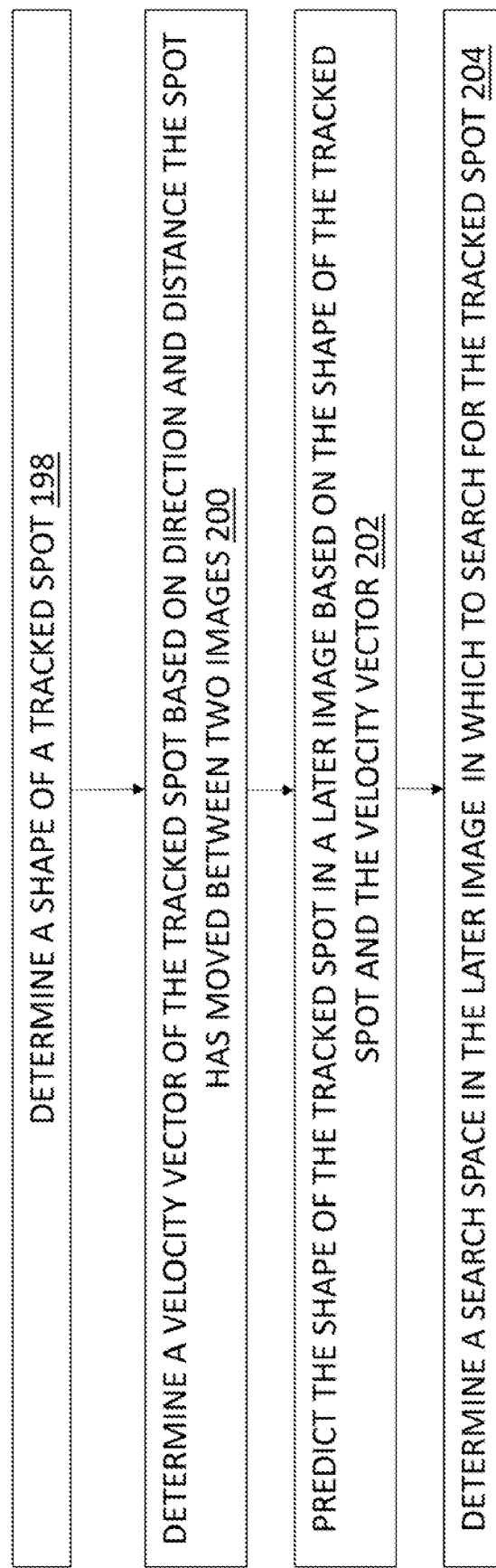

Reference is now made to FIG. 32, which is a flow chart outlining a method for finding a tracked spot 33s' in a later image, in accordance with some applications of the present invention. FIG. 32 also applies to finding other tracked features in a later image. The determination of a velocity vector for a tracked spot 33s' may also be used to help determine a search space in which to look for the tracked spot, i.e., if the spot is moving faster it will have moved farther between consecutive frames, and thus processor 96 may set a larger search space in which to search for the tracked spot. The inventors have realized that the shape of a tracked spot 33s' and the direction in which it is moving may be indicative of the velocity of the spot. For example, for some applications, if a spot that was projected as round appears elliptical then the spot is likely to be falling on an inclined surface with respect to projectors 22 and/or cameras 24. Similarly, as described hereinabove, a spot moving along an inclined surface in the direction of the incline will move faster than when moving not in the direction of the incline, and the steeper the incline of the surface, the faster the spot will move. Additionally, if the spot is appearing stretched into an elliptical shape due to the inclined surface, it will likely appear stretched in the direction of the incline, i.e., the major axis of the ellipse is in the direction of the incline. Thus, an elliptical spot moving along its major axis is indicative that the spot is moving up or down and incline, and is therefore faster than if the elliptical spot were moving along its minor axis (which may indicate that although being projected on an inclined surface, the spot is not moving in the direction of the incline).

Thus, for some applications, after determining the shape of a tracked spot 33s' (step 198), based on the direction and distance the tracked spot 33s' has moved between two consecutive images, processor 96 may determine a velocity vector of the tracked spot 33s' (step 200). Processor 96 may then use the determined velocity vector and/or the shape of the tracked spot 33s' to predict the shape of the tracked spot 33s' in a later image, e.g., in the next image (step 202). Subsequently to predicting the shape of the tracked spot 33s', processor 96 may use the combination of the velocity vector and the predicted shape of the tracked spot 33s' to determine a search space in the later image, e.g., in the next image, in which to search for the tracked spot 33s'. Referring again to the above example of an elliptical spot, if the shape of the spot is determined to be elliptical and the spot is determined to be moving along its major axis then a larger search space will be designated, versus if the elliptical spot were moving along its minor axis.

Figure 33:
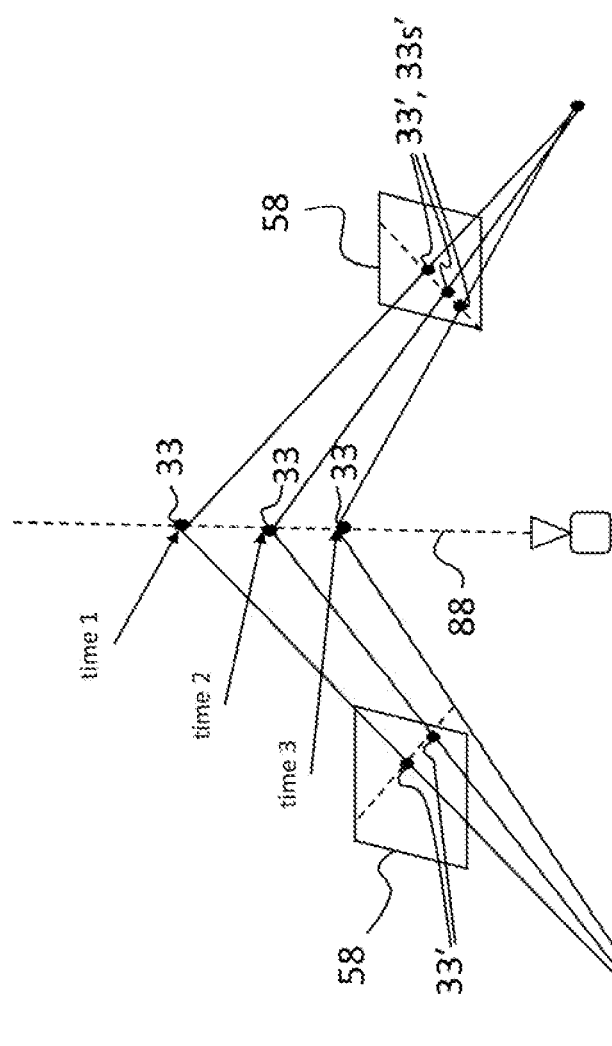
FIG. 33 is a schematic illustration depicting an example of how spot tracking helps to identify a detected spot as being projected from a particular projector ray, in accordance with some applications of the present invention.

Reference is now made to FIG. 33, which is a schematic illustration depicting an example of how spot tracking helps to identify a detected spot 33' as being projected from a particular projector ray 88, in accordance with some applications of the present invention. This is useful for cases where the correspondence algorithm did not present a solution for a particular detected spot 33', for example, in cases where a detected spot 33' in a particular frame is only seen by one camera 24. In such a case, if it is identified that the detected spot 33' is a tracked spot 33s' moving along a particular camera sensor path 90 of pixels corresponding to a particular projector ray 88, then, as described hereinabove, it can be assumed that that particular projector ray 88 projected the spot. Based on the solved correspondence of the tracked spot 33s' in the previous frames, the correspondence may be solved for the frame in which only one camera detected spot 33'. Thus, for some applications, after running a correspondence algorithm, such as the correspondence algorithm described hereinabove with reference to FIGS. 7-17, if it is determined that detected spot 33' is a tracked spot 33s' moving along a particular path 90 on a camera sensor 58 corresponding to a particular projector ray 88, then it can be assumed that that particular projector ray 88 produced the detected spot 33'. That is, processor 96 can identify a detected spot 33' as being from a particular projector ray 88 by identifying the detected spot 33' as being a tracked spot 33s' moving along the path 90 of pixels of a camera sensor 58 corresponding to the particular projector ray 88.

In the example shown in FIG. 33, in two consecutive frames taken at time 1 and at time 2, respectively, each of two camera sensors 58 detected a spot 33' projected from projector ray 88. The correspondence algorithm, as described hereinabove, has solved the correspondence for the detected spot 33' in frame 1 and frame 2, determining that projector ray 88 produced detected spot 33' in frame 1 and frame 2. In a third frame however, only one camera detects the spot 33'. For this example, it is assumed that the correspondence algorithm was unable to solve the correspondence for the detected spot 33' in frame 3. Processor 96, however determines that the detected spot 33' in frame 3 is a tracked spot 33s' moving along the same projector ray 88 that produced spots 33' in frame 1 and frame 2. Thus, processor 96 identifies detected spot 33' in frame 3 as being produced by projector ray 88.

Figure 34B:
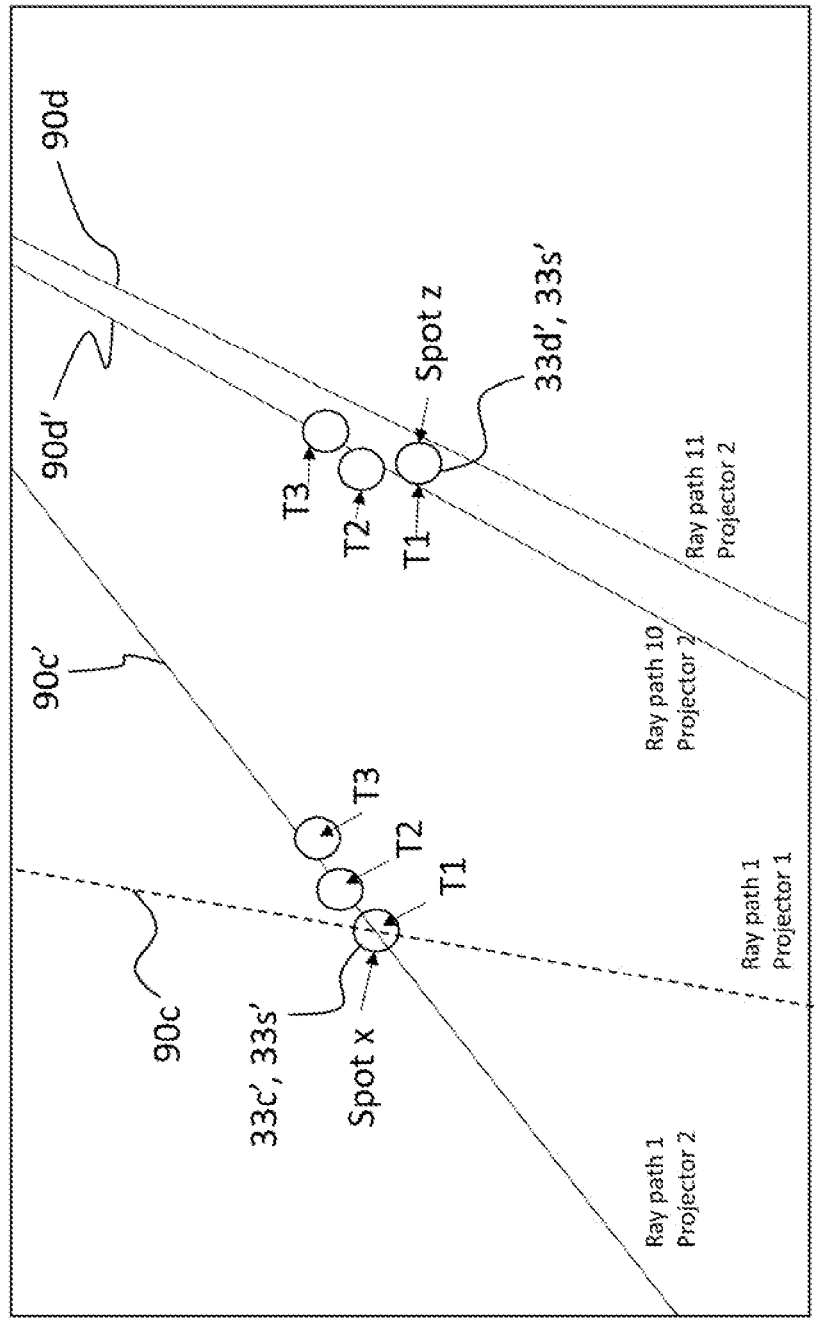

Reference is now made to FIGS. 34A-B, which are simplified schematic illustrations of a camera sensor 58 showing two detected spots 33c' and 33d', in accordance with some applications of the present invention. In FIG. 34A, for each of the detected spots there is an ambiguity as to which projector ray produced the spot, i.e., as to which camera sensor path 90 of pixels the detected spot falls on. For some applications, processor 96 is able to solve these ambiguities using spot tracking. Thus, for some applications, after running a correspondence algorithm (such as the correspondence algorithm described hereinabove with reference to FIGS. 7-17), if a detected spot 33' is identified as being from two distinct candidate projector rays 88 and 88' based on the three-dimensional position computed by the correspondence algorithm, processor 96 may identify the detected spot 33' as being from only one of the two distinct candidate projector rays 88 and 88' by identifying that the detected spot 33' is a tracked spot 33s' moving along either path 90 or path 90'.

An example of such an ambiguity is represented by detected spot 33c' in FIG. 34A. Spot 33c' is located at the intersection of two different paths 90c and 90c'. The correspondence algorithm may have found such a detected spot 33c' to be produced by both a projector ray 88 corresponding to path 90c and a projector ray 88' corresponding to path 90c'. Another type of such an ambiguity is represented by detected spot 33d' in FIG. 34A. Spot 33d' is very close to two different paths 90d and 90d' but not at an intersection between paths 90 and 90d. Due to noise in the signal it may have been unclear during the correspondence algorithm if spot 33d' was produced by a projector ray 88 corresponding to path 90d or by a projector ray 88' corresponding to path 90d'.

As shown in FIG. 34B, processor 96 may identify which projector rays produced each of spots 33c' and 33d' by identifying spots 33c' and 33d' as tracked spots 33s' each moving along a particular one of the paths. Detected spot 33c' is identified as a tracked spot 33s' moving along path 90c', thus detected spot 33c' is identified as being produced by projector ray 88' corresponding to path 90c'. Detected spot 33d' is identified as a tracked spot 33s' moving along path 90d', thus detected spot 33d' is identified as being produced by projector ray 88' corresponding to path 90d'.

Figure 35:
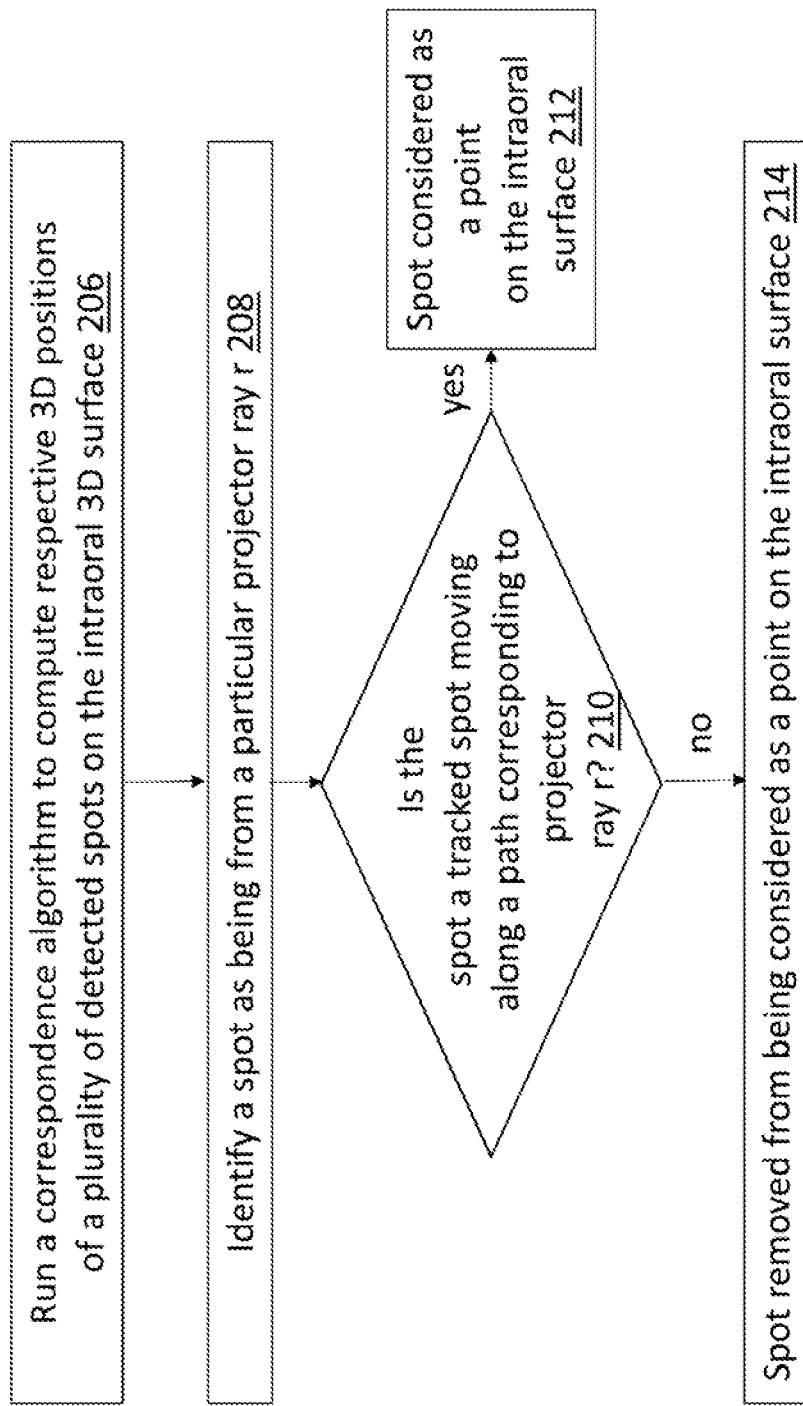
FIGS. 35-36 are flow charts outlining respective ways in which spot tracking may be used, in accordance with some applications of the present invention.

Reference is now made to FIG. 35, which is a flow chart outlining an additional or alternative way in which spot tracking may be used, in accordance with some applications of the present invention. The concepts shown in FIG. 35 also apply to ways of using other feature tracking. For some applications, processor 96 may be able to use spot tracking to remove a falsely detected spot 33' from being considered as a point on the intraoral three-dimensional surface. For some applications, after running a correspondence algorithm (step 206), such as the correspondence algorithm described hereinabove with reference to FIGS. 7-17, processor 96 may identify a detected spot 33' as being from a particular projector ray 88 based on the correspondence algorithm (step 208). Step 206 typically occurs following step 186 of the method outlined in the flowchart of FIG. 28. Additionally, processor 96 may identify a series of spots detected across a plurality of consecutive images that are all tracked spots 33s' moving along the path 90 of pixels that corresponds to the same particular projector ray 88. As indicated by decision diamond 210, if the detected spot 33' is one of the tracked spots 33s', then detected spot 33' may be considered as a point on the intraoral three-dimensional surface (step 212). However, if the detected spot 33' is not identified as a tracked spot 33s' moving along the path 90 of pixels corresponding to that particular projector ray 88, then it may be assumed that the detected spot 33' was a false positive detection of a spot and the detected spot 33' is removed from being considered as a point on the intraoral three-dimensional surface (step 214).

Figure 36:
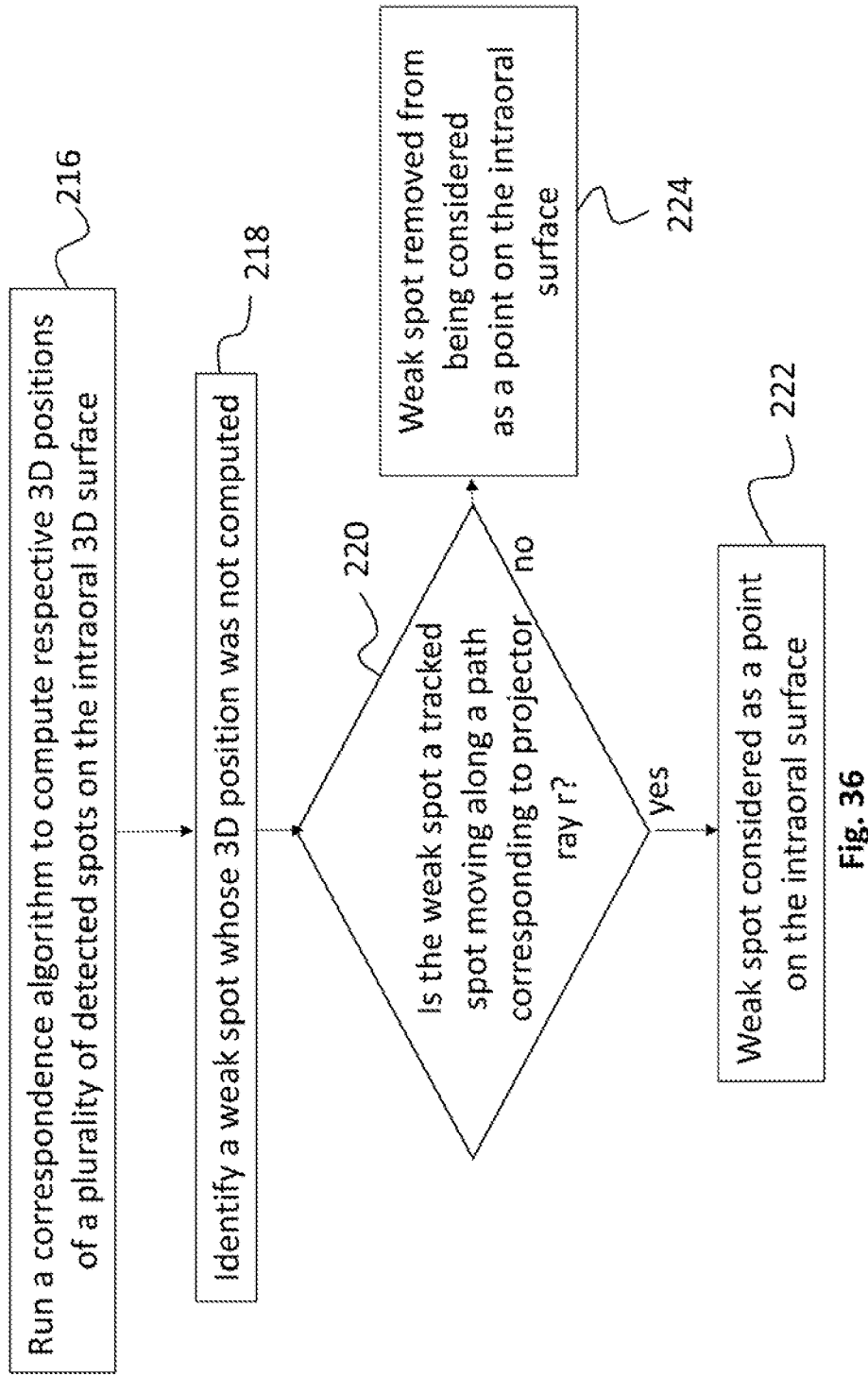

Reference is now made to FIG. 36, which is a flow chart outlining an additional or alternative way in which spot tracking may be used, in accordance with some applications of the present invention. The concepts shown in FIG. 36 also apply to ways of using other feature tracking. In order to reduce the occurrence of cameras 24 detecting many false positive spots, processor 96 may set an intensity threshold, and any detected spots 33' that are below the threshold are not included as candidate spots in the correspondence algorithm. However, this may also result in falsely mis-detected spots, i.e., this may result in a spot that may have provided useful information not being considered due to it being a weak spot (having an intensity below the threshold value). For example, in hard to capture regions of the intraoral scene it may be the case that some of the projected spots 33 appear below the intensity threshold. Thus, for some applications, after running a correspondence algorithm (step 216), such as the correspondence algorithm described hereinabove with reference to FIGS. 7-17, processor 96 may identify a weak spot 33' whose three-dimensional position was not computed by the correspondence algorithm (step 218), e.g., by lowering the intensity threshold and considering spots 33' that were not considered by the correspondence algorithm. As indicated by decision diamond 220, if the weak spot 33' is identified as being a tracked spot 33s' moving along a path 90 of pixels corresponding to a particular projector ray 88, then the weak spot 33' is identified as being projected from that particular projector ray 88 and is considered to be a point on the intraoral three-dimensional surface (step 222). If a weak spot is not identified as being a tracked spot 33s', then the weak spot is removed from being considered as a point on the intraoral three-dimensional surface (step 224).

For some applications, for a tracked spot 33s' processor 96 may determine a plurality of possible camera sensor paths 90 of pixels along which the tracked spot 33s' is moving, the plurality of paths 90 corresponding to a respective plurality of possible projector rays 88. For example, it may be the case that more than one projector ray 88 closely corresponds to a path 90 of pixels on the camera sensor 58 of a given camera. Processor 96 may run a correspondence algorithm to identify which of the possible projector rays 88 produced the tracked spot 33s', in order to compute three-dimensional positions on the surface for respective locations of the tracked spot 33s'.

For a given camera sensor 58, for each of the plurality of possible projector rays 88, a three-dimensional point in space exists at the intersection of each of the possible projector rays 88 and the camera ray corresponding to the detected tracked spot 33s' in the given camera sensor 58. For each of the possible projector rays 88, processor 96 considers camera sensor paths 90 that correspond to the possible projector ray 88 on each of the other camera sensors 58 and identifies how many other camera sensors 58 also detected a spot 33' on their respective camera sensor paths 90 corresponding to that possible projector ray 88, whose camera ray intersects with that three-dimensional point in space, i.e., how many other cameras agree on that tracked spot 33s' being projected by that projector ray 88. The process is repeated for all the possible projector rays 88 corresponding to the tracked spot 33s'. The possible projector ray 88 for which the highest number of other cameras agree is determined to be the particular projector ray 88 that produced the tracked spot 33s'. Once the particular projector ray 88 for the tracked spot 33s' is determined, the camera sensor path 90 along which the spot is moving is known, and respective three-dimensional positions on the surface are computed at the intersection of the particular projector ray 88 and the respective camera rays corresponding to the tracked spot 33s' in each of the consecutive images across which the spot 33s' was tracked.

Figure 37B:
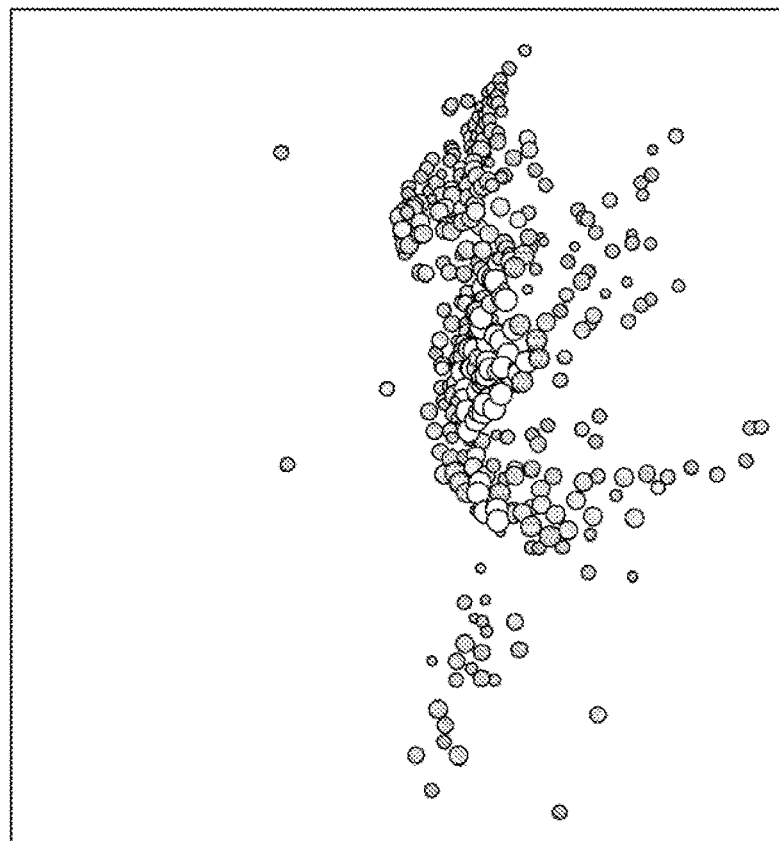
FIGS. 37A-B are schematic illustrations showing points used for three-dimensional reconstruction before and after the processor has implemented spot tracking, in accordance with some applications of the present invention.
Figure 37A:
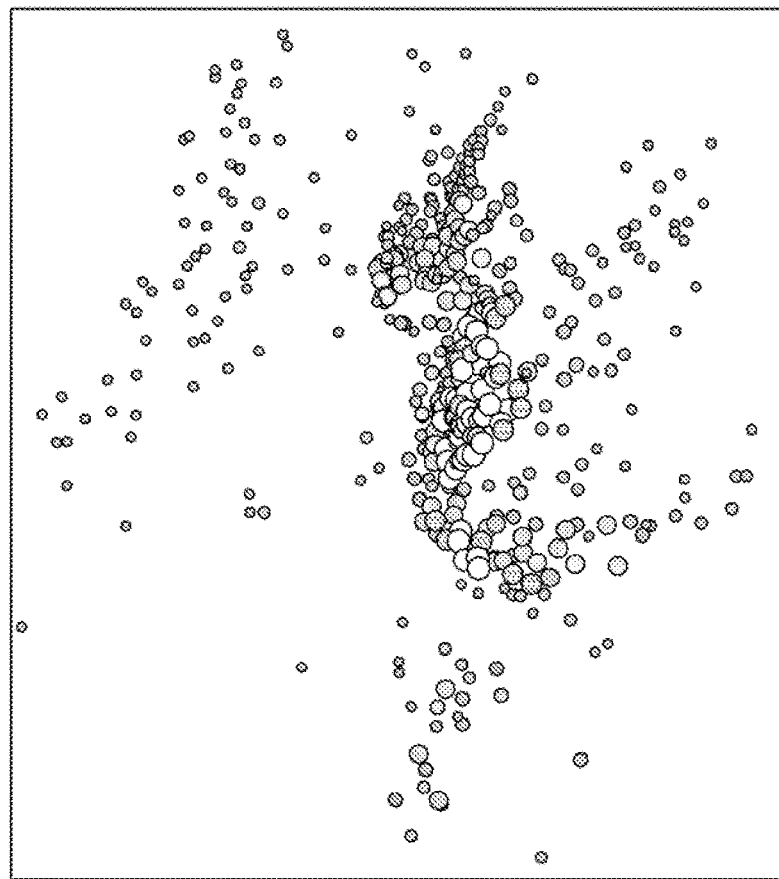

Reference is now made to FIGS. 37A-B, which are schematic illustrations showing points used for three-dimensional reconstruction before and after processor 96 has implemented spot tracking, in accordance with some applications of the present invention. The size of each data point represents how many cameras were used to solve the point, i.e., the larger the point the higher the number of cameras that saw that spot. It is noted that size of the data points is used in the figure to differentiate only between how many cameras saw any given point, and is not indicative of the size of the projected spots on the surface. In FIG. 37A there are many smaller points that seem to be located in the periphery and do not appear to be points on the intraoral surface. These smaller points refer to detected spots that were seen by very few cameras, e.g., only one, and yet were assigned a three-dimensional position in space based on the correspondence algorithm. After running the correspondence algorithm, processor 96 may perform spot tracking and thus determine that these lighter points in the periphery are actually false positive points (by determining that they are not tracked spots). Thus, as shown in FIG. 37B, after spot tracking, most of the spots that spot tracking determined to be false positive spots have been removed from being considered as points on the intraoral surface.

Figure 38:
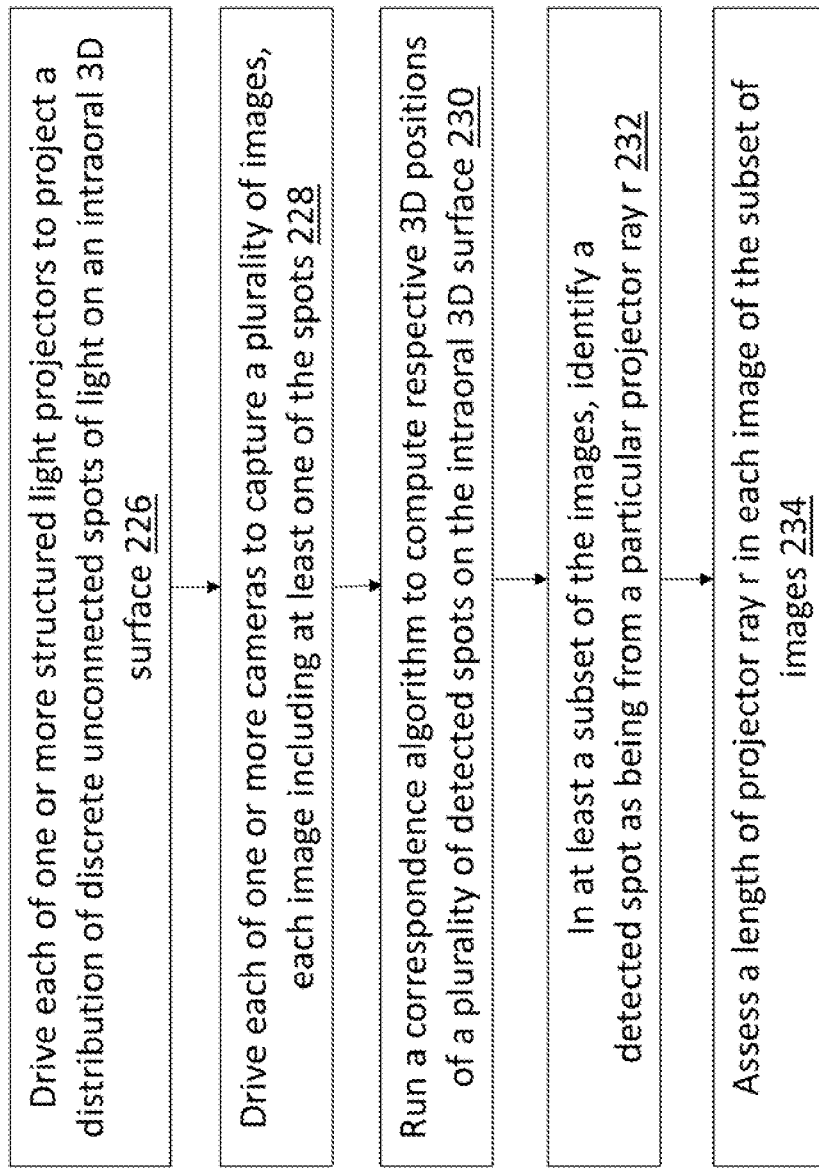
FIG. 38 is a flow chart outlining steps of a method for generating a digital three-dimensional image, referred to hereinbelow as "ray-tracking," in accordance with some applications of the present invention.

Reference is now made to FIG. 38, which is a flow chart outlining steps of a method for generating a digital three-dimensional image, referred to hereinbelow as "ray-tracking," in accordance with some applications of the present invention. For some applications alternatively or additionally to tracking detected spots and/or other features within two-dimensional images (as described hereinabove), the length of each projector ray 88 can be tracked in three-dimensional space. The length of a projector ray 88 is defined as the distance between the origin of the projector ray 88, i.e., the light source, and the three-dimensional position at which the projector ray 88 intersects the intraoral surface.

In step 226 of the method outlined in FIG. 38, each structured light projector 22 is driven to project a pattern of light, such as a distribution 34 of discrete unconnected spots 33 of light, on an intraoral three-dimensional surface, and in step 228 each camera 24 is driven to capture a plurality of images, each image including at least a feature of the projected pattern (e.g., at least one of spots 33). The method is described with reference to spots, but also works with other types of features. Based on the stored calibration values indicating (a) a camera ray 86 corresponding to each pixel on camera sensor 58 of each camera 24, and (b) a projector ray 88 corresponding to each projected spot 33 of light from each structured light projector 22, processor 96 is used in step 230 to run a correspondence algorithm, such as the correspondence algorithm described hereinabove with reference to FIGS. 7-17. As a result of the correspondence algorithm, each solved projector ray 88 in each image frame yields a reconstructed three-dimensional point in space, which in turn defines the length of the solved projector ray 88 in that frame.

Thus, in step 232, in at least a subset of the captured images, e.g., in a series of images or a plurality of consecutive images, processor 96 identifies the computed three-dimensional position of a detected spot 33' (as computed from the correspondence algorithm) as corresponding to particular projector ray 88. In step 234, based on each three-dimensional position corresponding to the projector ray 88 in the subset of images, processor 96 assesses, e.g., computes, a length of projector ray 88 in each image of the subset of images. Due to cameras 24 capturing images at a relatively high frame rate, e.g., about 100 Hz, the geometry of the spots as seen by each camera does not change significantly between frames. Thus, if the assessed, e.g., computed, length of projector ray 88 is tracked and plotted with respect to time, the data points will follow a relatively smooth curve, although some discontinuity may occur as further discussed hereinbelow. Thus, the length of a projector ray over time forms a relatively smooth univariate function with respect to time. As described hereinabove, the detected spots 33' corresponding to the projector ray 88 over the plurality of consecutive images will appear to move along a one-dimensional line that is the path 90 of pixels in the camera sensor corresponding to projector ray 88.

In one embodiment, a method for generating a digital three-dimensional image includes driving each one of one or more structured light projectors to project a pattern on an intraoral three-dimensional surface and driving each one of one or more cameras to capture an image, the image including at least a portion of the pattern. The method further includes using a processor to run a correspondence algorithm to compute respective three-dimensional positions of a plurality of features of the pattern on the intraoral three-dimensional surface, as captured in a series of images. The processor further identifies the computed three-dimensional position of a detected feature of the imaged pattern as corresponding to one or more particular projector ray r, in at least a subset of the series of images. Based on the three-dimensional position of the detected feature corresponding to the one or more projector ray r in the subset of images, the processor assesses, e.g., computes, a length associated with the one or more projector ray r in each image of the subset of images. In one embodiment, the processor computes an estimated length of the one or more projector ray r in at least one of the series of images in which a three-dimensional position of the projected feature from the one or more projector ray r was not identified. In one embodiment, each one of the one or more cameras comprises a camera sensor comprising an array of pixels, wherein computation of the respective three-dimensional positions of the plurality of features of the pattern on the intraoral three-dimensional surface and identification of the computed three-dimensional position of a detected feature of the pattern as corresponding to a particular projector ray r is performed based on stored calibration values indicating (i) a camera ray corresponding to each pixel on the camera sensor of each one of the one or more cameras, and (ii) a projector ray corresponding to each one of the features of the projected pattern of light from each one of the one or more projectors, whereby each projector ray corresponds to a respective path of pixels on at least one of the camera sensors. In one embodiment, the pattern comprises a plurality of spots, and each of the plurality of features of the pattern comprises a spot of the plurality of spots.

Figure 39:
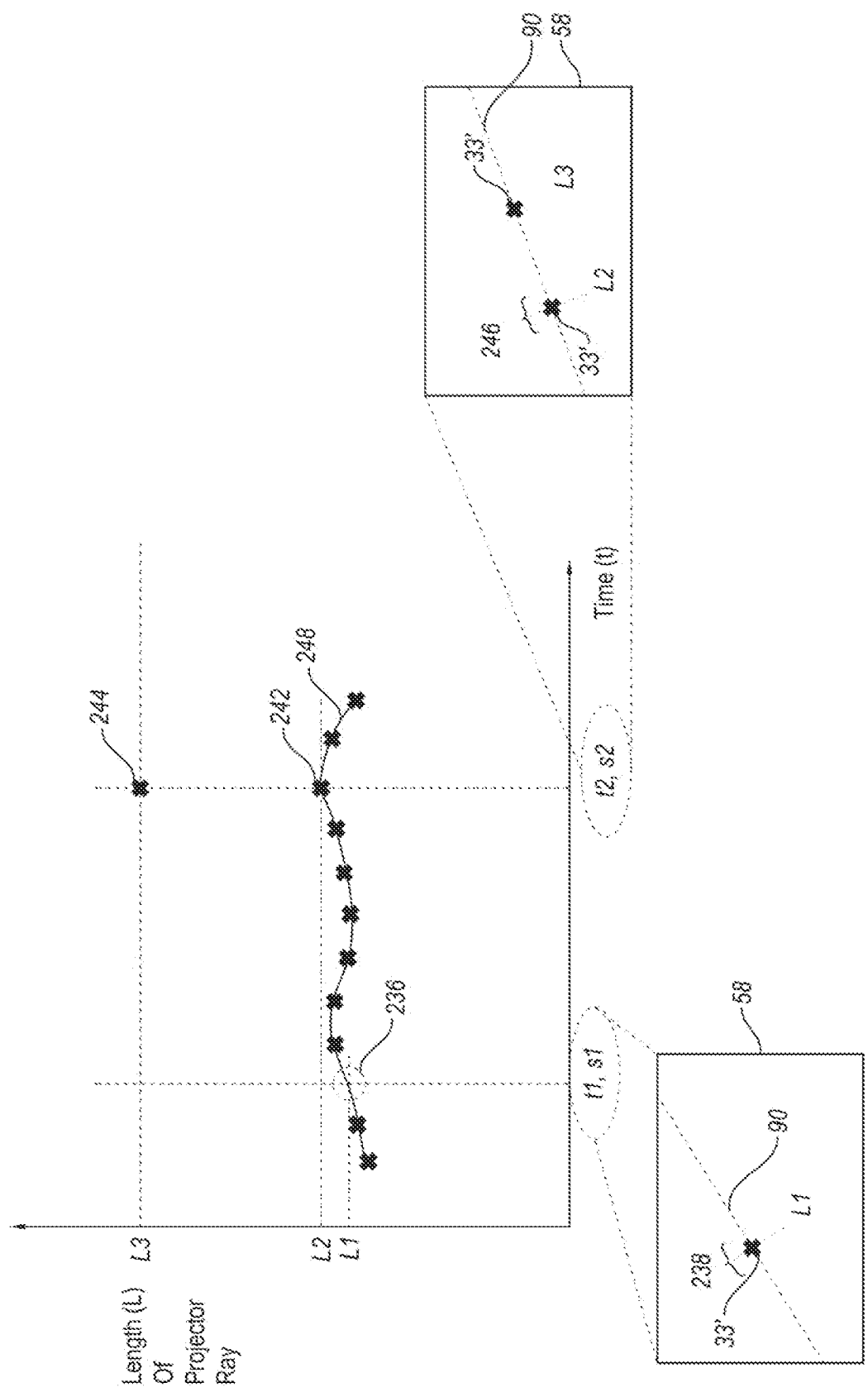
FIG. 39 is a graph showing the tracking of the length of a projector ray over time, and specific simplified views of a camera sensor corresponding to specific image frames, in accordance with some applications of the present invention.

Reference is now made to FIG. 39, which is a graph showing the tracking of the length of a projector ray 88 over time, and specific simplified views of a camera sensor 58 corresponding to specific image frames, in accordance with some applications of the present invention. The inventors have realized a plurality of uses for the above-described ray tracking. For some applications, there may be at least one image, from the plurality of consecutive images, in which a three-dimensional position of a projected spot 33 (or other feature) from a particular projector ray 88 was not identified in step 232 of the method shown in FIG. 38. For example, the projected spot (or other feature) in a particular frame may have been below the intensity threshold and was not considered by the correspondence algorithm, or there may have been a false mis-detection of the spot in a particular frame. However, due to the projector ray's length being tracked over time, processor 96 may compute an estimated length of the particular projector ray 88 in that image.

For example, in the exemplary graph show in FIG. 39, no three-dimensional position of the projected spot 33 was identified, based on the correspondence algorithm, for scan-frame s1 taken at time t1, and thus, as illustrated by dashed circle 236, there is no data point corresponding to the length of the projector ray 88 for scan-frame s1. However, due to the length of the ray being tracked through the plurality of consecutive images, an estimated length L1 of the projector ray 88 can be computed, e.g., by interpolation, for scan-frame s1. As described hereinabove, all points that are projected by a particular projector ray 88 appear on a particular path 90 of pixels in camera sensor 58 that corresponds to that particular projector ray 88. Thus, for scan-frame s1, in which a three-dimensional position of spot 33 corresponding to particular projector ray 88 was not identified in step 232, processor 96 may determine a one-dimensional search space 238 in scan-frame s1 in which to search for a projected spot from that particular projector ray 88. One-dimensional search space 238 is along the respective path 90 of pixels corresponding to the particular projector ray 88. This is in contrast to the spot tracking algorithm as described hereinabove, where processor 96 searches in two-dimensions within the images for spots that are close enough to each other from one frame to the next in order to be considered a tracked spot produced by the same projector ray in each of the image frames.

For some applications, based on the estimated length L1 of projector ray 88 in at least one of the plurality of images, processor 96 may determine a one-dimensional search space in respective pixel arrays, e.g., camera sensors 58, of a plurality of cameras 24, e.g., all cameras 24. For each of the respective pixel arrays, the one-dimensional search space is along the respective path 90 of pixels corresponding to projector ray 88 in that particular pixel array, e.g., camera sensor 58. Length L1 of projector ray 88 corresponds to a three-dimensional point in space, which corresponds to a two-dimensional location on a camera sensor 58. All the other camera 24 also have respective two-dimensional locations on their camera sensors 58 corresponding to the same three-dimensional point in space. Thus, the length of a projector ray in a particular frame may be used to define a one-dimensional search space in a plurality of the camera sensors 58, e.g., all of camera sensors 58, for that particular frame.

For some applications, in contrast to a false mis-detection where an expected spot (or other feature) was not detected, there may be at least one of the plurality of consecutive images in which more than one candidate three-dimensional position was computed for a projected spot 33 (or other feature) from a particular projector ray 88, i.e., a false positive detection of projected spot 33 (or other feature) occurred. For example, in the exemplary graph shown in FIG. 39, based on the correspondence algorithm, for a scan-frame s2 taken at time t2, two candidate detected spots 33' and 33" were computed to both be from particular projector ray 88, and thus two candidate three-dimensional positions of projected spot 33 were computed, and processor 96 computed two candidate lengths of projector ray 88 corresponding to each of the candidate three-dimensional positions for that frame. For example, processor 96 computes that for candidate detected spot 33' the candidate length of projector ray 88 is L2 (represented by data point 242 in FIG. 39), and for candidate detected spot 33" the candidate length of projector ray 88 is L3 (represented by data point 244 in FIG. 39). Due to the length of projector ray 88 being tracked over the plurality of consecutive images, when the ray length data for scan-frame s2 is added, it becomes apparent which candidate length, L2 or L3, is the estimated length of projector ray 88 for scan-frame s2. Thus, processor 96 is able to determine which of the more than one candidate three-dimensional positions of projected spot 33 is the correct three-dimensional position of projected spot 33, by determining which of the candidate three-dimensional positions corresponds to the estimated length of projector ray 88 for that image.

Based on the estimated length of projector ray 88 in the at least one of the plurality of images, e.g., in scan-frame s2, processor 96 may determine a one-dimensional search space 246 in scan-frame s2. Subsequently, processor 96 may determine which of the more than one candidate three-dimensional positions of projected spot 33 is the correct three-dimensional position of projected spot 33 produced by the projector ray 88, by determining which of the more than one candidate three-dimensional positions corresponds to a spot 33', produced by projector ray 88, and found within one-dimensional search space 246. Prior to the additional information provided by the ray tracking, camera sensor 58 for scan-frame s2 would have shown two candidate detected spots 33' and 33" both on path 90 of pixels corresponding to projector ray 88. Processor 96 computing the estimated length of projector ray 88 based on the length of the ray being tracked over the plurality of consecutive images, allows processor 96 to determine one-dimensional search space 246, and to determine that candidate detected spot 33' was indeed the correct spot. Candidate detected spot 33" is then removed from being considered as a point on the three-dimensional intraoral surface.

For some applications, processor 96 may define a curve 248 based on the assessed, e.g., computed, length of projector ray 88 in each image of the subset of images, e.g., the plurality of consecutive images. The inventors hypothesize that it can be reasonably assumed that any detected point whose three-dimensional position, based on the correspondence algorithm, corresponds to a length of projector ray r that is at least a threshold distance away from defined curve 248, may be considered a false positive detection and may be removed from being considered as a point on the three-dimensional intraoral surface.

Reference is now made to FIGS. 40A-B, which are graphs showing an experimental set of data before and after ray tracking, in accordance with some applications of the present invention. In FIG. 40A, the length of a particular projector ray 88 is plotted for every spot and/or other feature that was computed by the correspondence algorithm. Before ray tracking is applied, the ray lengths corresponding to spots and/or other features that appear far from the general curve defined by projector ray 88 are included in the data. FIG. 40B represents how the data appear after ray tracking is applied and used to determine which false positive spots and/or other features should be removed from being considered a point on the three-dimensional intraoral surface.

Reference is now made to FIG. 41, which is a schematic illustration of a plurality of camera sensors and a projector projecting a spot or other feature, in accordance with some applications of the present invention. For some applications, after running a correspondence algorithm, such as the correspondence algorithm described hereinabove with reference to FIGS. 7-17, depending on how many cameras 24 detected a given projected spot 33 (or other feature) on their respective pixel arrays (i.e., camera sensors 58), processor 96 can determine with a certain degree of certainty a candidate three-dimensional position of projected spot 33 (or other feature). The candidate three-dimensional position of projected spot 33 (or other feature) in FIG. 41 is marked by the dashed circle 250.

The higher the number of cameras 24 that saw projected spot 33 (or other feature), the higher the degree of certainty is for candidate three-dimensional position 250. Thus, using data from at least two of the cameras 24, processor 96 may identify candidate three-dimensional position 250 of a given spot 33 (or other feature) corresponding to a particular projector ray 88. Assuming the identification of candidate three-dimensional position 250 was determined substantially not using data from at least another camera 24', then it is possible there may be some error in the candidate three-dimensional position 250, and that candidate three-dimensional position 250 could be refined if processor 96 has data from other camera 24'.

Thus, assuming, after correspondence, at least two cameras 24 saw projected spot 33 (or other feature), at this point processor 96 knows (a) which projector ray 88 produced the projected spot 33 (or other feature) and (b) candidate three-dimensional position 250 of the spot (or other feature). Combining (a) and (b) allows processor 96 to determine a one-dimensional search space 252 in the pixel array, i.e., camera sensor 58', of another camera 24' in which to search for a spot (or other feature) from projector ray 88. One-dimensional search space 252 is along the path 90 of pixels on camera sensor 58' of the other camera 24', and may be along the particular segment of path 90 that corresponds to candidate three-dimensional position 250. If a spot 33' (or other feature) from projector ray 88, e.g., a falsely mis-detected spot 33' that was not considered by the correspondence algorithm (for example, because it was of sub-threshold intensity), is identified within the one-dimensional search space 252 then, using the now-achieved data from other camera 24', processor 96 may refine candidate three-dimensional position 250 of the spot 33 (or other feature) to be refined three-dimensional position 254.

Figure 42A:
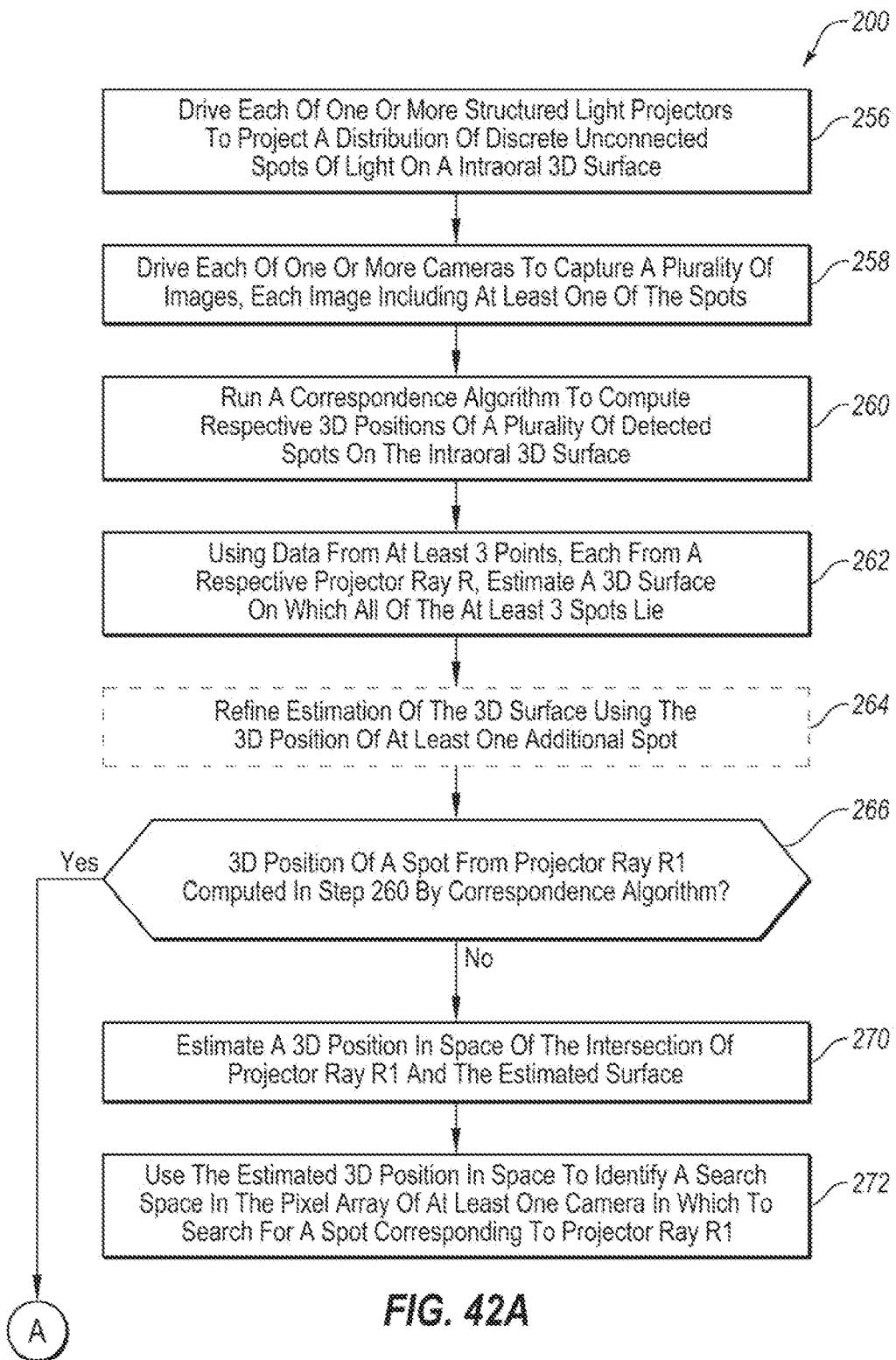
FIGS. 42A-B illustrate a flow chart outlining a method for generating a three-dimensional image, in accordance with some applications of the present invention.
Figure 42B:
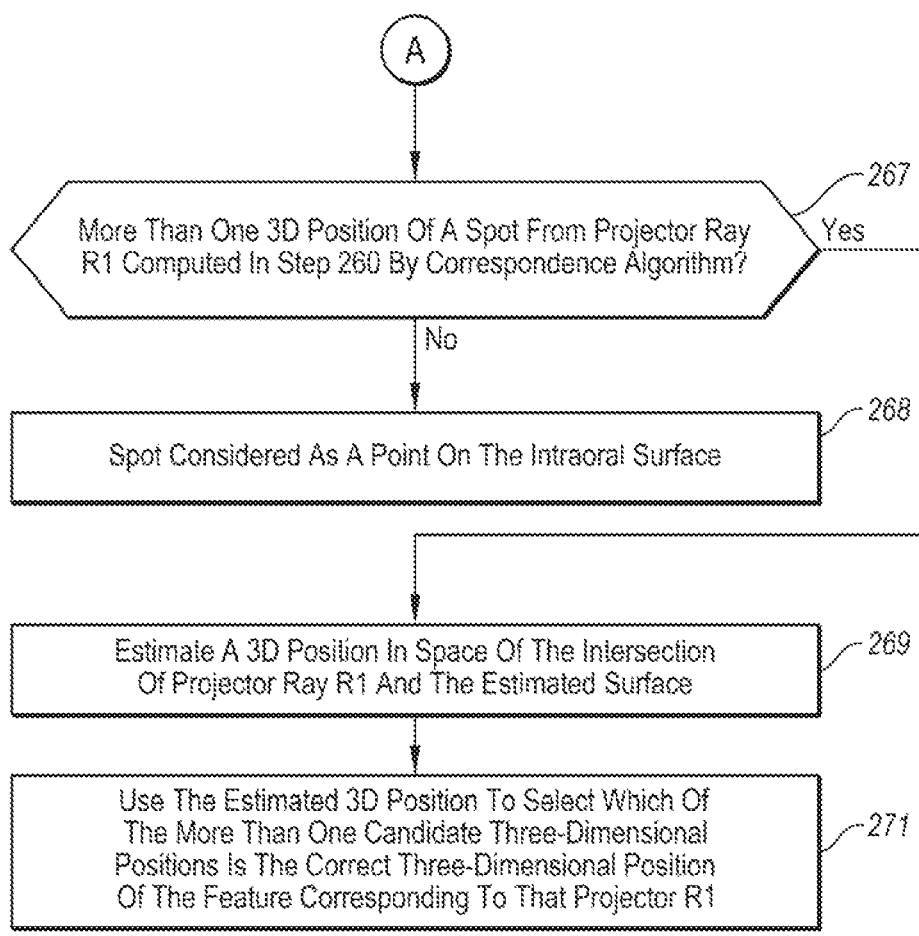

Reference is now made to FIGS. 42A-B, which illustrate a flow chart outlining a method for generating a three-dimensional image, in accordance with some applications of the present invention. For some applications, once three-dimensional positions are identified for at least three projected spots 33 (or other feature) from three distinct projector rays 88, a three-dimensional surface may be estimated such that all three of the identified three-dimensional positions lie on the estimated surface. For another projector ray 88', for which a three-dimensional position of its projected spot 33 (or other feature) was not determined, e.g., because projected spot 33 was of sub-threshold intensity, a candidate three-dimensional position may be computed at the intersection of other projector ray 88' and the estimated three-dimensional surface. Similarly to as described hereinabove with reference to FIG. 41, processor 96 may use the combination of (a) knowing the specific projector ray, i.e., knowing which path 90 on the sensor to look at, and (b) knowing the candidate three-dimensional position, to determine a one-dimensional search space in at least one camera sensor 58 along which to search for a detected spot 33' from other projector ray 88'.

Thus, in step 256 of the method outlined in FIGS. 42A-B, each structured light projector 22 is driven to project a structured light pattern, e.g., a distribution 34 of discrete unconnected spots 33 of light, on an intraoral three-dimensional surface, and in step 258 each camera 24 is driven to capture a plurality of images, each image including at least one of the spots. Based on the stored calibration values indicating (a) a camera ray 86 corresponding to each pixel on camera sensor 58 of each camera 24, and (b) a projector ray 88 corresponding to each projected spot 33 of light from each structured light projector 22, processor 96 is used in step 260 to run a correspondence algorithm (such as the correspondence algorithm described hereinabove with reference to FIGS. 7-17) to compute respective three-dimensional positions on the intraoral three-dimensional surface of a plurality of detected spots 33' for each of the plurality of images. In step 262, using data corresponding to the respective three-dimensional positions of at least three detected spots 33', each detected spot 33' corresponding to a respective projector ray 88, processor 96 estimates a three-dimensional surface on which all of the at least three detected spots 33' lie. Processor 96 then considers another projector ray 88'. As indicated by decision hexagon 266, if the correspondence algorithm already identified one three-dimensional position of a detected spot 33' from other projector ray 88' in step 260, then that detected spot 33' from other projector ray 88' may be considered to be a point on the intraoral surface (step 268) at that three-dimensional position. However, for another projector ray 88', for which a three-dimensional position of a spot 33 corresponding to other projector ray 88' was not computed in step 260, processor 96 may estimate a three-dimensional position in space of the intersection of other projector ray 88' and the estimated three-dimensional surface (step 270). In step 272, processor 96 uses the estimated three-dimensional position in space to identify a search space (e.g., a one-dimensional search space) in the pixel array (e.g., camera sensor 58) of at least one camera 24 along which to search for a detected spot 33' corresponding to the other projector ray 88'.

As described hereinabove, in order to reduce the occurrence of cameras 24 detecting many false positive spots, processor 96 may set a threshold, e.g., an intensity threshold, and any detected features, e.g., spots 33', that are below the threshold are not considered by the correspondence algorithm. Thus, for example, a three-dimensional position of a spot 33 corresponding to other projector ray 88' may not have been computed in step 260 due to the detected spot 33' being of sub-threshold intensity. In step 272, to search for the feature, e.g., a detected spot 33', the processor may lower the threshold in order to consider features that were not initially considered by the correspondence algorithm.

As used throughout the present application, including in the claims, when a search space is identified in which to search for a detected feature, e.g., a detected spot 33', it may be in the case of:
 (a) a falsely mis-detected spot (for example, a sub-threshold spot that was not initially considered by the correspondence algorithm, or a spot that was blocked by moving tissue), in which case processor 96 may lower the threshold in order to re-search that particular region, i.e., the identified search space, for a detected spot 33', or
 (b) a false positive spot, i.e., more than one candidate three-dimensional position for a spot being identified by the correspondence algorithm, in which case processor 96 may determine which spot is the correct spot based on re-searching that particular region, i.e., the identified search space, for the detected spot 33'.

For some applications, in step 260 the correspondence algorithm may identify more than one candidate three-dimensional position of a detected spot 33' from projector ray 88'. As indicated by decision hexagon 267, for the projector ray 88' for which more than one candidate three-dimensional position was identified for detected spot 33', processor 96 may estimate a three-dimensional position in space of the intersection of projector ray 88' and the estimated three-dimensional surface (step 269). In step 271, processor 96 selects which of the candidate three-dimensional positions of detected spot 33' from projector ray 88' is the correct position based on the three-dimensional position of the intersection of projector ray 88' and the estimated three-dimensional surface.

For some applications, in step 262, processor 96 uses data corresponding to the respective three-dimensional positions of at least three detected spots 33' that were all captured in one of the plurality of images. Furthermore, after the three-dimensional surface is estimated, the estimation may be refined by adding in data points from subsequent images, i.e., using data corresponding to the three-dimensional position of at least one additional spot whose three-dimensional position was computed based on another one of the plurality of images, such that all the spots (the three used for the original estimation and the at least one additional spot) lie on the refined estimated three-dimensional surface. For some applications, in step 262, processor 96 uses data corresponding to the respective three-dimensional positions of at least three detected spots 33' that were each captured in a separate image, i.e., in a respective one of the plurality of images.

It is noted that discussed hereinabove are falsely mis-detected projected spots. It is also possible that a mis-detected projected spot is a true mis-detection, and a spot corresponding to a particular projector ray was in reality not projected onto the intraoral surface, e.g., due to being occluded by moving tissue such as, for example, the patient's tongue, the patient's cheek, or the practitioner's fingers.

In one embodiment, a method for generating a digital three-dimensional image includes driving each one of one or more structured light projectors to project a pattern of light on an intraoral three-dimensional surface and driving each one of one or more cameras to capture a plurality of images, each image including at least a portion of the projected pattern, each one of the one or more cameras comprising a camera sensor comprising an array of pixels. The method further includes using a processor to run a correspondence algorithm to compute respective three-dimensional positions on the intraoral three-dimensional surface of a plurality of detected features of the projected pattern for each of the plurality of images. The processor uses data corresponding to the respective three-dimensional positions of at least three features, each feature corresponding to a respective projector ray r, to estimate a three-dimensional surface on which all of the at least three features lie. For a projector ray r1 for which a three-dimensional position of a feature corresponding to that projector ray r1 was not computed, or for which more than one three-dimensional position of a feature corresponding to that projector ray r1 was computed, the processor estimates a three-dimensional position in space of an intersection of projector ray r1 and the estimated three-dimensional surface. The processor then uses the estimated three-dimensional position in space to identify a search space in the pixel array of at least one camera in which to search for a feature corresponding to projector ray r1. In one embodiment, the correspondence algorithm is run based on stored calibration values indicating (a) a camera ray corresponding to each pixel on the camera sensor of each one of the one or more cameras, and (b) a projector ray corresponding to each feature of the projected pattern from each one of the one or more structured light projectors, whereby each projector ray corresponds to a respective path of pixels on at least one of the camera sensors. In one embodiment, the search space in the data comprises a search space defined by one or more thresholds. In one embodiment, the pattern of light comprises a distribution of discrete spots, and each of the features comprises a spot from the distribution of discrete spots.

Figure 43A:
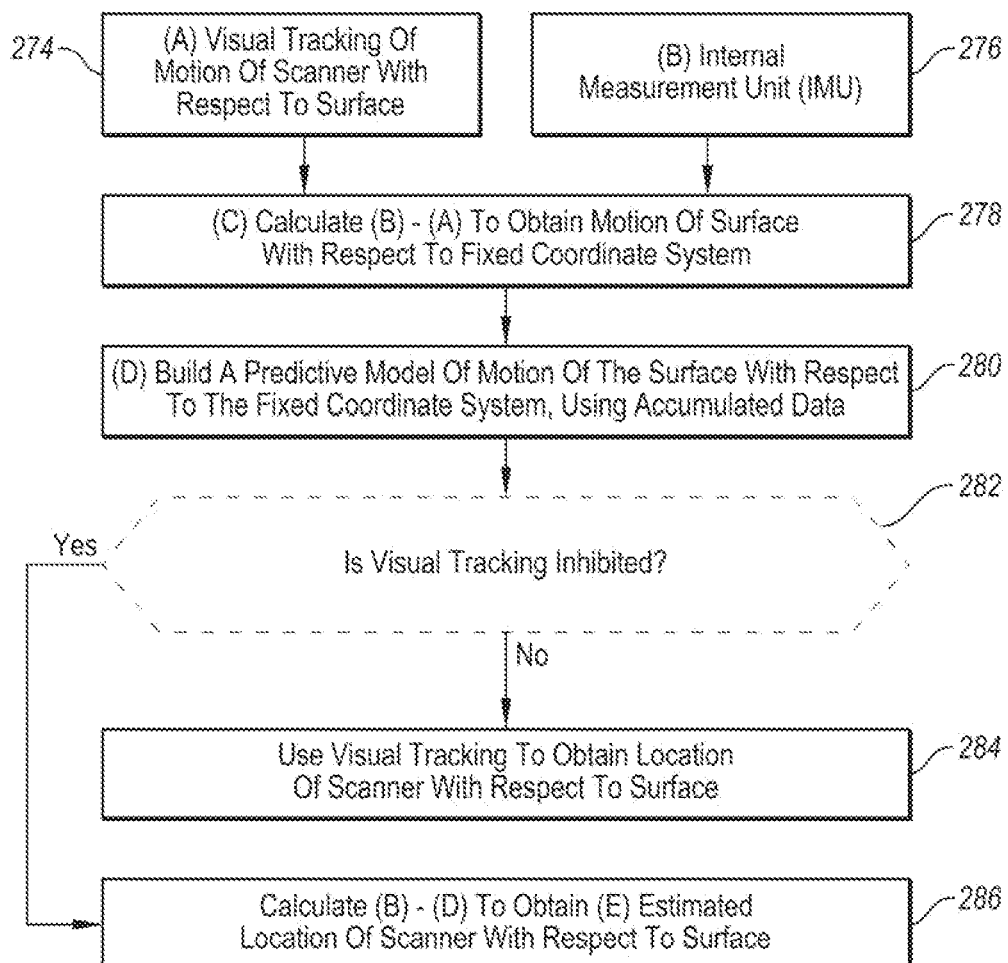
FIGS. 43A-B are flow charts outlining respective methods for tracking motion of the intraoral scanner, in accordance with some applications of the present invention.
Figure 43B:
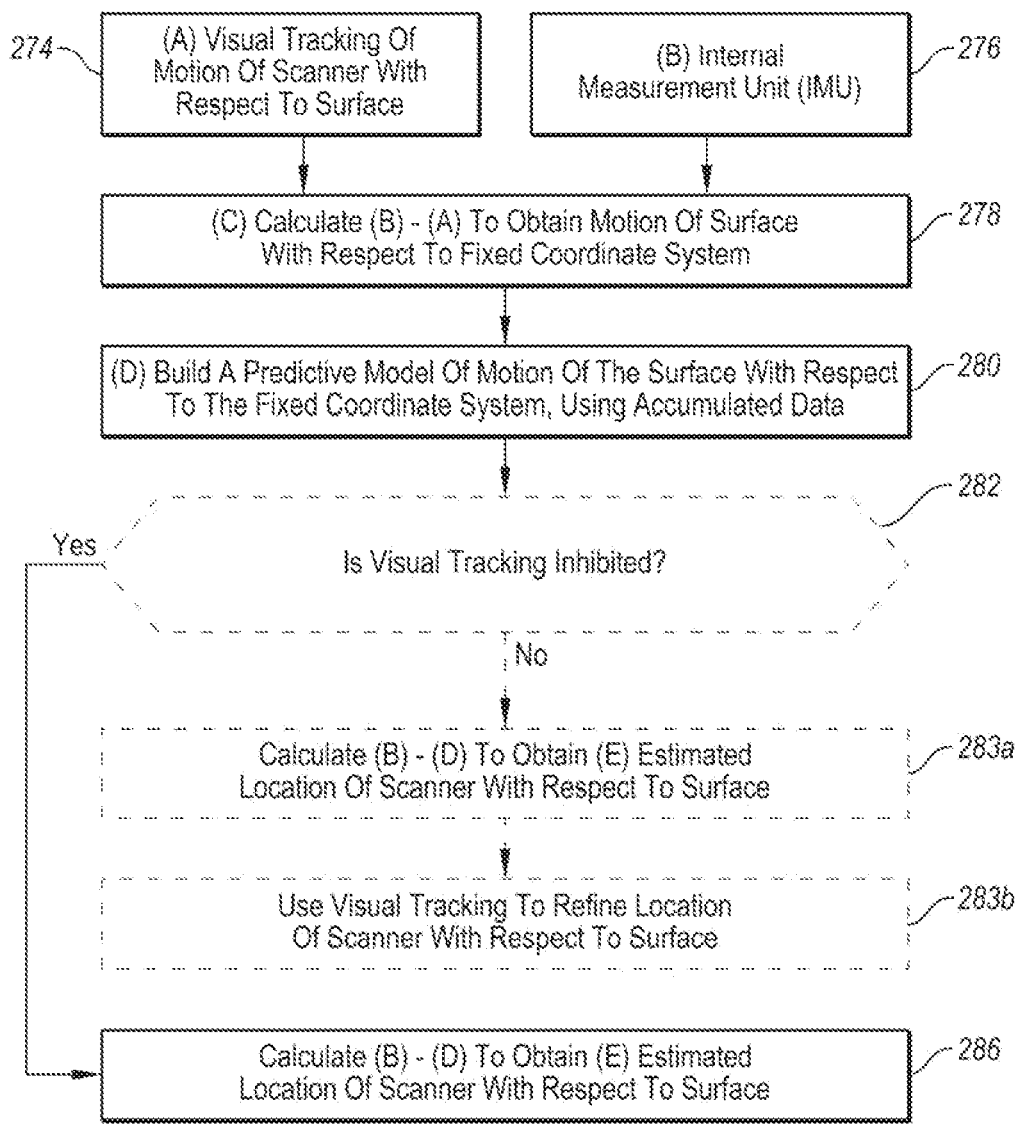

Reference is now made to FIGS. 43A-B, which are flow charts outlining respective methods for tracking motion of the intraoral scanner, i.e., handheld wand 20, in accordance with some applications of the present invention. For the purpose of object scanning, an estimation of the location of the scanner with respect to object 32 being scanned, i.e., the three-dimensional intraoral surface, is desirable at all times during a scan. Generally, the intraoral scanner may use at least one camera 24 that is coupled to the intraoral scanner to measure motion of the intraoral scanner with respect to object 32 being scanned via visual tracking (step 274). The visual tracking of the motion of the intraoral scanner with respect to object 32 being scanned is obtained by stitching of the respective surfaces or point clouds obtained from adjacent image frames or by a simultaneous localization and mapping (SLAM) algorithm, which in turn provides information on how the intraoral scanner has moved between one frame and the next. However, there may be times during a scan where sufficient visual tracking of the motion of the intraoral scanner with respect to object 32 is not available, e.g., in a hard to capture region of the intraoral scene, or if moving tissue blocks the camera, such as, for example, the patient's tongue, the patient's cheek, or the practitioner's fingers. An inertial measurement unit (IMU) coupled to the intraoral scanner may measure motion of the intraoral scanner with respect to a fixed coordinate system. However, using an IMU alone is generally not sufficient, in and of itself, in order to determine a location of the intraoral scanner with respect to object 32 being scanned, because object 32 is part of a subject's head, which itself may move.

Thus, the inventors have developed a method of combining (a) visual tracking of the scanner's motion with (b) inertial measurement of the scanner's motion to (i) accommodate for times when sufficient visual tracking is unavailable, and optionally (ii) when visual tracking is available, help provide an initial guess for movement of the intraoral scanner with respect to object 32 from one frame to the next so as to leave only refinement of the location of intraoral scanner to be obtained from visual tracking, thus reducing stitching time. In step 274, at least one camera, e.g., camera 24, coupled to the intraoral scanner is used to measure (A) motion of the intraoral scanner with respect to an intraoral surface being scanned. In step 276, at least one IMU coupled to the intraoral scanner is used to measure (B) motion of the intraoral scanner with respect to a fixed coordinate system (i.e., the Earth's frame of reference). In step 278 a processor, e.g., processor 96, is used to calculate motion of the intraoral surface with respect to the fixed coordinate system by subtracting (A) motion of the intraoral scanner with respect to the intraoral surface from (B) motion of the intraoral scanner with respect to the fixed coordinate system. Alternatively, the motion of the intraoral surface with respect to the fixed coordinate system may be otherwise calculated based on (A) the motion of the intraoral scanner with respect to the intraoral surface and (B) motion of the intraoral scanner with respect to the fixed coordinate system. The motion of the intraoral surface may be calculated by calculating a difference between the motion of the intraoral scanner with respect to the fixed coordinate system and the motion of the intraoral surface with respect to the fixed coordinate system. Typically, motion of the intraoral surface includes motion of the subject's upper and/or lower jaw.

While scanning, processor 96 may accumulate data of motion of the intraoral surface with respect to the fixed coordinate system collected in step 278. In step 280, based on accumulated data of motion of the intraoral surface with respect to the fixed coordinate system, the processor may build a predictive model of (D) motion of the intraoral surface with respect to the fixed coordinate system. The predictive model may be used to calculate (E) an estimated location of the intraoral scanner with respect to the intraoral surface. The predictive model is based on two assumptions. The first assumption is that the motion frequency of the subject's head, e.g., upper and/or lower jaw, is substantially slower than (a) the frame-rate capture of the camera that is performing the visual tracking, and (b) the sampling frequency of the IMU. The second assumption is that the motion frequency of the subject's head, e.g., upper and/or lower jaw, is also substantially slower than the motion frequency of the intraoral scanner with respect to the subject's head, e.g., upper and/or lower jaw. Thus, between any two captured frames it can be assumed that the motion of the subject's head is minimal and relatively smooth.

Reference is now made specifically to FIG. 43A. For some applications, as indicated by decision hexagon 282, as long as visual tracking of (A) motion of the intraoral scanner with respect to the intraoral surface is not inhibited, then the visual tracking may be used to obtain the location of the intraoral scanner with respect to the intraoral surface (step 284). However, if processor 96 determines that visual tracking is inhibited, i.e., sufficient visual tracking is unavailable, processor 96 may calculate (E) an estimated location of the intraoral scanner with respect to the intraoral surface by subtracting (D) the prediction of the motion of the intraoral surface with respect to the coordinate system, derived based on the predictive model, from (B) motion of the intraoral scanner with respect to the coordinate system as measured by the IMU. Alternatively, processor 96 may otherwise calculate an estimated location of the intraoral scanner with respect to the intraoral surface based on (A) the prediction of the motion of the intraoral surface with respect to the fixed coordinate system, derived from the predictive motion model, and (B) motion of the intraoral scanner with respect to the fixed coordinate system, as measured by the IMU.

Reference is now made specifically to FIG. 43B. FIG. 43B is similar to FIG. 43A, except for steps 283A and 283B, which take the place of step 284 in FIG. 43A. For some applications, even when visual tracking is not inhibited, the estimated location of the intraoral scanner with respect to the intraoral surface as calculated by subtracting (D) from (B) (as described above) may be used to provide an initial guess of the movement of intraoral scanner with respect to object 32 from one frame to the next (step 283A). The visual tracking may then be used to refine the location via stitching (step 282B). This may significantly reduce the amount of stitching time even when the intraoral scanner is relying on visual tracking.

Figure 44A:
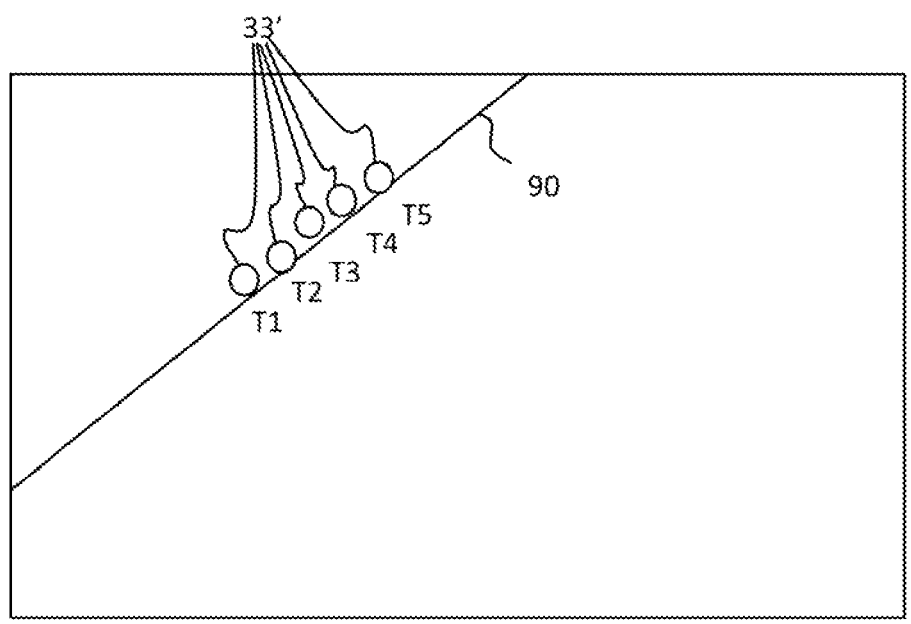
FIGS. 44A, 44B, and 45 are schematic illustrations showing a simplified view of a camera image with a plurality of detected spots from a single projector ray that were all captured at respective times and have been superimposed on the same image, in accordance with some applications of the present invention.
Figure 44B:
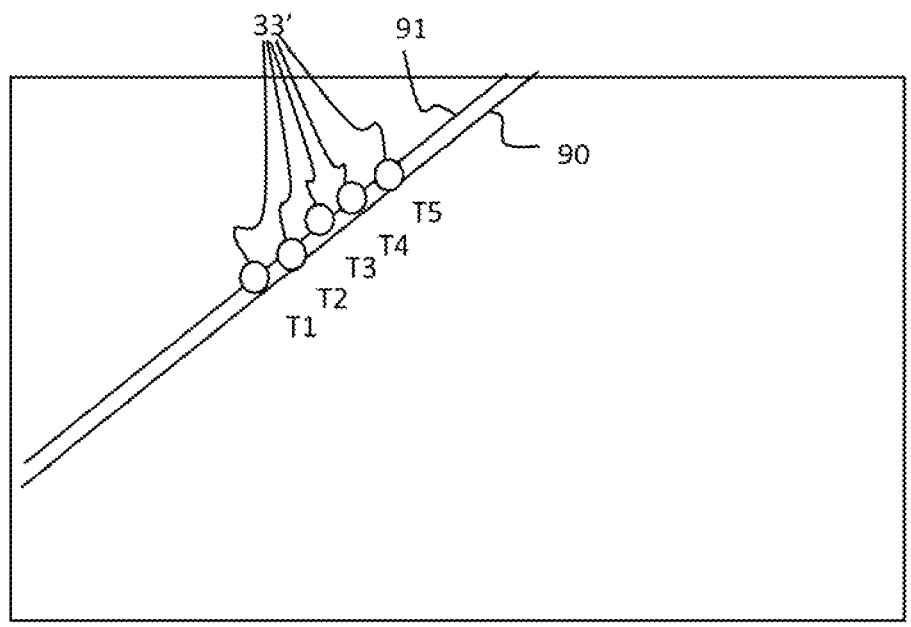

Reference is now made to FIGS. 44A-B, which are schematic illustrations showing a simplified view of a camera image with a plurality of detected spots 33' from a single projector ray 88 that were all captured at respective times T and have been superimposed on the same image, in accordance with some applications of the present invention. As described hereinabove, the correspondence algorithm, spot-tracking, and ray-tracking are all based on stored calibration values indicating (a) a camera ray 86 corresponding to each pixel on camera sensor 58 of each camera 24, and (b) a projector ray 88 corresponding to each projected spot 33 of light from each structured light projector 22, whereby each projector ray corresponds to a respective path 90 of pixels on at least one of the camera sensors. However, it is possible that, over time, at least one of cameras 24 and/or at least one of projectors 22 may move (e.g., by rotation or translation), the optics of at least one of cameras 24 and/or at least one of projectors 22 may be altered, or the wavelengths of the lasers may be altered, resulting in the stored calibration values no longer accurately corresponding to camera rays 86 and projector rays 88. Thus, the inventors have realized a way to use processor 96 to assess, based on data accumulated while the intraoral scanner, e.g., handheld wand 20 is being used to scan, the accuracy of the stored calibration values.

For any given projector ray 88, if processor 96 collects data including the computed respective three-dimensional positions on the intraoral surface of a plurality of detected spots 33' from that projector ray 88, that were detected at different points in time, and superimposes them on one image, the spots should all fall on the camera sensor path 90 of pixels that corresponds to that projector ray 88. If something has altered the calibration of either the camera or the projector, then it may appear as though the detected spots 33' from that particular projector ray 88 do not fall on the expected camera sensor path 90 as per the stored calibration values. FIG. 44A shows a simplified example of five detected spots 33' all produced by a particular projector ray 88 that were detected at a respective plurality of times T1 through T5. Camera sensor path 90 is the camera sensor path 90 corresponding to the particular projector ray 88 based on the stored calibration values. As can be seen, all of the spots 33' seem to be shifted such that they are not falling on the expected camera sensor path 90.

Thus, for some applications, after running a correspondence algorithm, such as the correspondence algorithm described hereinabove with reference to FIGS. 7-17, processor 96 collects data at a plurality of points in time, the data including the computed respective three-dimensional positions on the intraoral surface of a plurality of detected spots 33'. For each projector ray 88, based on the collected data, processor 96 defines an updated path 91 of pixels on each camera sensor 58, such that all of the computed three-dimensional positions corresponding to the plurality of detected spots 33' produced by projector ray 88 correspond to locations along the respective updated path 91 of pixels for each camera sensor 58. Processor 96 then compares each updated path 91 of pixels to the path 90 of pixels corresponding to that projector ray 88 on each camera sensor 58 from the stored calibration values.

FIG. 44B shows updated camera sensor path 91 for the simplified example shown in FIG. 44A. As can be seen, all five of the detected spots 33' are indeed falling on a camera sensor path, however it is not the original camera sensor path 90 from the stored calibration values. Thus, if for at least one camera sensor 58, updated path 91 of pixels corresponding to projector ray 88 differs from the path 90 of pixels corresponding to projector ray 88 from the stored calibration values, it may be an indication that either one or more projectors 22 have moved, or the optics of one or more projectors 22 may have changed, and/or it may be an indication that one or more cameras 24 have moved, or the optics of one or more cameras 24 have changed.

An assessment of a current calibration state may automatically be performed on a periodic basis (e.g., every scan, every $10^{th}$ scan, every month, every few months, etc.) or in response to certain criteria being met (e.g., in response to a threshold number of scans having been made). As a result of the assessment, the system may determine whether a state of the calibration is accurate or inaccurate (e.g., is good, bad, or approaching bad). Such a determination can be made automatically and without the use of any special calibration target. Based on the assessment, processing logic may determine a degree to which one or more components of the intraoral scanner are out of calibration, and may automatically perform a recalibration and/or compensate for drift or the degree to which the component(s) is out of calibration. Such automatic calibration and/or compensation may be performed without use of a special calibration target in embodiments.

In one embodiment, as a result of the assessment the system determines whether the calibration state is drifting. For example, the previous calibration may still be accurate enough to produce high quality scans, but the system may have deviated such that in the future it will no longer be able to produce accurate scans if a detected trend continues. In one embodiment, the system determines a rate of drift, and projects that rate of drift into the future to determine a projected date/time at which the calibration will no longer be accurate. In one embodiment, automatic calibration or manual calibration may be scheduled for that future date/time. In an example, processing logic assesses a state of calibration through time (e.g., by comparing states of calibration at multiple different points in time, and from such a comparison determines a rate of drift. From the rate of drift, the processing logic can predict when calibration should be performed based on the trend data.

In one embodiment, a method of assessing the calibration of an intraoral scanner is performed on a periodic basis or when certain criteria are met. In one embodiment, processing logic tracks a number of scans that have been performed by the intraoral scanner (e.g., a number of scans since an assessment of the calibration was last performed). If the number of scans meets a threshold, then an assessment may be performed. Alternatively, an assessment may automatically be performed after every scan session, after every scan, or on a periodic basis (e.g., once a day, once a week, once a month, etc.).

To perform the assessment, processing logic receives scan data of a patient's intraoral cavity from the intraoral scanner. Processing logic then assesses a calibration of the intraoral scanner based on at least some of the received scan data of the patient's intraoral cavity. The assessment of the calibration may be performed as described in detail herein above and below. Processing logic then outputs an indication associated with the assessed calibration. The indication may be output to a display and/or to a user. The indication may be a textual, visual and/or audio indication. The calibration assessment may include one or more calibration assessment values. Depending on a result of the calibration assessment, the indication may include a notification to recalibrate the intraoral scanner. For example, if the calibration assessment indicates that the intraoral scanner is out of calibration, or will soon be out of calibration, then the indication may include a notification to recalibrate the intraoral scanner.

Assessing the calibration may include comparing the calibration assessment values for the calibration to a threshold. In one embodiment, the indication is an indication that the intraoral scanner should be recalibrated, and this indication is outputted in response to one or more of the calibration assessment values exceeding the threshold. In some embodiments, the recalibration is automatically performed responsive to determining that a recalibration is warranted, and the notification is a notification that the intraoral scanner has been recalibrated. Some types of recalibration may be performed automatically, and some types of calibration may be performed with user interaction in embodiments. In other embodiments, all types of recalibration can be performed automatically.

In one embodiment, the calibration of the intraoral scanner is monitored over time. With each assessment of the calibration, a set of calibration assessment values associated with the assessment may be stored (e.g., along with a time stamp). Processing logic may monitor the calibration of the intraoral scanner based on the currently assessed calibration (e.g., current calibration assessment values) and previous calibration assessment values (i.e., results of previous calibration assessments) of the intraoral scanner. Each of the sets of calibration assessment values may include calibration assessment values that represent an amount of deviation from a calibrated state (e.g., optionally measured in terms of distance, such as between a path of a projector ray as included in stored calibration data and an estimated path of the projector ray as measured from the calibration assessment). In one embodiment, processing logic determines a rate of change of the calibration assessment values based on the current set of calibration assessment values and one or more previous sets of calibration assessment values. The rate of change of the calibration assessment values may indicate a drift or trend of the intraoral scanner away from a calibrated state. The rate of change of the calibration assessment values may be projected into the future. The projection of the rate of change of the calibration assessment values into the future may be used to determine a date/time at which the calibration assessment values will satisfy a recalibration criterion (e.g., a point in time at which a calibration assessment value will meet or exceed a threshold). The threshold may represent a maximum amount of acceptable deviation from a calibrated state.

In one embodiment, scan data of a patient's intraoral cavity is received from an intraoral scanner. Processing logic assesses a calibration of the intraoral scanner based on at least some of the received scan data of the patient's intraoral cavity, wherein assessing the calibration comprises determining a calibration assessment value. Processing logic compares the calibration assessment value to a threshold. In response to the calibration assessment value exceeding the threshold, processing logic automatically recalibrates the intraoral scanner. The automatic recalibration may be performed according to the recalibration methods described herein above and below in embodiments.

In one embodiment, when processor 96 determines that it is a projector 22 that has moved or changed, as further described hereinbelow, processor 96 may perform a recalibration of the projector rays 88. For some applications, the calibration data for projector rays 88 is stored as an indexed list of all the projector rays 88, and their corresponding camera sensor paths. In this case, to recalibrate the projector rays 88 for a projector 22, each projector ray 88 for that particular projector 22 is re-assigned based on the corresponding updated path 91 of pixels. For some applications, the calibration data for the projector rays 88 is stored in a parametrized projector calibration model that defines each projector ray 88 for a given projector 22. In this case, to recalibrate the projector rays 88 of a particular projector 22, processor 96 varies the parameters in the stored calibration model so as to reduce the difference between (i) updated path 91 of pixels corresponding to projector ray 88 for that particular projector 22 and (ii) path 90 of pixels corresponding to projector ray 88 for that particular projector 22 from the stored calibration data.

When processor 96 determines that it is a camera 24 that has moved or changed, as further described hereinbelow, processor 96 recalibrates camera 24 by varying the stored calibration values indicating the camera rays 86 corresponding to each pixel on at least one camera sensor 58. Recalibrating camera 24 typically includes redefining a parametrized camera calibration function that takes a given three-dimensional position in space and translates it to a given pixel in the two-dimensional pixel array of camera sensor 58. Processor 96 thus redefines camera rays 86 by varying one or more parameters of the camera calibration function in order to reduce the difference between (i) the collected values indicating the actual three-dimensional positions of a plurality of detected spots 33' projected from a plurality of respective projector rays 88, and (ii) the stored calibration values indicating respective camera rays 86 corresponding to the respective pixels on camera sensor 58 where the respective plurality of detected spots 33', projected from respective projector rays 88, should have been detected.

Thus, based on the accumulated data while handheld intraoral scanner 20 is being used to scan, processor 96 (A) recalibrates at least one projector 22 such that the projector ray 88 now corresponds to updated camera sensor path 91 along which spots produced by that projector ray 88 are being detected, and/or (B) recalibrates at least one camera 24 by redefining camera rays 86 for at least one camera sensor 58.

For some applications, in response to determining that for at least one camera sensor 58, updated path 91 of pixels corresponding to projector ray 88 differs from the path 90 of pixels corresponding to projector ray 88 from the stored calibration values, processor 96 may not perform a recalibration, but rather only determines that the stored calibration values for one or more projectors 22 are incorrect, and/or the calibration values for one or more cameras 24 are incorrect. For example, based on the determination that the stored calibration values are incorrect, a user may be prompted to return the intraoral scanner to the manufacturer for maintenance and/or recalibration, or request a new scanner.

Figure 45:
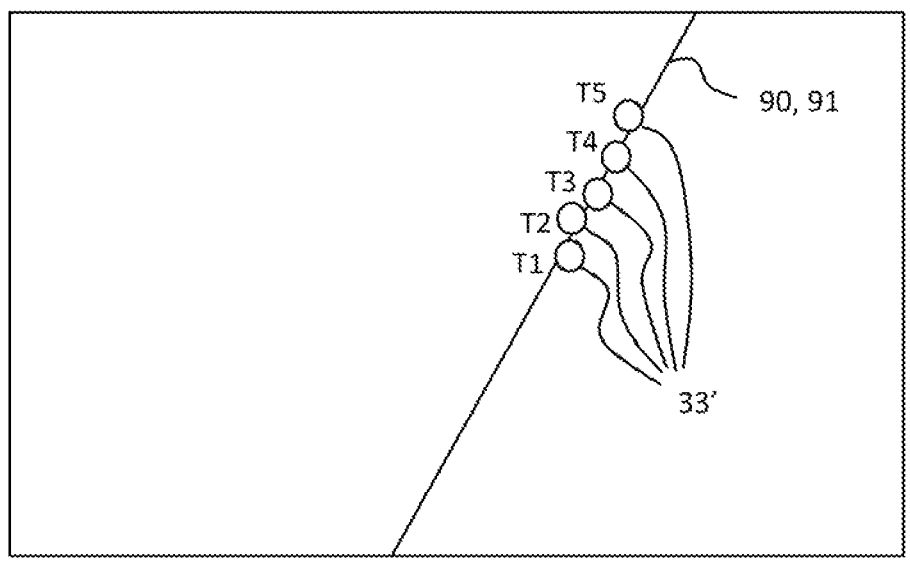

Reference is now made to FIG. 45, which is a schematic illustration showing a simplified example of when updated path 91 of pixels matches path 90 of pixels from the stored calibration values, indicating that recalibration as described hereinabove is not needed, in accordance with some applications of the present invention.

Figure 46B:
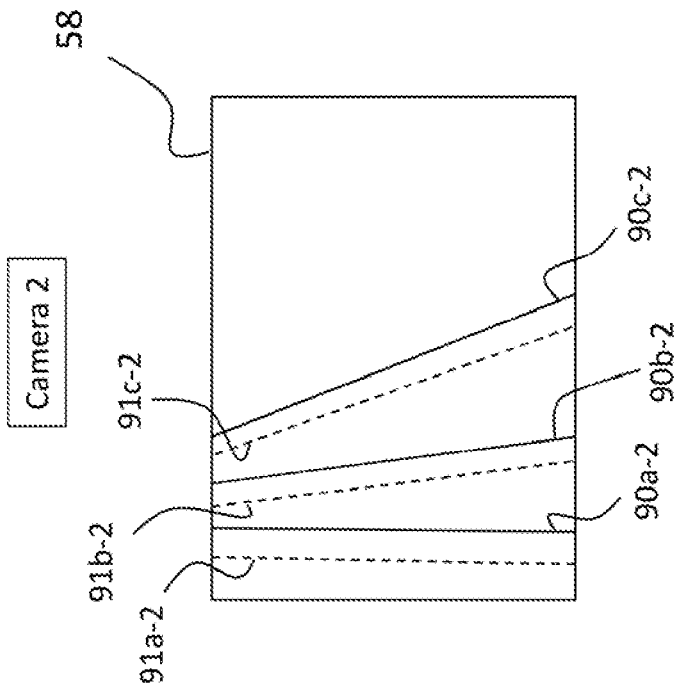
Figure 46A:
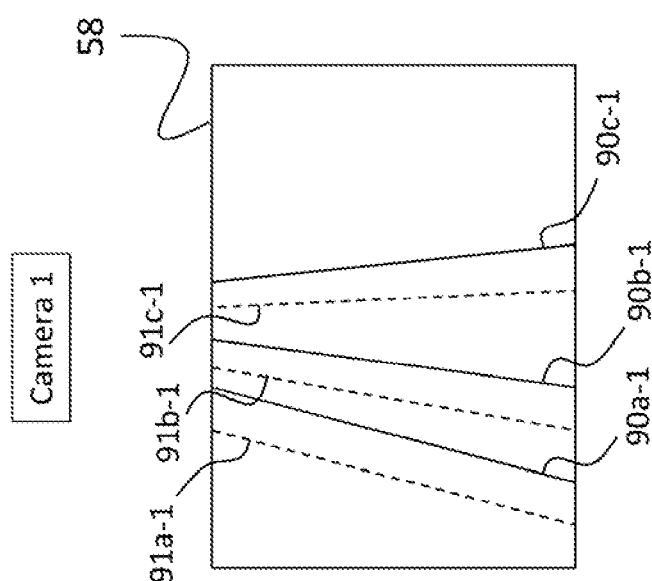

Reference is now made to FIGS. 46A-D, which show a simplified scenario in which processor 96 may identify that it is a particular projector that should be recalibrated and not any of the cameras, i.e., projector rays 88 from that projector 22 should be redefined, in accordance with some applications of the present invention. FIG. 46A shows camera sensor 58 of a first camera (camera 1). Three camera sensor paths 90*a*-1, 90*b*-1, and 90*c*-1, based on the stored calibration values, are shown on camera sensor 58 of camera 1. These three paths shown on camera 1 correspond, respectively, to three projector rays 88*a*, 88*b*, and 88*c* that all originate from a particular projector 22. FIG. 46B shows camera sensor 58 of a second camera (camera 2). Three camera sensor paths 90, based on the stored calibration values, are shown on camera sensor 58 of camera 2 (paths 90*a*-2, 90*b*-2, and 90*c*-2). These three paths shown on camera 2 correspond, respectively, to the same three projector rays that the paths on camera 1 correspond to, namely, projector rays 88*a*, 88*b*, and 88*c*.

In one embodiment, a method of recalibration is performed. The method includes driving each one of one or more structured light projectors to project a pattern of light on an intraoral three-dimensional surface and driving each one of one or more cameras to capture a plurality of images, each image including at least a portion of the projected pattern, each one of the one or more cameras comprising a camera sensor comprising an array of pixels. Based on stored calibration values indicating (a) a camera ray corresponding to each pixel on the camera sensor of each one of the one or more cameras, and (b) a projector ray corresponding to each feature of the projected pattern of light from each one of the one or more structured light projectors, whereby each projector ray corresponds to a respective path p of pixels on at least one of the camera sensors, a processor is used to perform a set of operations. The operations include running a correspondence algorithm to compute respective three-dimensional positions on the intraoral three-dimensional surface of a plurality of features of the projected pattern. The operations further include collecting data at a plurality of points in time, the data including the computed respective three-dimensional positions on the intraoral three-dimensional surface of the plurality of features. The operations further include, for each projector ray r, based on the collected data, defining an updated path p' of pixels on each of the camera sensors, such that all of the computed three-dimensional positions corresponding to features produced by projector ray r correspond to locations along the respective updated path p' of pixels for each of the camera sensors. The operations further include using the data to recalibrate the stored calibration values.

In one embodiment, to recalibrate the stored calibration values, the processor performs additional operations. The additional operations include comparing each updated path p' of pixels to the path p of pixels corresponding to that projector ray r on each camera sensor from the stored calibration values. If for at least one camera sensor s, the updated path p' of pixels corresponding to projector ray r differs from the path p of pixels corresponding to projector ray r from the stored calibration values, the difference between the updated path p' of pixels corresponding to each projector ray r and the respective path p of pixels corresponding to each projector ray r from the stored calibration values is reduced by varying stored calibration data. The stored calibration data may be include (i) the stored calibration values indicating a camera ray corresponding to each pixel on the camera sensors of each one of the one or more cameras and/or (ii) the stored calibration values indicating a projector ray r corresponding to each one of the projected features from each one of the one or more structured light projectors.

FIGS. 46A and 46B also show updated camera sensor paths for each of the projector rays, based on collected data as described hereinabove. In FIG. 46A, updated paths 91*a*-1, 91*b*-1, and 91*c*-1 are shown, corresponding, respectively to projector rays 88*a*, 88*b*, and 88*c* as seen by camera 1, and in FIG. 46B, updated paths 91*a*-2, 91*b*-2, and 91*c*-2 are shown, corresponding, respectively to projector rays 88*a*, 88*b*, and 88*c* as seen by camera 2. In this example, in camera sensors 58 of both camera 1 and camera 2, all of the updated paths 91*a*, 91*b*, and 91*c*, corresponding respectively to projector rays 88*a*, 88*b*, and 88*c* from a particular projector 22 are shifted in generally the same manner, e.g., the updated paths on each camera sensor all translate in the same direction, with little or no rotation. Thus, it may be reasonable to assume that the particular projector 22 has shifted, resulting in the same shift being observed on both cameras 1 and 2.

However, for some applications, in order to conclusively determine that it is that particular projector 22 that has shifted, as opposed to camera 1 and camera 2 both having shifted, the updated paths 91 corresponding to projector rays 88 from a different projector should be considered, as seen by the same cameras 1 and 2, such as is shown in FIGS. 46C-D. The particular projector 22 of FIGS. 46A-B is now referred to as a first projector 22-1. FIGS. 46C-D show the same camera sensor paths for the first projector 22-1 (90*a*-1, 90*b*-1, 90*c*-1, 90*a*-2, 90*b*-2, and 90*c*-2) as in FIGS. 46A-B, and the same updated paths for the first projector 22-1 (91*a*-1, 91*b*-1, 91*c*-1, 91*a*-2, 91*b*-2, and 91*c*-2) as seen in FIGS. 46A-B.

FIG. 46C additionally shows (i) three camera sensor paths (90*d*-1, 90*e*-1, 90*f*-1) for three respective projector rays 88*d*, 88*e*, and 88*f* of the second projector 22-2, and (ii) corresponding updated paths (91*d*-1, 91*e*-1, and 91*f*-1) for the three respective projector rays 88*d*, 88*e*, and 88*f* of the second projector 22-2, as seen by camera 1. FIG. 46D additionally shows (i) the same three camera sensor paths (90*d*-2, 90*e*-2, and 90*f*-2) for the three respective projector rays 88*d*, 88*e*, and 88*f* from second projector 22-2, and (ii) corresponding updated paths (91*d*-2, 91*e*-2, 91*f*-2) for the three respective projector rays 88 of the second camera 24-2, as seen by camera 2.

It is observed that, for second projector 22-2, both camera 1 and camera 2 see the updated paths (91*d*-1, 91*e*-1, and 91*f*-1 on camera 1 and 91*d*-2, 91*e*-2, and 91*f*-2 on camera 2), corresponding respectively to projector rays 88*d*, 88*e*, and 88*f* of second projector 22-2 as not having shifted, while for first projector 22-1, both camera 1 and camera 2 see the updated paths (91*a*-1, 91*b*-1, 91*c*-1 on camera 1 and 91*a*-2, 91*b*-2, and 91*c*-2 on camera 2) corresponding respectively to projector rays 88*a*, 88*b*, and 88*c* of first projector 22-1 as having shifted in the same manner, such as described above with reference to FIGS. 46A-B. It can thus be concluded, that the first projector 22-1 has shifted and the first projector 22-1 should be recalibrated as described hereinabove.

Reference is now made to FIGS. 47A-B, which show a simplified scenario in which processor 96 identifies that it is a camera that should be recalibrated and not any of the projectors, i.e., camera rays 86 for all pixels in camera sensor 58 of a particular camera 24 should be redefined, in accordance with some applications of the present invention. FIG. 47A shows camera sensor 58 of a first camera (camera 1). Three camera sensor paths 90*a*-1, 90*b*-1, and 90*c*-1, based on stored calibration values, are shown on camera sensor 58 of camera 1, corresponding, respectively, to three projector rays 88*a*, 88*b*, and 88*c* from a first projector 22. Another three camera sensor paths 90*d*-1, 90*e*-1, and 90*f*-1, based on stored calibration values, are shown on camera sensor 58 of camera 1, corresponding, respectively, to three projector rays 88*d*, 88*e*, and 88*f* from a second projector 22. FIG. 47A also shows updated camera sensor paths for each of the projector rays, based on collected data as described hereinabove. Updated paths 91*a*-1, 91*b*-1, and 91*c*-1 correspond, respectively, to projector rays 88*a*, 88*b*, and 88*c* from the first projector 22, and updated paths 91*d*-1, 91*e*-1, and 91*f*-1 correspond, respectively, to projector rays 88*d*, 88*e*, and 88*f* from the second projector 22. As is apparent from FIG. 47A, all the updated camera sensor paths from more than one projector are appearing shifted in the camera sensor of camera 1 with respect to their corresponding camera sensor paths from the stored calibration values. At this point in the analysis it could be concluded that either (i) camera 1 has shifted, or a change has occurred in the optics of camera 1, or (ii) that both projector 1 and projector 2 have shifted, or changes have occurred in the respective optics of projector 1 and projector 2.

FIG. 47B shows camera sensor 58 of a second camera (camera 2). Three camera sensor paths 90*a*-2, 90*b*-2, and 90*c*-2, based on stored calibration values, are shown on camera sensor 58 of camera 2. The three paths 90*a*-2, 90*b*-2, and 90*c*-2 correspond, respectively, to the same three projector rays that paths 90*a*-1, 90*b*-1, and 90*c*-1 on camera 1 correspond to, namely, projector rays 88*a*, 88*b*, and 88*c* from the first projector 22. Another three paths 90*d*-2, 90*e*-2, and 90*f*-2, based on stored calibration values, are shown on camera sensor 58 of camera 2. The three paths 90*d*-2, 90*e*-2, and 90*f*-2 correspond, respectively, to the same three projector rays that paths 90*d*-1, 90*e*-1, and 90*f*-1 on camera 1 correspond to, namely, projector rays 88*d*, 88*e*, and 88*f* from the second projector 22. FIG. 47B also shows updated camera sensor paths for each of the projector rays, based on collected data as described hereinabove. Updated paths 91*a*-2, 91*b*-2, and 91*c*-2 correspond, respectively, to projector rays 88*a*, 88*b*, and 88*c* from the first projector, and updated paths 91*d*-2, 91*e*-2, and 91*f*-2 correspond, respectively, to projector rays 88*d*, 88*e*, and 88*f* from the second projector. As is apparent from the figure, all of the updated camera sensor paths in camera 2, which correspond to the same projector rays from the same two projectors as on camera 1, appear to match their corresponding camera sensor paths from the stored calibration values. It can therefore reasonably be assumed that camera 1 has shifted and not the projectors.

Figures 48A, 48B:
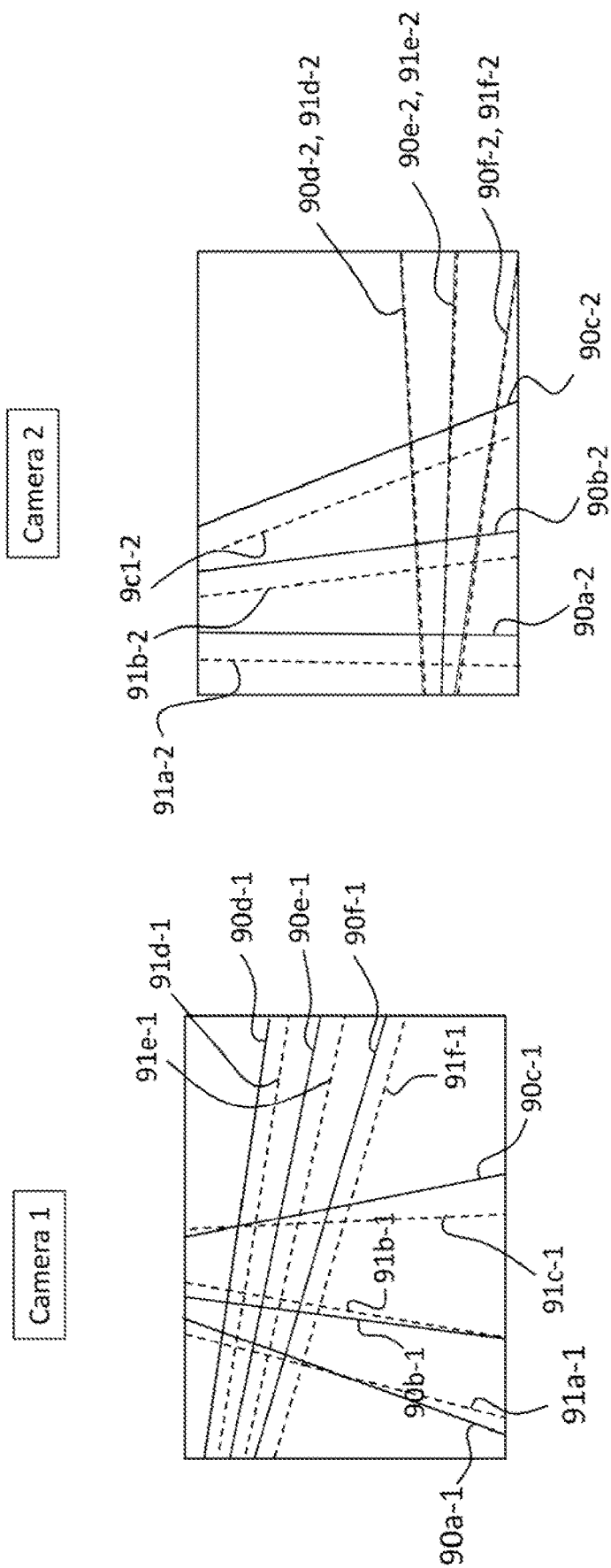
FIGS. 48A-B show a simplified scenario in which the processor cannot reasonably assume that a shift has occurred in only a camera or only a projector, in accordance with some applications of the present invention.

Reference is now made to FIGS. 48A-B, which show a simplified scenario in which processor 96 cannot reasonably assume that a shift has occurred in only a camera or only a projector, and processor 96 should (a) redefine projector rays 88 from at least one projector 22 (as described hereinabove by either re-assigning the values of indexed projector rays 88 or varying one or more parameters in the projector calibration model), and (b) also redefine camera rays 86 from at least one camera 24 (as described hereinabove by varying one or more parameters of the stored camera calibration function), in accordance with some applications of the present invention. Similarly to the above examples with reference to FIGS. 46A-B and FIGS. 47A-B, camera sensor paths 90*a*-1, 90*b*-1, and 90*c*-1 (based on stored calibration values and corresponding, respectively, to projector rays 88*a*, 88*b*, and 88*c* from a first projector 22) are shown on camera sensor 58 of camera 1. Corresponding updated camera sensor paths 91*a*-1, 91*b*-1, and 91*c*-1, based on collected data as described hereinabove, are shown as well. Additionally, camera sensor paths 90*d*-1, 90*e*-1, and 90*f*-1, based on stored calibration values and corresponding, respectively, to projector rays 88*d*, 88*e*, and 88*f* from a second projector 22, are shown on camera sensor 58 of camera 1. Corresponding updated camera sensor paths 91*d*-1, 91*e*-1, and 91*f*-1, based on collected data as described hereinabove, are shown as well.

FIG. 48B shows camera sensor 58 of a second camera (camera 2). Three camera sensor paths 90*a*-2, 90*b*-2, and 90*c*-2, based on stored calibration values, are shown on camera sensor 58 of camera 2. The three paths 90*a*-2, 90*b*-d, and 90*c*-2 correspond, respectively, to the same three projector rays that paths 90*a*-1, 90*b*-1, and 90*c*-1 on camera 1 correspond to, namely, projector rays 88*a*, 88*b*, and 88*c* from the first projector 22. Another three paths 90*d*-2, 90*e*-2, and 90*f*-2, based on stored calibration values, are shown on camera sensor 58 of camera 2. The three paths 90*d*-2, 90*e*-2, and 90*f*-2 correspond, respectively, to the same three projector rays that paths 90*d*-1, 90*e*-1, and 90*f*-1 on camera 1 correspond to, namely, projector rays 88*d*, 88*e*, and 88*f* from the second projector 22. FIG. 48B also shows updated camera sensor paths for each of the projector rays, based on collected data as described hereinabove. Updated paths 91*a*-2, 91*b*-2, and 91*c*-2 correspond, respectively, to projector rays 88*a*, 88*b*, and 88*c* from the first projector, and updated paths 91*d*-2, 91*e*-2, and 91*f*-2 correspond, respectively, to projector rays 88*d*, 88*e*, and 88*f* from the second projector.

In the example of FIGS. 48A-B, the updated camera sensor paths corresponding to the projector rays of the second projector appear to all be shifted in generally the same manner on camera sensor 58 of camera 1 (e.g., the updated camera sensor paths all appear to translate in the same direction with little to no rotation). However, the updated camera sensor paths corresponding to the projector rays of the first projector appear to all be shifted in different respective directions on camera sensor 58 of camera 1 (the shifting including rotating of the updated camera sensor paths to varying extents and not all in the same direction). Furthermore, the updated camera sensor paths corresponding to the projector rays of the first projector appear to all be shifted in generally the same manner on camera sensor 58 of camera 2, and the updated camera sensor paths corresponding to the projector rays of the second projector do not appear to be shifted at all on camera sensor 58 of camera 2. It can therefore, in this example, not be assumed that either camera 1, or camera 2, or projector 1 or projector 2 can alone be recalibrated to solve the entire scenario. In addition, in this example, it can be seen that camera 2 and projector 2 do not need to be recalibrated.

Thus, for some applications, processor 96 recalibrates projectors 22 and cameras 24 by performing an optimization algorithm that iteratively varies the respective parameters in the stored calibration data for (a) projector rays 88 from at least one projector 22, and (b) camera rays 86 from at least one camera 24, until a solution is found that reduces the difference between each (i) updated path 91 of pixels corresponding to a projector ray 88 and (ii) the path 90 of pixels corresponding to the projector ray 88 from the stored calibration values.

Reference is now made to FIGS. 49A-B, which are schematic illustrations, respectively, of three-dimensional and two-dimensional calibration objects 288, in accordance with some applications of the present invention. For some applications, in order to further improve the optimization algorithm, a calibration object having known features, i.e., parameters, e.g., dimensions such as the dimensions illustrated by arrows 290, may be used. Each of cameras 24 is driven to capture a plurality of images of calibration object 288. For some applications, calibration object 288 may be a three-dimensional calibration object with predetermined, i.e., known, dimensions and shapes, such as the dimensions of the illustrative calibration object 288 illustrated by arrows 290 in FIG. 49A. Alternatively or additionally, calibration object 288 may be a two-dimensional calibration object that includes a pattern of visually-distinguishable, e.g., unique, features, with the distances between the visually-distinguishable features being predetermined, i.e., known, such as the distances illustrated by arrows 290 in FIG. 49B. It is noted that when using two-dimensional calibration object 288, each one of cameras 24 is driven to capture a plurality of images of two-dimensional calibration object 288 from a plurality of different viewpoints with respect to two-dimensional calibration object 288. Processor 96 performs a triangulation algorithm using the captured images of calibration object 288 in FIG. 49A or FIG. 49B in order to compute the respective parameters of calibration object 288, e.g., dimensions such as the dimensions illustrated by arrows 290, and thereby determine if cameras 24 are calibrated to the correct scale. The computed respective parameters of calibration object 288 are then used in the optimization algorithm, optionally along with the collected data from the collected accumulated data while handheld intraoral scanner 20 is being used to scan.

If (a) the dimensions, e.g., dimensions illustrated by arrows 290, of a 3D calibration object 288 as determined by triangulation from cameras 24 are the same as the known dimensions of the 3D calibration object 288, or (b) the distances between the visually-distinguishable (e.g., unique) features, e.g., distances illustrated by arrows 290, of a 2D calibration object 288 as determined by triangulation from cameras 24 are the same as the predetermined dimensions, i.e., known distances between the visually-distinguishable, e.g., unique, features, then cameras 24 are determined to be calibrated in the correct scale. If the triangulated dimensions or distances 290 are not the same as the known dimensions or distances 290 then processor 96 may determine what the difference in scale is. The resulting information regarding the scale in which cameras 24 are calibrated is fed into the optimization algorithm described hereinabove, such that when the optimization is complete, the calibrated scale of cameras 24 is correct.

Reference is again made to FIG. 1, and FIG. 2C-E. For some applications, there is at least one unstructured light projector 118 coupled to rigid structure 26. Unstructured light projector 118 may transmit unstructured light, which may be uniform light, non-coherent light and/or broad spectrum light (e.g., white light), onto object 32 being scanned. For example, unstructured light projector 118 may be a light emitting diode (LED), or other broad spectrum or non-coherent light source. For some applications, unstructured light projector 118 may be a near infrared (NIR) light source. At least one camera, e.g., one of cameras 24, captures two-dimensional images of object 32 using illumination from unstructured light projector 118, where the two-dimensional images may be two-dimensional color images. Processor 96 may run a surface reconstruction algorithm that combines at least one image captured using illumination from structured light projectors 22 with a plurality of images captured using illumination from unstructured light projector 118 in order to generate a digital three-dimensional image of the intraoral three-dimensional surface. Using a combination of structured light and unstructured light (e.g., uniform illumination) enhances the overall capture of the intraoral scanner and may help reduce the number of options that processor 96 considers when running the correspondence algorithm.

Figure 50:
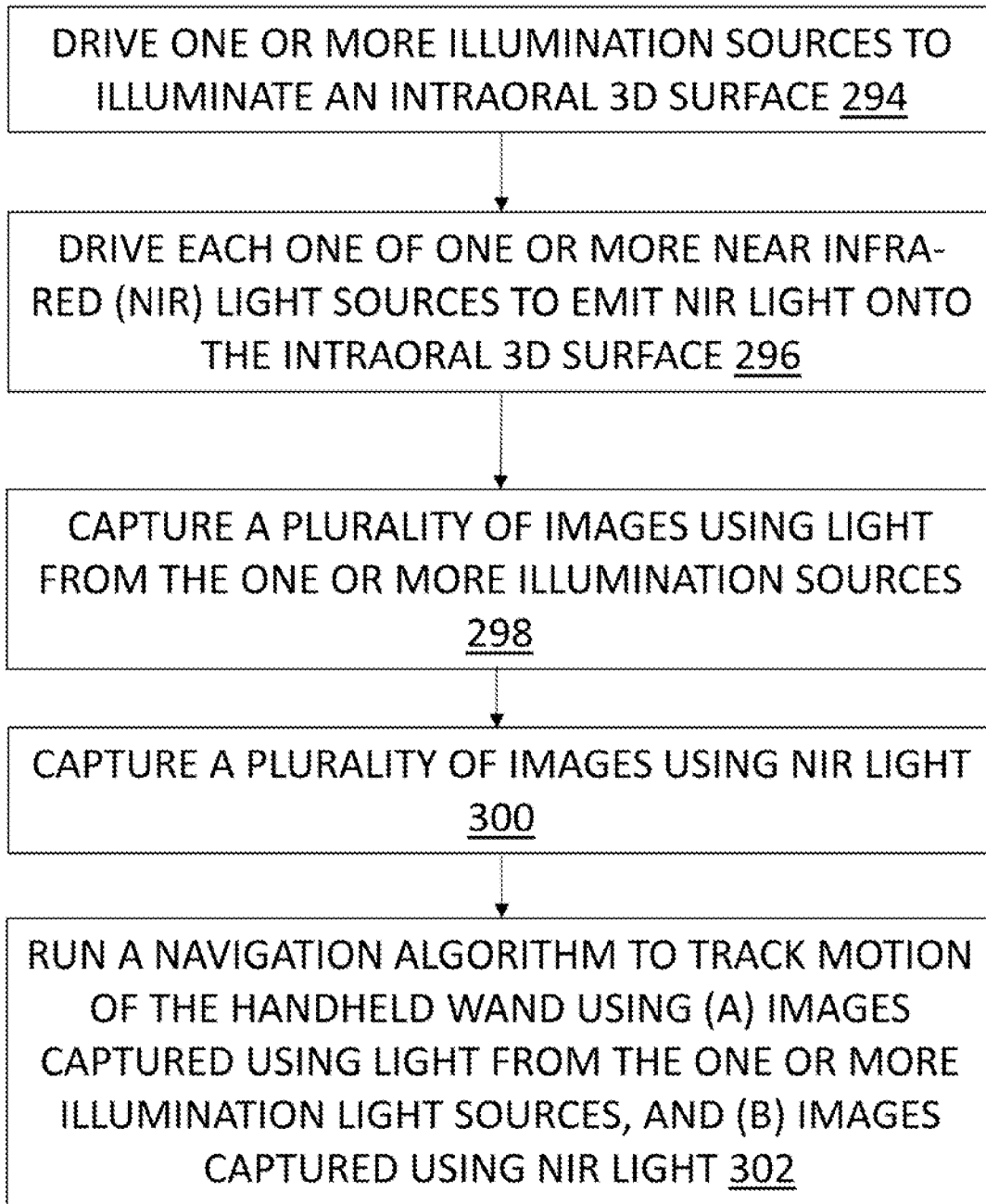
FIG. 50 is a flowchart depicting a method for tracking motion of the handheld wand, in accordance with some applications of the present invention.

Reference is now made to FIG. 50, which is a flowchart depicting a method for tracking motion of the intraoral scanner, i.e., handheld wand 20, in accordance with some applications of the present invention. As described hereinabove, the visual tracking of the motion of the intraoral scanner with respect to object 32 being scanned may be obtained by stitching of the respective surfaces or point clouds obtained from adjacent image frames. As described herein, for some applications, illumination of the intraoral cavity under near infrared (NIR) light may increase the number of visible features that can be used to stitch the respective surfaces or point clouds obtained from adjacent image frames. In particular, NIR light penetrates the teeth, such that images captured under NIR light include features that are inside the teeth, e.g., cracks within a tooth, as opposed to two-dimensional color images taken under broad spectrum illumination in which only features appearing on the surface of the teeth are visible. These additional sub-surface features may be used for stitching the respective surfaces or point clouds obtained from adjacent image frames.

Thus, for some applications:
one or more illumination light sources, e.g., one or more structured light projectors 22, and/or one or more unstructured light projectors 118, are driven to illuminate the intraoral three-dimensional surface (step 294),
one or more NIR light sources 292 are driven to emit NIR light onto the intraoral three-dimensional surface (step 296),
a plurality of images are captured, e.g., using cameras 24, using light from the illumination light sources (step 298),
a plurality of images are captured, e.g., using cameras 24, using NIR light (step 300), and
processor 96 runs a navigation algorithm to track motion of handheld wand 20 using (A) images captured using light from the illumination light sources, and (B) images captured using the NIR light (step 302).

For some applications processor 96 may use the two-dimensional images in a 2D-to-3D surface reconstruction of the intraoral three-dimensional surface, as further described hereinbelow. An advantage to using the two-dimensional images for three-dimensional reconstruction of the surface is that in each two-dimensional image there are typically hundreds of thousands of pixels which can be used for triangulation in the three-dimensional reconstruction algorithm, as opposed to the projected features (e.g., spots) from structured light projectors 22, which are on the order of magnitude of a few hundred projected spots from each structured light projector 22. Thus, using two-dimensional images may significantly increase the resolution of the three-dimensional reconstruction. Additionally, in some image frames there may be low capture from the structured light due to (a) the potentially low contrast of the structured light pattern on the intraoral surface, e.g., teeth, as described hereinabove, (b) potentially difficult-to-capture regions of the intraoral surface, e.g., narrow gaps, and/or (c) some of the projected spots potentially being blocked, e.g., by moving tissue such as the patient's tongue. Thus, as described herein, for some applications it is useful to augment the three-dimensional reconstruction of the intraoral three-dimensional surface with three-dimensional reconstruction from two-dimensional images. For some applications, the two-dimensional images are two-dimensional color images captured under illumination from a broad spectrum and/or incoherent light source, e.g., under illumination from a LED. Alternatively or additionally, the two-dimensional images may be monochromatic two-dimensional images captured using NIR light.

Typically, the capturing of the structured light and the capturing of the unstructured (e.g., broad spectrum, non-coherent, and/or NIR light) light is regulated so as to produce an alternating sequence of one or more image frames of structured light interspersed with one or more image frames of unstructured light. For example, an alternating pattern of three consecutive image frames of structured light and one image frame of unstructured light may be used. Alternatively, an alternating pattern of two consecutive image frames of structured light and two image frames of unstructured light may be used. Thus, as used herein, when referring to an image frame of unstructured light that is adjacent to an image frame of structured light, or vice versa, the adjacent image frame of unstructured light may be either before or after the image frame of structured light in the regulated sequence.

For some applications, all data points taken at a specific time, e.g., from a specific image frame of structured light, are used as a rigid point cloud, and multiple such point clouds are captured at a frame rate of over 10 captures per second. The plurality of point clouds are then stitched together using a registration algorithm, e.g., iterative closest point (ICP), to create a dense point cloud. For some applications, the registration algorithm uses the normal to the surface at each point, e.g., point-to-plane stitching, or plane-to-plane stitching. A surface reconstruction algorithm may then be used to generate a representation of the surface of object 32.

Figure 51A:
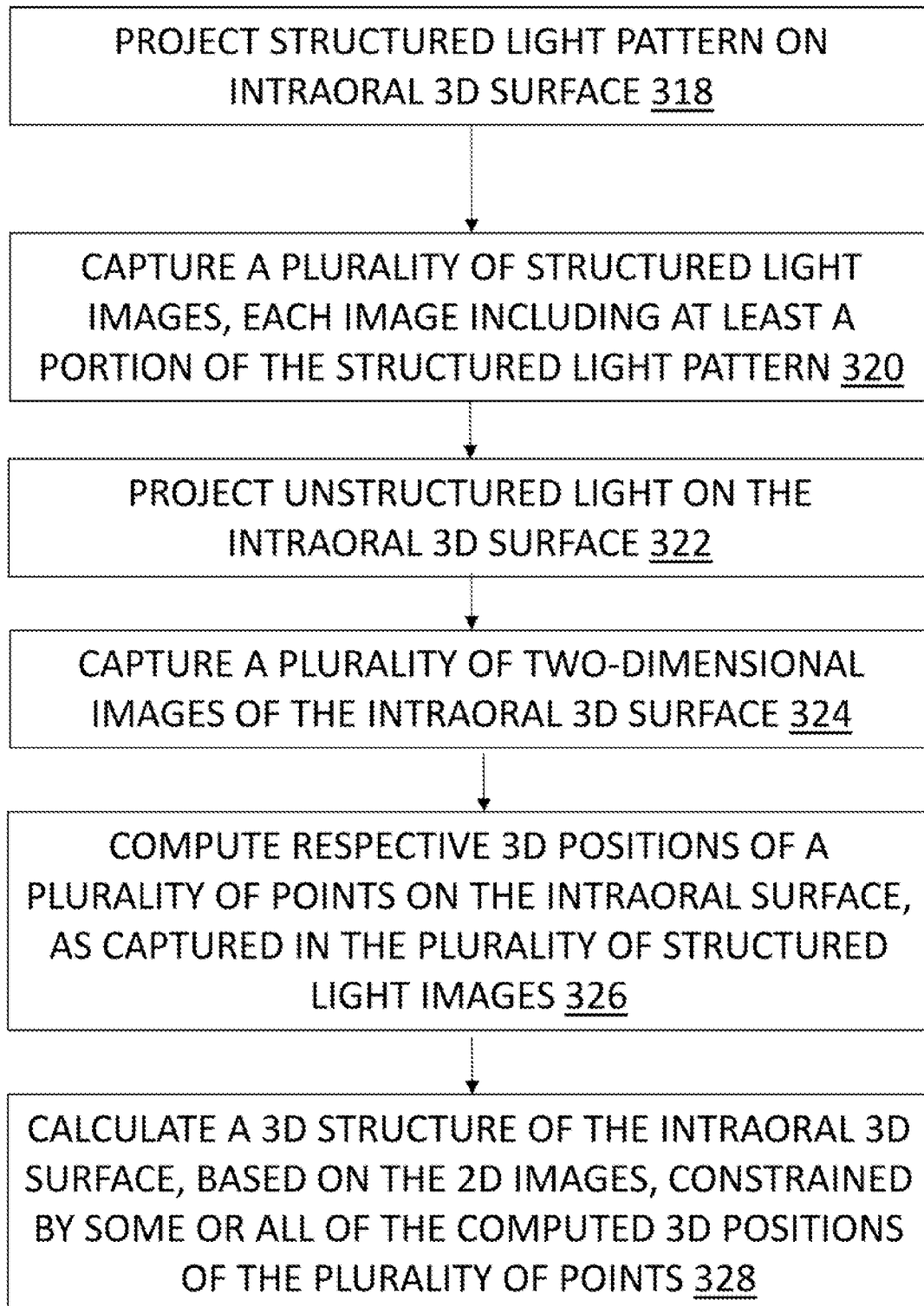
FIGS. 51A-F are flowcharts depicting a method for computing the three-dimensional structure of an intraoral three-dimensional surface, in accordance with some applications of the present invention.
Figure 51B:
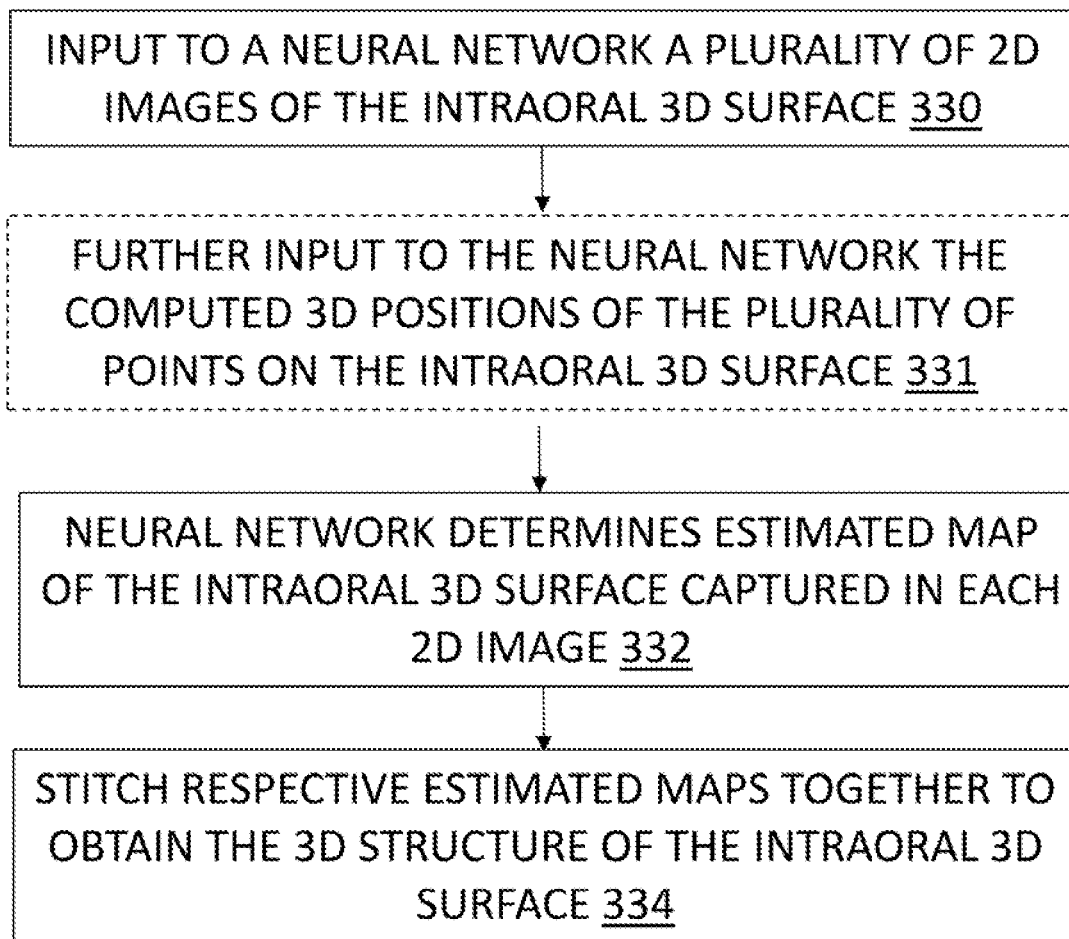

Reference is now made to FIGS. 51A-B, which are flowcharts depicting a method for computing the three-dimensional structure of an intraoral three-dimensional surface, in accordance with some applications of the present invention. One or more structured light projectors 22 are driven to project a structured light pattern, e.g., a distribution of discrete unconnected spots of light, on the intraoral three-dimensional surface (step 318). One or more cameras 24, e.g., each one of two or more cameras 24, are driven to capture a plurality of structured light images, each image including at least a portion of the structured light pattern (step 320). One or more unstructured light projectors 118 are driven to project unstructured light (e.g., broad spectrum light, non-coherent light, and/or NIR light) on the intraoral three-dimensional surface (step 322). Cameras 24 capture a plurality of two-dimensional images, using the unstructured light, e.g., two-dimensional color images or two-dimensional monochromatic images, of the intraoral three-dimensional surface (step 324). Processor 96 then (a) computes respective three-dimensional positions of a plurality of points on the intraoral three-dimensional surface, as captured in the plurality of structured light images, e.g., using the correspondence algorithm described hereinabove, (step 326), and (b) computes a three-dimensional structure of the intraoral three-dimensional surface, based on the plurality of two-dimensional images of the intraoral three-dimensional surface, constrained by some or all the computed three-dimensional positions of the plurality of points (step 328). Typically, the points that are used to constrain the computed three-dimensional structured of the intraoral three-dimensional surface are points in a particular region of interest for any given two-dimensional images.

FIG. 51B is a flowchart depicting how step 328 of FIG. 51A is performed, in accordance with some applications of the present invention. For some applications, the computation of the three-dimensional structure is performed by a neural network 400 (for example, shown in FIGS. 51G-I, 52B, 52D-F, 58, and 59A-B), as described herein below. The neural network may be, for example, a deep network, a recurrent neural network, a long short-term memory neural network, an auto encoder, a generative adversarial network (GAN), a convolutional network, and so on. In alternative embodiments, other types of machine learning algorithms or machine learning models may be used to perform the computation, which may be generated via supervised learning or unsupervised learning, depending on the machine learning model. Non-limiting examples of other types of machine learning models that may be used include support vector machines, decision trees, random forests, linear regression, logistic regression, k-nearest neighbors, gradient boosting algorithms, and so on. In some embodiments, a series of multiple machine learning models may be used, where an output of one machine learning model may be input into another machine learning model.

Figure 58:
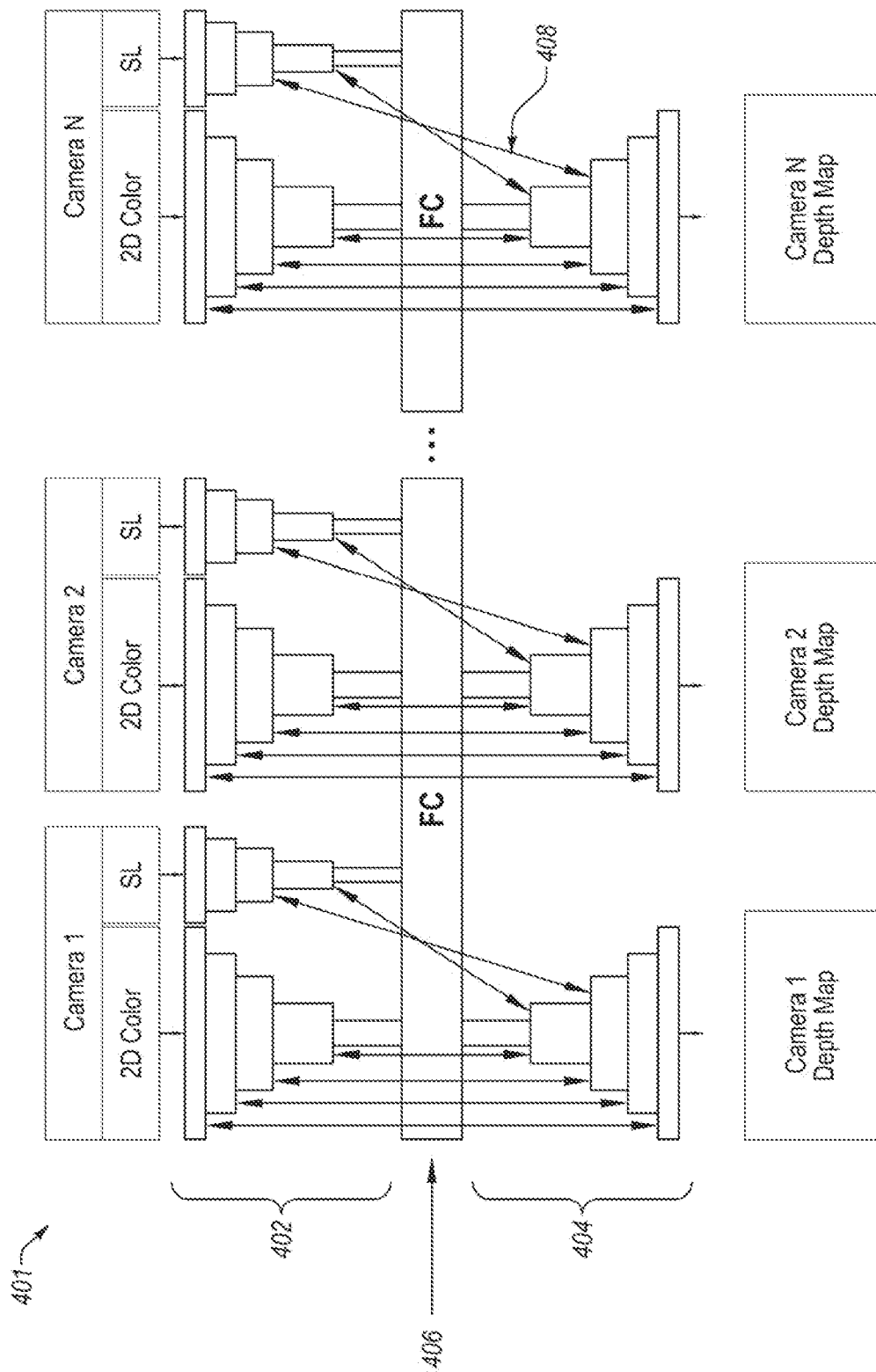
FIGS. 58 and 59A-B are schematic illustrations of a neural network in accordance with some applications of the present invention.
Figure 59A:
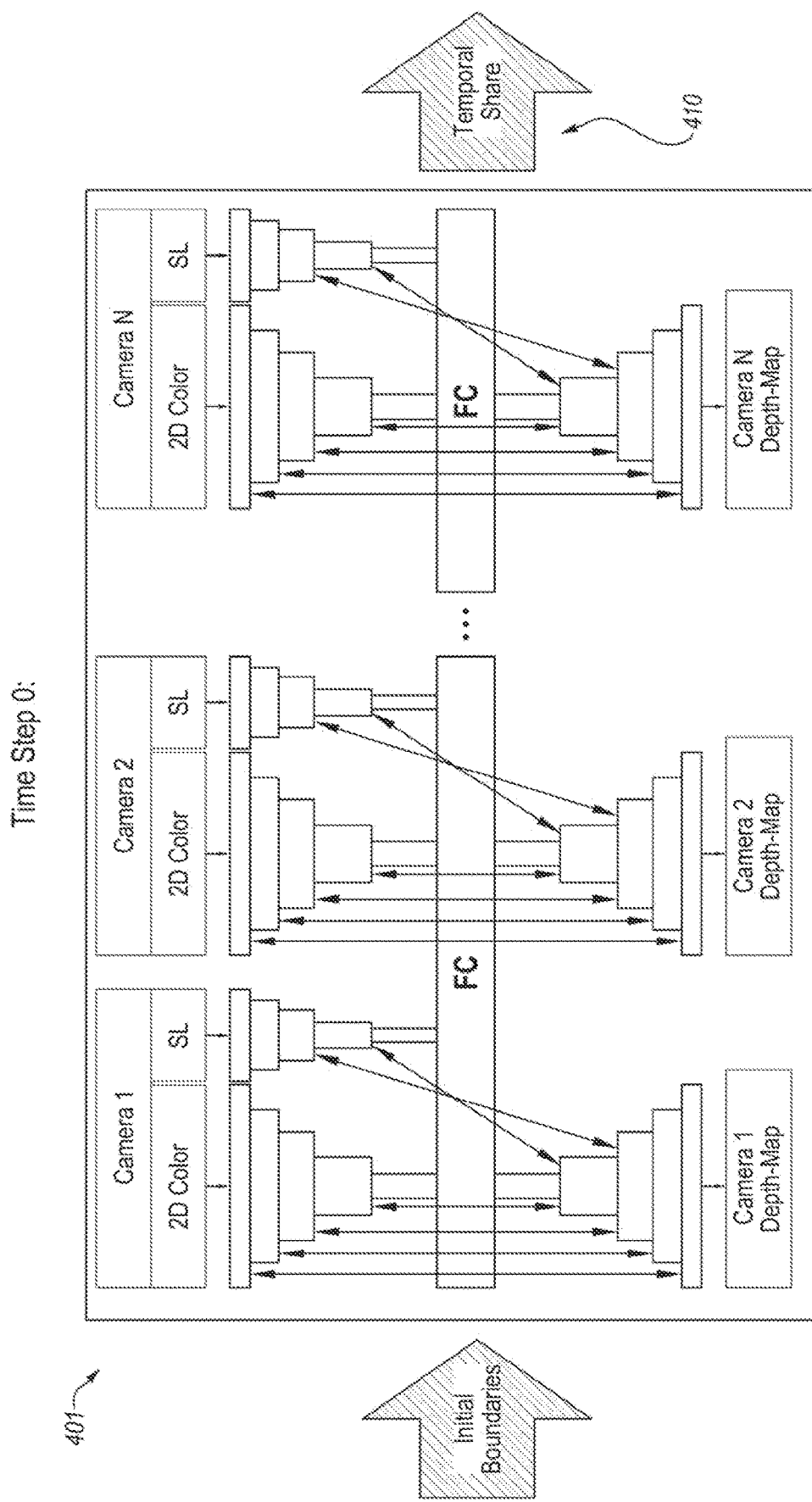
Figure 59B:
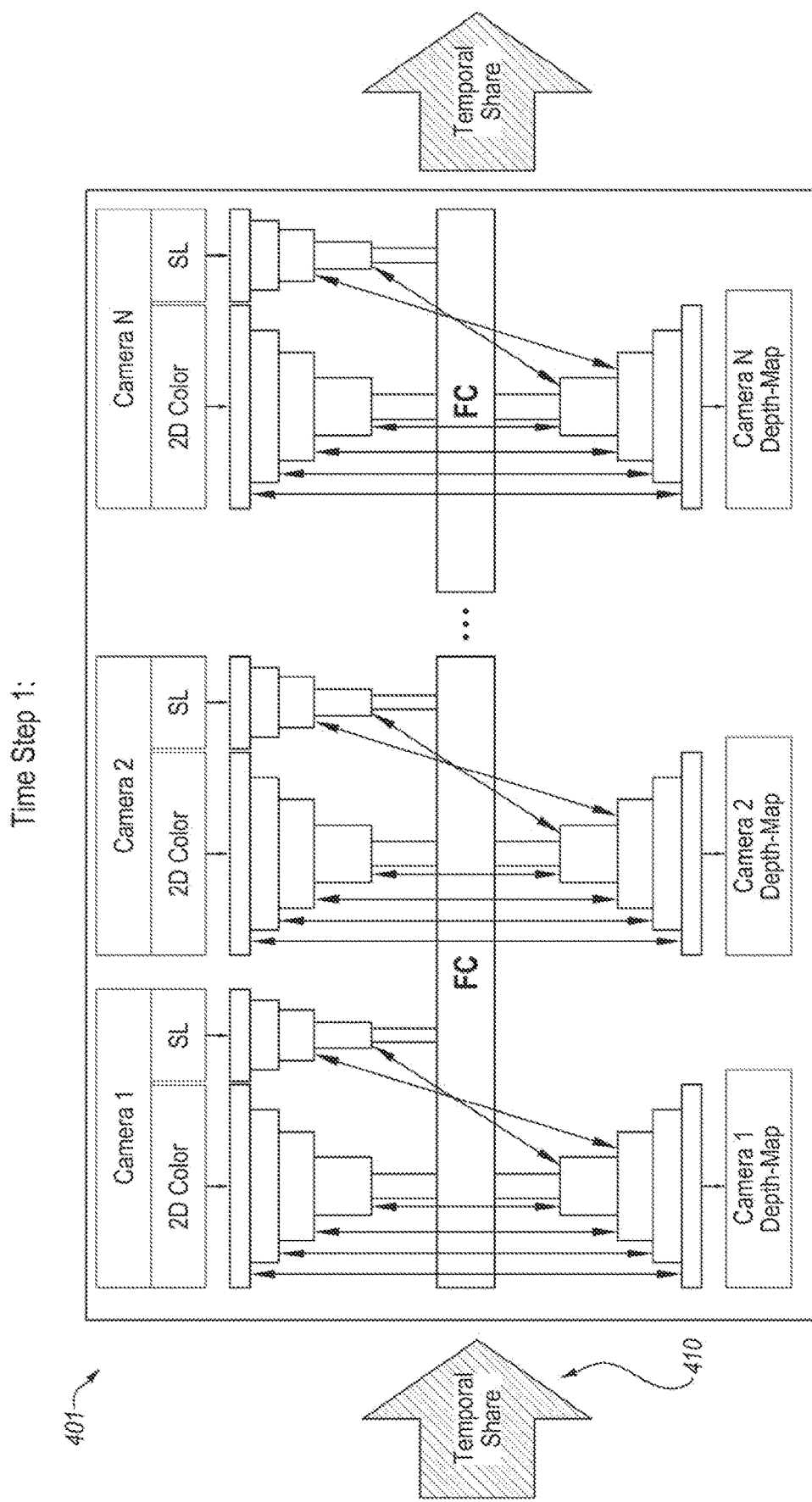

For some applications, processor 96 inputs to neural network 400 (or other machine learning model), e.g., neural network 401 as further described hereinbelow with reference to FIGS. 58, 59A, and 59B, (a) the plurality of two-dimensional images of the intraoral three-dimensional surface (step 330), and, optionally, (b) the computed respective three-dimensional positions of the plurality of points on the intraoral three-dimensional surface (step 331), and the neural network determines and returns a respective estimated map of the intraoral three-dimensional surface as captured in each of the two-dimensional images (step 332), further described hereinbelow. For some applications, the respective estimated maps are stitched together to obtain the three-dimensional structure of the intraoral three-dimensional surface (step 334).

Figure 51C:
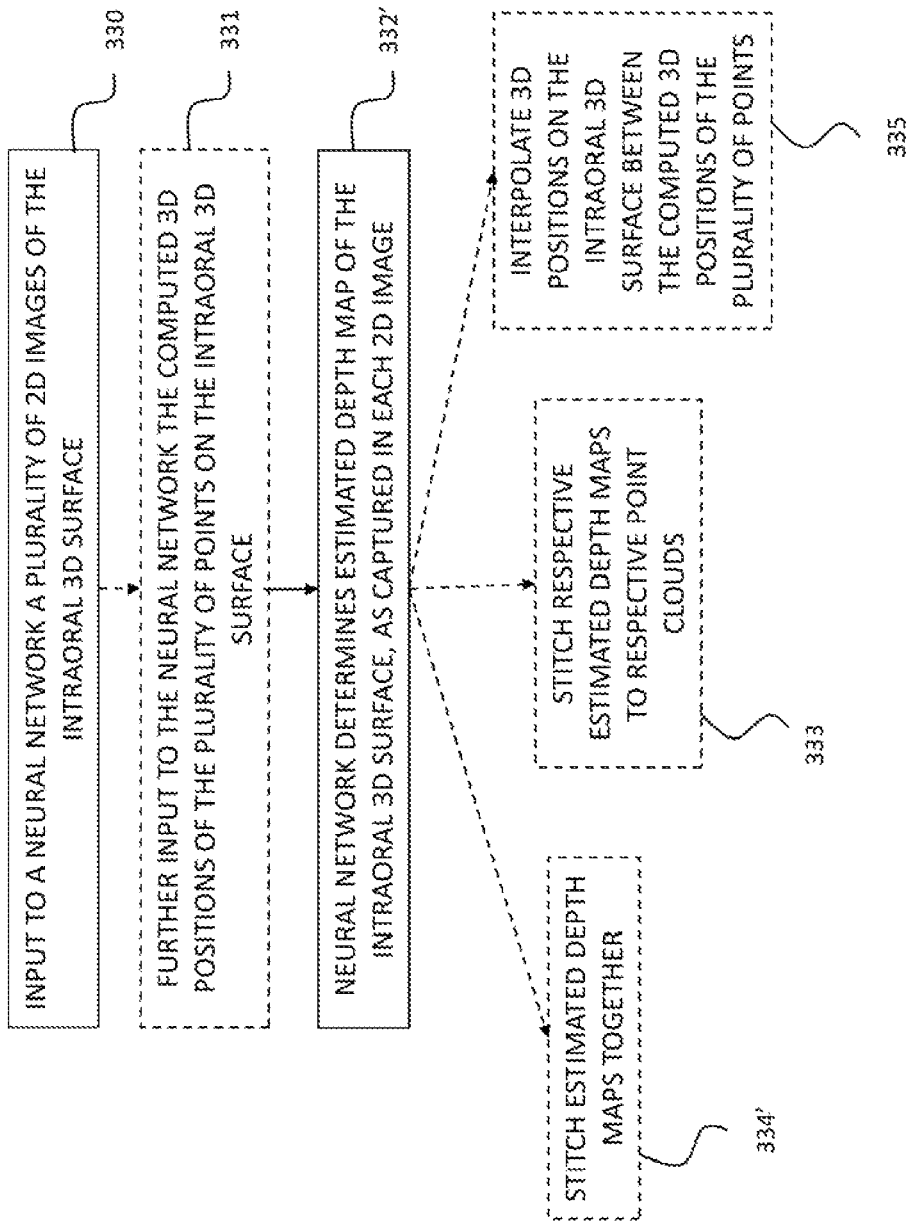

Reference is now made to FIG. 51C, which is a flow chart which depicts a specific application of step 332 of FIG. 51B, in accordance with some applications of the present invention. Steps 330 and 331 of FIG. 51C are the same as for FIG. 51B. For some applications, in step 332', neural network 400, e.g., neural network 401, determines and returns a respective estimated depth map (also known as a height map) of the intraoral three-dimensional surface as captured in each of the two-dimensional images. In step 334' the respective estimated depth maps, each being from a respective image frame of unstructured light, may be stitched together to obtain the three-dimensional structure of the intraoral three-dimensional surface. Alternatively or additionally, each depth map may be stitched to a respective point cloud from an adjacent image frame of structured light (step 333). The depth maps may also be used to interpolate three-dimensional positions on the intraoral three-dimensional surface (step 335) that are between the computed respective three-dimensional positions of the plurality of points on the intraoral three-dimensional surface as captured in the structured light images, thus increasing the resolution of the three-dimensional structured light reconstruction.

Figure 51D:
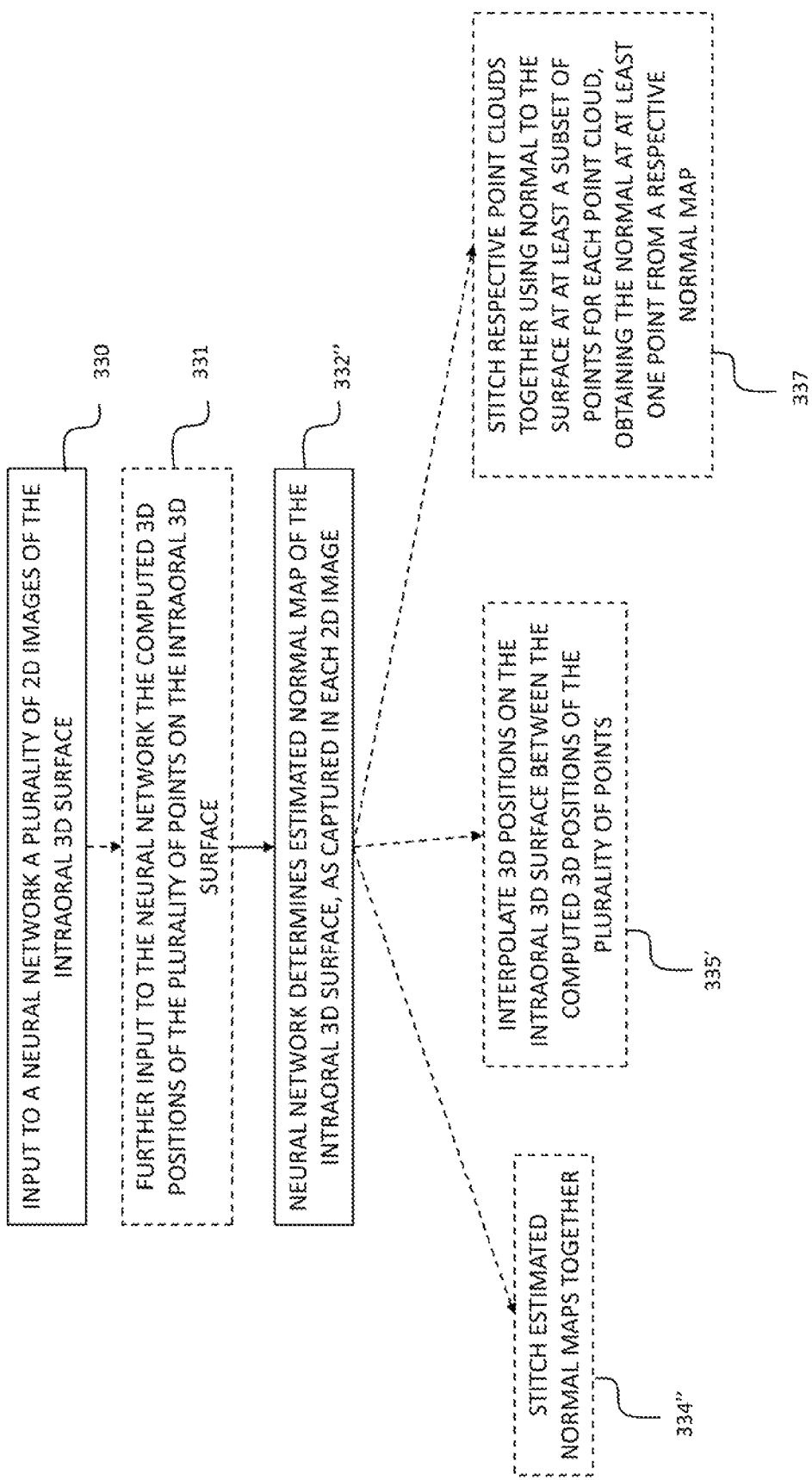

Reference is now made to FIG. 51D, which depicts a specific application of step 332 of FIG. 51B, in accordance with some applications of the present invention. Steps 330 and 331 of FIG. 51D are the same as for FIG. 51B. For some applications, in step 332", neural network 400, e.g., neural network 401, determines and returns a respective estimated normal map of the intraoral three-dimensional surface as captured in each of the two-dimensional images. The normal map represents the normal to the surface at every point on the intraoral surface as captured in the two-dimensional image, and is an integration of the depth map. In step 334" the respective estimated normal maps, each being from a respective image frame of unstructured light, may be stitched together to obtain the three-dimensional structure of the intraoral three-dimensional surface. For some applications, for each input neural network 400 may return both a depth map and the corresponding normal map.

Similarly to as described hereinabove with reference to the depth map, the normal maps may also be used to interpolate three-dimensional positions on the intraoral three-dimensional surface (step 335') that are between the computed three-dimensional positions of the plurality of points on the intraoral three-dimensional surface as captured in the structured light images. Without the information provided by the normal map, it is possible that when trying to interpolate between structured light points on the intraoral three-dimensional surface, the interpolation, i.e., integration, may result in a smooth surface where in reality there may be a sharp curve, edge, or other feature of the intraoral three-dimensional surface. Having the normal to the surface at each point from the respective normal maps helps the interpolation, i.e., integration, maintain any non-smooth surfaces that may otherwise have been missed.

As described hereinabove, for some applications, the registration, i.e., stitching, algorithm that is used by processor 96 to stitch respective point clouds together from respective structured light image frames uses the normal to the surface at each point of the point cloud. When the computed respective positions of the structured light points on the intraoral three-dimensional surface are close enough to each other, then the normal at each point may be calculated based on the positions of the neighboring points. However, in regions where the structured light points are sparse, processor 96 may not be able to calculate the normals based on neighboring points. In such cases, the missing normals may be obtained from the normal map as determined by the neural network (step 337).

Figure 51E:
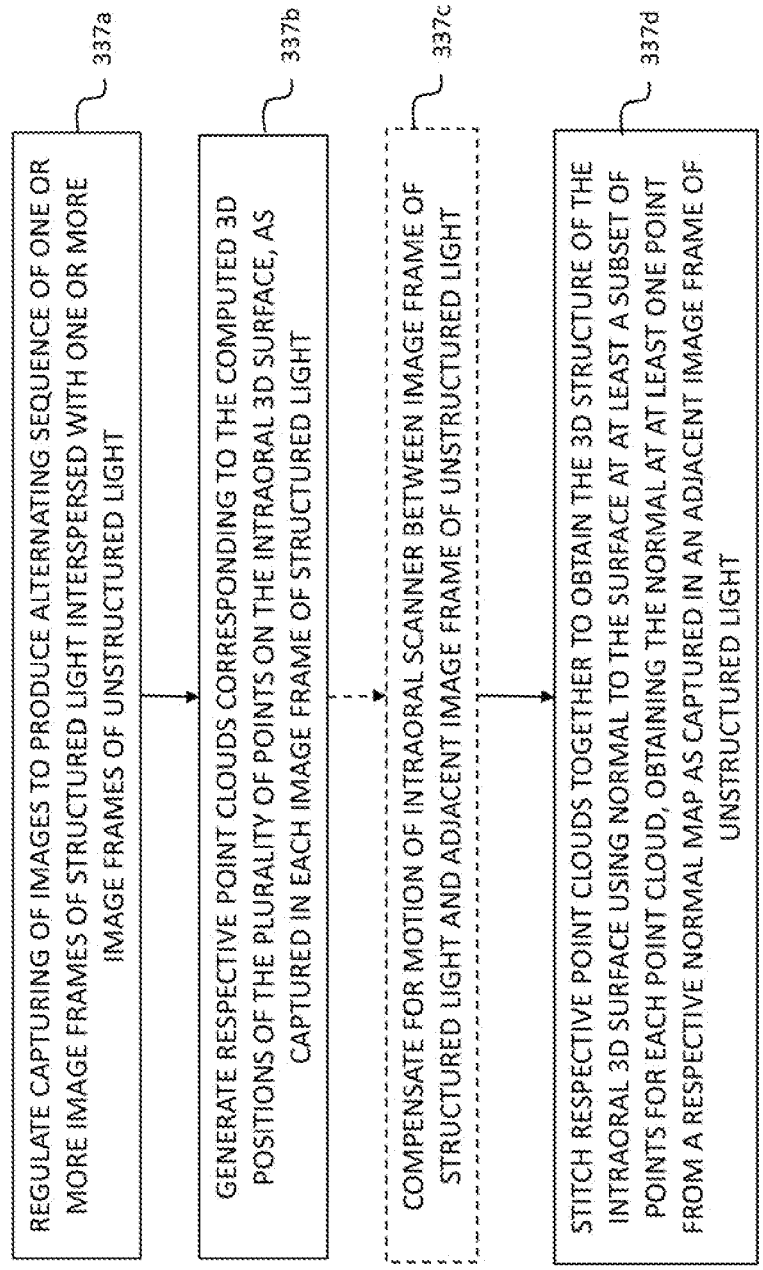

Reference is now made to FIG. 51E, which depicts step 337 from FIG. 51D in more detail, in accordance with some applications of the present invention. As described hereinabove, the capturing of the structured light and the capturing of the two-dimensional images using the unstructured light (e.g., broad spectrum, non-coherent, and/or NIR light) is regulated so as to produce an alternating sequence of one or more image frames of structured light interspersed with one or more image frames of unstructured light (step 337a). Processor 96 (a) generates a respective point cloud corresponding to the computed respective three-dimensional positions of the plurality of points on the intraoral three-dimensional surface, as captured in each image frame of structured light (step 337b), and (b) stitches the respective point clouds together using, as an input to the stitching, for at least a subset, e.g., some or all, of the plurality of points for each point cloud, the normal to the surface at each point of the subset of points (step 337d). For a given point cloud the normal to the surface at at least one point of the subset of points is obtained from the respective estimated normal map of the intraoral three-dimensional surface as captured in an adjacent image frame of unstructured light.

As described hereinabove, an adjacent image frame of unstructured light may be either before or after the image frame of structured light from which the point cloud was generated. Typically, the time between each image frame is at least 3 ms and/or less than 100 ms, such that a normal map obtained from an unstructured light image frame that is adjacent to a structured light image frame represents almost the exact same surface as the point cloud from the structured light image frame. Nevertheless, for some applications, even the slight motion of the intraoral scanner between the structured light image frame and the adjacent unstructured image frame may be compensated (step 337c) by estimating the motion of the intraoral scanner based on previous image frames, i.e., based on previous structured and/or unstructured image frames. By way of example and not limitation, motion estimation methods may be used such as an IMU, either alone or in combination with visual tracking, as described hereinabove, or a SLAM algorithm as further described hereinbelow.

Figure 51F:
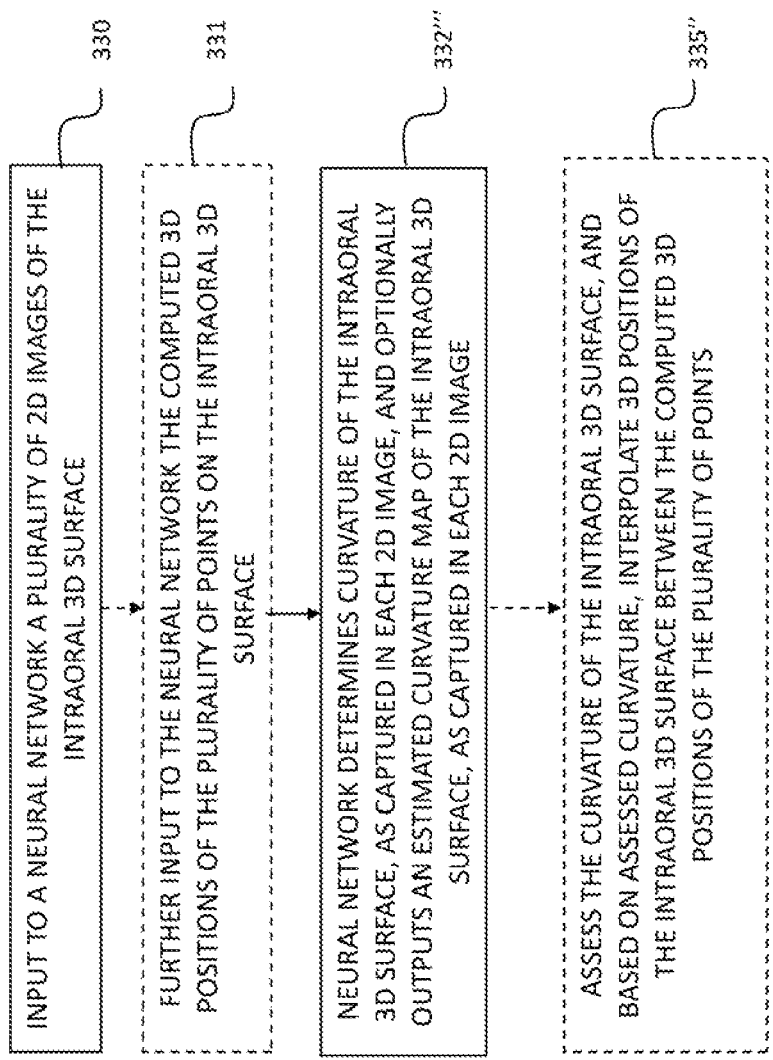

Reference is now made to FIG. 51F, which depicts a specific application of step 332 of FIG. 51B, in accordance with some applications of the present invention. Steps 330 and 331 of FIG. 51D are the same as for FIG. 51B. For some applications, in step 332", neural network 400, e.g., neural network 401, determines the curvature of the intraoral three-dimensional surface as captured in each of the two-dimensional images (step 332") and, optionally, returns a respective estimated curvature map of the intraoral three-dimensional surface as captured in each of the two-dimensional images. For some applications, processor 96 assesses the curvature of the intraoral three-dimensional surface and, based on the assessed curvature, interpolates three-dimensional positions on the intraoral three-dimensional surface (step 335") that are between the computed three-dimensional positions of the plurality of points on the intraoral three-dimensional surface as captured in the structured light images, i.e., processor 96 may integrate the surface based on the assessed curvature. Similarly to as described above with reference to the normal maps, the curvature of the intraoral three-dimensional surface also provides information as to where on the surface there are smooth regions which can be integrated, and where on the surface there is high curvature, e.g., a sharp edge or cliff.

Figure 51H:
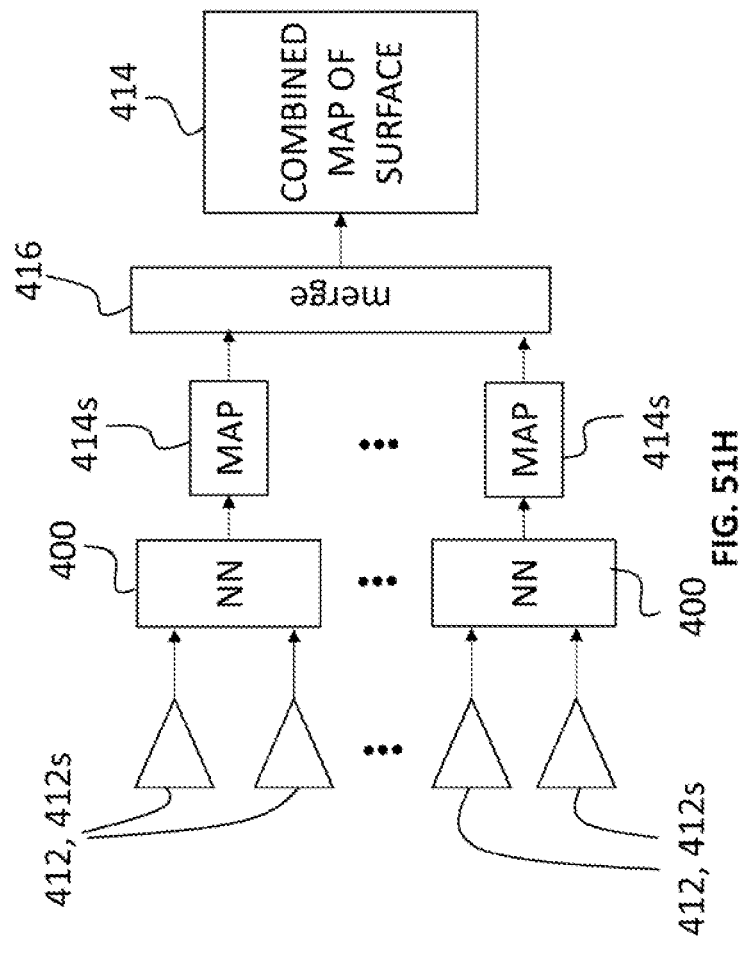
Figure 51G:
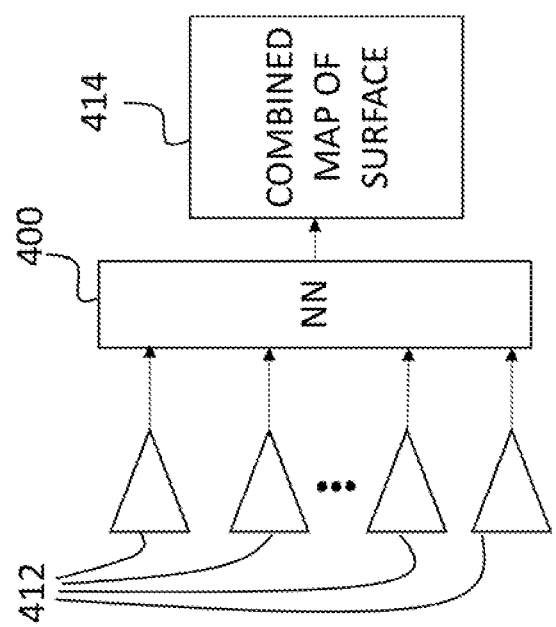
Figure 5I:
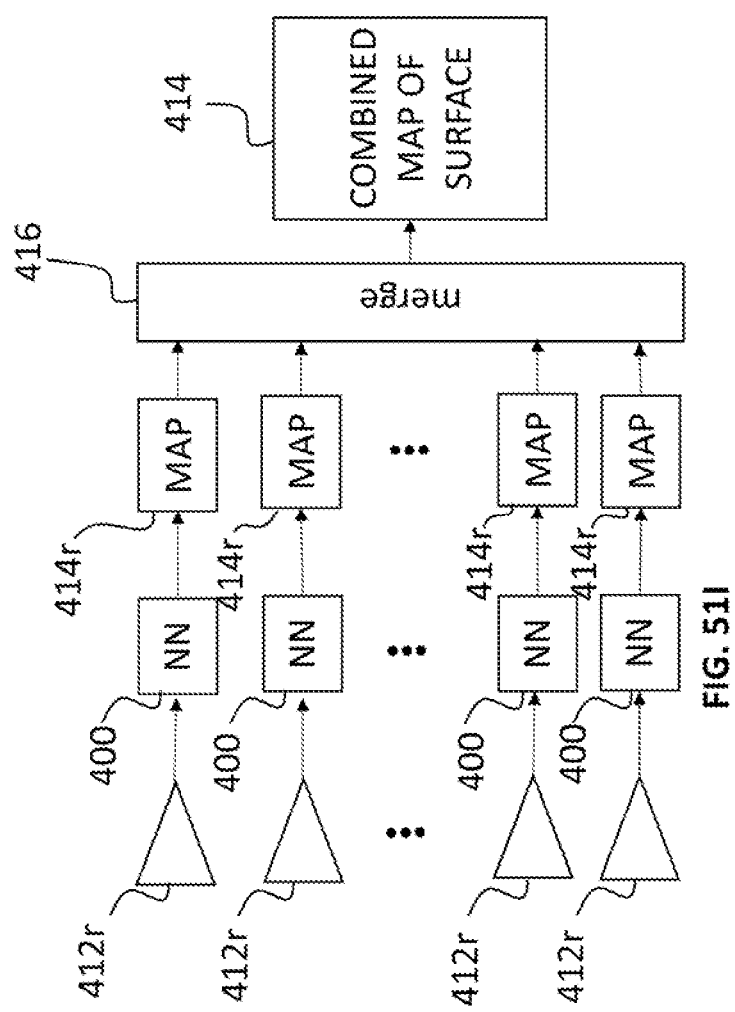

Reference is now made to FIGS. 51G-I, which are block diagrams showing different configurations of inputs to neural network 400, e.g., neural network 401, in accordance with some applications of the present invention. For some applications, there are two or more cameras 24 coupled to probe 28 of handheld wand 20 of an intraoral scanner. In a given image frame of unstructured light (e.g., broad spectrum, non-coherent, and/or NIR light), each of the two or more cameras 24 is driven to simultaneously capture a respective two-dimensional image of a respective portion of the intraoral three-dimensional surface.

For some applications, such as shown in FIG. 51G, all of the respective simultaneously captured two-dimensional images 412 from a given image frame of unstructured light (e.g., broad spectrum, non-coherent, and/or NIR light) are input to neural network 400 as a single input. This is graphically represented in FIG. 51G by the arrows from all of two-dimensional images 412 pointing toward a single representation of neural network 400. In such a case, neural network 400 determines for the given image frame an estimated depth map 414 of the intraoral three-dimensional surface that combines the respective portions of the intraoral surface as captured in each of the simultaneously captured two-dimensional images 412. Typically, in order for neural network 400 to combine the images and output a combined depth map, each of respective two-dimensional images 412 has an overlapping field of view with at least one other of the respective two-dimensional images 412.

For some applications, such as is shown in FIG. 51H, there are three or more cameras 24, e.g., six cameras 24, coupled to probe 28 of handheld wand 20 of an intraoral scanner. In a given image frame of unstructured light (e.g., broad spectrum, non-coherent, and/or NIR light) each one of the three or more cameras is driven to simultaneously capture a respective two-dimensional image of a respective portion of the intraoral three-dimensional surface. At least one subset 412s of the three or more simultaneously captured two-dimensional images 412 from each image frame of unstructured light is input to neural network 400 as a single input. Subset 412s typically contains at least two simultaneously captured two-dimensional images 412. Neural network 400 determines for the given image frame an estimated depth map 414s of the intraoral three-dimensional surface that combines the respective portions of the intraoral surface as captured in subset 412s of the simultaneously captured two-dimensional images 412. This is graphically represented in FIG. 51H by the arrows from subset 412s of simultaneously captured two-dimensional images 412 pointing toward a single representation of neural network 400. Typically, in order for neural network 400 to combine the subset of images and output a combined depth map for the subset, each image of the subset of respective two-dimensional images 412 has an overlapping field of view with at least one other of the subset of respective two-dimensional images 412.

For some applications, more than one subset 412s of simultaneously captured two-dimensional images 412 is input to neural network 400, and neural network 400 returns a respective estimated depth map 414s that combines the respective portions of the intraoral surface as captured in each subset 412s of the simultaneously captured two-dimensional images 412. This is graphically represented in FIG. 51H, which shows two subsets 412s, each with arrows pointing toward respective representations of neural network 400. It is noted that the representation of separate neural networks 400 is simply for graphical clarity, and that the scope of the present invention also covers one neural network 400 into which one or more subsets 412s of simultaneously captured two-dimensional images 412 is input. Processor 96 then merges the respective depth maps 414s (further described hereinbelow) to obtain an estimated depth map 414 of the intraoral three-dimensional surface that combines the respective portions of the intraoral surface as captured in all of the simultaneously captured two-dimensional images 412, i.e., the estimated depth map 414 of the intraoral three-dimensional surface as captured in that image frame. The merging of the respective depth maps 414s is graphically represented by rectangle 416 of FIG. 51H.

For some applications, such as is shown in FIG. 51I, each respective two-dimensional image 412r of the simultaneously captured two-dimensional images in a given frame of unstructured light (e.g., broad spectrum, non-coherent light, and/or NIR light) is input to neural network 400 as separate respective inputs. Neural network 400 determines a respective estimated depth map 414r of each portion of the intraoral three-dimensional surface as captured in each respective two-dimensional images by the two or more cameras 24, e.g., by each one of three or more cameras 24, e.g., each one of six cameras 24. This is graphically represented by an arrow from each of the simultaneously captured two-dimensional images 412r pointing toward a respective representation of neural network 400. It is noted that the representation of separate neural networks 400 is simply for graphical clarity, and that the scope of the present invention also covers one neural network 400 into which each one of simultaneously captured two-dimensional images 412r is input as a separate input. The inventors have realized that for this application, i.e., single-camera inputs (412r) and respective depth map outputs (414r), neural network 400 may be smaller and simpler to train. Due to the single-camera inputs, neural network 400 in this application does need to learn geometrical relationships between cameras and illumination conditions, thus enabling it to be trained using fewer examples. Processor 96 then merges the respective estimated depth maps 414r based on local calibration data of the intraoral scanner (further described hereinbelow) to obtain the estimated depth map 414 that combines the respective portions of the intraoral surface as captured in all of the simultaneously captured two-dimensional images 412r, i.e., the estimated depth map 414 of the intraoral three-dimensional surface as captured in that image frame. The merging of the respective depth maps 414s is graphically represented by rectangle 416 of FIG. 51I.

Typically, the combined field of view of all of cameras 24 spans a significant area of the intraoral three-dimensional surface. Using the neural network as described above to obtain an estimated depth map using two-dimensional images from each camera 24 allows for the computation of the three-dimensional structure of a significant portion of the intraoral three-dimensional surface from a single image frame.

It is noted that some applications are described herein with reference to two-dimensional color images. Examples of such operations include training neural network 400. It should be understood that such operations and other operations that are described with reference to two-dimensional color images also may be practiced with two-dimensional monochromatic images, e.g., two-dimensional monochromatic images captured under NIR light. Accordingly, discussions herein with reference to two-dimensional color images also apply to two-dimensional monochromatic images.

Figure 52A:
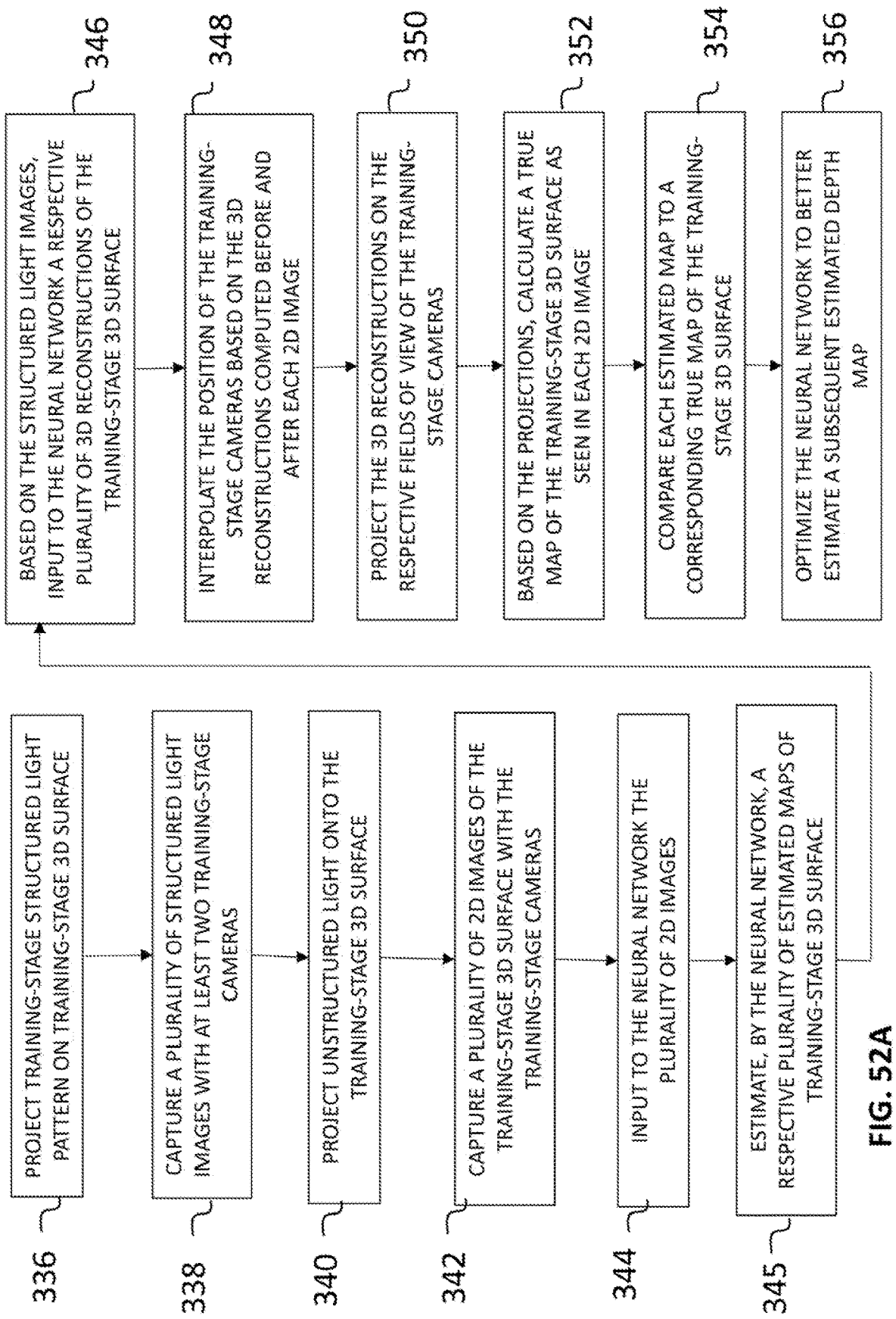
FIG. 52A is a flowchart that depicts a method of training a neural network, in accordance with some applications of the present invention.

Reference is now made to FIG. 52A, which is a flowchart that depicts a method of training the neural network, in accordance with some applications of the present invention. Training the neural network requires a large database that contains both two-dimensional images (e.g., two-dimensional color images and/or two-dimensional monochromatic images) and corresponding target outputs, e.g., a true depth map, for each two-dimensional image. For some applications, each true depth map is calculated using successful three-dimensional reconstructions based on the structured light illumination and three-dimensional reconstruction from structured light as described hereinabove. The three-dimensional reconstructions are projected on the field of view of each camera in order to calculate the true map for each two-dimensional image, e.g., each two-dimensional color or monochromatic image. During the training of the neural network, training-stage three-dimensional surfaces are used in order to train the neural network to be able to reliably estimate a map, e.g., a depth, normal, and/or curvature map, for almost any two-dimensional color image that may be input to the neural network during regular use of the intraoral scanner. For example, large numbers of differently shaped and colored teeth, e.g., polyurethane models of teeth, and differently shaped and colored crowns may be used as the training-stage three-dimensional surfaces. For some applications, intraoral three-dimensional surfaces from a large number of patients may be used as the training-stage three-dimensional surfaces.

Using steps of the method described hereinbelow, the neural network estimates an estimated map, e.g., a depth, normal, and/or curvature map, for each two-dimensional color image during training, which is then compared to a corresponding true map, e.g., true depth map, true normal map, and/or true curvature map, of the training-stage three-dimensional surface in order to optimize the neural network to better estimate a subsequent estimated map.

Thus, in accordance with some applications of the present invention, training neural network 400, e.g., neural network 401, to output estimated maps of a three-dimensional surface may be performed as follows:

(a) driving one or more structured light projectors 22 to project a training-stage structured light pattern on a training-stage three-dimensional surface (step 336), e.g., a distribution of discrete unconnected spots of light, (b) driving one or more training-stage cameras to capture a plurality of training-stage structured light images, each image including at least a portion of the training-stage structured light pattern (step 338), (c) driving one or more training-stage unstructured light projectors to project unstructured light onto the training-stage three-dimensional surface (step 340), (d) driving one or more training-stage cameras to capture a plurality of training-stage two-dimensional color images of the training-stage three-dimensional surface using illumination from the training-stage unstructured light projectors (step 342), (e) regulating the capturing of the training-stage structured light images and the capturing of the training-stage two-dimensional color images to produce an alternating sequence of one or more image frames of structured light images interspersed with one or more image frames of two-dimensional color images, (f) inputting to the neural network the plurality of training-stage two-dimensional color images (step 344), (g) estimating, by the neural network, an estimated map, e.g., depth, normal, and/or curvature map, of the training-stage three-dimensional surface as captured in each of the training-stage two-dimensional color images (step 345), (h) inputting to the neural network a respective plurality of three-dimensional reconstructions of the training-stage three-dimensional surface, based on structured light images of the training-stage three-dimensional surface, the three-dimensional reconstructions including computed three-dimensional positions of a plurality of points on the training-stage three-dimensional surface (step 346), (i) interpolating the position of the one or more training-stage cameras with respect to the training-stage three-dimensional surface for each two-dimensional color image frame based on the computed three-dimensional positions of the plurality of points on the training-stage surface as computed based on respective structured light image frames before and after each two-dimensional color image frame (step 348), (j) projecting the three-dimensional reconstructions on respective fields of view of each of the one or more training-stage cameras (step 350) and, based on the projections, calculating a true map, e.g., a true depth map, a true normal map computed from the true depth map, and/or true curvature map computed from the true depth map, of the training-stage three-dimensional surface as seen in each training-stage two-dimensional color image, constrained by the computed three-dimensional positions of the plurality of points (step 352), (k) comparing each estimated map of the training-stage three-dimensional surface to a corresponding true map of the training-stage three-dimensional surface (step 354), and (l) based on differences between each estimated map and the corresponding true map, optimizing the neural network to better estimate a subsequent estimated map (step 356).

With regard to step (j) in the above neural network training method, the inventors have realized that using the computed three-dimensional positions of a plurality of points on the surface as "anchors" for the estimated depth maps enables the neural network to produce more accurate and reliable depth maps.

Figure 52B:
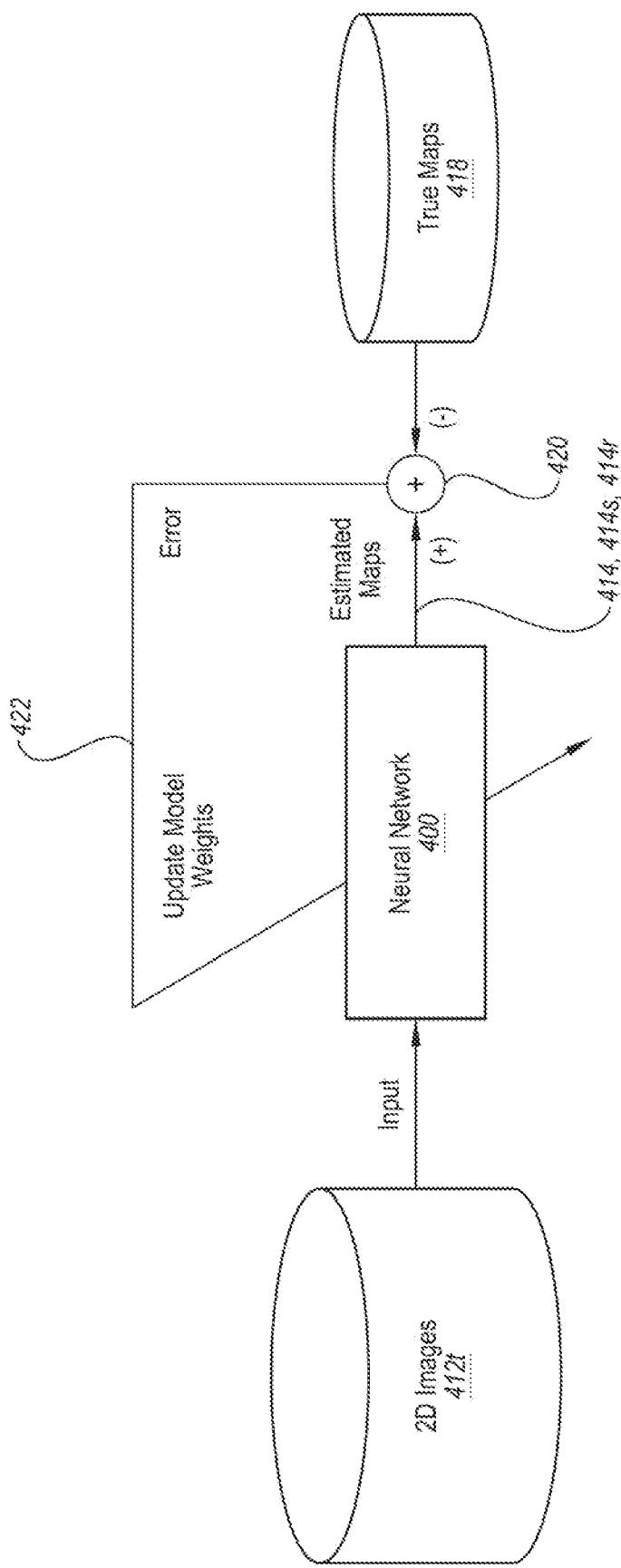
FIG. 52B is a block diagram of the training of the neural network, in accordance with some applications of the present invention.

Reference is now made to FIG. 52B, which depicts a block diagram of the training of neural network 400, as described hereinabove. Training-stage two-dimensional images 412*t* are input to neural network 400 (corresponding to step 344 of FIG. 52A), which outputs the estimated maps 414 (corresponding to step 345 of FIG. 52A). The true maps 418 are calculated using three-dimensional reconstructions that are projected on the field of view of each camera, as described hereinabove (corresponding to step 352 of FIG. 52A). The comparator 420 in FIG. 52B performs the comparison of each estimated map of the training-stage three-dimensional surface to a corresponding true map of the training-stage three-dimensional surface (corresponding to step 354 of FIG. 52B). Arrow 422 corresponds to step 356 of FIG. 52A, where the error, i.e., difference between each estimated map and the corresponding true map, is used to optimize neural network 400 to better estimate a subsequent estimated map, e.g., by updating the model weights.

For some applications, in order to train neural network 400 to output an estimated depth map 414*s* (or depth map 414 that combines respective portions of the intraoral surface as captured in two or more simultaneously captured two-dimensional images 412) as described hereinabove with reference to FIGS. 51G-H, training-stage two-dimensional images 412*t* input to neural network 400 during the training may be sets of two-dimensional images 412*t* of respective portions of the training surface, simultaneously captured by more than one training-stage camera, where each set is input to the neural network as a single input. In such a case, output estimated maps 414 are maps that combines the respective portions of the training surface as captured in all of the simultaneously captured training-stage two-dimensional images 412*t*.

Alternatively or additionally, in order to train neural network 400 to output a respective estimated depth map 414*r* for each individual two-dimensional image 412 as captured by each camera 24 in a given image frame, as described hereinabove with reference to FIG. 51I, each training-stage two-dimensional images 412*t* is an image captured by only one training-stage camera.

Figure 52C:
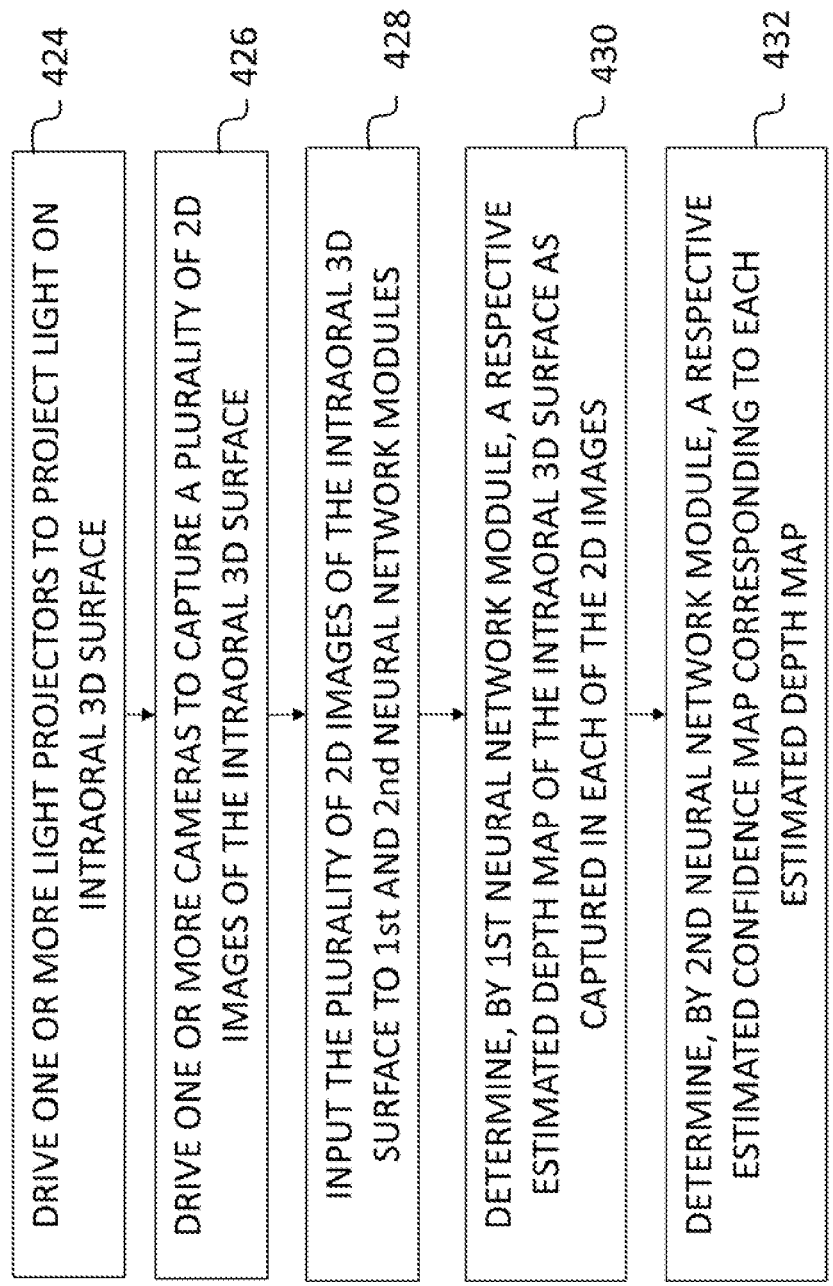
FIG. 52C is a flowchart depicting a method where the neural network outputs depth maps as well as corresponding confidence maps, in accordance with some applications of the present invention.

Reference is now made to FIG. 52C, which is a flowchart depicting a method where the neural network outputs depth maps as well as corresponding confidence maps, in accordance with some applications of the present invention. As described hereinabove, for some applications, estimated depth maps output by neural network 400 are merged based on local camera calibration data for any given handheld wand 20. For example, (a) respective estimated depth maps 414*r*, each from a respective two-dimensional image as captured by one camera 24, are merged to obtain a combined depth map for the image frame, (b) respective estimated depth maps 414*s*, each from a combined subset of two-dimensional images as captured by a subset of cameras 24, are merged to obtain a combined depth map for the image frame, or (c) respective estimated depth maps 414, each from a respective image frame of unstructured light, are merged. However, there may be cases where depth maps that are being merged may contradict each other in a particular region of the depth map. Thus, the inventors have developed a method of training the neural network to not only output a respective depth map corresponding to each respective input (i.e., single two-dimensional image inputs or combined two-dimensional image inputs), but to also output a respective estimated corresponding confidence map, each confidence map indicating a confidence level per region of the corresponding respective estimated depth map. For some applications, in response to determining a contradiction between corresponding regions in at least two estimated depth maps that are to be merged, processor 96 merges the depth maps based on the confidence level of each of the corresponding respective regions as indicated by the respective confidence maps for each of the depth maps. For example, for a particular contradicting region, if one of the depth maps has low confidence in that region, as indicated by the corresponding confidence map, and the contradiction depth map has high confidence in that region, processor 96 may rely more heavily on the depth map with high confidence for that particular reason.

Thus, in accordance with some applications of the present invention, a method is provided for computing a three-dimensional structure of an intraoral three-dimensional surface, including the following steps:

driving one or more light projectors, e.g., unstructured light projectors 118, to project light, e.g., unstructured light, on the intraoral three-dimensional surface (step 424), driving one or more cameras 24 to capture a plurality of two-dimensional images (412, 412s, 412r) of the intraoral three-dimensional surface (step 426), and using processor 96:

inputting the plurality of two-dimensional images of the intraoral three-dimensional surface to a first neural network module 434 (shown in FIGS. 52D-F) and to a second neural network module 436 (shown in FIGS. 52D-F) (step 428), determining, by first neural network module 434, a respective estimated depth map (414, 414s, 414r) of the intraoral three-dimensional surface as captured in each of the two-dimensional images (step 430), and determining, by second neural network module 436, a respective estimated confidence map 438 (shown in FIGS. 52D-F) corresponding to each estimated depth map (step 432), each confidence map indicating a confidence level per region of the respective estimated depth map.

For some applications, first neural network module 434 and second neural network module 436 are separate modules of a same neural network 400. In this case, neural network 400 comprises first neural network module 434 and second neural network module 436 within it. For example, second neural network module 436 may be implemented by appending and expanding some of the network layers of first neural network module 434. As further described hereinbelow, first neural network module 434 alone is initially trained to output depth maps as described hereinabove with reference to FIGS. 52A-B. For some applications, this may be done using a temporary model 434' of first neural network module 434. Subsequently, when second neural network module 436 is trained to output the corresponding confidence maps (further described hereinbelow), first neural network module 434 within the larger neural network 400 (which contains both modules) receives all the parameters/weights that were learned during the training of the temporary model 434' of first neural network module 434. Alternatively, for some applications, first neural network module 434 and second neural network module 436 are not separate modules of a same neural network, i.e., they are each a separate neural network.

Figure 52D:
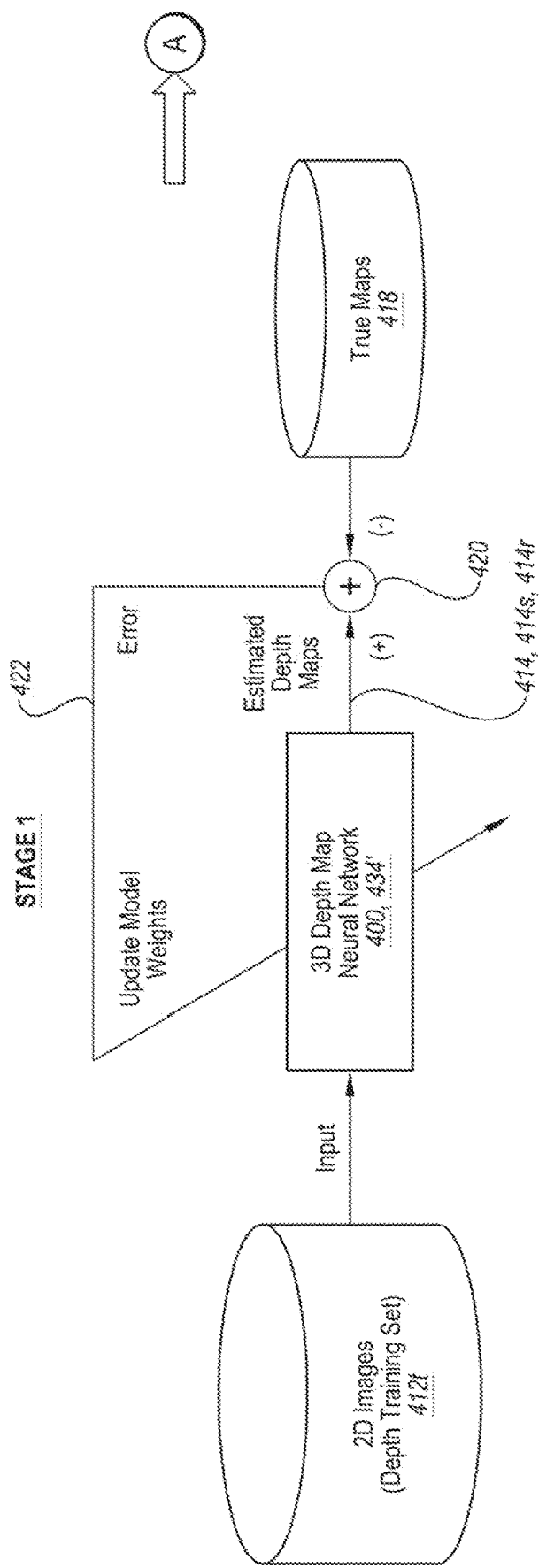
FIGS. 52D-F are schematic illustrations depicting training of a neural network to output depth maps as well as corresponding confidence maps, in accordance with some applications of the present invention.
Figure 52E:
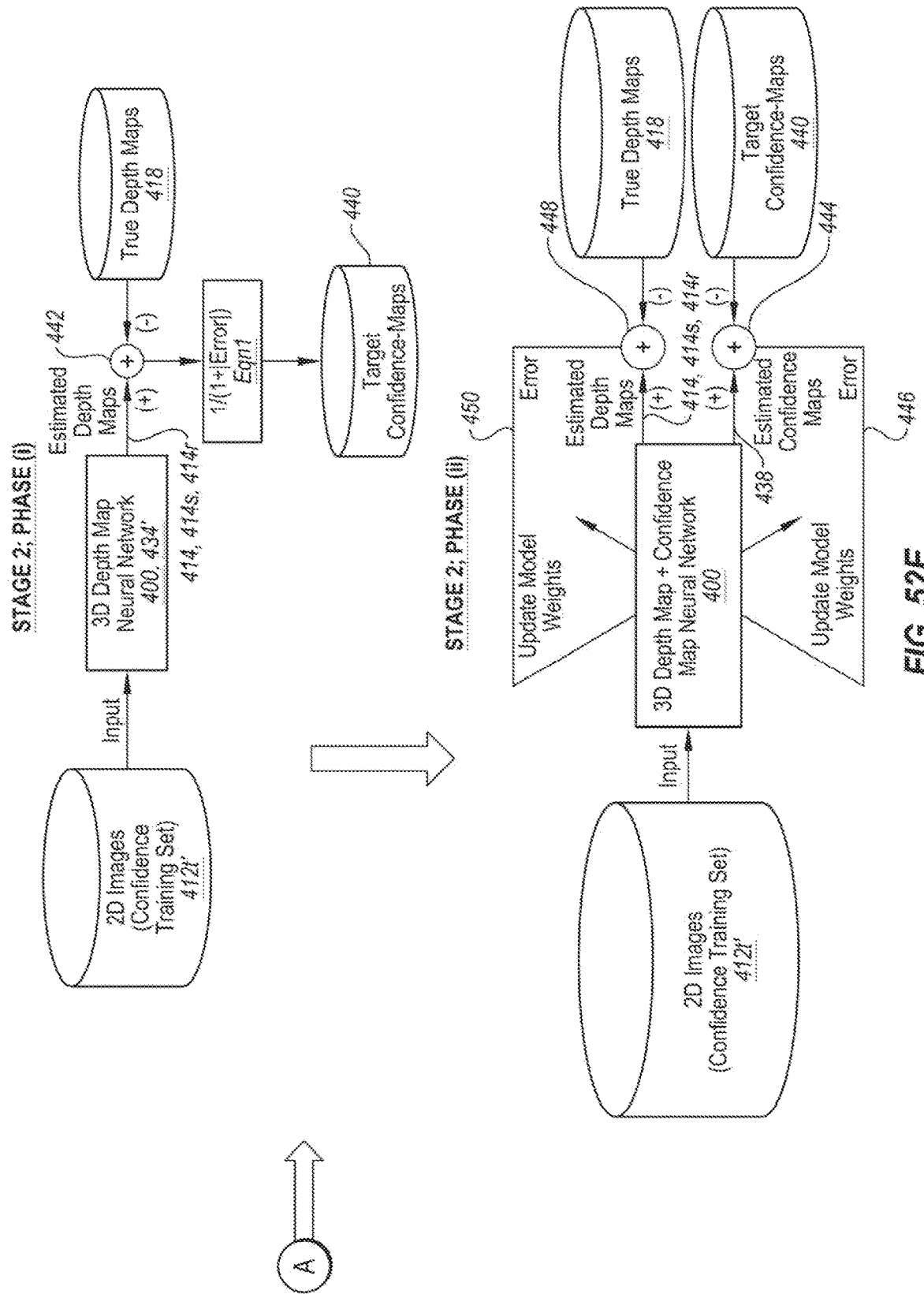
Figure 52F:
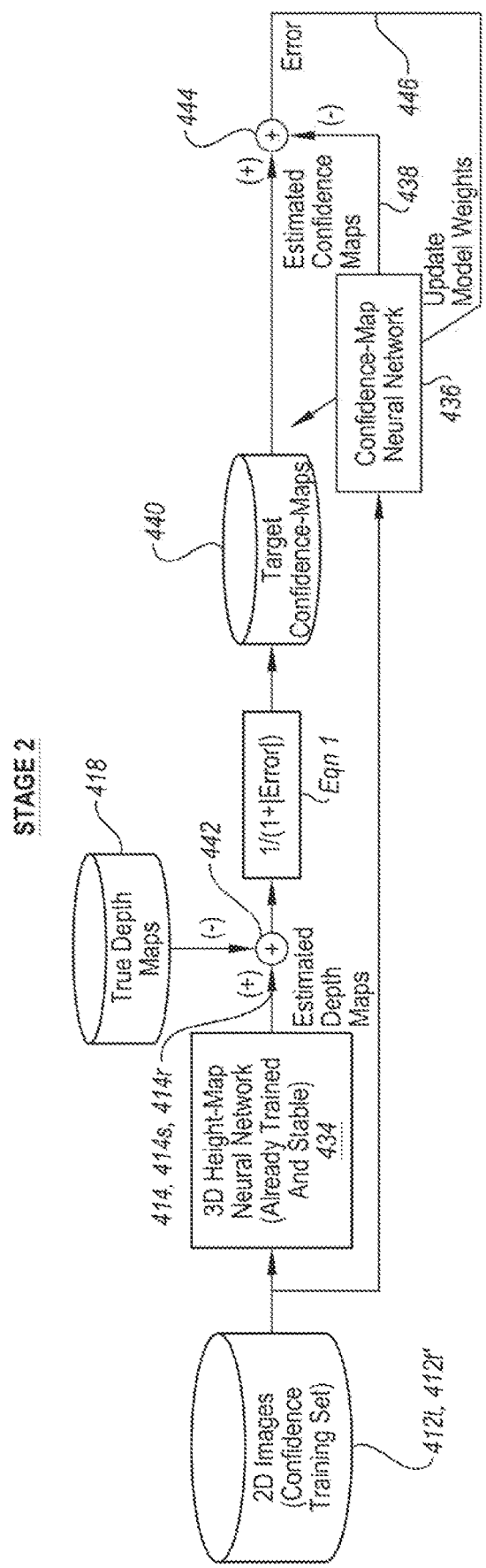

Reference is now made to FIGS. 52D-F, which are schematic illustrations depicting the training process of the neural network to output depth maps as well as corresponding confidence maps, in accordance with some applications of the present invention. The overall training is performed in two stages:

(1) training first neural network module 434 to output depth maps 414, 414s, and/or 414r (as described hereinabove with reference to FIGS. 52A-B), and (2) training second neural network module 436 to output the corresponding confidence maps.

During stage 1 of the training, training-stage two-dimensional images 412t are used as described hereinabove (for the purpose of the discussion below these are referred to as "depth-training-stage two-dimensional images" 412t). For some applications, during stage 2 of the training a separate set of confidence-training-stage two-dimensional images 412f are used that are not the same as depth-training-stage two-dimensional images 412t (further discussed hereinbelow). Alternatively or additionally, the same depth-training-stage two-dimensional images 412t may be used in stage 2 of the training. Stage 2 of the training itself has two phases:

(i) generating target confidence maps for each of the confidence-training-stage two-dimensional images 412t' (or for each of the depth-training-stage two-dimensional images 412t), and (ii) using the target confidence maps to train second neural network module 436 to output estimated confidence maps.

FIGS. 52D-E depict the training process when first neural network module 434 and second neural network module 436 are modules of a same neural network 400, and two separate sets of training-stage two-dimensional images are used for stage 1 and stage 2 respectively. Stage 1 includes initially training first neural network module 434, e.g., initially training a temporary model 434' of first neural network module 434, to determine the respective estimated depth maps 414, 414s, or 414r using a plurality of depth-training-stage two-dimensional images 412t.

Phase (i) of stage 2 includes using the trained first neural network module 434, e.g., trained temporary model 434', to generate the target confidence maps 440 to be used in phase (ii) of stage 2. Generating the target confidence maps may be performed as follows:

(a) inputting to trained first neural network module 434, e.g., trained temporary model 434', a plurality of confidence-training-stage two-dimensional images 412f of a training-stage three-dimensional surface, (b) determining, by first neural network module 434, e.g., trained temporary model 434', a respective estimated depth map 414, 414s, or 414r of the training-stage three-dimensional surface as captured in each of confidence-training-stage two-dimensional images 412f, and (c) computing a difference, represented by comparator 442, between each estimated depth map 414, 414s, or 414r and a corresponding respective true depth map 418 to obtain a respective target confidence map 440 corresponding to each estimated depth map 414, 414s, or 414r as determined by first neural network module 434.

Computing this difference provides the error in each estimated depth map, the inverse of which is then used to compute each target confidence map 440, i.e., in a region of an estimated depth map having low error (i.e., where the difference is low) the corresponding target confidence map will indicate high confidence for that region, and in a region of an estimated depth map having high error (i.e., where the difference is high) the corresponding target confidence map will indicate low confidence for that region. By way of example and not limitation, the following equation may be used to compute each target confidence map 440:

$$\text{conf} = 1/(1+|\text{error}|) \quad \text{[Eqn 1]}$$

Phase (ii) of stage 2 includes training second neural network module 436 to output estimated confidence maps 438 corresponding to depth maps 414, 414s, 414r that are output by first neural network module 434. Training second neural network module 436 may be performed as follows:

(a) inputting to second neural network module 436 the plurality of confidence-training-stage two-dimensional images 412t', (b) estimating, by second neural network module 436, a respective estimated confidence map 438 indicating a confidence level per region of each respective estimated depth map 414, 414s, and/or 414r, and (c) comparing each estimated confidence map 438 to the corresponding target confidence map 440, as represented by comparator 444, and based on the comparison, optimizing second neural network module 436 to better estimate a subsequent estimated confidence map 438, e.g., by updating the model weights, as represented by arrow 446.

For some applications, when (a) first and second neural network modules 434 and 436 are part of the same neural network 400 and (b) different sets of training-stage two-dimensional images are used for the training of first neural network module 434 and the training of second neural network module 436, respectively, then, concurrently with the training of second neural network module 436, first neural network module 434 can continue to optimize its depth map learning based on the new confidence-training-stage two-dimensional images 412t'. This is depicted in stage 2; phase (ii) of FIG. 52E. For each input of the confidence-training-stage two-dimensional images 412t' neural network 400 (including both modules) determines an estimated depth map 414, 414s, and/or 414r. Each of these estimated depth maps is compared to a corresponding true depth map 418, using comparator 448, and based on the comparison first neural network module 434 is optimized to better estimate a subsequent estimated depth map 414, 414s, and/or 414r, e.g., by updating the model weights, as represented by arrow 450.

Another advantage that the inventors have realized to using different sets of training-stage two-dimensional images 412t and 412t', is that using training-stage two-dimensional images that first neural network module 434, e.g., trained temporary model 434', has never seen before for the computation of target confidence maps 440 may avoid a phenomenon known as overfilling. Target confidence maps 440 are ultimately used in order to train second neural network module 436 to be able to accurately estimate the behavior of first neural network module 434, and to output an estimation of where first neural network module 434 may produce low error and where neural network module 434 may produce high error for every given estimated depth map 414, 414s, and/or 414r of first neural network module 434. If this training is based on images that first neural network module 434 has already received during its initial training, then it is possible that the error in each corresponding respective estimated depth maps 414, 414s, and/or 414r may be lower than if two-dimensional images that first neural network module 434 has never seen before are used. Nevertheless, the scope of the present invention includes both the use of different respective sets (412t and 412t') of training-stage two-dimensional images for training the two neural network modules respectively, and the use of the same training-stage two-dimensional images for training both neural network modules.

FIG. 52F depicts an alternative application of stage 2 of the training. For this application, the training-stage two-dimensional images (either depth-training-stage two-dimensional images 412t, or confidence-training-stage two-dimensional images 412t') are simultaneously input to (a) a stable already-trained first neural network module 434 and (b) second neural network module 436. First neural network module 434 outputs respective estimated depth maps 414, 414s, and/or 414r, and each depth map is compared to a corresponding true depth map 418 (using comparator 442) in order to compute a target confidence map 440 for each two-dimensional image input. Concurrently, second neural network module 436 outputs an estimated confidence map 438 for each two-dimensional image input, and each estimated confidence map 438 is compared to the corresponding target confidence map 440 for that same two-dimensional image input (using comparator 444), and based on the comparison, second neural network module 436 is optimized to better estimate a subsequent estimated confidence map 438, e.g., by updating the model weights, as represented by arrow 446.

Figure 52G:
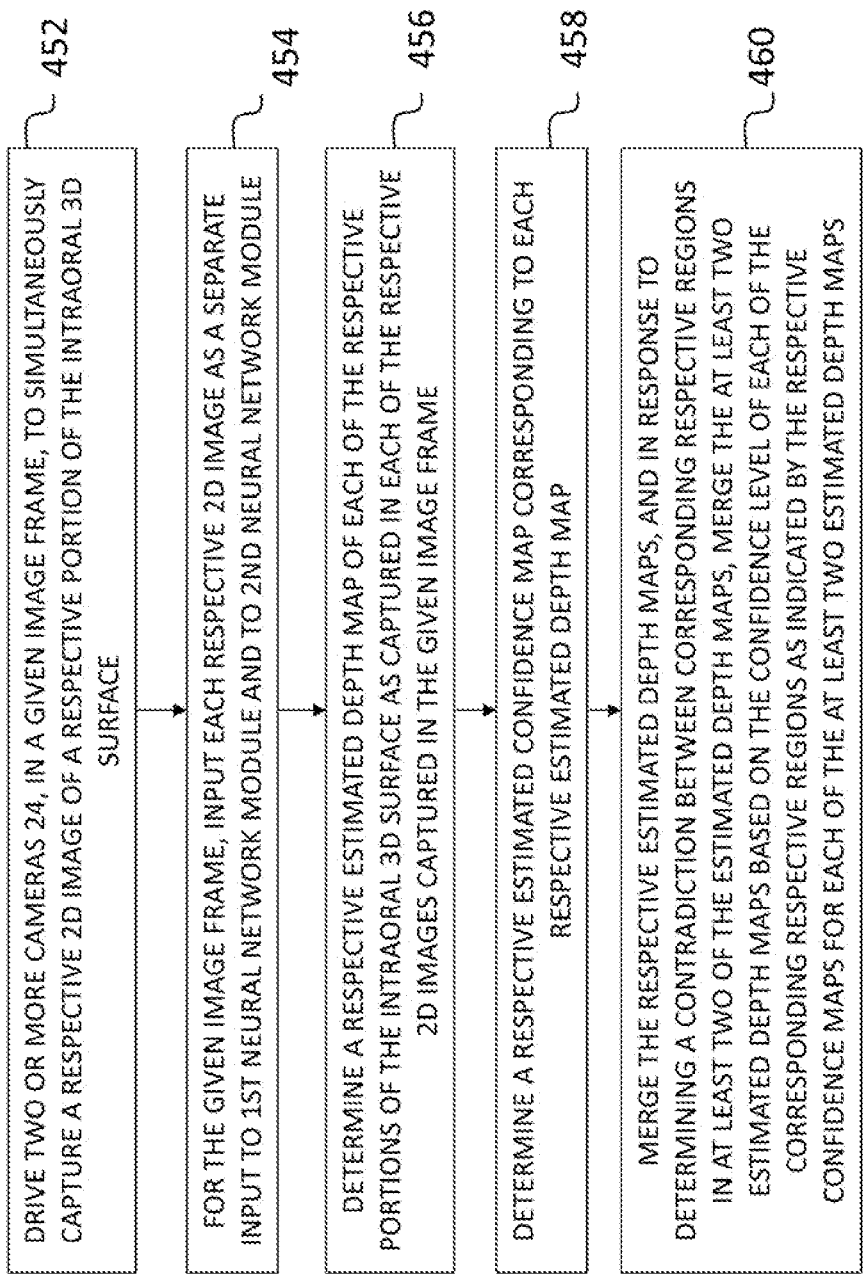
FIG. 52G is a flow chart depicting how the confidence maps may be used, in accordance with some applications of the present invention.

Reference is now made to FIG. 52G, which is a flow chart depicting a method of how the confidence maps may be used, in accordance with some applications of the present invention. As described hereinabove, there may be contradicting regions when processor 96 merges the estimated depth maps. Having a corresponding confidence map for each estimated depth may help resolve possible contradictions between respective depth maps. The method includes the following steps:

- driving each one of two or more cameras 24, in a given image frame, to simultaneously capture a respective two-dimensional image 412r of a respective portion of the intraoral three-dimensional surface (step 452),
- for the given image frame, inputting each one of the respective two-dimensional images 412r as a separate input to first neural network module 434 and to second neural network module 436 (step 454),
- for the given image frame, determining a respective estimated depth map 414r of each of the respective portions of the intraoral three-dimensional surface as captured in each of the respective two-dimensional images 412r captured in the given image frame (step 456),
- for the given image frame, determining a respective estimated confidence map 438 corresponding to each respective estimated depth map 414r of each of the respective portions of the intraoral three-dimensional surface as captured in each of the respective two-dimensional images 412r captured in the given image frame (step 458), and
- using processor 96, merging the respective estimated depth maps 414r to obtain a combined estimated depth map 414 of the intraoral three-dimensional surface as captured in the given image frame, and in response to determining a contradiction between corresponding respective regions in at least two of the estimated depth maps 414r, merging the at least two estimated depth maps 414r based on the confidence level of each of the corresponding respective regions as indicated by the respective confidence maps 438 for each of the at least two estimated depth maps 414r (step 460).

It is noted that the above method is described in the context of respective estimated depth maps 414r, each from a respective two-dimensional image as captured by one camera 24 in a given image frame, however the scope of the present invention includes using this method for merging estimated depth maps 414s, each from a combined subset of two-dimensional images as captured by a subset of cameras 24 in a given image frame, and/or for merging respective estimated depth maps 414, each from a respective image frame of unstructured light.

Typically, during the training, the three-dimensional reconstructions based on structured light images of the training-stage three-dimensional surface are obtained during long, slow scans. By doing so, the three-dimensional reconstructions are averaged over many samples and are therefore more accurate. Additionally, blue (or green) lasers may be used for the training scans in order to increase resolution (relative to red lasers). Once the intraoral scanner is in use, i.e., being used to scan actual intraoral three-dimensional surfaces, the training of the neural network may be updated/ "retrained" using actual intraoral scans, further described hereinbelow with reference to FIG. 62.

The architecture of the neural network may be of an Encoder-Decoder type, where a single image is fed into the model and the output is again an image with each pixel labeled according to the desired outcome. Neural network 401 shown in FIGS. 58 and 59A-B is trained and used as described hereinabove, in accordance with some applications of the present invention. Layers 402 represent the encoder for a single camera, layers 404 represent the decoder for a single camera, and layer 406 is a fully connected layer for shared information. Arrows 408 represent spatial information-passes between encoders and decoders. The respective outputs of the decoders are the predicted depth maps for each camera. FIGS. 59A-B show an architecture for neural network 401 in a temporally recurrent configuration, with arrow 410 representing temporal sharing of information, in accordance with some applications of the present invention.

It is noted that fully connected layer 406 is the part of neural network 400 that combines the two-dimensional images when more than one two-dimensional image is input to the net together as a single input, for example as shown in and described with reference to FIGS. 51G and 51H. For the embodiment described with reference to FIG. 51I, i.e., two-dimensional images from each camera input to the net each as a separate input, neural network 400 may be practiced as shown in FIGS. 58, and 59A-B, but without fully connected layer 406.

As described hereinabove, using the neural network to obtain three-dimensional reconstructions of the intraoral three-dimensional surface from two-dimensional images, e.g., two-dimensional color images and/or two-dimensional monochromatic images, as captured by six cameras 24 per frame allows for fast three-dimensional reconstruction of the intraoral surface at high resolution. However, it is possible that in use a particular two-dimensional image may be input to the neural network containing a feature such as a color, image, or shape (for example, a particular dental pathology or orthodontic fixture), that the neural network has not "learned." In this case, the depth map produced by the neural network may not be as accurate as in other instances. Thus, the inventors have realized that while use of the neural network for 2D-to-3D reconstruction, as described hereinabove, increases speed and resolution, the three-dimensional reconstruction based on the structured light from structured light projectors 22 (as described herein) may provide, in some cases, a more robust solution.

Thus, for some applications, processor 96 performs three-dimensional reconstruction of an intraoral three-dimensional surface using a combination of structured light and unstructured light as follows:

When three-dimensional reconstructions based on the structured light and three-dimensional reconstruction based on the unstructured light (e.g., broad spectrum light and/or non-coherent light) agree with each other, processor 96 uses the reconstructed surface from the unstructured light to refine the reconstructed surface from the structured light.

When structured light information is missing, e.g., due to low contrast or blocked spots, processor 96 fills in the missing region using the reconstructed surface from the unstructured light (and will typically mark the region as needing more scans for robustness).

When three-dimensional reconstructions based on the structured light and three-dimensional reconstruction based on the unstructured light disagree with each other, processor 96 analyses the disagreement characteristics. If the discrepancy relates to data from (for example) only a single structured light spot, then processor 96 may use the reconstructed surface from the unstructured light to fill it in. However, if the discrepancy is larger, processor 96 may rely on the reconstructed surface from the structured light if enough points were reliably solved, e.g., were detected by a high number of cameras as described hereinabove.

Figure 65:
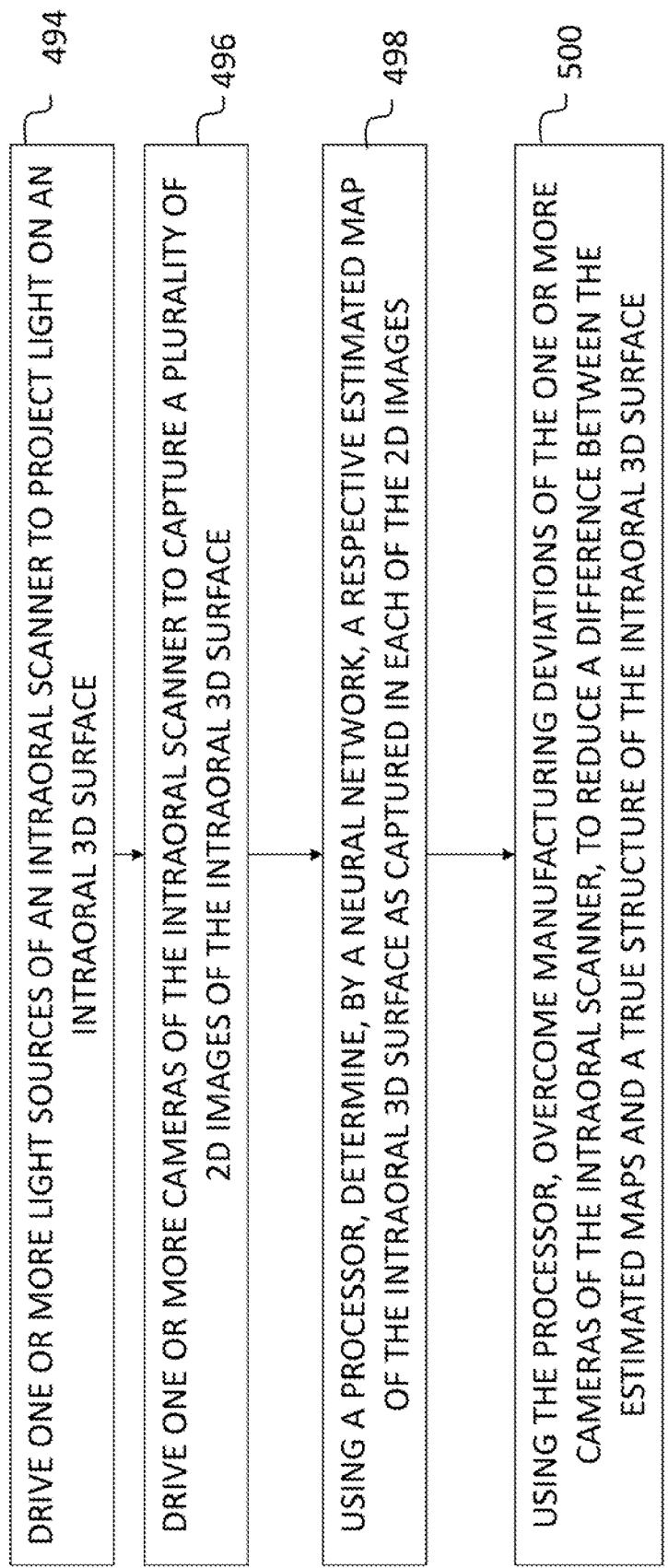
FIG. 65 is a flowchart depicting a method for overcoming manufacturing deviations between intraoral scanners, in accordance with some applications of the present invention.

Reference is now made to FIG. 65, which is a flowchart depicting a method for overcoming manufacturing deviations between intraoral scanners, in accordance with some applications of the present invention. The inventors have realized that a potential challenge in the use of neural network 400 is that neural network 400 is fixed to the specific cameras that were used to provide the training-stage two-dimensional images. However, in reality, when the intraoral scanners are commercially produced there may exist small manufacturing deviations that cause (a) the calibration of the cameras and projectors on each commercially-produced intraoral scanner to be slightly different than the calibration of the training-stage cameras and projectors, and/or (b) the illumination relationships between the cameras and the projectors on each commercially-produced intraoral scanner to be slightly different than those of the training-stage cameras and projectors. Other manufacturing deviations in the cameras and/or projectors may exist as well. The method includes the following steps:

driving one or more light sources, e.g., unstructured light projectors 118, of the intraoral scanner to project light on the intraoral three-dimensional surface (step 494), driving one or more cameras 24 of the intraoral scanner to capture a plurality of two-dimensional images of the intraoral three-dimensional surface (step 496), using processor 96, determining, by neural network 400, a respective estimated map of the intraoral three-dimensional surface as captured in each of the two-dimensional images (step 498), and using processor 96, overcoming manufacturing deviations of the one or more cameras 24 of the intraoral scanner, to reduce a difference between the estimated maps and a true structure of the intraoral three-dimensional surface (step 500).

The inventors have invented a number of ways in which to overcome these manufacturing deviations.

With reference to step 342 of FIG. 52A, the inventors have realized that one way to overcome manufacturing deviations in the form of illumination peculiarities and/or illumination relationships between the cameras and projectors, e.g., illumination origin, brightness, and rotation of the fields of view, is to train neural network 400 using training-stage images as captured by a plurality of training-stage handheld wands 20, each of the training-stage handheld wands 20 comprising one or more reference cameras, i.e., training-stage cameras. Each of the one or more cameras 24 of an intraoral scanner corresponds to a respective one of the one or more reference cameras on each of the training-stage handheld wands. For example, if the intraoral scanners are manufactured with six cameras 24, then each of the training-stage handheld wands has a corresponding six training-stage cameras. This method is based on the realization that if neural network 400 is trained using training-stage cameras from only one handheld wand 20, and that training-stage handheld wand 20 has some specific characteristic and/or peculiarity, then neural network 400 learns that characteristic and/or peculiarity. However, if training-stage images are input to neural network 400 from a plurality, e.g., many, different handheld wands 20, each perhaps with its own slightly differing characteristics and/or peculiarities, then neural network 400 will learn to output the estimated maps regardless of these differing characteristics and/or peculiarities, i.e., neural network 400 will learn to ignore these types of small differences between each intraoral scanner.

With reference to FIG. 51I, the inventors have realized that one way to overcome manufacturing deviations in the form of local calibration values of cameras 24 on an intraoral scanner differing slightly from the calibration values of the training-stage cameras, and/or spatial relationships between cameras 24 on an intraoral scanner differing slightly from those of the training-stage cameras, is to train neural network 400 to accept single-camera inputs, such as described hereinabove with reference to FIG. 51I, and to output a respective depth map for each single-camera input. The advantage here is that neural network 400 does not need to combine two-dimensional images and thus does not need to learn the relationships between the cameras. Each image from each camera is input to neural network 400, and once neural network 400 has determined the respective estimated depth maps, they may be merged based on the local calibration data of that specific handheld wand 20, as described hereinabove. For this application, the calibration data of and spatial relationships between the training-stage cameras is not relevant to the training or in-the-field use of neural network 400. As described hereinabove with reference to FIGS. 52C-E, neural network 400 may also determine a respective estimated confidence map corresponding to each estimated depth map, each confidence map indicating a confidence level per region of the respective estimated depth map. When the respective estimated depth maps are merged, in response to determining a contradiction between corresponding respective regions in at least two of the estimated depth maps, the merging may be performed based on the confidence level of each of the corresponding respective regions as indicated by the respective confidence maps for each of the at least two estimated depth maps, as described hereinabove.

Figure 62:
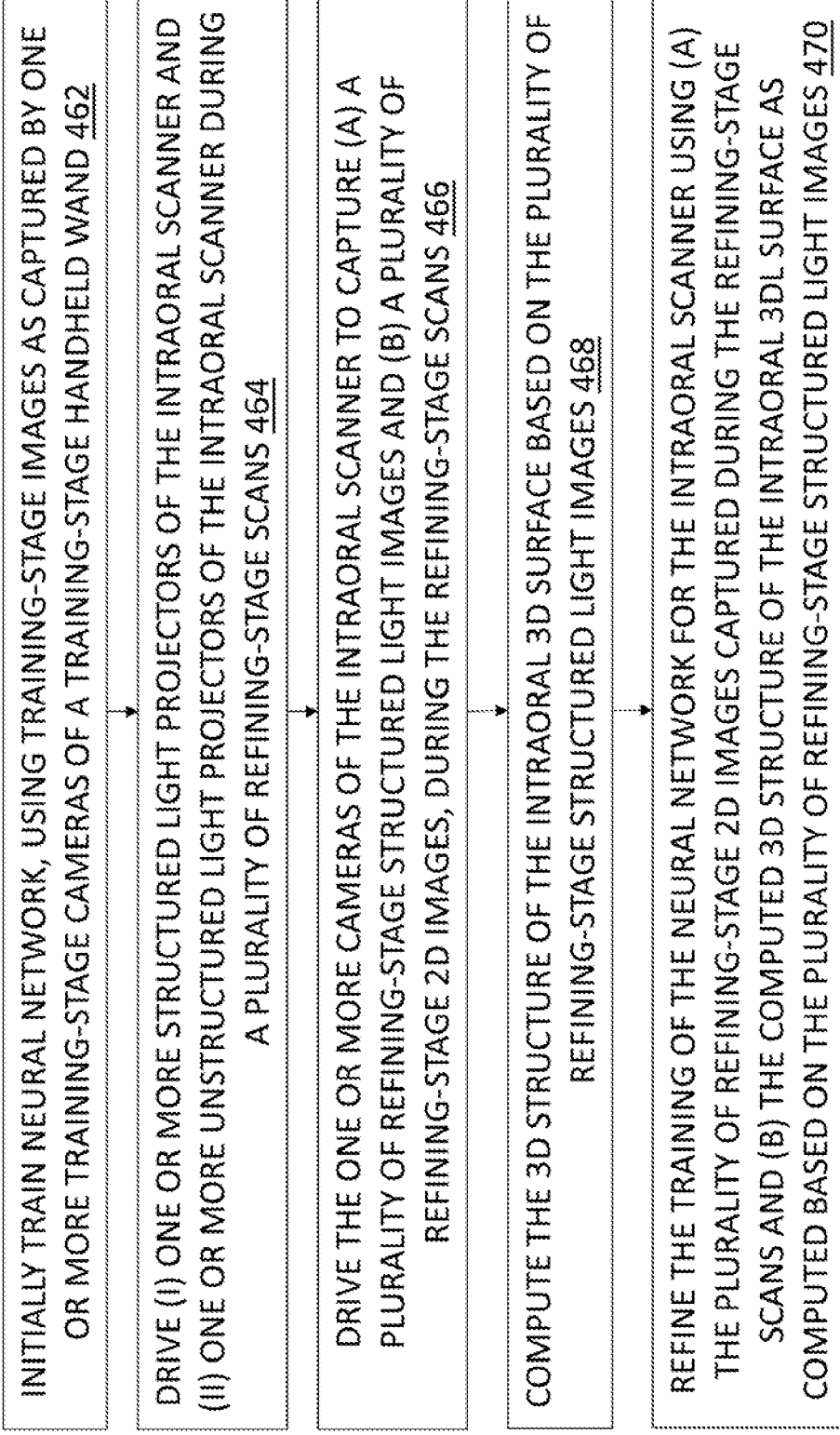
FIG. 62 is a flowchart depicting a method for overcoming manufacturing deviations between intraoral scanners, in accordance with some applications of the present invention.

Reference is now made to FIG. 62, which depicts another method that the inventors have invented for overcoming manufacturing deviations, in accordance with some applications of the present invention. For some applications, neural network 400 undergoes a refining stage in the field during which it continues to be trained based on two-dimensional images from the local cameras 24 of a given intraoral scanner. Thus, manufacturing differences, such as the types of differences described above, between a given intraoral scanner in the field and the training-stage handheld wand 20 are learned by neural network 400 for that specific intraoral scanner. The local structured light projectors 22, unstructured light projectors 118, and cameras 24 of a given intraoral scanner may be used to perform a plurality of refining-stage scans, that include capturing a plurality of refining-stage structured light images and a plurality of refining-stage two-dimensional images (steps 464-466). For each of the refining-stage scans the three-dimensional structure of the intraoral three-dimensional surface is computed based on the plurality of refining-stage structured light images (step 468). The training of neural network 400 then undergoes a refining stage (step 470) using (a) the plurality of refining-stage two-dimensional images captured during the refining-stage scans as inputs to neural network 400, and (b) the computed three-dimensional structure of the intraoral three-dimensional surface as computed based on the plurality of refining-stage structured light images as the respective target outputs to which each respective estimated map output by neural network 400 during the refining stage is compared. For the purposes of the present discussion, the term "in the field" refers to a commercially-manufactured intraoral scanner that is in use by an end-user of the product. The method includes the following steps using structured light projectors 22, unstructured light projectors 118, and cameras 24 of an intraoral scanner in the field:

- initially training neural network 400, using training-stage images as captured by one or more training-stage cameras of a training-stage handheld wand, each of the one or more cameras 24 of the intraoral scanner corresponding to a respective one of the one or more training-stage cameras (step 462),
- subsequently driving (i) the one or more structured light projectors 22 of the intraoral scanner and (ii) the one or more unstructured light projectors 118 of the intraoral scanner during a plurality of refining-stage scans (step 464),
- driving the one or more cameras 24 of the intraoral scanner to capture (a) a plurality of refining-stage structured light images and (b) a plurality of refining-stage two-dimensional images, during the refining-stage scans (step 466),
- computing the three-dimensional structure of the intraoral three-dimensional surface based on the plurality of refining-stage structured light images (step 468), and
- refining the training of the neural network for the intraoral scanner using (a) the plurality of refining-stage two-dimensional images captured during the refining-stage scans and (b) the computed three-dimensional structure of the intraoral three-dimensional surface as computed based on the plurality of refining-stage structured light images (step 470).

For some applications, with reference to step 470, the refining of the training of neural network 400 may be performed on only a part of neural network 400. For example, neural network 400 comprises a plurality of layers, and refining the training of neural network 400 may be practiced by constraining a subset of the layers.

For some applications, with reference to steps 464, 466, and 468, processor 96 may select from a plurality of scans, which of the plurality of scans to use as the refining-stage scans based on a quality level of each scan. Similarly to as described hereinabove for the initial training, the three-dimensional reconstructions of the intraoral three-dimensional surface (step 468) that are based on refining-stage structured light images of the intraoral three-dimensional surface are obtained during long, slow scans that have enough data for computing the three-dimensional structure based on the structured light images alone. Additionally, blue (or green) lasers may be used for the refining-stage training scans in order to increase resolution (relative to red lasers). Additionally, or alternatively, the three-dimensional reconstructions of step 468 may be based only on projected pattern features, e.g., spots, that are specific distances away from cameras 24 at which cameras 24 are in focus. This allows for a higher resolution reconstructed three-dimensional surface for neural network 400 to use in learning.

As further described hereinbelow, while the training of neural network 400 is being refined, the intraoral scanner is still usable to compute end-result three-dimensional structures of an intraoral three-dimensional surface for a user of the intraoral scanner, using only the structured light images from the refining-stage scans.

Figure 63:
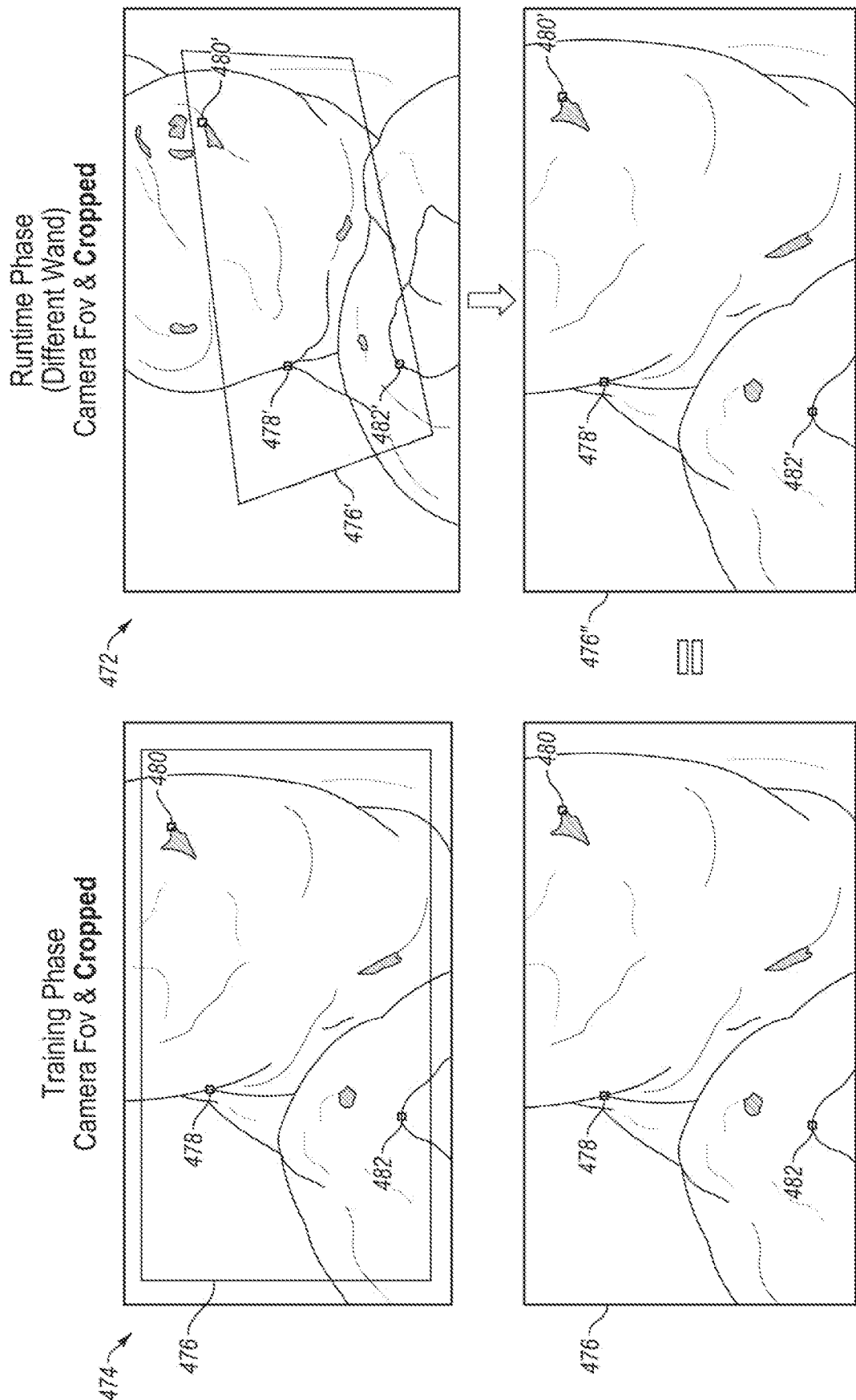
FIG. 63 is a schematic illustration of another method for overcoming manufacturing deviations between intraoral scanners, in accordance with some applications of the present invention.

Reference is now made to FIG. 63, which is a schematic illustration of another method for overcoming manufacturing deviations between intraoral scanners, in accordance with some applications of the present invention. Typically, each one of the one or more cameras 24 of an intraoral scanner corresponds to a respective one of one or more training-stage cameras (also referred to hereinbelow as "reference" cameras). The inventors have realized that based on the stored calibration data of the one or more cameras 24 of an intraoral scanner in relation to the stored calibration data of the reference cameras, each run-time two-dimensional image 472 captured in the field by a given intraoral scanner may be modified, e.g., morphed, so that it appears as though a corresponding one of the training-stage reference cameras captured that specific image. The morphed image is then used as the input to neural network 400, such that neural network 400 is always receiving images that are "as if" captured from the specific training-stage cameras with which it was trained. Furthermore, the training-stage images (e.g., image 474 of FIG. 63) from each of the reference cameras are slightly cropped such that neural network 400 is trained using images that correspond to only a subset of pixels of the camera array of each training-stage camera, i.e., on a cropped region 476 of the field of view of each reference camera. For some applications, cropped region 476 is 85-97% of a respective full field of view of each of the one or more reference cameras. This is to ensure that for two-dimensional run-time images 472 taken in the field, a corresponding cropped region 476' may be found within run-time two-dimensional image 472 that can be morphed to match cropped region 476 of the field of view of a corresponding reference camera.

Morphing the cropped region 476' of a run-time two-dimensional image 472 is typically performed by a transformation that rigidly maps each pixel in run-time cropped region 476' to a corresponding pixel in training-stage cropped region 476, and morphs the run-time cropped region 476' (represented by arrow 477) by changing the vales of the camera rays of each of those pixels in run-time cropped region 476' to be identical to the respective camera rays of the corresponding pixels in the training-stage cropped region 476. Thus, once the pixels are matched up, the run-time cropped region 476' is effectively stretched and/or compressed in various regions until the resulting cropped and morphed region 476" appears exactly as if the corresponding reference camera had captured the image. For example, pixel 478' in run-time cropped region 476' is mapped to pixel 478 of training-stage cropped region 476, and similarly, pixel 480' is mapped to pixel 480, and pixel 482' is mapped to pixel 482. It is noted that for graphical clarity the pixels as labeled in FIG. 63A are much larger than the actual pixels on the sensor array of each camera. It is also noted that while the description herein uses three pixels as an example, the morphing is typically performed for all of the pixels in run-time cropped region 476'. When the camera rays corresponding to pixels 478', 480', and 482' are changed to match the respective camera rays of corresponding pixels 478, 480, and 482, run-time cropped region 476' morphs to match training-stage cropped region 476. The result is a cropped and morphed image 476" from a given camera 24 that matches the cropped field of view, i.e., cropped region 476, of a corresponding one of the reference cameras.

For some applications, as described hereinabove, in-the-field intraoral three-dimensional surfaces may be used as the training-stage three-dimensional surfaces for training neural network 400. In this case, two-dimensional images of intraoral three-dimensional surfaces from multiple in-the-field intraoral scanners may be modified, e.g., cropped and morphed, so as to match the reference cameras (as described above), and subsequently the modified, e.g., cropped and morphed two-dimensional images, along with respective corresponding true maps computed based on structured light, may be used as training-stage images 412$t$ and/or 412$t'$ to train neural network 400.

Thus, in accordance with some applications of the present invention, a method is provided including the following steps:
  driving one or more light projectors of an intraoral scanner, e.g., one or more structured light projectors 118 (which may be broadband, non-coherent, or NIR) of an intraoral scanner to project light on an intraoral three-dimensional surface,
  driving one or more cameras 24 of the intraoral scanner to each capture a plurality of two-dimensional images (e.g., two-dimensional color images, or two-dimensional monochromatic NIR images) of the intraoral three-dimensional surface, each of the one or more cameras 24 of the intraoral scanner corresponding to a respective one of one or more reference cameras, and
  using processor 96:
    for each camera 24 of the intraoral scanner, modifying, e.g., cropping and morphing, at least one of the two-dimensional images 472 from camera 24 to obtain a plurality of cropped and morphed two-dimensional images, each cropped and morphed image corresponding to a cropped and morphed field of view (i.e., region) 476" of camera 24, the cropped and morphed field of view 476" of camera 24 matching the cropped field of view of a corresponding one of the reference cameras, and
    computing a three-dimensional structure of the intraoral three-dimensional surface, based on the plurality of modified, e.g., cropped and morphed, two-dimensional images of the intraoral three-dimensional surface by:
      inputting to neural network 400 the plurality of modified, e.g., cropped and morphed, two-dimensional images of the intraoral three-dimensional surface, and
      determining, by neural network 400, a respective estimated map (e.g., estimated depth map, normal map, and/or curvature map) of the intraoral three-dimensional surface as captured in each of the plurality of modified, e.g., cropped and morphed, two-dimensional images, neural network 400 having been trained (e.g., using the same training methods as described hereinabove with reference to FIGS. 52A-E) using training-stage images corresponding to the cropped fields of view of each of the one or more reference cameras.

Typically, the modification, e.g., cropping and morphing, is performed by processor 96 using (a) stored calibration values indicating a camera ray 86 corresponding to each pixel on the camera sensor 58 of each one of the one or more cameras 24, and (b) reference calibration values indicating (i) a camera ray 86 corresponding to each pixel on a reference camera sensor 58 of each one of one or more reference cameras, and (ii) a cropped field of view for each one of the one or more reference cameras.

It is noted that all of the above-described applications and methods relating to depth maps, normal maps, curvature maps, and the uses thereof, with reference to FIGS. 51C-I, may be performed based on the modified, e.g., cropped and morphed, run-time images in the field, mutatis mutandis. Similarly, the training of second neural network module 436 to produce estimated confidence maps and the use of the estimated confidence maps, as described hereinabove with reference to FIGS. 52C-F, may be performed based on the cropped and morphed run-time images in the field, mutatis mutandis.

The inventors have additionally realized that with regard to using estimated maps (e.g., depth, normal, curvature, and/or confidence maps) that are based on the modified, e.g., cropped and morphed, run-time images, the morphing that was performed in order to force the run-time image to match calibration data from a corresponding reference camera should be reversed in order to return the resulting estimated map to the local coordinate system of the intraoral scanner. These uses of the estimated maps include, for example, merging estimated maps together, merging estimated maps to respective point clouds, taking normals to the surface from an estimated normal map, interpolating positions on the intraoral surface based on the estimated maps, and/or using the confidence maps to help with merging contradicting depth maps. Thus, for each estimated map of the intraoral three-dimensional surface as captured in a cropped and morphed two-dimensional image, processor 96 performs a reverse of the morphing to obtain a respective non-morphed estimated map of the intraoral surface as seen in the two-dimensional image prior to the morphing.

It is within the scope of the present invention to combine any of the above-described methods for overcoming potential manufacturing deviations between commercially-produced intraoral scanners that all utilize the same neural network. It is possible that there are deviations that may not be fully overcome by using one method alone. For example, the cropping and morphing of each run-time image may not account for manufacturing deviations related to illumination peculiarities. Therefore, it may be advantageous to additionally perform the above-described method of refining the training of neural network 400 using a plurality of refining-stage scans for a given intraoral scanner, as described hereinabove with reference to FIG. 62, mutatis mutandis.

Figure 64:
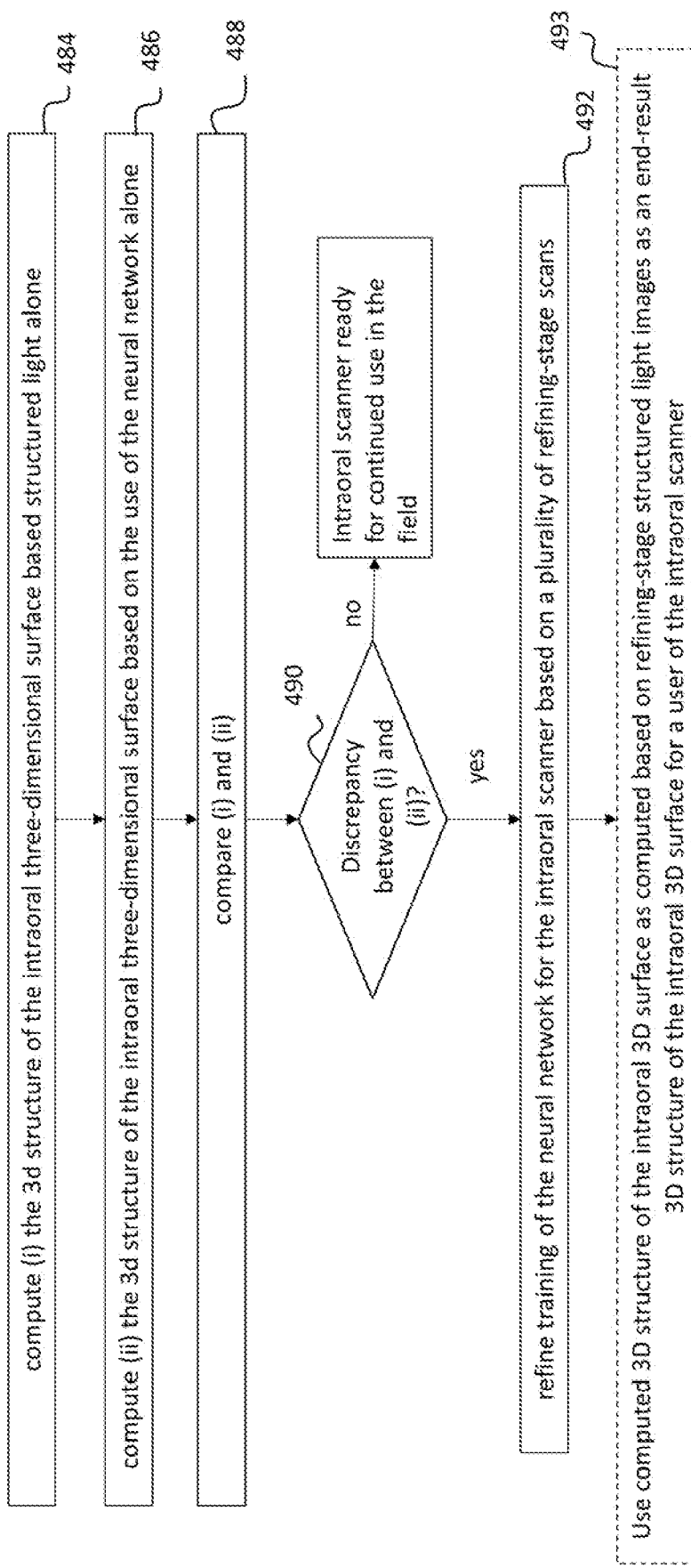
FIG. 64 is a flow chart depicting a method for testing if the cropping and morphing of each run-time image accurately accounts for possible manufacturing deviations for a given intraoral scanner, and if it does not, then refining the training of the neural network based on local refining-stage scans for that given intraoral scanner, in accordance with some applications of the present invention.

Reference is now made to FIG. 64, which is a flow chart depicting a method for testing if the modifying, e.g., cropping and morphing, of each run-time image accurately accounts for possible manufacturing deviations for a given intraoral scanner, and if it does not, then refining the training of neural network 400 based on local refining-stage scans for that given intraoral scanner, in accordance with some applications of the present invention. The method includes the following steps, using estimated depth maps of an intraoral three-dimensional surface, as captured in each of a plurality of cropped and morphed two-dimensional images for a given intraoral scanner:

(a) computing the three-dimensional structure of the intraoral three-dimensional surface based on structured light alone (step 484), i.e., based on computed respective three-dimensional positions of a plurality of points on the intraoral three-dimensional surface, as captured in a plurality of structured light images, (b) computing the three-dimensional structure of the intraoral three-dimensional surface based on the use of neural network 400 alone (step 486), i.e., based on respective estimated depth maps of the intraoral three-dimensional surface, as captured in each of a plurality of cropped and morphed two-dimensional images, (c) comparing (in step 488) (i) the three-dimensional structure of the intraoral three-dimensional surface as computed based on the computed respective three-dimensional positions of the plurality of points on the intraoral three-dimensional surface and (ii) the three-dimensional structure of the intraoral three-dimensional surface as computed based on the respective estimated depth maps of the intraoral three-dimensional surface, and as represented by decision diamond 490, and (d) in response to determining a discrepancy between (i) and (ii), refining the training of neural network 400 for the intraoral scanner based on a plurality of refining-stage scans (step 492) as follows:

driving (A) the one or more structured light projectors 22 of the intraoral scanner and (B) the one or more unstructured light projectors 118 of the intraoral scanner, during a plurality of refining-stage scans, driving the one or more cameras 24 of the intraoral scanner to capture (a) a plurality of refining-stage structured light images and (b) a plurality of refining-stage two-dimensional images, during the plurality of refining-stage scans, computing the three-dimensional structure of the intraoral three-dimensional surface based on the plurality of refining-stage structured light images, and refining the training of the neural network for the intraoral scanner using (a) the plurality of two-dimensional images captured during the refining-stage scans and (b) the computed three-dimensional structure of the intraoral three-dimensional surface as computed based on the plurality of refining-stage structured light images.

It is noted that while the above method for checking if the image modification method accurately accounts for possible manufacturing deviations for a given intraoral scanner is described using depth maps, the same method may be performed using normal maps of the intraoral three-dimensional surface. For example, from the three-dimensional structure of the intraoral three-dimensional based on structured light alone, the true normal map may be computed. This may then be compared to a normal map determined by neural network 400. If a discrepancy is found, neural network 400 may be refined for that intraoral scanner as described hereinabove.

For some applications, while the training of the neural network is being refined, the intraoral scanner is still usable to compute end-result three-dimensional structures of an intraoral three-dimensional surface for a user of the intraoral scanner, using only the structured light images from the refining-stage scans. Therefore, although the intraoral scanner may operate slower than if computing the three-dimensional structure using both structured and unstructured light, the intraoral scanner is fully operational and may be used for run-time in-the-field scans of an intraoral surface even while the training of neural network 400 is being refined for a particular intraoral scanner. Thus, the method further includes, during the refining-stage scans, using the computed three-dimensional structure of the intraoral three-dimensional surface as computed based on the plurality of refining-stage structured light images as an end-result three-dimensional structure of the intraoral three-dimensional surface for a user of the intraoral scanner (step 493).

Reference is now made to FIG. 66, which is a flowchart depicting a method for training neural network 400, in accordance with some applications of the present invention. For some applications, neural network 400 is trained using intraoral two-dimensional images. It may be the case though that in a given intraoral two-dimensional image there is moving tissue, e.g., a subject's tongue, lips, or cheek, that is blocking part of the intraoral three-dimensional surface from cameras 24. The inventors have realized that it is advantageous to the training of neural network 400 to exclude parts of the two-dimensional images that include moving tissue from being included in the training-stage images that are used to optimize neural network 400, e.g., training-stage images 412*t* or 412*t'*. Thus, as indicated by decision diamond 502 in FIG. 66, if moving tissue is identified in a two-dimensional image, then the two-dimensional image may be processed so as to exclude at least a portion of the moving tissue (step 504) prior to inputting the two-dimensional image to neural network 400. Thus, the method includes the following steps:

- inputting to neural network 400 a plurality of two-dimensional images, e.g., two-dimensional images 412*t* or 412*t'*, of an intraoral three-dimensional surface (step 506),
- estimating, by neural network 400, an estimated map (414, 414*s*, and/or 414*r*) of the intraoral three-dimensional surface as captured in each of the two-dimensional images (step 508),
- based on a plurality of structured light images of the intraoral three-dimensional surface, computing a true map 418 of the intraoral three-dimensional surface as seen in each of the two-dimensional images (step 510),
- comparing each estimated map of the intraoral three-dimensional surface to a corresponding true map of the intraoral three-dimensional surface (step 512), and
- based on differences between each estimated map and the corresponding true map, optimizing neural network 400 to better estimate a subsequent estimated map (step 514), wherein, for a two-dimensional image in which moving tissue is identified, processing the image so as to exclude at least a portion of the moving tissue prior to inputting the two-dimensional image to neural network 400 (as indicated by decision diamond 502 and step 504).

For some applications, as described hereinabove, one or more structured light projectors 22 are driven to project a structured light pattern on the intraoral three-dimensional surface and one or more cameras 24 are driven to capture the structured light images, each image including at least a portion of the structured light pattern. One or more unstructured light projectors 118 are used to project unstructured light onto the intraoral three-dimensional surface, and the one or more cameras 24 are driven to capture the plurality of two-dimensional images of the intraoral three-dimensional surface using illumination from the unstructured light projectors. Typically, the capturing of the structured light images and the capturing of the two-dimensional images are regulated to produce an alternating sequence of one or more image frames of structured light interspersed with one or more image frames of two-dimensional images, as described hereinabove. As described hereinabove with reference to FIG. 52A, steps 346, 348, 350, and 352, computing the true map of the intraoral three-dimensional surface as seen in each of the two-dimensional images may include the following steps:

- inputting to neural network 400 a respective plurality of three-dimensional reconstructions of the intraoral three-dimensional surface, based on structured light images of the intraoral three-dimensional surface, the three-dimensional reconstructions including computed three-dimensional positions of a plurality of points on the intraoral three-dimensional surface,
- interpolating a position of the one or more cameras with respect to the intraoral three-dimensional surface for each two-dimensional image frame based on the computed three-dimensional positions of the plurality of points on the intraoral three-dimensional surface as computed based on respective structured light image frames before and after each two-dimensional image frame, and
- projecting the three-dimensional reconstructions on respective fields of view of each of the one or more cameras and, based on the projections, calculating a true map of the intraoral three-dimensional surface as seen in each two-dimensional image, constrained by the computed three-dimensional positions of the plurality of points.

For some applications, structured light projectors 22 are simultaneously driven to project their respective distributions 34 of discrete unconnected spots 33 of light on the intraoral three-surface. Alternatively, structured light projectors 22 may be driven to project their respective distributions 34 of discrete unconnected spots 33 of light on the intraoral three-surface at different respective times, e.g., in a predetermined order, or in an order that is dynamically determined during a scan. Alternatively, for some applications, a single structured light projector 22 may be driven to project distribution 34.

Dynamically determining which structured light projectors 22 to activate during a scan may improve overall signal quality of the scan as some of the structured light projectors may have better signal quality in some regions of the intraoral cavity relative to other regions. For example, when scanning a subject's palate (upper jaw region) the red projectors tend to have better signal quality than the blue projectors. Additionally, hard-to-see regions within the intraoral cavity may be encountered during a scan, e.g., an area with missing teeth or narrow cracks between big teeth. In these types of cases, dynamically determining which structured light projector 22 to activate during a scan allows specific projectors that may have better line of sight to the region in question to be activated.

For some applications, different structured light projectors 22 may be configured to focus at different object focal planes. Dynamically determining which structured light projectors 22 to activate during a scan allows for activating specific structured light projectors 22 according to their respective object focal planes depending on a distance from a region currently being scanned.

For some applications, at least one temperature sensor 52 is coupled to rigid structure 26 and measures a temperature of rigid structure 26. Temperature control circuitry 54 disposed within handheld wand 20 (*a*) receives data from temperature sensor 52 indicative of the temperature of rigid structure 26 and (b) activates a temperature control unit 56 in response to the received data. Temperature control unit 56, e.g., a PID controller, keeps probe 28 at a desired temperature (e.g., between 35 and 43 degrees Celsius, between 37 and 41 degrees Celsius, etc.). Keeping probe 28 above 35 degrees Celsius, e.g., above 37 degrees Celsius, reduces fogging of the glass surface of handheld wand 20, through which structured light projectors 22 project and cameras 24 view, as probe 28 enters the intraoral cavity, which is typically around or above 37 degrees Celsius. Keeping probe 28 below 43 degrees, e.g., below 41 degrees Celsius, prevents discomfort or pain.

Additionally, in order for the stored calibration values of the camera rays and the projector rays to be of use during a scan, the temperature of cameras 24 and structured light projectors 22 may be prevented from varying so as to maintain geometrical integrity of the optics. A variation in temperature can cause the length of probe 28 to change due to thermal expansion, which in turn may cause the respective camera and projector positions to shift. Due to different types of stress that may build up within probe 28 during such thermal expansion, twisting can also occur, causing the angles of the respective camera rays and projector rays to shift as well. Within the cameras and projectors, geometric changes may occur due to temperature variation as well. For example, DOE 39 may expand and alter the projected pattern, temperature variations may affect the refractive index of the camera lenses, or temperature variations may change the wavelengths transmitted by laser diodes 36. Therefore, in addition to keeping probe 28 at a temperature within the range described above, temperature control unit 56 may further prevent the temperature of probe 28 from varying by more than 1 degree when handheld wand 20 is in use, so as to maintain geometrical integrity of the optics disposed within probe 28. For example, if temperature control unit 56 is keeping probe 28 at a temperature of 39 degrees Celsius then temperature control unit 56 will further ensure that during use the temperature of probe 28 does not go below 38 degrees Celsius or above 40 degrees Celsius.

For some applications, probe 28 is maintained at its controlled temperature through the use of a combination of heating and cooling. For example, temperature control unit 56 may include a heater, e.g., a plurality of heaters, and a cooler, e.g., a thermoelectric cooler. If the temperature of probe 28 drops below 38 degrees Celsius the heater(s) may be used to raise the temperature of probe 28, and if the temperature of probe 28 goes above 40 degrees Celsius, the thermoelectric cooler may be used to lower the temperature of probe 28.

Alternatively, for some applications, probe 28 is maintained at its controlled temperature through the use of heating only, without cooling. The use of laser diodes 36 and diffractive and/or refractive pattern generating optical elements helps maintain an energy efficient structured light projector so as to limit probe 28 from heating up during use; laser diodes 36 may use less than 0.2 Watts of power while transmitting at a high brightness and diffractive and/or refractive pattern generating optical elements utilize all the transmitted light (in contrast, for example, to a mask which stops some of the rays from hitting the object). External environmental temperatures, such as those encountered within a subject's intraoral cavity, may however cause heating of probe 28. To overcome this, heat may be drawn out of the probe 28 via a heat conducting element 94, e.g., a heat pipe, that is disposed within handheld wand 20, such that a distal end 95 of heat conducting element 94 is in contact with rigid structure 26 and a proximal end 99 is in contact with a proximal end 100 of handheld wand 20. Heat is thereby transferred from rigid structure 26 to proximal end 100 of handheld wand 20. Alternatively or additionally, a fan disposed in a handle region 174 of handheld wand 20 may be used to draw heat out of probe 28.

For some applications, alternatively or additionally to maintaining geometric integrity of the optics by preventing the temperature of probe 28 from varying by more than a threshold change in temperature, processor 96 may select between a plurality of sets of calibration data corresponding to different temperatures respectively. For example, the threshold change may be 1 degree Celsius. Based on data received from temperature sensor 52 indicative of the temperature of structured light projectors 22 and cameras 24, processor 96 may select between a plurality of sets of stored calibration data corresponding to a plurality of respective temperatures of structured light projectors 22 and cameras 24, each set of stored calibration data indicating for a respective temperature (a) the projector ray corresponding to each of the projected spots of light from each one of the one or more projectors, and (b) the camera ray corresponding to each pixel on the camera sensor of each one of the one or more cameras. If processor 96 only has access to stored calibration data for a specific plurality of temperatures, processor 96 may interpolate between the plurality of sets of stored calibration data based on data received from temperature sensor 52, in order to obtain calibration data for temperatures between the respective temperatures corresponding to each set of calibration data.

Figure 18:
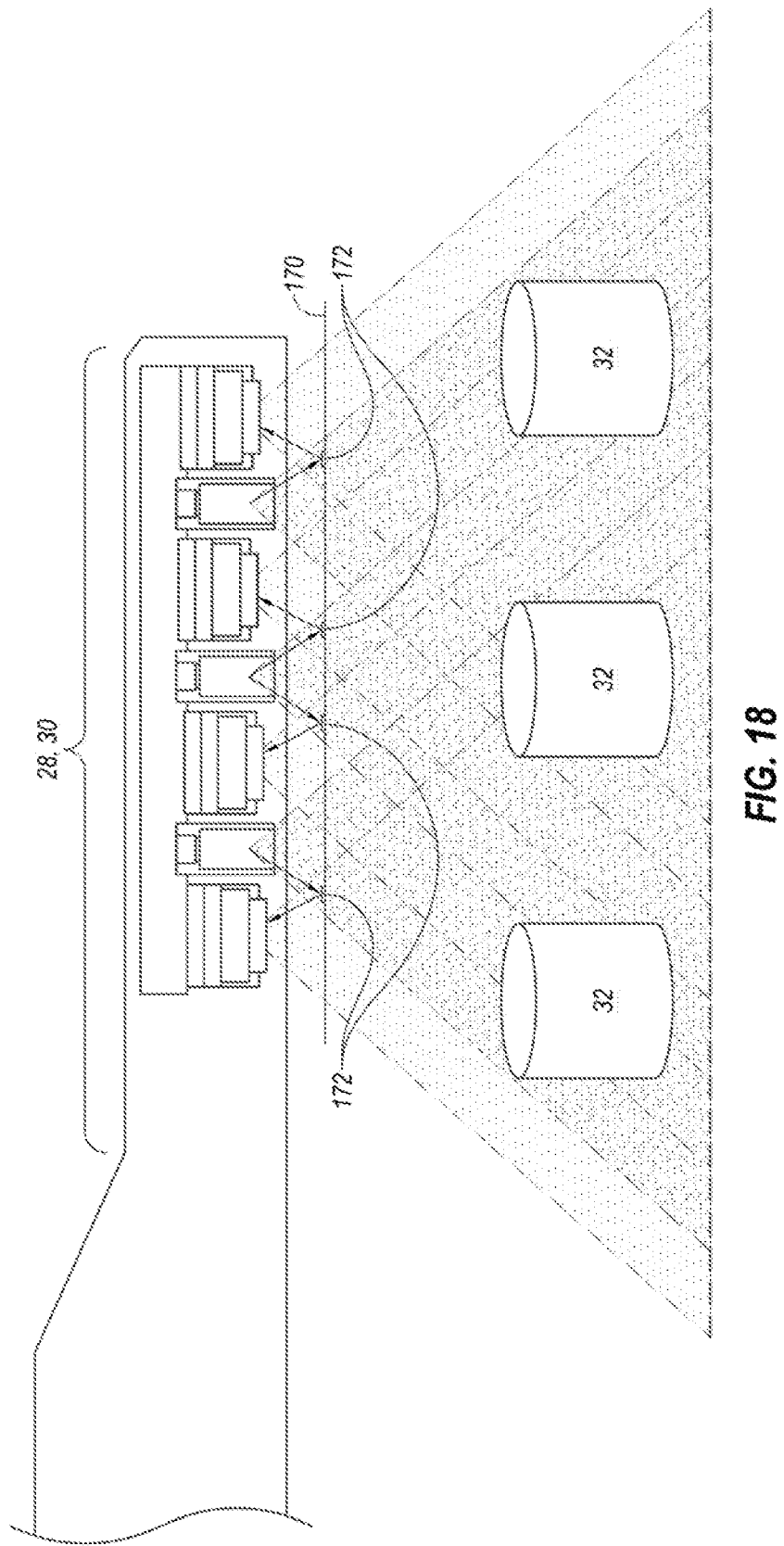
FIG. 18 is a schematic illustration of the probe including a diffuse reflector, in accordance with some applications of the present invention.

Reference is now made to FIG. 18, which is a schematic illustration of probe 28, in accordance with some applications of the present invention. For some applications, probe 28 further includes a diffuse reflector 170 having a plurality of regions 172 disposed within probe 28 (or, as shown in FIG. 18, adjacent to probe 28). In some applications, (a) each structured light projector 22 may have at least one region 172 of diffuse reflector 170 in its field of illumination, (b) each camera 24 has at least one region 172 of diffuse reflector 170 in its field of view, and (c) a plurality of regions 172 of diffuse reflector 170 are in the field of view of a camera 24 and in the field of illumination of a structured light projector 22. Alternatively or additionally to maintaining geometric integrity of the optics by preventing the temperature of probe 28 from varying by more than a threshold temperature change, processor 96 may (a) receive data from cameras 24 indicative of the position of the diffuse reflector with respect to distribution 34 of discrete unconnected spots 33 of light, (b) compare the received data to a stored calibration position of diffuse reflector 170, wherein a discrepancy between (i) the received data indicative of the position of diffuse reflector 170 and (ii) the stored calibration position of diffuse reflector 170, indicates a shift of projector rays 88 and cameras rays 86 from their respective stored calibration values, and (c) run the correspondence algorithm based on the shift of projector rays 88 and cameras rays 86.

Alternatively or additionally, a discrepancy between (i) the received data indicative of the position of diffuse reflector 170 and (ii) the stored calibration position of diffuse reflector 170 may indicate a change in temperature of probe 28. In this case the temperature of probe 28 may be regulated based on the comparison of the received data and the stored calibration position of diffuse reflector 170.

Hereinbelow is described a plurality of applications for structured light projectors 22.

Figure 19B:
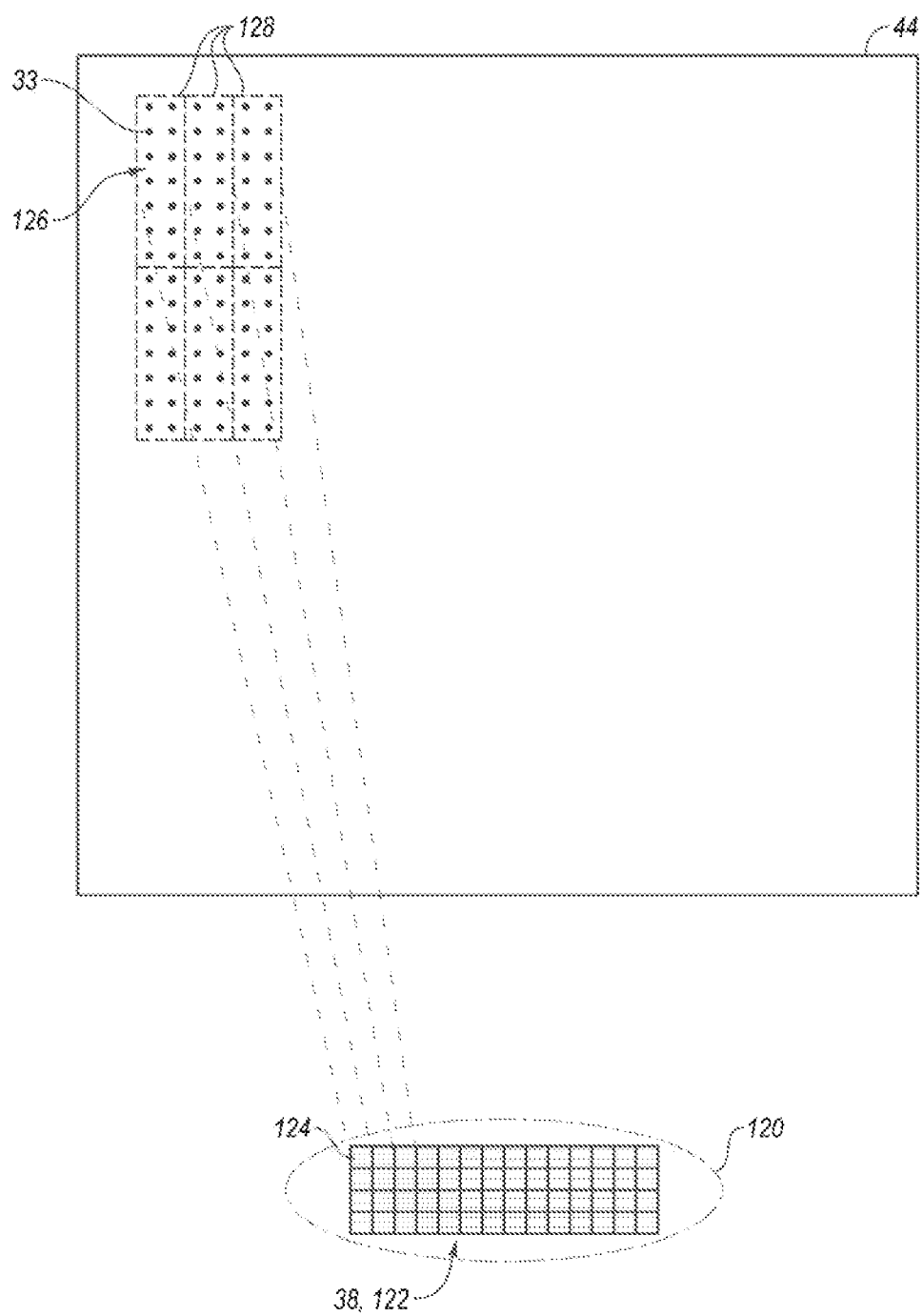

Reference is now made to FIG. 19A-B, which are schematic illustrations of structured light projector 22 and a cross-section of a beam 120 of light transmitted by a laser diode 36, with a pattern generating optical element 38 shown disposed in the light path of the beam, in accordance with some applications of the present invention. In some applications, each laser diode 36 transmits an elliptical beam 120 whose elliptical cross-section has (a) a long axis of at least 500 microns and/or less than 700 microns and (b) a short axis of at least 100 microns and/or less than 200 microns. For some applications, a small area beam splitter may be used in order to generate a tightly focused spot array, e.g., a DOE having a side length of less than 100 microns may be used in order to maintain projected spots 33 in tight focus over the entire focus range of interest. However, such a small DOE would utilize only a fraction of the light transmitted via elliptical laser beam 120.

Therefore, for some applications, pattern generating optical element 38 is a segmented DOE 122 that is segmented into a plurality of sub-DOE patches 124 that are arranged in an array. The array of sub-DOE patches 124 is positioned so as to (a) be contained within elliptical beam 120 of light and (b) utilize a high percentage, e.g., at least 50% of the light transmitted via elliptical laser beam 120. In some applications, the array is a rectangular array including at least 16 and/or less than 72 sub-DOE patches 124 and has a longest dimension of at least 500 microns and/or less than 800 microns. Each sub-DOE patch 124 may have a square cross-section having a side of length of at least 30 microns and/or less than 75 microns, the cross-section being taken perpendicular to the optical axis of the DOE.

Each sub-DOE patch 124 generates a respective distribution 126 of discrete unconnected spots 33 of light in a different area 128 of the field of illumination. For this application of structured light projector 22, distribution 34 of discrete unconnected spots 33 of light, as described hereinabove with reference to FIG. 4, is a combination of respective distributions 126 generated by respective sub-DOE patches 124. FIG. 19B shows an orthogonal plane 44, on which is shown respective distributions 126 of discrete unconnected spots 33 of light, each respective distribution 126 being in a different area 128 of the field of illumination. Since each sub-DOE patch 124 is responsible for a different area 128 of the field of illumination, each sub-DOE patch 124 has a different design so as to direct its respective distribution 126 in a different direction and avoid beam crossing in order to avoid overlap between projected spots 33.

Figure 20A:
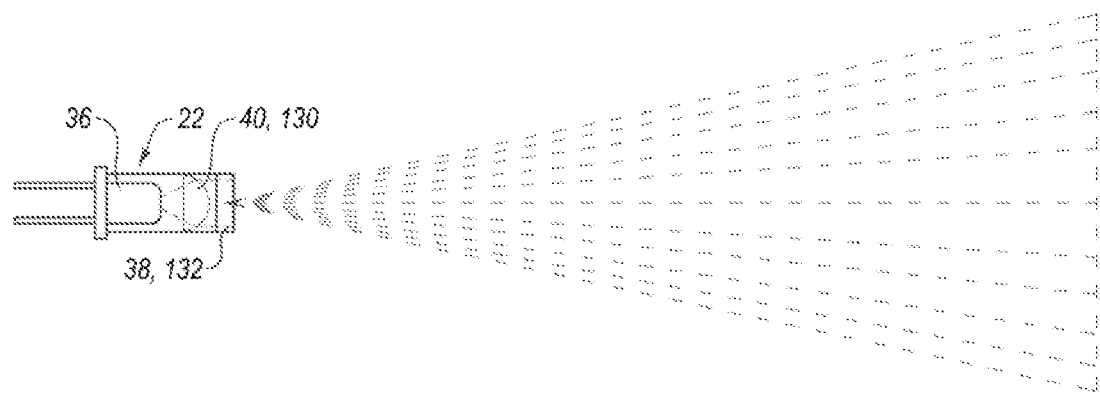
FIGS. 20A-E are schematic illustrations of a micro-lens array used as a pattern generating optical element in a structured light projector, in accordance with some applications of the present invention.
Figure 20B:
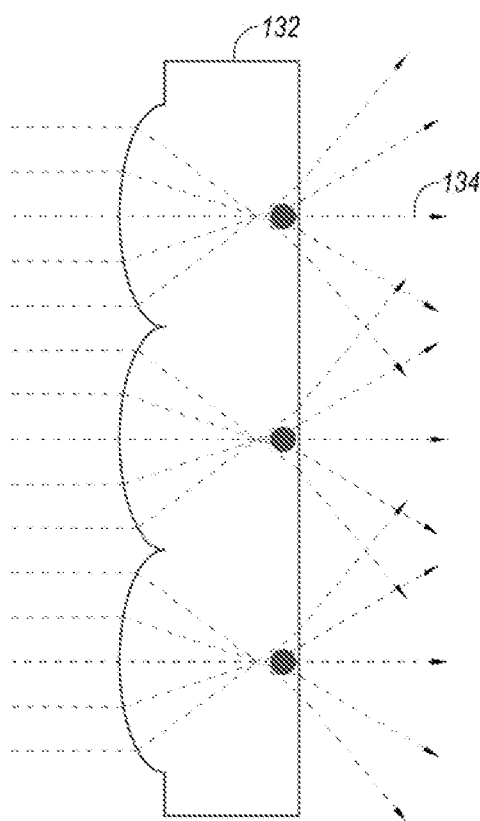
Figure 20C:
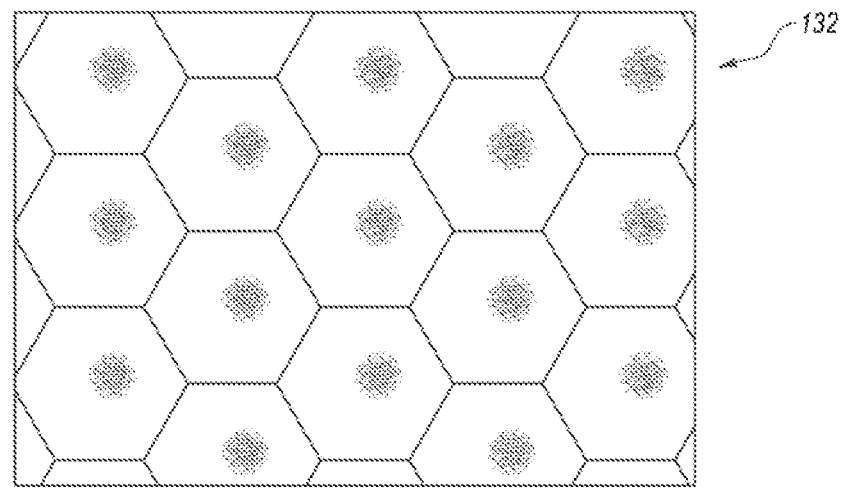
Figure 20D:
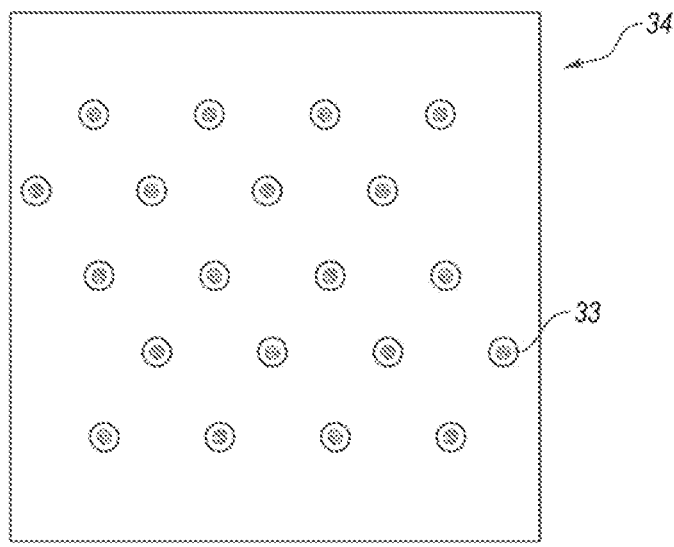
Figure 20E:
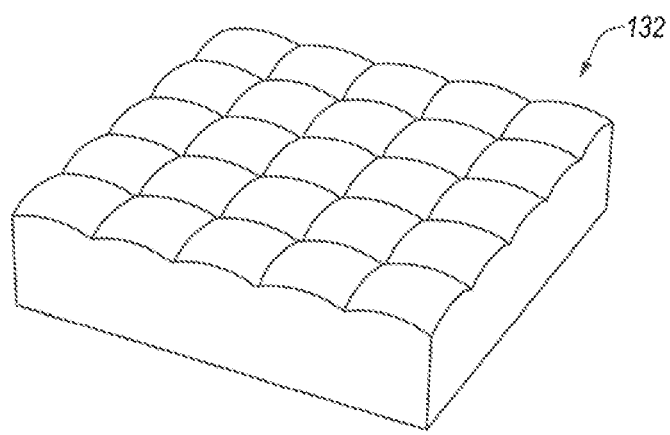

Reference is now made to FIGS. 20A-E, which are schematic illustrations of a micro-lens array 132 as pattern generating optical element 38, in accordance with some applications of the present invention. A micro-lens array can be used as spot generator since it is periodic and the profile variation of each lens in the array is in the wavelength scale. The pitch of micro-lens array 132 is tuned for the desired angular pitch between the spots. The numerical aperture (NA) of micro-lens array 132 is tuned to provide the desired angular field of illumination, as described hereinabove. In some applications, the NA of micro-lens array 132 is at least 0.2 and/or less than 0.7. Micro-lens array 132 may be, for example, a hexagonal micro-lens array, such as is shown in FIG. 20C, or a rectangular micro-lens array, such as is shown in FIG. 20E.

Structured light projectors 22 that have micro-lens array 132 as pattern generating optical element 38 may include laser diode 36, collimating lens 130, an aperture, and micro-lens array 132. The aperture defines a smaller input beam diameter in order to maintain tightly focused spots at a near focal distance, e.g., at least 1 mm and/or less than 30 mm, e.g., at least 4 mm and/or less than 24 mm, from micro-lens array 132. FIG. 20B shows the collimated laser beam illuminating micro-lens array 132, and micro-lens array then generating diverging beams 134 of light, the interference of these diverging beams generating an array of spots 33, e.g., distribution 34 (FIG. 20D). For some applications, the aperture is a chrome film that is applied to the laser-diode-side of collimating lens 130. Alternatively, for some applications, the aperture is a chrome film disposed on the collimating-lens-side of micro-lens array 132. In some applications, the aperture may span a distance of at least 10 times the pitch of micro-lens array 132 and has a diameter of at least 50 microns and/or less than 200 microns.

Figure 21A:
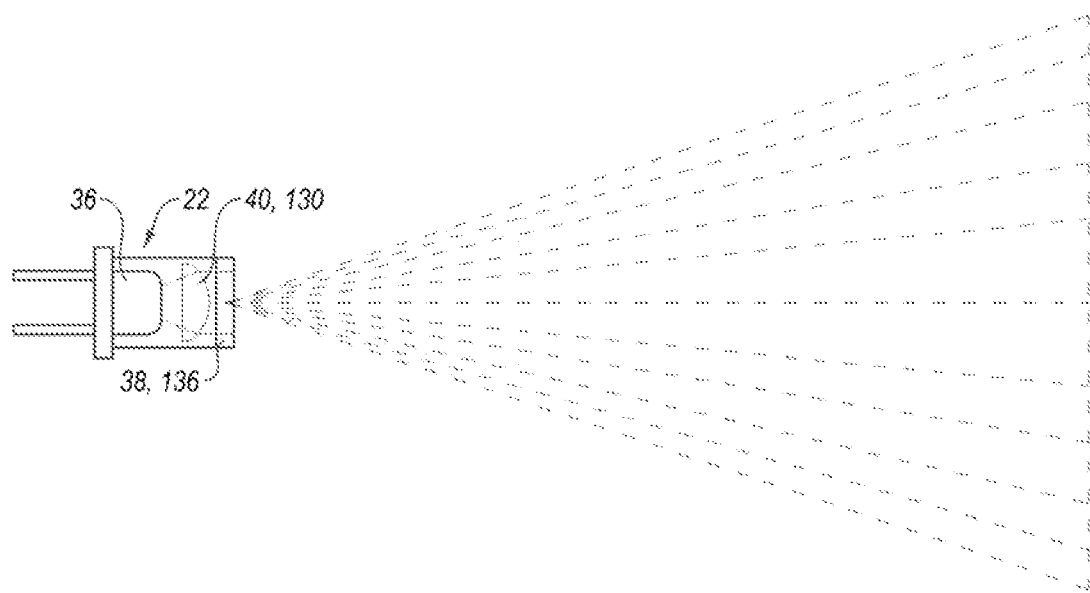
FIGS. 21A-C are schematic illustrations of a compound 2-D diffractive periodic structure used as a pattern generating optical element in a structured light projector, in accordance with some applications of the present invention.
Figure 21B:
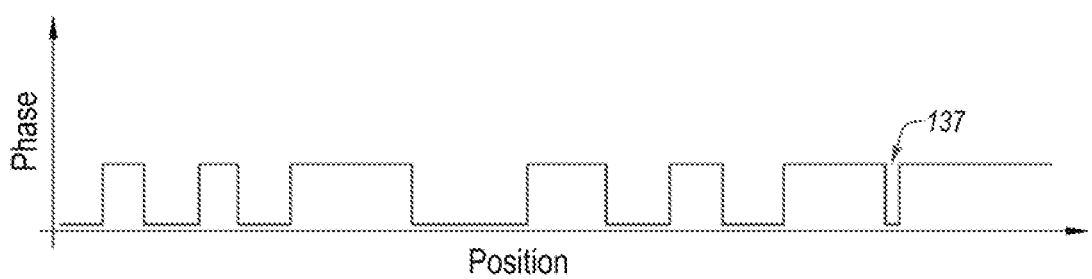
Figure 21C:
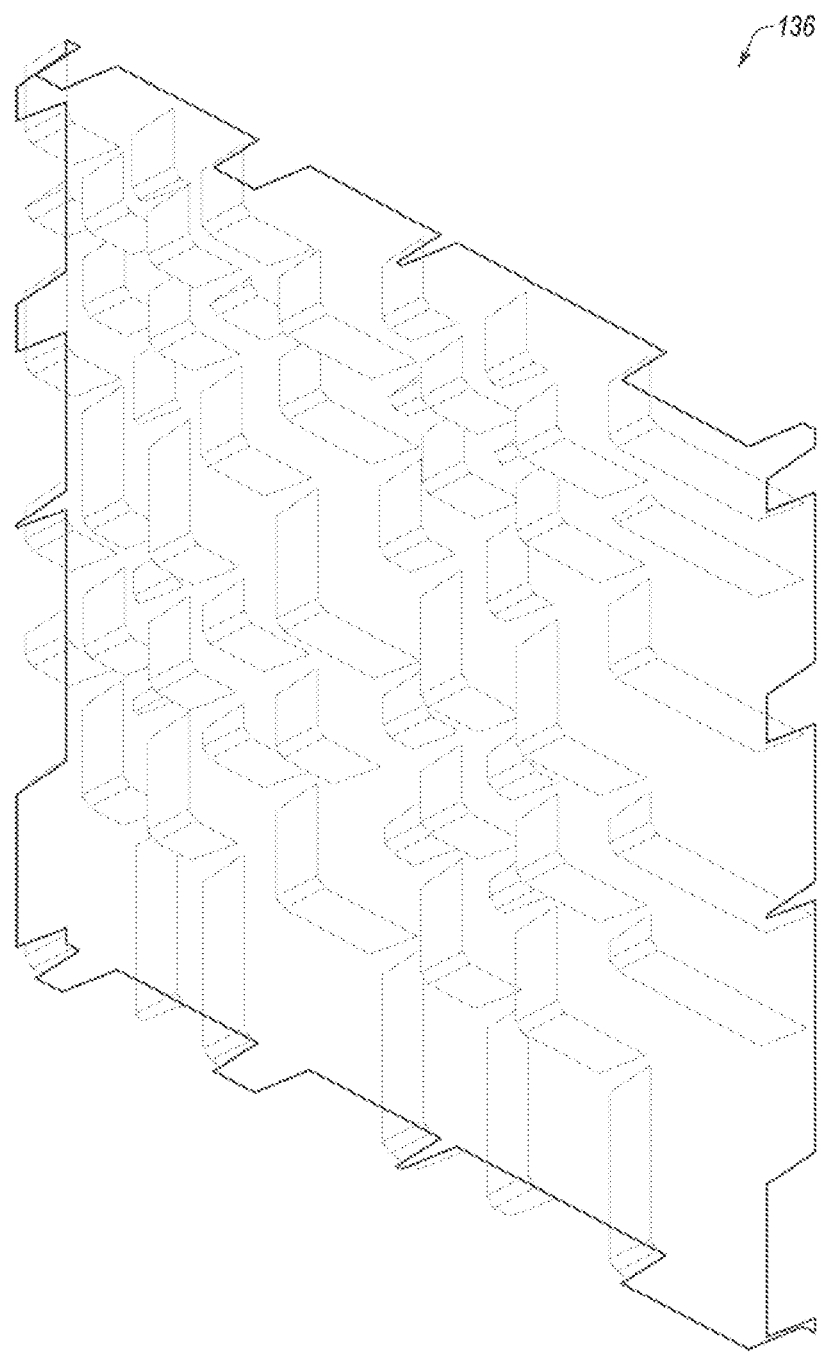

Reference is now made to FIGS. 21A-C, which are schematic illustrations of a compound 2-D diffractive periodic structure 136, e.g., a diffractive grating such as a Dammann grating, as pattern generating optical element 38, in accordance with some applications of the present invention. Compound diffractive periodic structure 136 may have a periodic structure feature size 137 of at least 100 nm and/or less than 400 nm. The large field of illumination as described hereinabove may be obtained by small sub-features that are around 300 nm. The period of compound diffractive periodic structure 136 may be tuned to provide a desired angular pitch of the projected beams of light.

Structured light projectors 22 that have compound diffractive periodic structure 136 as pattern generating optical element 38 may include laser diode 36, collimating lens 130, an aperture, and compound diffractive periodic structure 136. The aperture defines a smaller input beam diameter in order to maintain tightly focused spots at a near focal distance, e.g., at least 1 mm and/or less than 30 mm, e.g., at least 4 mm and/or less than 24 mm, from compound diffractive periodic structure 136. For some applications, the aperture is chrome film that is over the periodic structure features of compound diffractive periodic structure 136. In some applications, the aperture may span a distance of at least 10 periods of compound diffractive periodic structure 136 and has a diameter of at least 50 microns and/or less than 200 microns.

For some applications, beam shaping optical element 40 (such as is shown in FIG. 3) is a collimating lens 130 disposed between laser diode 36 and pattern generating optical element 38. With respect to the applications described hereinabove with reference to FIGS. 19A-B, 20A-E, and 21A-C, collimating lens 130 may be disposed between laser diode 36 and segmented DOE 122 (FIG. 19A), between laser diode 36 and micro-lens array 132 (FIG. 20A), and between laser diode 36 and compound diffractive periodic structure 136 (FIG. 21A).

Figure 22A:
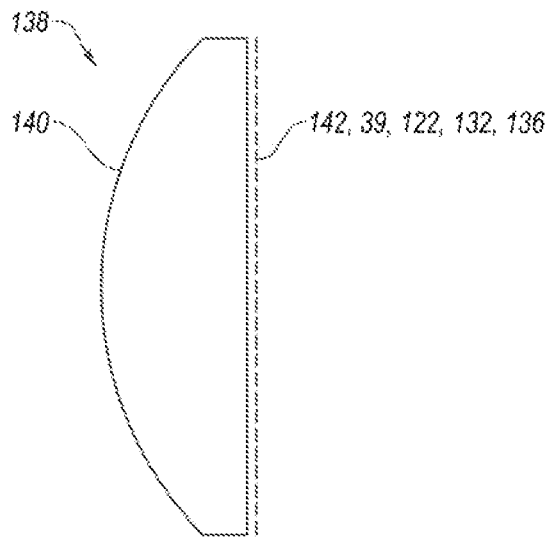
FIGS. 22A-B are schematic illustrations showing a single optical element that has an aspherical first side and a planar second side, opposite the first side, and a structured light projector including the optical element, in accordance with some applications of the present invention.
Figure 22B:
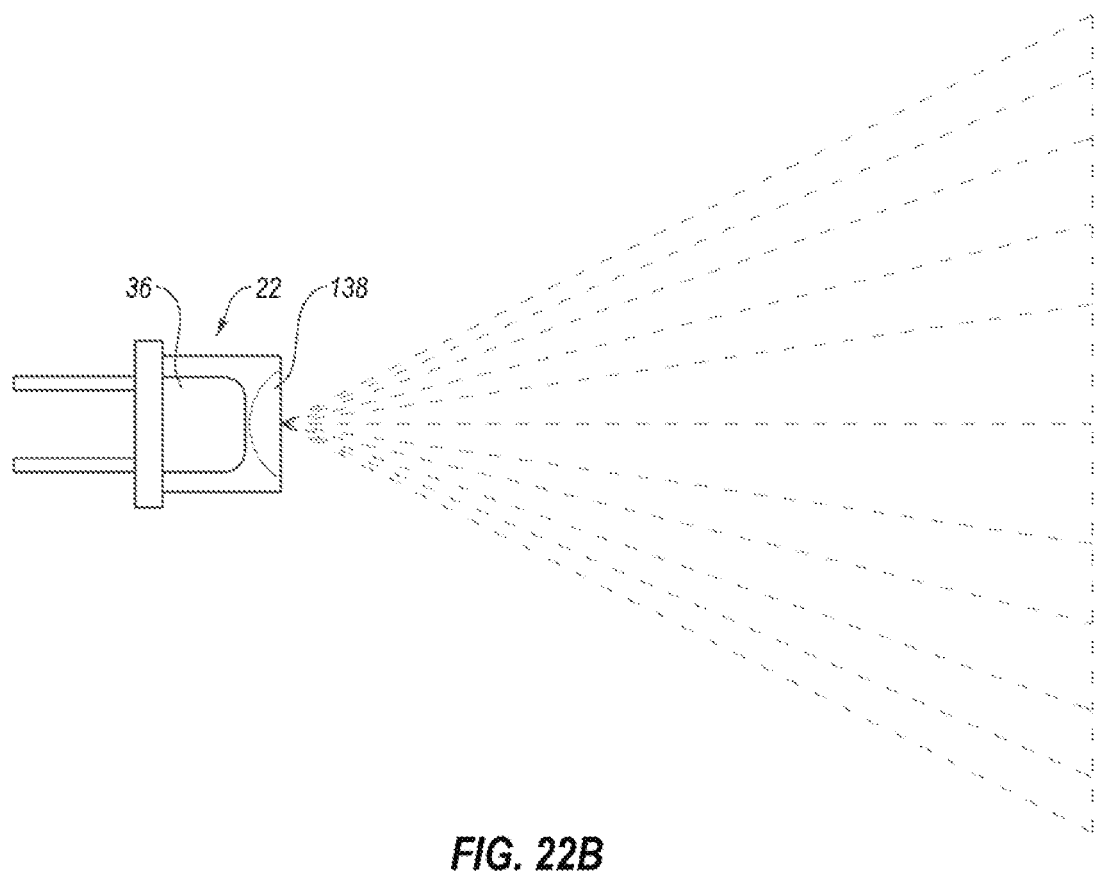

Reference is now made to FIGS. 22A-B, which are schematic illustrations showing a single optical element 138 that has an aspherical first side and a planar second side, opposite the first side, and structured light projector 22 including optical element 138, in accordance with some applications of the present invention. For some applications, collimating lens 130 and pattern generating optical element 38 may be fabricated as single optical element 138, a first aspherical side 140 of which collimates the light transmitted from laser diode 36, and a second planar side 142 of which generates distribution 34 of discrete unconnected spots 33 of light. Planar side 142 of single optical element 138 may be shaped to define DOE 39, segmented DOE 122, micro-lens array 132, or compound diffractive periodic structure 136.

Figure 23A:
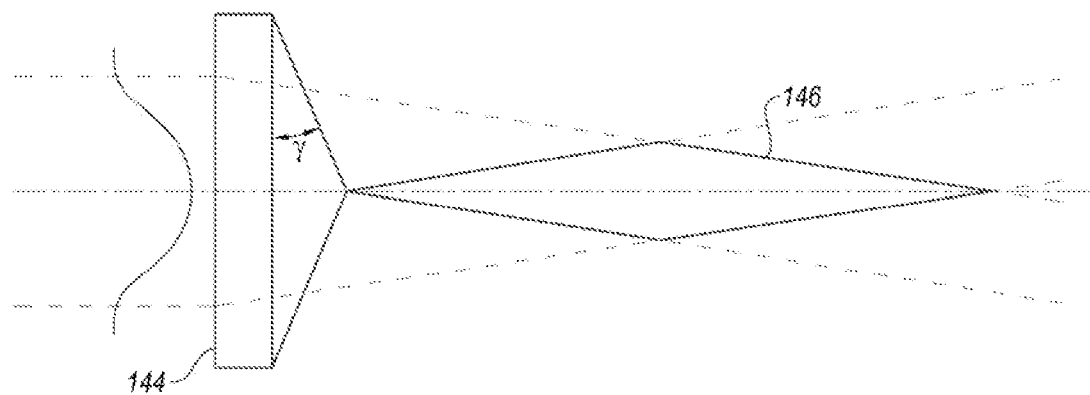
FIGS. 23A-B are schematic illustrations of an axicon lens and a structured light projector including the axicon lens, in accordance with some applications of the present invention.
Figure 23B:
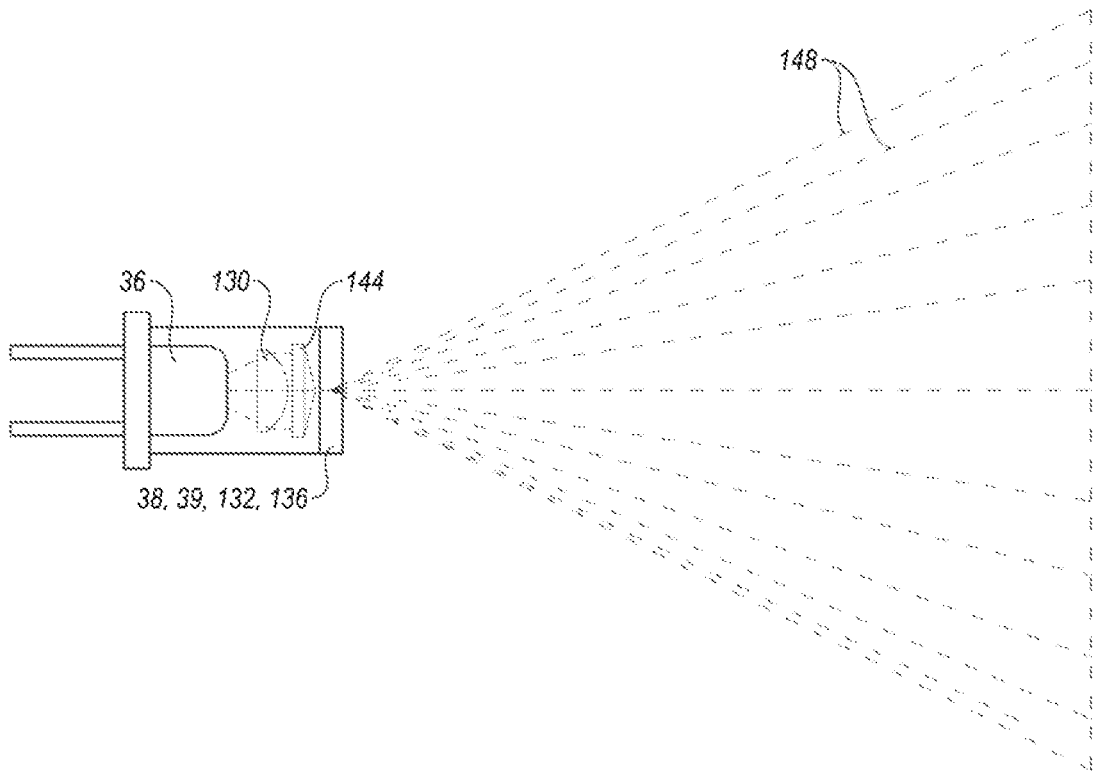

Reference is now made to FIGS. 23A-B, which are schematic illustrations of an axicon lens 144 and structured light projector 22 including axicon lens 144, in accordance with some applications of the present invention. Axicon lenses are known to generate a Bessel beam, which is a beam of light that is focused throughout a desired depth range depending on the input beam diameter and the axicon head angle. For some applications, axicon lens 144, having a head angle γ (gamma) of at least 0.2 degrees and/or less than 2 degrees, is disposed between collimating lens 130 and pattern generating optical element 38. Axicon lens 144 generates a focused Bessel beam 146 when laser diode 36 transmits light through axicon lens 144. Focused Bessel beam 146 is split into many beams 148 by pattern generating optical element 38, each beam 148 being an exact copy of the Bessel beam 146 generated by axicon lens 144. Pattern generating optical element 38 may be DOE 39, micro-lens array 132, or compound diffractive periodic structure 136.

Figure 24A:
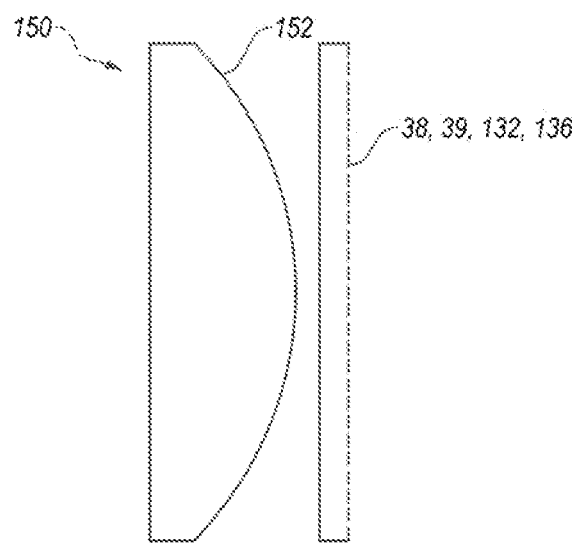
FIGS. 24A-B are schematic illustrations showing an optical element that has an aspherical surface on a first side and a planar surface on a second side, opposite the first side, and a structured light projector including the optical element, in accordance with some applications of the present invention.
Figure 24B:
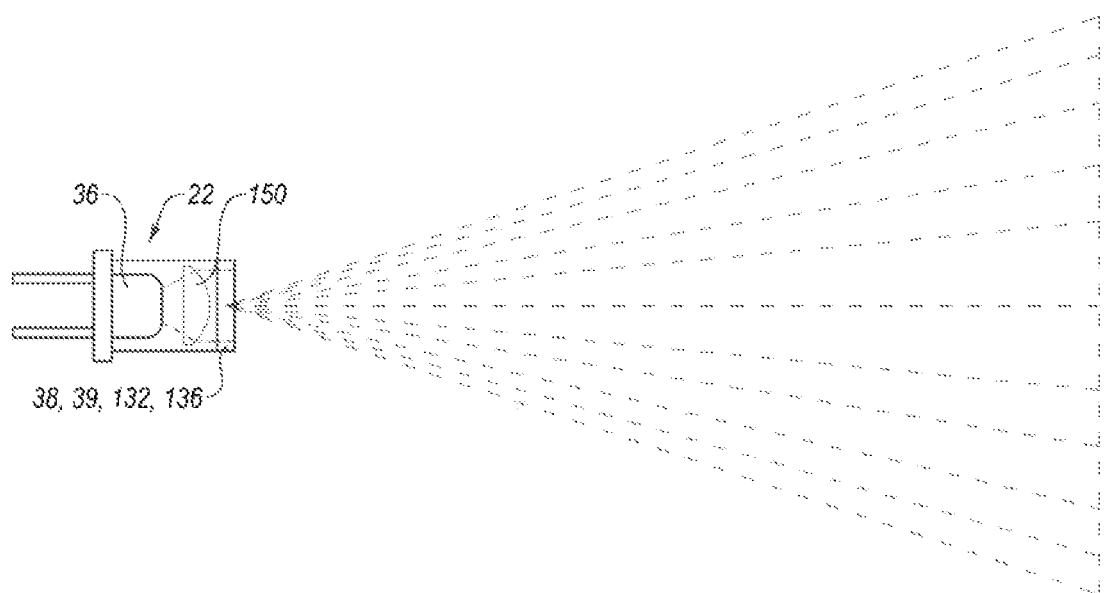

Reference is now made to FIGS. 24A-B, which are schematic illustrations showing an optical element 150 that has an aspherical surface 152 on a first side and a planar surface on a second side, opposite the first side, and structured light projector 22 including optical element 150, in accordance with some applications of the present invention.

For some applications, collimating lens 130 and axicon lens 144 may be fabricated as single optical element 150. Aspherical surface 152 of single optical element 150 generates a Bessel beam directly from a diverging beam of light when laser diode 36 transmits light through optical element 150. As the light then travels through pattern generating optical element 38, distribution 34 of discrete unconnected spots 33 of light is generated such that discrete unconnected spots 33 of light have a substantially uniform size at any orthogonal plane located between 1 mm and 30 mm, e.g., between 4 mm and 24 mm, from pattern generating optical element 38. Pattern generating optical element 38 may be DOE 39, micro-lens array 132, or compound diffractive periodic structure 136. As used herein throughout the present application, including in the claims, spots having a "substantially uniform size" means that the size of the spots does not vary by more than 40%.

Figure 25:
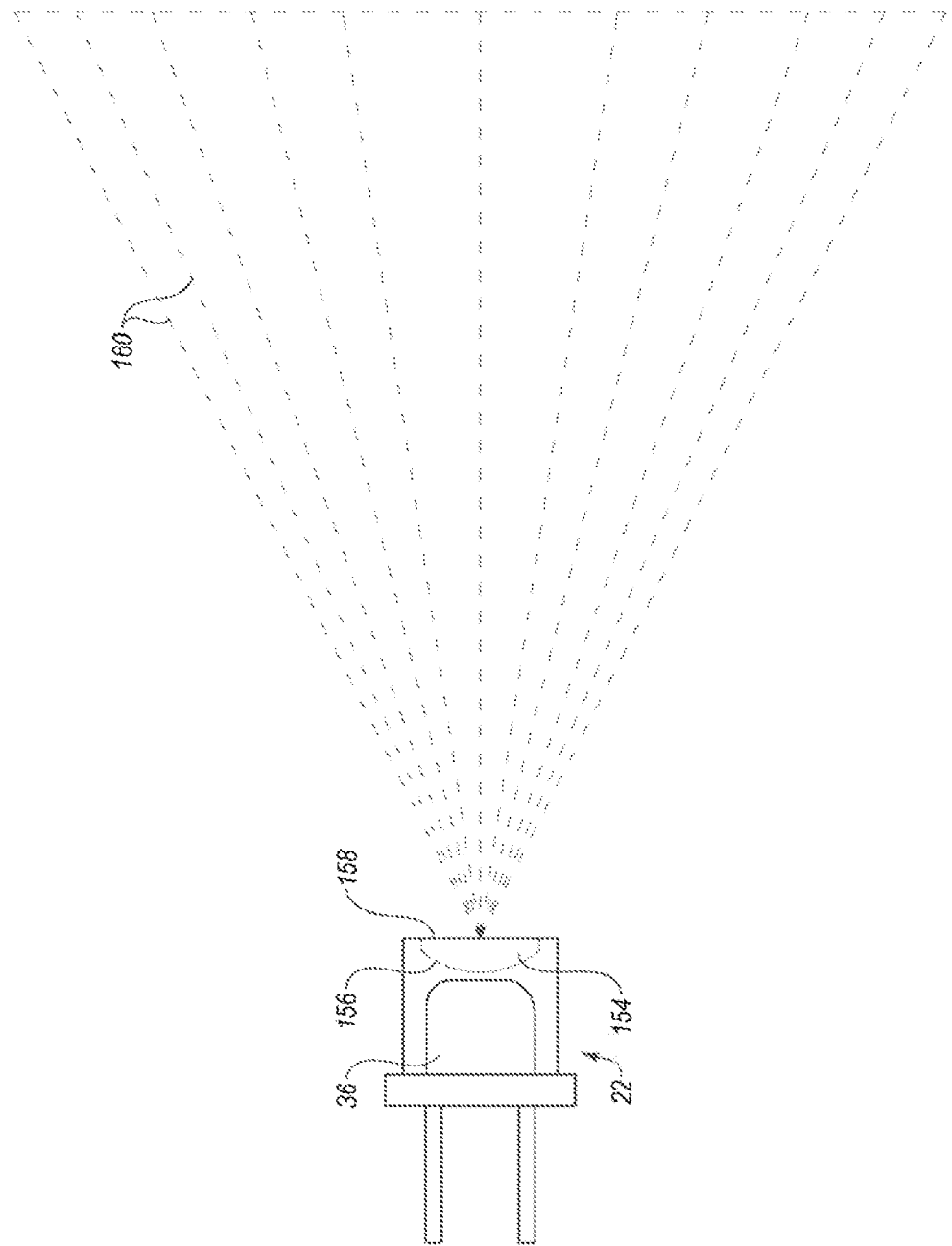
FIG. 25 is a schematic illustration of a single optical element in a structured light projector, in accordance with some applications of the present invention.

Reference is now made to FIG. 25, which is a schematic illustration of a single optical element 154 in structured light projector 22, in accordance with some applications of the present invention. For some applications, single optical element 154 may perform the functions of the collimating lens, axicon lens, and pattern generating optical element. Single optical element 154 includes an aspherical surface 156 on a first side and a planar surface 158 on a second side, opposite the first side. Aspherical surface 156 generates a Bessel beam directly from a diverging beam of light when laser diode 36 transmits a diverging beam of light through the single optical element 154. Planar surface 158 is shaped to define pattern generating optical element 38 and thus splits the Bessel beam into an array of discrete Bessel beams 160 so as to generate distribution 34 of discrete unconnected spots 33 of light, such that discrete unconnected spots 33 of light have a substantially uniform size at any orthogonal plane located between 1 mm and 30 mm, e.g., between 4 mm and 24 mm, from pattern generating single optical element 154. Planar surface 158 may be shaped to define DOE 39, micro-lens array 132, or compound diffractive periodic structure 136.

Figure 26A:
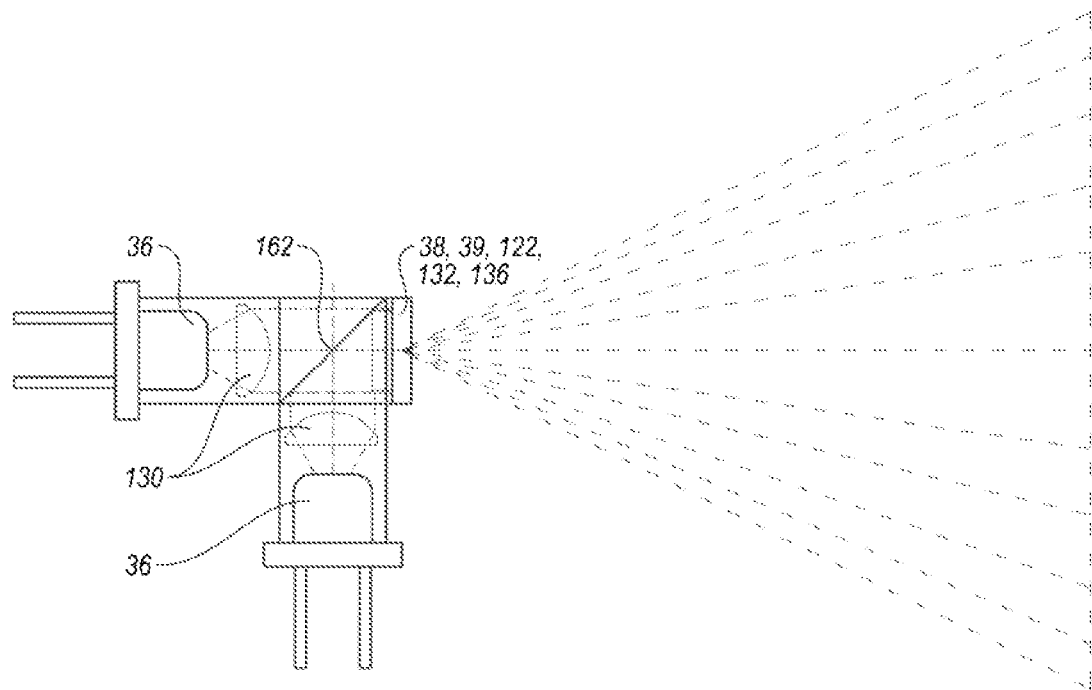
FIGS. 26A-B are schematic illustrations of a structured light projector with more than one laser diode, in accordance with some applications of the present invention.
Figure 26B:
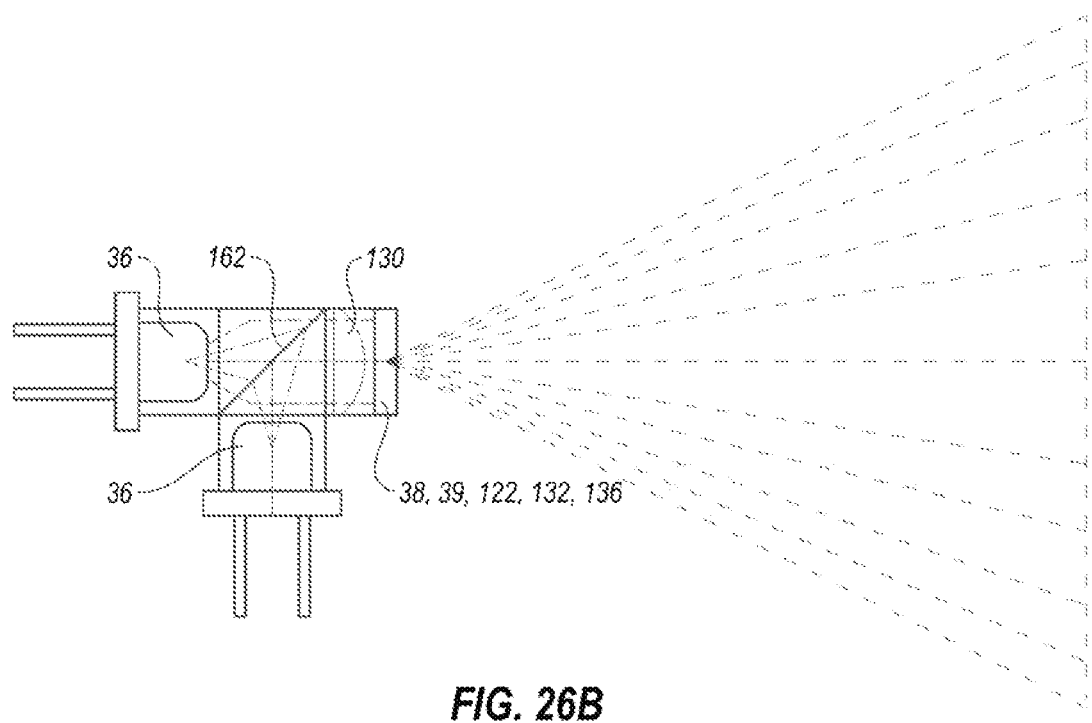

Reference is now made to FIGS. 26A-B, which are schematic illustrations of structured light projector 22 with more than one light source (e.g., laser diodes 36), in accordance with some applications of the present invention. When using a laser diode, laser speckles may give rise to spatial noise. The speckle effect is a result of interference of many waves of the same frequency but different phases and amplitudes. When all added together, the resultant wave is a wave whose amplitude varies randomly across the beam profile. For some applications, the speckle effect may be reduced by combining a plurality of laser diodes 36 of the same wavelength. Different lasers having the same wavelength are not coherent to one another, so combining them into the same spatial space, or the same diffractive beam splitter 162, will lower the speckles by at least a factor of the square root of the number of different laser diodes 36.

Beam splitter 162 may be a standard 50/50 splitter, lowering the efficiency of both beams to under 50%, or a polarizing beam splitter (PBS), keeping the efficiency at greater than 90%. For some applications, each laser diode 36 may have its own collimating lens 130, such as is shown in FIG. 26A. Alternatively, the plurality of laser diodes 36 may share a collimating lens 130, the collimating lens being disposed between beam splitter 162 and pattern generating optical element 38, such as is shown in FIG. 26B. Pattern generating optical element 38 may be DOE 39, segmented DOE 122, micro-lens array 132, or compound diffractive periodic structure 136.

As described hereinabove, a sparse distribution 34 improves capture by providing an improved balance between reducing the amount of projected light while maintaining a useful amount of information. For some applications, in order to provide a higher density pattern without reducing capture, a plurality of laser diodes 36 having different wavelengths may be combined. For example, each structured light projector 22 may include at least two, e.g., at least three, laser diodes 36 that transmit light at distinct respective wavelengths. Although projected spots 33 may be nearly overlapping in some cases, the different color spots may be resolved in space using the camera sensors' color distinguishing capabilities. Optionally, red, blue, and green laser diodes may be used. All of the structured light projector configurations described hereinabove may be implemented using a plurality of laser diodes 36 in each structured light projector 22.

Figure 27B:
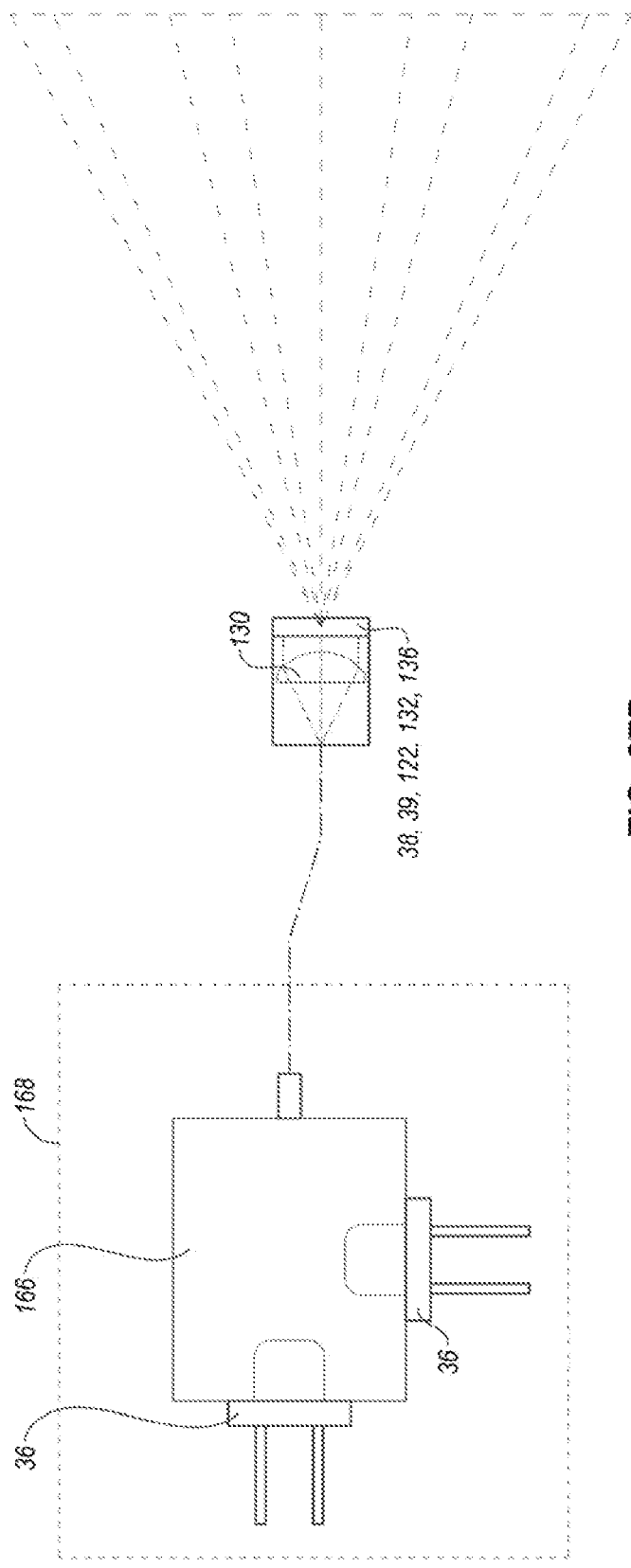

Reference is now made to FIGS. 27A-B, which are schematic illustrations of different ways to combine laser diodes of different wavelengths, in accordance with some applications of the present invention. Combining two or more lasers of different wavelengths into the same diffractive element can be done using a fiber coupler 164 (FIG. 27A) or a laser combiner 166 (FIG. 27B). For laser combiner 166 the combining element may be a dichroic two-way or three-way dichroic combiner. Within each structured light projector 22 all laser diodes 36 transmit light through a common pattern generating optical element 38, either simultaneously or at different times. The respective laser beams may hit slightly different positions in pattern generating optical element 38 and create different patterns. These patterns will not interfere with each other due to different colors, different times of pulse, or different angles. Using fiber coupler 164 or laser combiner 166 allows for laser diodes 36 to be disposed in a remote enclosure 168. Remote enclosure 168 may be disposed in a proximal end of handheld wand 20, thus allowing for a smaller probe 28.

For some applications, structured light projectors 22 and cameras 24 may be disposed in proximal end 100 of probe 28.

Figure 53A:
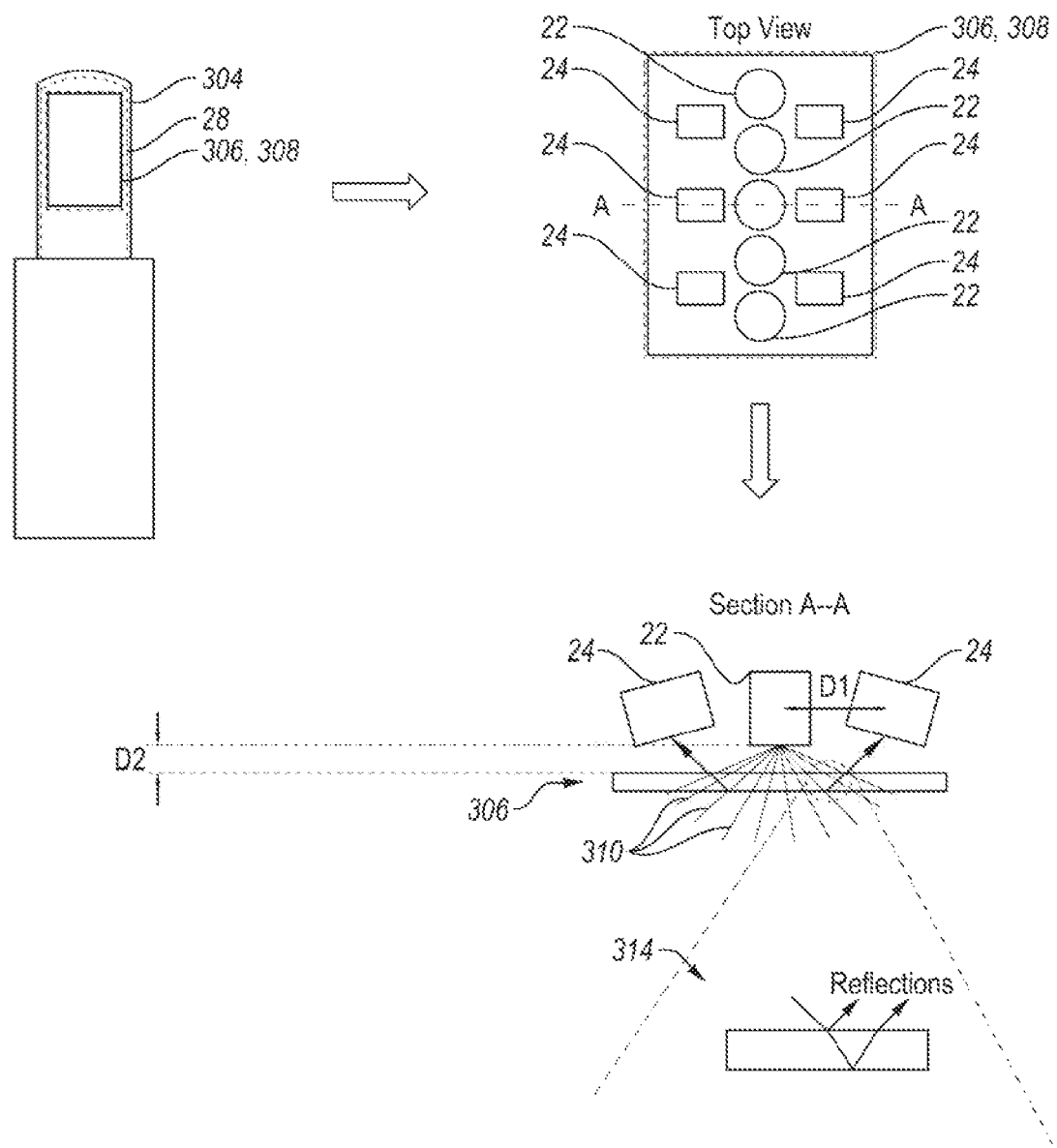
FIG. 53A is a schematic illustration of a disposable sleeve placed over the distal end of the intraoral scanner prior to the probe being placed inside a patient's mouth, in order to prevent cross contamination between patients, in accordance with some applications of the present invention.

Reference is now made to FIG. 53A, which is a schematic illustration of a disposable sleeve 304 placed over the distal end of the intraoral scanner, e.g. over probe 28, prior to probe 28 being placed inside a patient's mouth, in order to prevent cross contamination between patients, in accordance with some applications of the present invention. In order to reduce costs the sleeve may be made of a unitary piece of plastic, with a portion 306 of the sleeve that is disposed directly over the glass surface of handheld probe 28 (i.e., a window 308 of probe 28 through which light enters and exit probe 28) typically being of a high quality optical surface. Light entering and exiting probe 28 through the exit window will also encounter the portion 306 of the sleeve. FIG. 53 shows sleeve 304 disposed over probe 28, with portion 306 of the sleeve directly over window 308 of probe 28. The enlarged view of portion 306 and window 308 shows a possible positioning of structured light projectors 22 and cameras 24 within probe 28.

For some applications, each structured light projector 22 within probe 28 has a field of illumination of at least 30 degrees, e.g., at least 70 degrees, e.g., 90 degrees, and comprises a laser that emits polarized laser light. Each structured light projector 22 also has a pattern generating optical element, e.g., DOE 39, that generates a pattern of light when the laser diode is activated to transmit light through the pattern generating optical element. The inventors have realized that, due to the positioning of structured light projectors 22, i.e., the laser of each structured light projector 22, and neighboring cameras 24 within probe 28 (such as is shown, for example, in FIGS. 2D-E and FIG. 53A), the lasers may be positioned at a distance with respect to one or more neighboring cameras 24, such that when probe 28 is disposed in the sleeve, a portion of the pattern of light is reflected off of the sleeve and reaches camera sensor 58 of camera 24. Typically, each camera 24 has a field of view of at least 30 degrees, e.g., at least 70 degrees, e.g., 85 degrees, such that there is overlap between the field of illumination of a structured light projector 22 and its neighboring cameras 24. Typically, distance D1 between a structured light projector 22 and a neighboring camera 24 may be 1-6 times a distance D2 between structured light projector 22 and sleeve 304, when handheld wand 20, e.g., probe 28, is disposed in sleeve 304.

Cross-section A-A in FIG. 53A shows laser light rays 310 of the pattern of light being emitted from a structured light projector 22, with some of rays 310, i.e., portions 312 of the pattern of light, reflecting off portion 306 of sleeve 304 directly into respective neighboring cameras 24. Enlarged view 314 shows the laser light hitting portion 306 of sleeve 304, with some of the light reflecting off a near side of portion 306 and some of the light reflecting off a far side of portion 306.

Figure 53B:
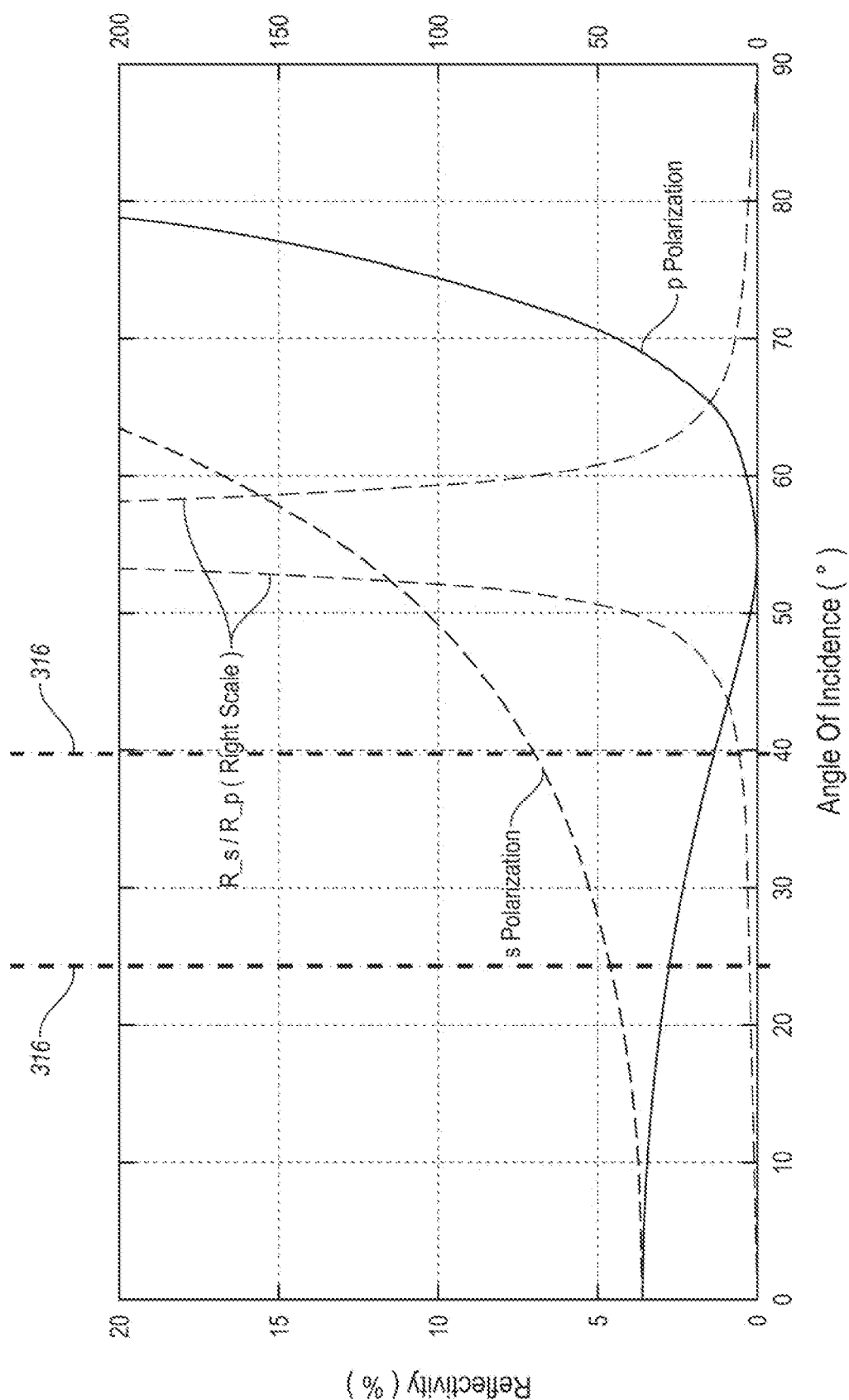
FIG. 53B is a graph showing reflectivity of polarized laser light according to the Fresnel equations, and the use thereof, in accordance with some applications of the present invention.

Reference is now made to FIG. 53B, which is a graph showing the reflectivity of the laser light as it encounters portion 306 of sleeve 304, according to the Fresnel equations. The inventors have realized that the polarization of the laser light may be used in order to reduce the reflections from the sleeve. According to the Fresnel equations, in a certain range of angles of incidence, the reflectivity of p-polarized light (i.e., polarized light with the electric field of the wave oriented parallel to the surface defined by the normal to the reflective surface and the incident light ray) is significantly lower than the reflectivity of s-polarized light (i.e., polarized light with the electric field of the wave oriented perpendicular to the surface defined by the normal to the reflective surface and the incident light ray).

Due to the above described relative positioning of structured light projectors 22 with respective neighboring cameras 24 and sleeve 304, the angles of incidence (e.g., at least 25 degrees, and/or less than 40 degrees, as illustrated by the range of angles in between dashed lines 316 in FIG. 53B) corresponding to portion 312 of the pattern of light that is reflected by portion 306 into a neighboring camera 24 are such that, due to the polarization of the pattern of light, the extent of reflection by sleeve 304 of portion 312 of the pattern of light is less than a threshold reflection for all possible rotational angles of the laser with respect to its optical axis. In one embodiment, an extent of reflection by the sleeve 304 of the portion 312 of the pattern is less than 70% (e.g., less than 60%, 15%-60%, etc.) of a maximum reflection for all possible rotational angles of the laser with respect to its optical axis. That is, the laser may be rotated around its own optical axis such that a polarization angle of the laser light with respect to portion 306 of sleeve 304 is found so as to reduce the extent of the reflections.

As shown in FIG. 53B, for an angle of incidence of for example 30 degrees, if the laser is rotated around its own optical axis so as to obtain p-polarization, then the reflectivity of the light is slightly less than 50% of the maximum reflectivity (which would occur for s-polarization). Additionally, for example, for an angle of incidence of 40 degrees, if the laser is rotated around its own optical axis so as to obtain p-polarization, then the reflectivity of the light is around 20% of the maximum reflectivity (which would occur for s-polarization).

It is noted that similar reflections into the camera may occur from window 308 of probe 28. The rotation of the lasers as described hereinabove also reduces the reflections from window 308. Typically, however, window 308 of probe 28 is coated with an anti-reflective coating so as to minimize reflections. To reduce costs, sleeve 304 being designated for single use typically does not have such an anti-reflective coating.

Reference is now made to FIGS. 54A-B, 55, and 56A-B, which depict methods for generating a three-dimensional image using handheld wand 20, in accordance with some applications of the present invention. Simultaneous localization and mapping (SLAM) is a known technique in the fields of robotics and camera navigation. A SLAM algorithm iterates between (i) computing visible feature locations in three-dimensional space (i.e., mapping) and computing the position of the camera, often referred to as self or ego location (i.e., localization). Traditionally, SLAM is performed using two or more cameras seeing generally the same image, but from slightly different angles. This allows both the scale of the features in three-dimensional space and the ego-movement of the cameras to be obtained.

For some applications, due to the positioning of cameras 24 within probe 28, and the close positioning of probe 28 to the object being scanned, i.e., the intraoral three-dimensional surface, it is often not the case that two or more cameras 24 see generally the same image. Solving a SLAM algorithm using only one camera presents a challenge in determining the scale of features that appear to have moved from one image to the next. That is, with only one camera, it is difficult to determine if an object is near to the camera and has moved a small amount or is far from the camera and has moved a large amount. Furthermore, some of the surfaces in an intraoral cavity are smooth and relatively featureless, e.g., smooth sides of a tooth, and some surfaces in an intraoral cavity may be moving tissue, e.g., a patient's tongue. The inventors have invented a number of ways to overcome these challenges in order to utilize SLAM to track the motion of handheld wand 20 and generate three-dimensional images of an intraoral three-dimensional surface.

Figures 54A, 54B:
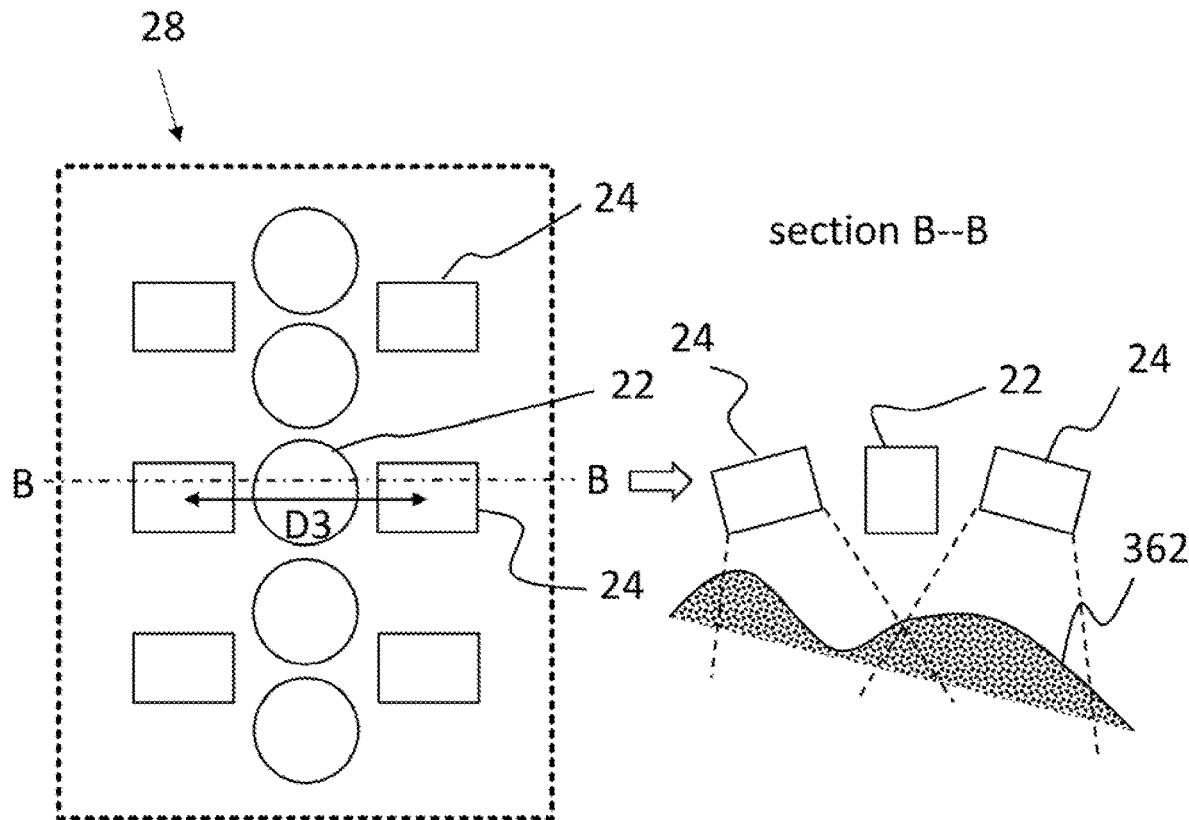
FIGS. 54A-B are, respectively, a flowchart depicting a method for generating a three-dimensional image using the handheld wand, and a schematic illustration of the positioning of the projectors and the cameras, in accordance with some applications of the present invention.

Reference is now made in particular to FIGS. 54A-B, which are, respectively, a flowchart depicting a method for generating a three-dimensional image using handheld wand 20, and a schematic illustration of the positioning of projectors 22 and cameras 24 within probe 28 and the positioning of cameras 24 with respect to an intraoral three-dimensional surface 362 during a scan, in accordance with some applications of the present invention. As described hereinabove, all of the cameras and projectors within probe 28 of handheld wand 20 are connected to a rigid structure, i.e., they are rigidly coupled to each other. This means that it is necessarily the case that when handheld wand 20 is moved, all of cameras 24 move together, i.e., all the cameras 24 share the same ego-motion.

The inventors have developed a SLAM algorithm which may be solved for cameras 24 that are rigidly connected to handheld wand 20, such that respective fields of view of each of cameras 24 have non-overlapping portions. Cameras 24 tend to have non-overlapping portions of their respective fields of view because the camera-spacing-distance D3 (shown in FIG. 54B) between adjacent cameras 24 is significant with respect to the close proximity of the cameras to the object being scanned, i.e., the intraoral three-dimensional surface. The cross-section B—in FIG. 54B shows a side view of two cameras and their respective fields of view. Because the intraoral three-dimensional surface is close to the cameras 24, the respective fields of view of the two cameras 24 have non-overlapping portions.

Two or more of cameras 24 capture a plurality of images of an intraoral three-dimensional surface (step 358 of FIG. 54A). Processor 96 runs a SLAM algorithm using captured images from camera 24 for the non-overlapping portions of the respective fields of view (step 360 of FIG. 54A), the localization of each of the cameras 24 being solved based on the motion of each of the cameras 24 being the same as the motion of every other one of the cameras 24, i.e., by constraining the solution of the ego-motion for all the cameras to be same as the ego-motion for every other one of the cameras.

For some applications, there may be times during a scan when the respective fields of view of a first one of cameras 24 and a second one of cameras 24 also have overlapping portions. In this case a plurality of images of the intraoral three-dimensional surface may be captured such that a feature of the intraoral three-dimensional surface that is in the overlapping portion of the respective fields of view appears in the images captured by the first and second cameras 24, and processor 96 runs a SLAM algorithm using the features of the intraoral three-dimensional surface that appear in the images of at least two of cameras 24.

Figure 55:
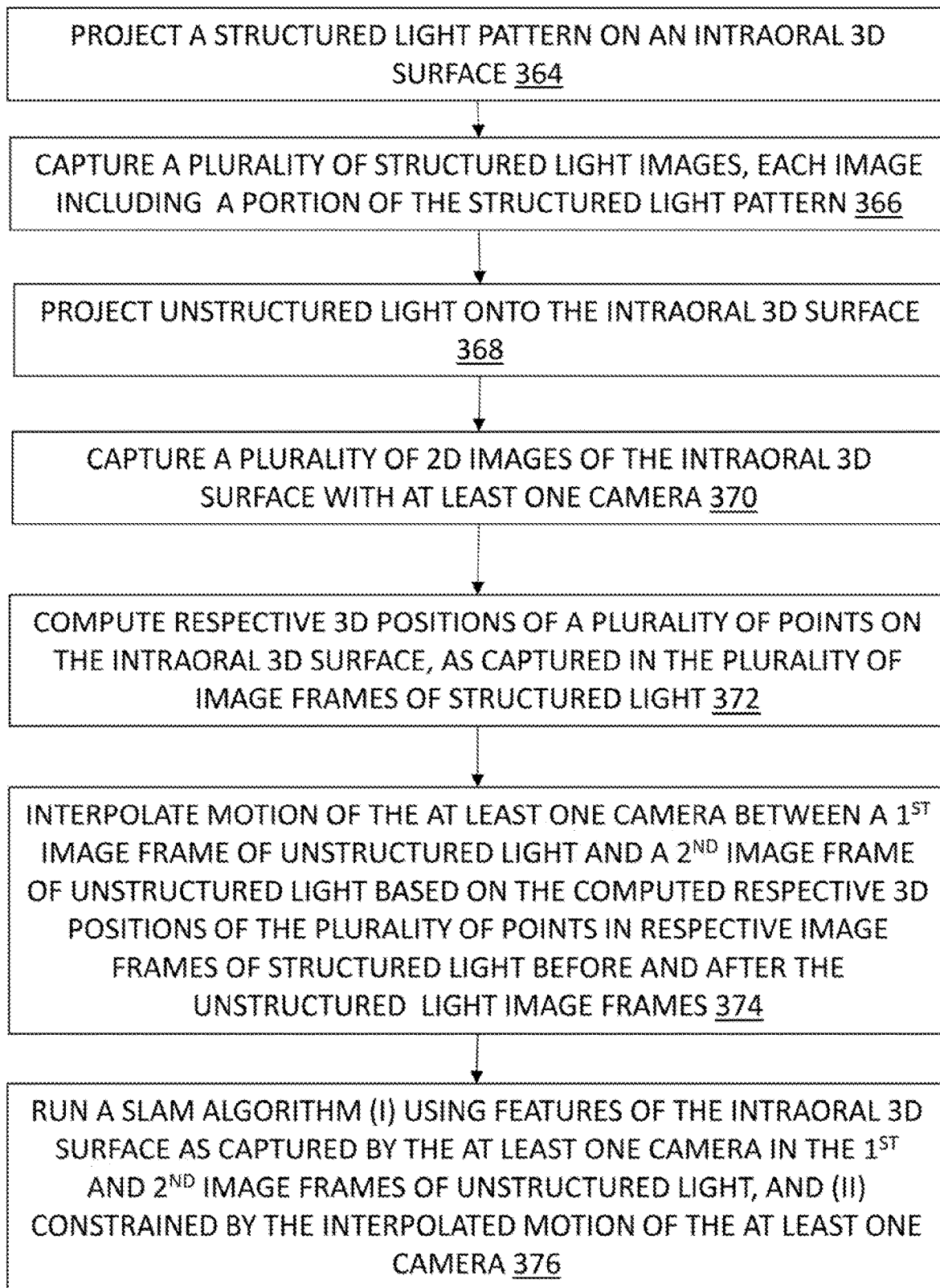
FIG. 55 is a flowchart depicting a method for generating a three-dimensional image using the handheld wand, in accordance with some applications of the present invention.

Reference is now made in particular to FIG. 55, which is a flowchart depicting a method for generating a three-dimensional image using handheld wand 20, in accordance with some applications of the present invention. As described hereinabove, the capturing of structured light and the capturing of unstructured light (e.g., broad spectrum, non-coherent light, and/or NIR light) using handheld wand 20 may be regulated so as to produce an alternating sequence of one or more image frames of structured light interspersed with one or more image frames of unstructured light. For example, an alternating pattern of three consecutive image frames of structured light and one image frame of unstructured light may be used. Alternatively, an alternating pattern of two consecutive image frames of structured light and two image frames of unstructured light may be used. The inventors have realized that when solving a SLAM algorithm for a single camera 24, the information obtained from structured light image frames before and after the unstructured light image frames may be used to interpolate the motion, i.e., localization, of the camera 24.

Thus, the following method may be used:
(a) driving one or more structured light projectors 22 to project a structured light pattern, e.g., a distribution of discrete unconnected spots of light, on an intraoral three-dimensional surface (step 364),
(b) driving one or more cameras 24 to capture a plurality of structured light images, each image including at least a portion of the structured light pattern (step 366),
(c) driving one or more unstructured light projectors 118 to project unstructured light (which may be broad spectrum light, non-coherent light, and/or NIR) onto the intraoral three-dimensional surface (step 368),
(d) driving at least one camera 24 to capture two-dimensional images (e.g., two-dimensional color images and/or two-dimensional monochromatic NIR images) of the intraoral three-dimensional surface using illumination from the uniform light projectors (step 370),
(e) regulating the capturing of the structured light and the capturing of the unstructured light to produce an alternating sequence of one or more image frames of structured light interspersed with one or more image frames of unstructured light, as described hereinabove,
(f) computing respective three-dimensional positions of a plurality of points on the intraoral three-dimensional surface, as captured in the plurality of image frames of structured light (step 372),
(g) interpolating the motion of camera 24 between a first image frame of unstructured light and a second image frame of unstructured light based on the computed three-dimensional positions of the plurality of points in respective structured light image frames before and after the image frames of unstructured light, further described hereinbelow, (step 374), and
(h) running a SLAM algorithm (i) using features of the intraoral three-dimensional surface as captured by the at least one camera 24 in the first and second image frames of unstructured light, and (ii) constrained by the interpolated motion of camera 24 between the first image frame of unstructured light and the second image frame of unstructured light (step 376).

With regard to step (g), for some applications, each unstructured light image frame may be between two structured light images frames. For example, an alternating pattern of three consecutive structured light image frames and one unstructured light image frame may be used. In this case, the interpolation of the motion camera 24 is based on the computed three-dimensional positions of the plurality of points on the intraoral three-dimensional surface in (a) respective structured light image frames before and after the first unstructured light image frame and (b) respective structured light image frames before and after the second unstructured light image frame.

Alternatively, for some applications, consecutive unstructured light image frames may be taken, with structured light image frames taken before and after the consecutive unstructured light image frames. For example, an alternating pattern of two consecutive structured light image frames and two consecutive unstructured light image frames may be used, i.e., there is no structured light image frame between the first and second unstructured light image frames. In this case, the interpolation of the motion of camera 24 is based on the computed three-dimensional positions of the plurality of points on the intraoral three-dimensional surface in a respective structured light image frame before the first unstructured light image frame and a respective structured light image frame after the second unstructured light image frame.

Figure 56A:
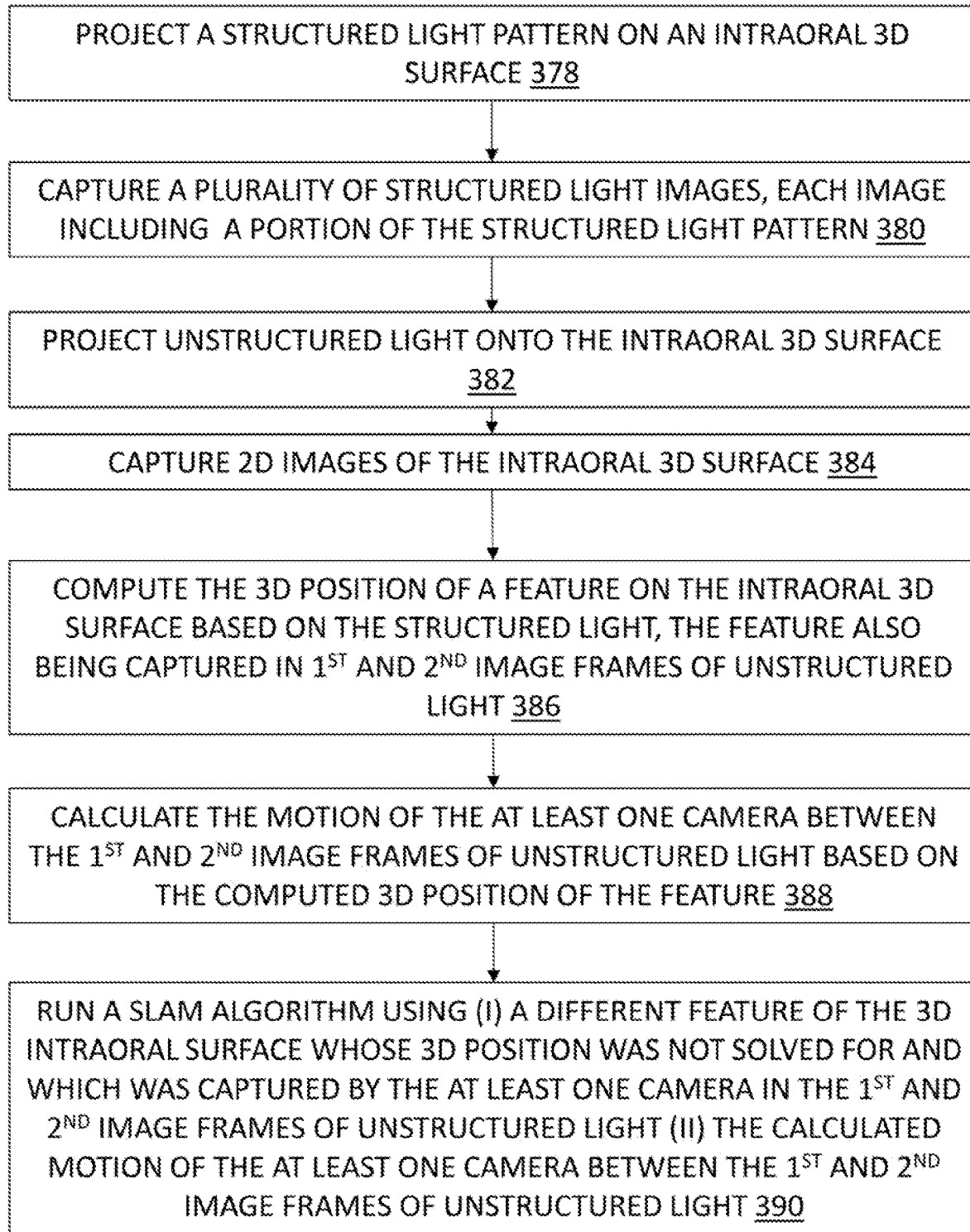
FIGS. 56A-B are, respectively, a flowchart depicting a method for generating a three-dimensional image using the handheld wand, and a schematic illustration of two image frames of unstructured light and two features of an intraoral three-dimensional surface, in accordance with some applications of the present invention.
Figure 56B:
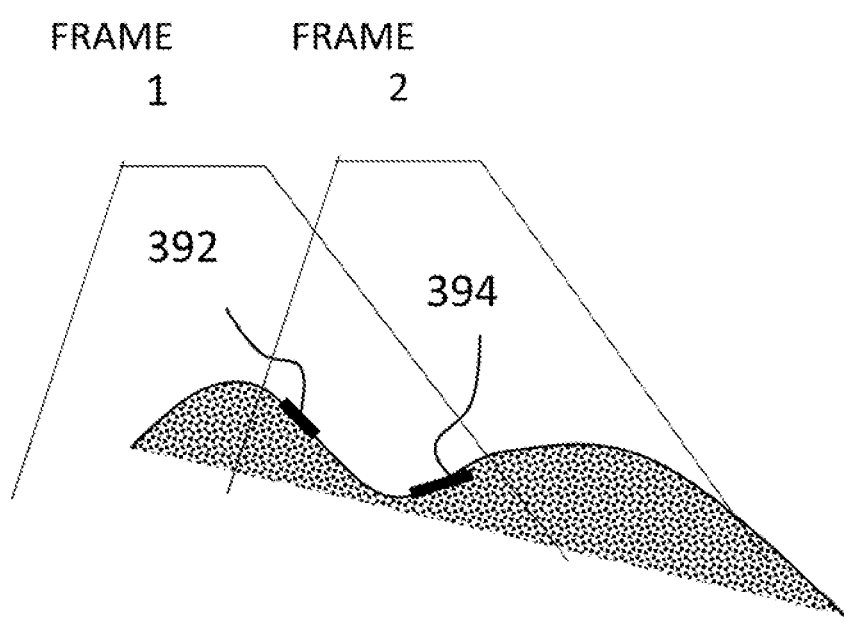

Reference is now made in particular to FIGS. 56A-B, which are, respectively, a flowchart depicting a method for generating a three-dimensional image using handheld wand 20, and a schematic illustration of two image frames of unstructured light and two features 392 and 394 of an intraoral three-dimensional surface, in accordance with some applications of the present invention. As described herein, utilizing a three-dimensional feature 392 of the intraoral three-dimensional surface whose three-dimensional position was solved for based on structured light can allow for the calculation of the motion of a camera 24 that sees that same solved—for feature 392 in a first unstructured light image frame (FRAME 1 of FIG. 56B) and in a second unstructured light image frame (FRAME 2 of FIG. 56B). Once the motion of the camera is calculated, processor 96 may run a SLAM algorithm using a different feature 394 that was (i) not solved for based on structured light, and (ii) was captured in the first and second unstructured light image frames.

Thus, the following method may be used:
(a) driving one or more structured light projectors 22 to project a structured light pattern, e.g., a distribution of discrete unconnected spots of light, on an intraoral three-dimensional surface (step 378),
(b) driving one or more cameras 24 to capture a plurality of structured light images, each image including at least a portion of the structured light pattern (step 380),
(c) driving one or more unstructured light projectors 118 to project unstructured light onto the intraoral three-dimensional surface (step 382),
(d) driving the one or more cameras 24 to capture two-dimensional images (e.g., two-dimensional color images and/or two-dimensional monochromatic NIR images) of the intraoral three-dimensional surface using illumination from unstructured light projectors 118 (step 384),
(e) regulating the capturing of the structured light and the capturing of the unstructured light to produce an alternating sequence of one or more image frames of structured light interspersed with one or more image frames of unstructured light,
(f) computing the three-dimensional position of a feature, e.g., feature 392 (FIG. 56B) on the intraoral three-dimensional surface, based on the image frames of structured light, the feature also being captured in a first image frame of unstructured light (FRAME 1) and a second image frame of unstructured light (FRAME 2) (step 386),
(g) calculating the motion of the at least one camera between the first image frame of unstructured light and the second image frame of unstructured light based on the computed three-dimensional position of feature 392 (step 388), and
(h) running a SLAM algorithm using (i) a different feature 394 of the intraoral three-dimensional surface for which the three-dimensional position was not computed based on the image frames of structured light, as captured by the at least one camera in the first and second image frames of unstructured light, and (ii) the calculated motion of the camera between the first and second image frames of unstructured light (step 390).

In FIG. 56B, feature 392 of the intraoral surface has a known three-dimensional position, as computed based on image frames of structured light. Feature 392 is seen in FRAME 1 and FRAME 2. Therefore, the motion of the camera 24 between FRAME 1 and FRAME 2 can be calculated. Once the motion is calculated, the SLAM algorithm may be solved for feature 394, which is also seen by camera 24 in FRAME 1 and FRAME 2.

Figure 57:
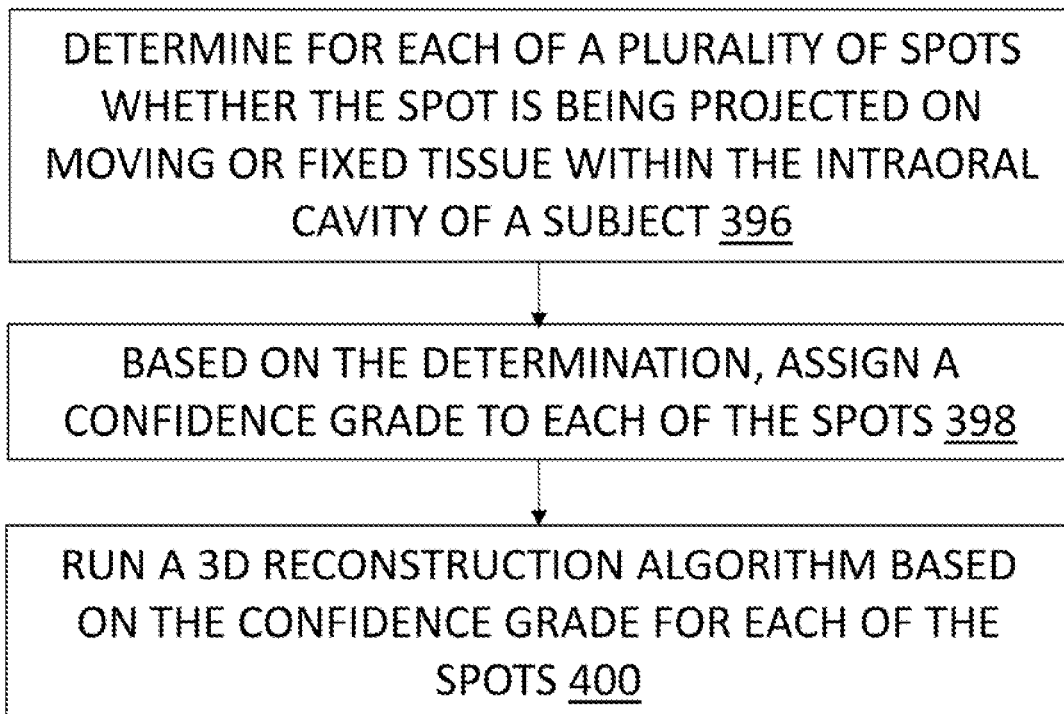
FIG. 57 is a flowchart depicting a method for computing the three-dimensional structure of an intraoral three-dimensional surface within an intraoral cavity of a subject, in accordance with some applications of the present invention.

Reference is now made to FIG. 57, which is a flowchart depicting a method for computing the three-dimensional structure of an intraoral three-dimensional surface within an intraoral cavity of a subject, in accordance with some applications of the present invention. For some applications, it is possible that as structured light projectors 22 are projecting their distributions of spots on the intraoral surface, some of the spots may land on moving tissue (e.g., the patient's tongue). For improvement of accuracy of the three-dimensional reconstruction algorithm, such as described hereinabove, spots that fall on moving tissue should generally not be relied upon for reconstruction of the intraoral three-dimensional surface. As described herein, whether a spot has been projected on moving or stable tissue within the intraoral cavity may be determined (step 396) based on image frames of unstructured light (e.g., broad spectrum light, non-coherent light, and/or NIR light) interspersed through image frames of structured light, as described hereinabove. Typically, the determination will be based on the most recent image frame of unstructured light prior to the image frame of structured light in which the spot was detected. Based on the determination for each of a plurality of detected spots as to whether they were projected on fixed or moving tissue, a confidence grade is given to each spot (step 398), with high confidence being for fixed tissue and low confidence being for moving tissue. Based on the confidence grade for each of the plurality of spots, processor 96 runs a three-dimensional reconstruction algorithm using the detected spots.

For some applications, a fixed-tissue threshold value is defined, and processor 96 runs the three-dimensional reconstruction algorithm using only a subset of the detected spots, the subset consisting of spots that were assigned a confidence grade above the fixed-tissue threshold value. Alternatively, for some applications, a respective weight is assigned to each of the detected spots based on the respective confidence grade that was assigned to each spot, with low weight being assigned to a spot that was assigned a low confidence grade and high weight being assigned to a spot that was assigned a high confidence grade. Processor 96 runs the three-dimensional reconstruction algorithm using the respective weights for each of the detected spots.

In one embodiment of a method for computing a three-dimensional structure of an intraoral three-dimensional surface within an intraoral cavity of a subject, the method comprises driving one or more structured light projectors to project a pattern of structured light on the intraoral three-dimensional surface (the pattern comprising a plurality of features), driving one or more cameras to capture a plurality of structured light images (each structured light image including at least one of the features of the structured light pattern), driving one or more unstructured light projectors to project unstructured light onto the intraoral three-dimensional surface, and driving at least one camera to capture two-dimensional images of the intraoral three-dimensional surface using illumination from the one or more unstructured light projectors. The method further includes regulating capturing of the structured light and capturing of the unstructured light to produce an alternating sequence of one or more image frames of structured light interspersed with one or more image frames of unstructured light. A processor is used to determine for one or more features of the plurality of features of the structured light pattern whether the feature is being projected on moving or stable tissue within the intraoral cavity, based on the two-dimensional images. Based on the determination, the processor assigns a respective confidence grade for each of the one or more features, high confidence being for fixed tissue and low confidence being for moving tissue. Based on the confidence grade for each of the one or more features, the processor runs a three-dimensional reconstruction algorithm using the one or more features. In one embodiment, the unstructured light comprises broad spectrum light, and the two-dimensional images are two-dimensional color images. In one embodiment, the plurality of features comprise a plurality of spots, and driving the one or more structured light projectors to project the structured light pattern comprises driving the one or more structured light projectors to each project a distribution of discrete unconnected spots of light on the intraoral three-dimensional surface. In one embodiment, running the three-dimensional reconstruction algorithm is performed using only a subset of the plurality of features, the subset consisting of features that were assigned a confidence grade above a fixed-tissue threshold value. In one embodiment, running the three-dimensional reconstruction algorithm comprises, (a) for each feature, assigning a weight to that feature based on the respective confidence grade assigned to that feature, and (b) using the respective weights for each feature in the three-dimensional reconstruction algorithm.

Applications of the invention described herein can take the form of a computer program product accessible from a computer-usable or computer-readable medium (e.g., a non-transitory computer-readable medium) providing program code for use by or in connection with a computer or any instruction execution system, such as processor 96. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. In some embodiments, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., processor 96) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., processor 96) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Processor 96 is typically a hardware device programmed with computer program instructions to produce a special purpose computer. For example, when programmed to perform the methods described herein, the computer processor typically acts as a special purpose 3-D surface reconstruction computer processor. Typically, the operations described herein that are performed by computer processors transform the physical state of a memory, which is a real physical article, to have a different magnetic polarity, electrical charge, or the like depending on the technology of the memory that is used.

Alternatively, processor 96 may take the form of a field programmable gate array (FPGA), an application-specific integrated circuit (ASIC), or a neural network implemented on a specialized chip.

Figure 60:
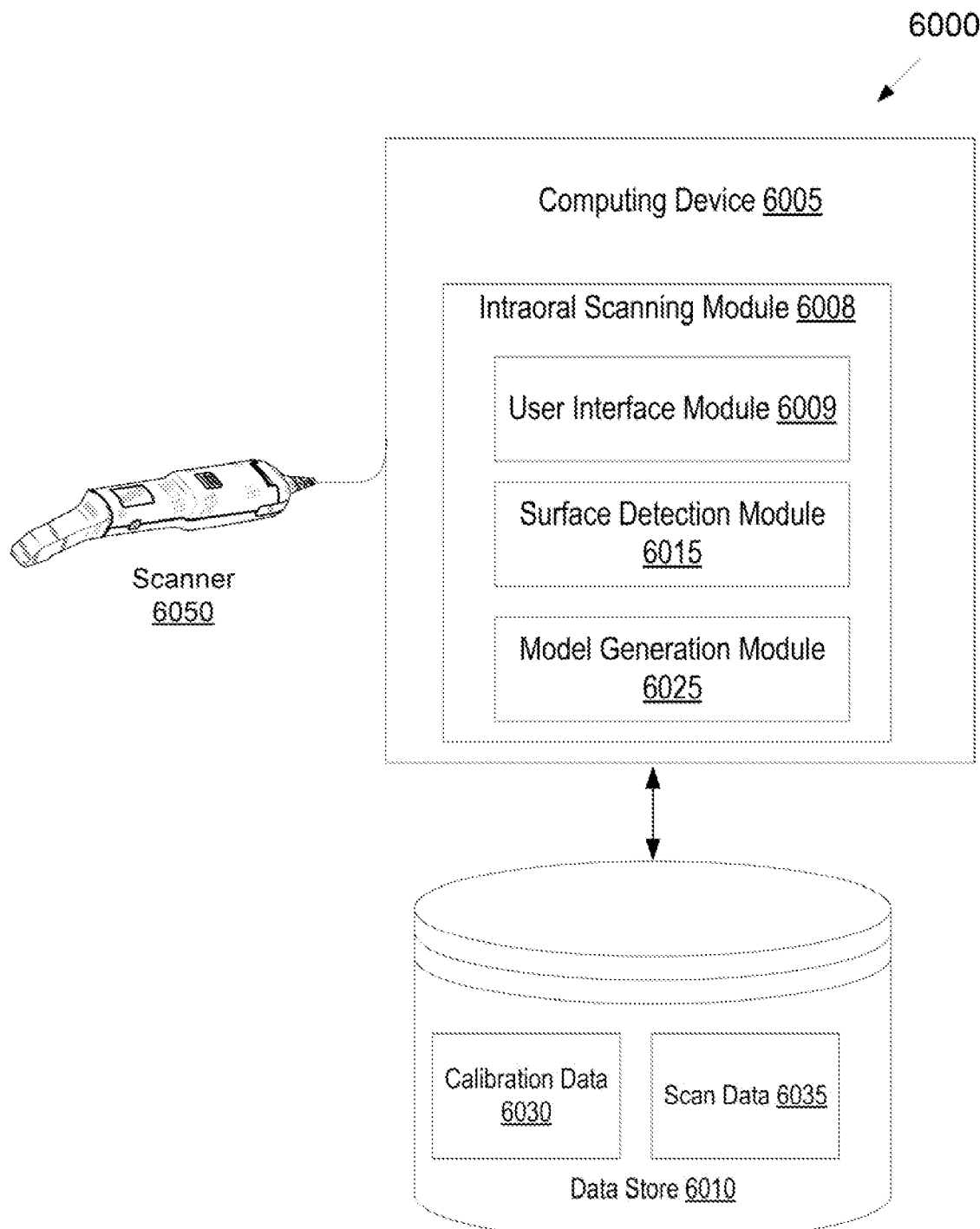
FIG. 60 illustrates one embodiment of a system for performing intraoral scanning and generating a virtual 3D model of a dental arch.

FIG. 60 illustrates one embodiment of a system 6000 for performing intraoral scanning and/or generating a virtual 3D model of a dental arch. In one embodiment, system 6000 carries out one or more operations of above described methods. System 6000 includes a computing device 6005 that may be coupled to an intraoral scanner 6050 (also referred to simply as a scanner 6050) and/or a data store 6010. Intraoral scanner 6050 may correspond to elongate handheld wand 20 of the preceding figures in embodiments. Computing device 6005 may include processor 96 of the preceding figures in embodiments.

Computing device 6005 may include one or more processing device (e.g., processor 96), memory, secondary storage, one or more input devices (e.g., such as a keyboard, mouse, tablet, and so on), one or more output devices (e.g., a display, a printer, etc.), and/or other hardware components. Computing device 6005 may be connected to a data store 6010 either directly or via a network. The network may be a local area network (LAN), a public wide area network (WAN) (e.g., the Internet), a private WAN (e.g., an intranet), or a combination thereof. The computing device and the memory device may be integrated into the scanner 6050 in some embodiments to improve performance and/or mobility.

Data store 6010 may be an internal data store, or an external data store that is connected to computing device 6005 directly or via a network. Examples of network data stores include a storage area network (SAN), a network attached storage (NAS), and a storage service provided by a cloud computing service provider. Data store 6010 may include a file system, a database, or other data storage arrangement.

In some embodiments, a scanner 6050 for obtaining three-dimensional (3D) data of a dental site in a patient's oral cavity is operatively connected to the computing device 6005. Scanner 6050 may include a probe (e.g., a hand held probe) for optically capturing three dimensional structures, as described above.

In some embodiments, the scanner 6050 includes an elongate handheld wand 20 including a probe at a distal end of the handheld wand; a rigid structure disposed within a distal end of the probe; one or more structured light projectors coupled to the rigid structure; and one or more cameras coupled to the rigid structure. In some applications, each structured light projector may have a field of illumination of 45-120 degrees. Optionally, the one or more structured light projectors may utilize a laser diode light source. Further, the structure light projector(s) may include a beam shaping optical element. Further still, the structured light projector(s) may include a pattern generating optical element.

The pattern generating optical element may be configured to generate a distribution of discrete unconnected spots of light. The distribution of discrete unconnected spots of light may be generated at all planes located between specific distances (e.g., 1-30 mm, 1-50 mm, 1-80 mm, etc.) from the pattern generating optical element when the light source (e.g., laser diode) is activated to transmit light through the pattern generating optical element. In some applications, the pattern generating optical element utilizes diffraction and/or refraction to generate the distribution. Optionally, the pattern generating optical element has a light throughput efficiency of at least 90%.

For some applications, the structured light projectors and the cameras are positioned such that each structured light projector faces an object outside of the wand placed in its field of illumination. Optionally, each camera may face an object outside of the wand placed in its field of view. Further, in some applications, at least 20% of the discrete unconnected spots of light are in the field of view of at least one of the cameras.

The scanner 6050 may be used to perform intraoral scanning of a patient's oral cavity. A result of the intraoral scanning may be a sequence of intraoral scans that have been discretely generated (e.g., by pressing on a "generate scan" button of the scanner for each intraoral scan). Alternatively, a result of the intraoral scanning may be one or more videos of the patient's oral cavity. An operator may start recording the video with the scanner 6050 at a first position in the oral cavity, move the scanner 6050 within the oral cavity to a second position while the video is being taken, and then stop recording the video. In some embodiments, recording may start automatically as the scanner identifies that it has been positioned at a particular station (e.g., at a particular position and orientation in a patient's oral cavity). In either case, the scanner 6050 may transmit the discrete intraoral scans or intraoral video (referred to collectively as scan data 6035) to the computing device 6005. Note that in some embodiments the computing device may be integrated into the scanner 6050. Computing device 6005 may store the scan data 6035 in data store 6010. Alternatively, scanner 6050 may be connected to another system that stores the scan data in data store 6010. In such an embodiment, scanner 6050 may not be connected to computing device 6005.

Scanner 6050 may drive each one of one or more structured light projectors to project a distribution of discrete unconnected spots of light on an intraoral three-dimensional surface. Scanner 6050 may further drive each one of one or more cameras to capture an image, the image including at least one of the spots. Each one of the one or more cameras may include a camera sensor including an array of pixels. The images captured together at a particular time may together form an intraoral scan. The intraoral scans may be transmitted to computing device 6005 and/or stored in data store 6010 as scan data 6035.

Computing device 6005 may include an intraoral scanning module 6008 for facilitating intraoral scanning and generating 3D models of dental arches from intraoral scans.

Intraoral scanning module 6008 may include a surface detection module 6015 and a model generation module 6025 in some embodiments. Surface detection module 6015 may analyze received image data 6035 to identify objects in the intraoral scans of the image data 6035. In some embodiments, surface detection module executes a correspondence algorithm on intraoral scans to determine the depths of spots or points in the intraoral scans, as described above. The surface detection module 6015 may access stored calibration data 6030 indicating (a) a camera ray corresponding to each pixel on the camera sensor of each one of the one or more cameras, and (b) a projector ray corresponding to each of the projected spots of light from each one of the one or more projectors, where each projector ray corresponds to a respective path of pixels on at least one of the camera sensors. Using the calibration data 6030 and the correspondence algorithm, surface detection module 6015 may, (1) for each projector ray i, identify for each detected spot j on a camera sensor path corresponding to ray i, how many other cameras, on their respective camera sensor paths corresponding to ray i, detected respective spots k corresponding to respective camera rays that intersect ray i and the camera ray corresponding to detected spot j. Ray i is identified as the specific projector ray that produced a detected spot j for which the highest number of other cameras detected respective spots k. Surface detection module 6015 may further (2) compute a respective three-dimensional position on an intraoral three-dimensional surface at the intersection of projector ray i and the respective camera rays corresponding to the detected spot j and the respective detected spots k. For some applications, running the correspondence algorithm further includes, following operation (1), using the processor to remove from consideration projector ray i, and the respective camera rays corresponding to the detected spot j and the respective detected spots k, and running the correspondence algorithm again for a next projector ray i.

Model generation module 6025 may perform surface registration between intraoral scans (e.g., may stitch together the intraoral scans as discussed above). Model generation module 6025 may then generate a virtual 3D model of a dental arch from the registered intraoral scans, as discussed above.

In some embodiments, intraoral scanning module 6008 includes a user interface module 6009 that provides a user interface that may display the generated virtual 3D model. Additionally, user interface module 6009 may direct a user to position a probe of the scanner 6050 at a particular position and orientation (e.g., a particular station) for generation of a specific intraoral scan.

Figure 61:
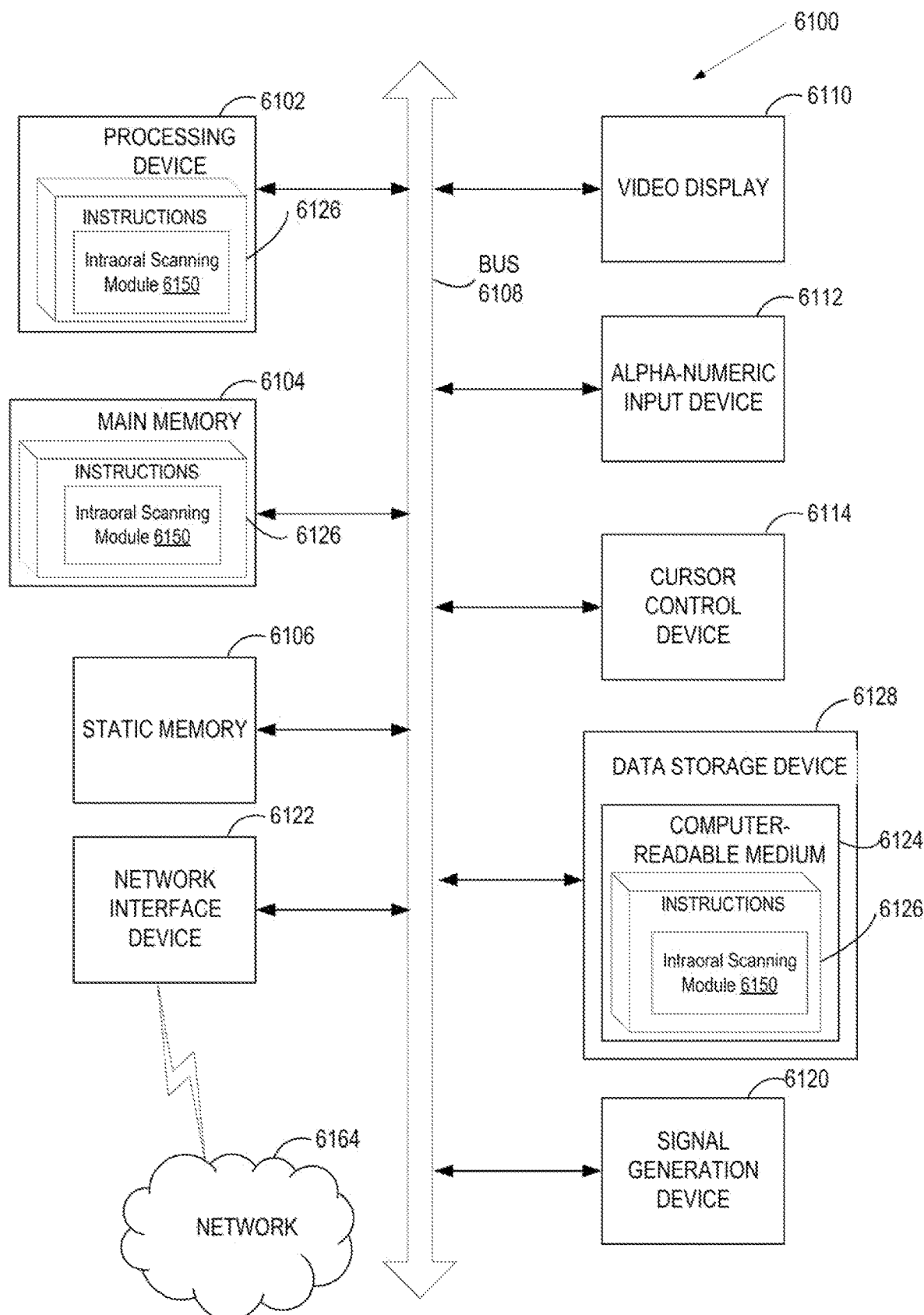
FIG. 61 illustrates a block diagram of an example computing device, in accordance with embodiments of the present disclosure.

FIG. 61 illustrates a diagrammatic representation of a machine in the example form of a computing device 6100 within which a set of instructions, for causing the machine to perform any one or more of the methodologies discussed herein, may be executed. The computing device 6100 may be operatively connected to a scanner (e.g., to an elongate handheld wand) discussed above. In some embodiments, the computing device 6100 may be connected (e.g., networked) to other machines in a Local Area Network (LAN), an intranet, an extranet, or the Internet. The computing device 6100 may operate in the capacity of a server or a client machine in a client-server network environment, or as a peer machine in a peer-to-peer (or distributed) network environment. The computing device 6100 may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 6100 includes a processing device 6102, a main memory 6104 (e.g., read-only memory (ROM), flash memory, dynamic random access memory (DRAM) such as synchronous DRAM (SDRAM), etc.), a static memory 6106 (e.g., flash memory, static random access memory (SRAM), etc.), and a secondary memory (e.g., a data storage device 6128), which communicate with each other via a bus 6108.

In some embodiments, processing device 6102 corresponds to processor 96. Processing device 6102 may represent one or more general-purpose processors such as a microprocessor, central processing unit, or the like. More particularly, the processing device 6102 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 6102 may also be one or more special-purpose processing devices such as an application specific integrated circuit (ASIC), a field programmable gate array (FPGA), a digital signal processor (DSP), network processor, or the like. Processing device 6102 may also be a graphics processing unit (GPU) or a general-purpose graphics processing unit (GPGPU). Processing device 6102 is configured to execute the processing logic (instructions 6126) for performing operations and operations discussed herein.

The computing device 6100 may further include a network interface device 6122 for communicating with a network 6164. The computing device 6100 also may include a video display unit 6110 (e.g., a liquid crystal display (LCD) or a cathode ray tube (CRT)), an alphanumeric input device 6112 (e.g., a keyboard), a cursor control device 6114 (e.g., a mouse), and a signal generation device 6120 (e.g., a speaker).

The data storage device 6128 may include a machine-readable storage medium (or more specifically a non-transitory computer-readable storage medium) 6124 on which is stored one or more sets of instructions 6126 embodying any one or more of the methodologies or functions described herein. A non-transitory storage medium refers to a storage medium other than a carrier wave. The instructions 6126 may also reside, completely or at least partially, within the main memory 6104 and/or within the processing device 6102 during execution thereof by the computer device 6100, the main memory 6104 and the processing device 6102 also constituting computer-readable storage media.

The computer-readable storage medium 6124 may also be used to store an intraoral scanning module 6150, which may correspond to intraoral scanning module 6008 of FIG. 60. The computer readable storage medium 6124 may also store a software library containing methods that call an intraoral scanning module 6150, a scan registration module and/or a model generation module. While the computer-readable storage medium 6124 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

In accordance with some applications of the present invention, there is provided the following list of inventive concepts:

Inventive Concept 1. A method for generating a digital three-dimensional image, the method comprising:
  driving each one of one or more structured light projectors to project a pattern on an intraoral three-dimensional surface;
  driving each one of one or more cameras to capture a plurality of images, each image including at least a portion of the projected pattern; and
  using a processor to:
    compare a series of images captured by the one or more cameras;
    determine which of the portions of the projected pattern can be tracked across the series of images based on the comparison of the series of images; and
    construct a three-dimensional model of the intraoral three-dimensional surface based at least in part on the comparison of the series of images.

Inventive Concept 2. The method according to Inventive Concept 1, wherein using the processor further comprises using the processor to:
  solve a correspondence algorithm for the tracked portions of the projected pattern in at least one of the series of images; and
  use the solved correspondence algorithm for the tracked portions in the at least one of the series of images to solve the correspondence algorithm for the tracked portions of the projected pattern in at least another image of the series of images, wherein the solution to the correspondence algorithm is used to construct the three-dimensional model.

Inventive Concept 3. The method according to Inventive Concept 1, wherein using the processor further comprises using the processor to:
  solve a correspondence algorithm for the tracked portions of the projected pattern based on positions of the tracked portions in each image throughout the series of images, wherein constructing the three-dimensional model comprises using the solution to the correspondence algorithm to construct the three-dimensional model.

Inventive Concept 4. The method according to Inventive Concept 1, wherein the one or more structured light projectors project a pattern that is spatially fixed relative to the one or more cameras.

Inventive Concept 5. The method according to any one of Inventive Concepts 1-4, wherein the projected pattern comprises a plurality of projected spots of light, and wherein the portion of the projected pattern corresponds to a projected spot s of the plurality of projected spots of light.

Inventive Concept 6. The method according to Inventive Concept 5, wherein using the processor to compare the series of images comprises using the processor to compare the series of images based on stored calibration values indicating (a) a camera ray corresponding to each pixel on a camera sensor of each one of the one or more cameras, and (b) a projector ray corresponding to each one of the projected spots of light from each one of the one or more structured light projectors, wherein each projector ray corresponds to a respective path of pixels on at least one of the camera sensors, wherein determining which portions of the projected pattern can be tracked comprises determining which of the projected spots s can be tracked across the series of images, and wherein each tracked spot s moves along a path of pixels corresponding to a respective projector ray r.

Inventive Concept 7. The method according to Inventive Concept 6, wherein using the processor further comprises using the processor to determine, for each tracked spot s, a plurality of possible paths p of pixels on a given one of the cameras, paths p corresponding to a respective plurality of possible projector rays r.

Inventive Concept 8. The method according to Inventive Concept 7, wherein using the processor further comprises using the processor to run a correspondence algorithm to:
for each of the possible projector rays r:
identify how many other cameras, on their respective paths p1 of pixels corresponding to projector ray r, detected respective spots q corresponding to respective camera rays that intersect projector ray r and the camera ray of the given one of the cameras corresponding to the tracked spot s;
identify a given projector ray r1 for which the highest number of other cameras detected respective spots q; and
identify projector ray r1 as the particular projector ray r that produced the tracked spot s.

Inventive Concept 9. The method according to Inventive Concept 6, wherein using the processor further comprises using the processor to:
run a correspondence algorithm to compute respective three-dimensional positions of a plurality of detected spots on the intraoral three-dimensional surface, as captured in the series of images; and
in at least one of the series of images, identify a detected spot as being from a particular projector ray r by identifying the detected spot as being a tracked spot s moving along the path of pixels corresponding to the particular projector ray r.

Inventive Concept 10. The method according to Inventive Concept 6, wherein using the processor further comprises using the processor to:
run a correspondence algorithm to compute respective three-dimensional positions of a plurality of detected spots on the intraoral three-dimensional surface, as captured in the series of images, and
remove from being considered as a point on the intraoral three-dimensional surface a spot that (i) is identified as being from particular projector ray r based on the three-dimensional position computed by the correspondence algorithm, and (ii) is not identified as being a tracked spot s moving along the path of pixels corresponding to particular projector ray r.

Inventive Concept 11. The method according to Inventive Concept 6, wherein using the processor further comprises using the processor to:
run a correspondence algorithm to compute respective three-dimensional positions of a plurality of detected spots on the intraoral three-dimensional surface, as captured in the series of images; and
for a detected spot which is identified as being from two distinct projector rays r based on the three-dimensional position computed by the correspondence algorithm, identify the detected spot as being from one of the two distinct projector rays r by identifying the detected spot as a tracked spot s moving along the one of the two distinct projector rays r.

Inventive Concept 12. The method according to Inventive Concept 6, wherein using the processor further comprises using the processor to:
run a correspondence algorithm to compute respective three-dimensional positions of a plurality of detected spots on the intraoral three-dimensional surface, as captured in the series of images, and
identify a weak spot whose three-dimensional position was not computed by the correspondence algorithm as being a projected spot from a particular projector ray r, by identifying the weak spot as being a tracked spot s moving along the path of pixels corresponding to particular projector ray r.

Inventive Concept 13. The method according to Inventive Concept 6, wherein using the processor further comprises using the processor to compute respective three-dimensional positions on the intraoral three-dimensional surface at an intersection of the projector ray r and the respective camera rays corresponding to the tracked spot s in each of the series of images across which spot s was tracked.

Inventive Concept 14. The method according to any one of Inventive Concepts 1-4, wherein the three-dimensional model is constructed using a correspondence algorithm, wherein the correspondence algorithm uses, at least in-part, the portions of the projected pattern that are determined to be trackable across the series of images.

Inventive Concept 15. The method according to any one of Inventive Concepts 1-4, wherein using the processor further comprises using the processor to:
determine a parameter of a tracked portion of the projected pattern in at least two adjacent images from the series of images, the parameter selected from the group consisting of: a size of the portion, a shape of the portion, an orientation of the portion, an intensity of the portion, and a signal-to-noise ratio (SNR) of the portion; and
based on the parameter of the tracked portion of the projected pattern in the at least two adjacent images, predict the parameter of the tracked portion of the projected pattern in a later image.

Inventive Concept 16. The method according to Inventive Concept 15, wherein using the processor further comprises, based on the predicted parameter of the tracked portion of the projected pattern, using the processor to search for the portion of the projected pattern having substantially the predicted parameter in the later image.

Inventive Concept 17. The method according to Inventive Concept 15, wherein the selected parameter is the shape of the portion of the projected pattern, and wherein using the processor further comprises using the processor to, based on the predicted shape of the tracked portion of the projected pattern, determine a search space in a next image in which to search for the tracked portion of the projected pattern.

Inventive Concept 18. The method according to Inventive Concept 17, wherein using the processor to determine the search space comprises using the processor to determine a search space in the next image in which to search for the tracked portion of the projected pattern, the search space having a size and aspect ratio based on a size and aspect ratio of the predicted shape of the tracked portion of the projected pattern.

Inventive Concept 19. The method according to Inventive Concept 15, wherein the selected parameter is the shape of the portion of the projected pattern, and wherein using the processor further comprises using the processor to:
- based on a direction and distance that the tracked portion of the projected pattern has moved between the at least two adjacent images from the series of images, determine a velocity vector of the tracked portion of the projected pattern;
- in response to the shape of the tracked portion of the projected pattern in at least one of the at least two adjacent images, predict the shape of the tracked portion of the projected pattern in a later image; and
- in response to (i) the determination of the velocity vector of the tracked portion of the projected pattern in combination with (ii) the predicted shape of the tracked portion of the projected pattern, determine a search space in the later image in which to search for the tracked portion of the projected pattern.

Inventive Concept 20. The method according to Inventive Concept 15, wherein the parameter is the shape of the portion of the projected pattern, and wherein using the processor further comprises using the processor to:
- based on a direction and distance that the tracked portion of the projected pattern has moved between the at least two adjacent images from the series of images, determine a velocity vector of the tracked portion of the projected pattern;
- in response to the determination of the velocity vector of the tracked portion of the projected pattern, predict the shape of the tracked portion of the projected pattern in a later image; and
- in response to (i) the determination of the velocity vector of the tracked portion of the projected pattern in combination with (ii) the predicted shape of the tracked portion of the projected pattern, determine a search space in the later image in which to search for the tracked portion of the projected pattern.

Inventive Concept 21. The method according to Inventive Concept 20, wherein using the processor comprises using the processor to predict the shape of the tracked portion of the projected pattern in the later image in response to (i) the determination of the velocity vector of the tracked portion of the projected pattern in combination with (ii) the shape of the tracked portion of the projected pattern in at least one of the two adjacent images.

Inventive Concept 22. The method according to any one of Inventive Concepts 1-4, wherein using the processor further comprises using the processor to:
- based on a direction and distance that a tracked portion of the projected pattern has moved between two consecutive images in the series of images, determine a velocity vector of the tracked portion of the projected pattern; and
- in response to the determination of the velocity vector of the tracked portion of the projected pattern, determine a search space in a later image in which to search for the tracked portion of the projected pattern.

Inventive Concept 23. A method for generating a digital three-dimensional image, the method comprising:
- driving each one of one or more structured light projectors to project a pattern of light on an intraoral three-dimensional surface, the pattern of light comprising a plurality of projected features, each feature projected by a respective projector ray;
- driving each one of one or more cameras to capture an image, the image including at least a portion of the pattern; and
- using a processor to:
  - run a correspondence algorithm to compute respective three-dimensional positions of a plurality of features of the pattern on the intraoral three-dimensional surface, as captured in a series of images;
  - identify the computed three-dimensional position of a detected feature of the pattern as corresponding to a particular projector ray r, in at least a subset of the series of images; and
  - based on the three-dimensional position of the detected feature corresponding to the particular projector ray r in the subset of images, assess a length corresponding to the projector ray r in each image of the subset of images.

Inventive Concept 24. The method according to Inventive Concept 23, wherein the pattern comprises a plurality of spots, and wherein each of the plurality of features of the pattern comprises a spot of the plurality of spots.

Inventive Concept 25. The method according to any one of Inventive Concepts 23-24, wherein using the processor further comprises using the processor to compute an estimated length of the projector ray r in at least one of the series of images in which a three-dimensional position of the projected feature from the projector ray r was not identified.

Inventive Concept 26. The method according to any one of Inventive Concepts 23-25, wherein each one of the one or more cameras comprises a camera sensor comprising an array of pixels, wherein computation of the respective three-dimensional positions of the plurality of features of the pattern on the intraoral three-dimensional surface and identification of the computed three-dimensional position of the detected feature of the pattern as corresponding to particular projector ray r is performed based on stored calibration values indicating (i) a camera ray corresponding to each pixel on the camera sensor of each one of the one or more cameras, and (ii) a projector ray corresponding to each one of the features of the projected pattern of light from each one of the one or more projectors, whereby each projector ray corresponds to a respective path of pixels on at least one of the camera sensors.

Inventive Concept 27. The method according to Inventive Concept 26, wherein using the processor further comprises using the processor to:
- compute an estimated length of the projector ray r in at least one of the series of images in which a three-dimensional position of the projected feature from the projector ray r was not identified, and
- based on the estimated length of projector ray r in the at least one of the series of images, determine a one-dimensional search space in the at least one of the series of images in which to search for a projected feature from projector ray r, the one-dimensional search space being along the respective path of pixels corresponding to projector ray r.

Inventive Concept 28. The method according to Inventive Concept 26, wherein using the processor further comprises using the processor to,
- compute an estimated length of the projector ray r in at least one of the series of images in which a three-dimensional position of the projected feature from the projector ray r was not identified, and
- based on the estimated length of projector ray r in the at least one of the series of images, determine a one-dimensional search space in respective pixel arrays of a plurality of the cameras in which to search for a projected spot from projector ray r, for each of the respective pixel arrays, the one-dimensional search space being along the respective path of pixels corresponding to ray r.

Inventive Concept 29. The method according to Inventive Concept 28, wherein using the processor to determine the one-dimensional search space in respective pixel arrays of a plurality of the cameras comprises using the processor to determine a one-dimensional search space in respective pixel arrays of all of the cameras, in which to search for a projected feature from projector ray r.

Inventive Concept 30. The method according to any one of Inventive Concepts 23-25, wherein using the processor further comprises using the processor to:
based on the correspondence algorithm, in each of at least one of the series of images that is not in the subset of images, identify more than one candidate three-dimensional position of the projected feature from the projector ray r, and compute an estimated length of projector ray r in the at least one of the series of images in which more than one candidate three-dimensional position of the projected feature from projector ray r was identified.

Inventive Concept 31. The method according to Inventive Concept 30, wherein using the processor further comprises using the processor to determine which of the more than one candidate three-dimensional positions is a correct three-dimensional position of the projected feature by determining which of the more than one candidate three-dimensional positions corresponds to the estimated length of projector ray r in the at least one of the series of images.

Inventive Concept 32. The method according to Inventive Concept 30, wherein using the processor further comprises using the processor to, based on the estimated length of projector ray r in the at least one of the series of images:
determine a one-dimensional search space in the at least one of the series of images in which to search for a projected feature from projector ray r; and
determine which of the more than one candidate three-dimensional positions of the projected feature is a correct three-dimensional position of the projected feature produced by projector ray r by determining which of the more than one candidate three-dimensional positions corresponds to a feature produced by projector ray r found within the one-dimensional search space.

Inventive Concept 33. The method according to any one of Inventive Concepts 23-25, wherein using the processor further comprises using the processor to:
define a curve based on the assessed length of projector ray r in each image of the subset of images; and
remove from being considered as a point on the intraoral three-dimensional surface a detected feature which was identified as being from projector ray r if the three-dimensional position of the projected feature corresponds to a length of projector ray r that is at least a threshold distance away from the defined curve.

Inventive Concept 34. A method for generating a digital three-dimensional image, the method comprising:
driving each one of one or more structured light projectors to project a pattern of light on an intraoral three-dimensional surface, the pattern of light comprising a plurality of projected features;
driving each of a plurality of cameras to capture an image, the image including at least a portion of the projected pattern, each one of the plurality of cameras comprising a camera sensor comprising an array of pixels; and
using a processor to:
run a correspondence algorithm to compute respective three-dimensional positions on the intraoral three-dimensional surface of a plurality of features of the projected pattern;
using data from a first camera of the plurality of cameras, identify a candidate three-dimensional position of a given feature of the projected pattern corresponding to a particular projector ray r, wherein data from a second camera of the plurality of cameras is not used to identify that candidate three-dimensional position;
using the candidate three-dimensional position as seen by the first camera, identify a search space on the second camera's pixel array in which to search for a feature of the projected pattern from projector ray r; and
if a feature of the projected pattern from projector ray r is identified within the search space, then, using the data from the second camera, refine the candidate three-dimensional position of the feature of the projected pattern.

Inventive Concept 35. The method according to Inventive Concept 34, wherein:
to identify the candidate three-dimensional position of a given spot corresponding to a particular projector ray r, the processor uses data from at least two of the cameras,
the data from the second camera comprises data from another one of the cameras that is not one of the at least two cameras, and
to identify the search space, the processor uses the candidate three-dimensional position as seen by at least one of the at least two cameras.

Inventive Concept 36. The method according to Inventive Concept 34, wherein the processor uses stored calibration values indicating (a) a camera ray corresponding to each pixel on the camera sensor of each one of the plurality of cameras, and (b) a projector ray corresponding to each one of the features of the projected pattern of light from each one of the one or more structured light projectors, whereby each projector ray corresponds to a respective path of pixels on at least one of the camera sensors.

Inventive Concept 37. The method according to any one of Inventive Concepts 34-36, wherein the pattern of light comprises a distribution of discrete unconnected spots of light, and wherein the feature of the projected pattern comprises a projected spot from the unconnected spots of light.

Inventive Concept 38. A method for generating a digital three-dimensional image, the method comprising:
driving each one of one or more structured light projectors to project a pattern of light on an intraoral three-dimensional surface along a plurality of projector rays;
driving each one of one or more cameras to capture a plurality of images, each image including at least a portion of the projected pattern, each one of the one or more cameras comprising a camera sensor comprising an array of pixels; and
using a processor to:
run a correspondence algorithm to compute respective three-dimensional positions on the intraoral three-dimensional surface of a plurality of detected features of the projected pattern for each of the plurality of images;
using data corresponding to the respective three-dimensional positions of at least three of the detected features, estimate a three-dimensional surface based on the at least three features, each feature corresponding to a respective projector ray r of the plurality of projector rays;

for a projector ray r1 of the plurality of projector rays for which a three-dimensional position of a feature corresponding to that projector ray r1 was not computed, estimate a three-dimensional position in space of an intersection of projector ray r1 and the estimated three-dimensional surface; and using the estimated three-dimensional position in space, identify a search space in the pixel array of at least one camera in which to search for a feature corresponding to projector ray r1.

Inventive Concept 39. The method according to Inventive Concept 38, wherein:

the correspondence algorithm is run based on stored calibration values indicating (a) a camera ray corresponding to each pixel on the camera sensor of each one of the one or more cameras, and (b) a projector ray corresponding to each feature of the projected pattern from each one of the one or more structured light projectors, whereby each projector ray corresponds to a respective path of pixels on at least one of the camera sensors.

Inventive Concept 40. The method according to Inventive Concept 38, wherein the pattern of light comprises a distribution of discrete spots, and wherein each of the features comprises a spot from the distribution of discrete spots.

Inventive Concept 41. The method according to any one of Inventive Concepts 38-40, wherein to run the correspondence algorithm, the processor sets a threshold, such that a detected feature that is below the threshold is not considered by the correspondence algorithm, and wherein to search for the feature corresponding to projector ray r1 in the identified search space, the processor lowers the threshold in order to consider features that were not considered by the correspondence algorithm.

Inventive Concept 42. The method according to Inventive Concept 41, wherein the threshold is an intensity threshold.

Inventive Concept 43. The method according to any one of Inventive Concepts 38-40, wherein using data corresponding to the respective three-dimensional positions of at least three features comprises using data corresponding to the respective three-dimensional positions of at least three features that were all captured in one of the plurality of images.

Inventive Concept 44. The method according to Inventive Concept 43, further comprising refining the estimation of the three-dimensional surface using data corresponding to a three-dimensional position of at least one additional feature of the projected pattern, the at least one additional feature having a three-dimensional position that was computed based on another one of the plurality of images.

Inventive Concept 45. The method according to Inventive Concept 44, wherein refining the estimation of the three-dimensional surface comprises refining the estimation of the three-dimensional surface such that all of the at least three features and the at least one additional feature lie on the three-dimensional surface.

Inventive Concept 46. The method according to any one of Inventive Concepts 38-40, wherein using data corresponding to the respective three-dimensional positions of at least three features comprises using data corresponding to at least three features, each captured in a respective one of the plurality of images.

Inventive Concept 47. A method for generating a digital three-dimensional image, the method comprising:

driving each one of one or more structured light projectors to project a pattern of light on an intraoral three-dimensional surface along a plurality of projector rays;

driving each one of one or more cameras to capture a plurality of images, each image including at least a portion of the projected pattern, each one of the one or more cameras comprising a camera sensor comprising an array of pixels; and using a processor to:

run a correspondence algorithm to compute respective three-dimensional positions on the intraoral three-dimensional surface of a plurality of detected features of the projected pattern for each of the plurality of images;

using data corresponding to the respective three-dimensional positions of at least three of the detected features, estimate a three-dimensional surface based on the at least three features, each feature corresponding to a respective projector ray r of the plurality of projector rays;

for a projector ray r1 of the plurality of projector rays for which more than one candidate three-dimensional position of a feature corresponding to that projector ray r1 was computed, estimate a three-dimensional position in space of an intersection of projector ray r1 and the estimated three-dimensional surface; and using the estimated three-dimensional position in space of the intersection of projector ray r1, select which of the more than one candidate three-dimensional positions is the correct three-dimensional position of the feature corresponding to that projector r1.

Inventive Concept 48. The method according to Inventive Concept 47, wherein:

the correspondence algorithm is run based on stored calibration values indicating (a) a camera ray corresponding to each pixel on the camera sensor of each one of the one or more cameras, and (b) a projector ray corresponding to each feature of the projected pattern from each one of the one or more structured light projectors, whereby each projector ray corresponds to a respective path of pixels on at least one of the camera sensors.

Inventive Concept 49. The method according to Inventive Concept 47, wherein the pattern of light comprises a distribution of discrete spots, and wherein each of the features comprises a spot from the distribution of discrete spots.

Inventive Concept 50. The method according to any one of Inventive Concepts 47-49, wherein using data corresponding to the respective three-dimensional positions of at least three features comprises using data corresponding to the respective three-dimensional positions of at least three features that were all captured in one of the plurality of images.

Inventive Concept 51. The method according to Inventive Concept 50, further comprising refining the estimation of the three-dimensional surface using data corresponding to a three-dimensional position of at least one additional feature of the projected pattern, the at least one additional feature having a three-dimensional position that was computed based on another one of the plurality of images.

Inventive Concept 52. The method according to Inventive Concept 51, wherein refining the estimation of the three-dimensional surface comprises refining the estimation of the three-dimensional surface such that all of the at least three features and the at least one additional feature lie on the three-dimensional surface.

Inventive Concept 53. The method according to any one of Inventive Concepts 47-49, wherein using data corresponding to the respective three-dimensional positions of at least three features comprises using data corresponding to at least three features, each captured in a respective one of the plurality of images.

Inventive Concept 54. A method for tracking motion of an intraoral scanner, the method comprising:
using at least one camera coupled to the intraoral scanner, measuring motion of the intraoral scanner with respect to an intraoral surface being scanned;
using at least one inertial measurement unit (IMU) coupled to the intraoral scanner, measuring motion of the intraoral scanner with respect to a fixed coordinate system; and
using a processor:
calculating motion of the intraoral surface with respect to the fixed coordinate system based on (a) motion of the intraoral scanner with respect to the intraoral surface and (b) motion of the intraoral scanner with respect to the fixed coordinate system;
based on accumulated data of motion of the intraoral surface with respect to the fixed coordinate system, building a predictive model of motion of the intraoral surface with respect to the fixed coordinate system; and
calculating an estimated location of the intraoral scanner with respect to the intraoral surface based on (a) a prediction of the motion of the intraoral surface with respect to the fixed coordinate system, derived based on the predictive model of motion, and (b) motion of the intraoral scanner with respect to the fixed coordinate system, measured by the IMU.

Inventive Concept 55. The method according to Inventive Concept 54, wherein the calculating of the motion is performed by calculating a difference between (a) the motion of the intraoral scanner with respect to the intraoral surface and (b) the motion of the intraoral scanner with respect to the fixed coordinate system.

Inventive Concept 56. The method according to any one of Inventive Concepts 54-55, further comprising:
determining whether measuring motion of the intraoral scanner with respect to the intraoral surface using the at least one camera is inhibited; and
in response to determining that the measuring of the motion is inhibited, calculating the estimated location of the intraoral scanner with respect to the intraoral surface.

Inventive Concept 57. A method comprising:
driving each one of one or more light sources to project light on an intraoral three-dimensional surface;
driving each one of one or more cameras to capture a plurality of images of the intraoral three-dimensional surface; and
based on stored calibration data for the one or more light sources and for the one or more cameras:
using a processor:
running a correspondence algorithm to compute respective three-dimensional positions on the intraoral three-dimensional surface of a plurality of features of the projected light;
collecting data at a plurality of points in time, the data including the computed respective three-dimensional positions on the intraoral three-dimensional surface of the plurality of features; and
based on the collected data, determining that at least some of the stored calibration data is incorrect.

Inventive Concept 58. The method according to Inventive Concept 57, wherein:
the one or more light sources are one or more structured light projectors,
driving each one of the one or more light sources to project light comprises driving each one of the one or more structured light projectors to project a pattern of light on the intraoral three-dimensional surface,
driving each one of one or more cameras comprises driving each one of the one or more cameras to capture a plurality of images of the intraoral three-dimensional surface, each image including at least a portion of the projected pattern,
each one of the one or more cameras comprises a camera sensor comprising an array of pixels, and
the stored calibration data comprises stored calibration values indicating (a) a camera ray corresponding to each pixel on the camera sensor of each one of the one or more cameras, and (b) a projector ray corresponding to each feature of the projected pattern of light from each one of the one or more structured light projectors, whereby each projector ray corresponds to a respective path p of pixels on at least one of the camera sensors.

Inventive Concept 59. The method according to Inventive Concept 58, wherein determining that at least some of the stored calibration data is incorrect comprises, using the processor:
for each projector ray r, based on the collected data, defining an updated path p' of pixels on each of the camera sensors, such that all of the computed three-dimensional positions corresponding to features produced by projector ray r correspond to locations along the respective updated path p' of pixels for each of the camera sensors;
comparing each updated path p' of pixels to the path p of pixels corresponding to that projector ray r on each camera sensor from the stored calibration values; and
in response to the updated path p' for at least one camera sensor s differing from the path p of pixels corresponding to that projector ray r from the stored calibration values, determining that at least some of the stored calibration values are incorrect.

Inventive Concept 60. A method comprising:
driving each one of one or more light sources to project light on an intraoral three-dimensional surface;
driving each one of one or more cameras to capture a plurality of images of the intraoral three-dimensional surface; and
based on stored calibration data for the one or more light sources and for the one or more cameras:
using a processor:
running a correspondence algorithm to compute respective three-dimensional positions on the intraoral three-dimensional surface of a plurality of features of the projected light;
collecting data at a plurality of points in time, the data including the computed respective three-dimensional positions on the intraoral three-dimensional surface of the plurality of features; and
using the collected data to recalibrate the stored calibration data.

Inventive Concept 61. The method according to Inventive Concept 60, wherein:
the one or more light sources are one or more structured light projectors,
driving each one of the one or more light sources to project light comprises driving each one of the one or more structured light projectors to project a pattern of light on the intraoral three-dimensional surface,
driving each one of one or more cameras comprises driving each one of the one or more cameras to capture a plurality of images of the intraoral three-dimensional surface, each image including at least a portion of the projected pattern, each one of the one or more cameras comprises a camera sensor comprising an array of pixels, and the stored calibration data comprises stored calibration values indicating (a) a camera ray corresponding to each pixel on the camera sensor of each one of the one or more cameras, and (b) a projector ray corresponding to each feature of the projected pattern of light from each one of the one or more structured light projectors, whereby each projector ray corresponds to a respective path p of pixels on at least one of the camera sensors.

Inventive Concept 62. The method according to Inventive Concept 61, wherein using the collected data to recalibrate the stored calibration data comprises, using a processor:

for each projector ray r, based on the collected data, defining an updated path p' of pixels on each of the camera sensors, such that all of the computed three-dimensional positions corresponding to features produced by projector ray r correspond to locations along the respective updated path p' of pixels for each of the camera sensors; and using the updated paths p' to recalibrate the stored calibration values.

Inventive Concept 63. The method according to Inventive Concept 62, wherein to recalibrate the stored calibration values, the processor performs operations comprising:

comparing each updated path p' of pixels to the path p of pixels corresponding to that projector ray r on each camera sensor from the stored calibration values; and if for at least one camera sensor s, the updated path p' of pixels corresponding to projector ray r differs from the path p of pixels corresponding to projector ray r from the stored calibration values:

reducing the difference between the updated path p' of pixels corresponding to each projector ray r and the respective path p of pixels corresponding to each projector ray r from the stored calibration values, by varying stored calibration data selected from the group consisting of:

the stored calibration values indicating a camera ray corresponding to each pixel on the camera sensor s of each one of the one or more cameras, and the stored calibration values indicating a projector ray r corresponding to each one of the projected features from each one of the one or more structured light projectors.

Inventive Concept 64. The method according to Inventive Concept 63, wherein:

the stored calibration data that is varied comprises the stored calibration values indicating a camera ray corresponding to each pixel on the camera sensor of each one of the one or more cameras; and varying the stored calibration data comprises varying one or more parameters of a parametrized camera calibration function that defines the camera rays corresponding to each pixel on at least one camera sensor s, in order to reduce the difference between:

the computed respective three-dimensional positions on the intraoral three-dimensional surface of the plurality of features of the projected pattern; and the stored calibration values indicating respective camera rays corresponding to each pixel on the camera sensor where a respective one of the plurality of features should have been detected.

Inventive Concept 65. The method according to Inventive Concept 63, wherein the stored calibration data that is varied comprises the stored calibration values indicating a projector ray corresponding to each one of the plurality of features from each one of the one or more structured light projectors, and wherein varying the stored calibration data comprises varying:

an indexed list assigning each projector ray r to a path p of pixels, or one or more parameters of a parametrized projector calibration model that defines each projector ray r.

Inventive Concept 66. The method according to Inventive Concept 65, wherein varying the stored calibration data comprises varying the indexed list by re-assigning each projector ray r based on the respective updated paths p' of pixels corresponding to each projector ray r.

Inventive Concept 67. The method according to Inventive Concept 63, wherein varying the stored calibration data comprises varying:

the stored calibration values indicating a camera ray corresponding to each pixel on the camera sensor s of each one of the one or more cameras, and the stored calibration values indicating a projector ray r corresponding to each one of the plurality of features from each one of the one or more structured light projectors.

Inventive Concept 68. The method according to Inventive Concept 67, wherein varying the stored calibration values comprises iteratively varying the stored calibration values.

Inventive Concept 69. The method according to Inventive Concept 62, further comprising:

driving each one of the one or more cameras to capture a plurality of images of a calibration object having predetermined parameters; and using a processor:

running a triangulation algorithm to compute the respective parameters of the calibration object based on the captured images; and running an optimization algorithm:

to reduce a difference between (i) updated path p' of pixels corresponding to projector ray r and (ii) the path p of pixels corresponding to projector ray r from the stored calibration values, using the computed respective parameters of the calibration object based on the captured images.

Inventive Concept 70. The method according to Inventive Concept 69, wherein the calibration object is a three-dimensional calibration object of known shape, and wherein driving each one of the one or more cameras to capture a plurality of images of the calibration object comprises driving each one of the one or more cameras to capture images of the three-dimensional calibration object, and wherein the predetermined parameters of the calibration object are dimensions of the three-dimensional calibration object.

Inventive Concept 71. The method according to Inventive Concept 70, wherein to run the optimization algorithm the processor further uses the collected data.

Inventive Concept 72. The method according to Inventive Concept 69, wherein the calibration object is a two-dimensional calibration object having visually-distinguishable features, wherein driving each one of the one or more cameras to capture a plurality of images of the calibration object comprises driving each one of the one or more cameras to capture images of the two-dimensional calibration object, and wherein the predetermined parameters of the two-dimensional calibration object are respective distances between respective visually-distinguishable features.

Inventive Concept 73. The method according to Inventive Concept 72, wherein to run the optimization algorithm the processor further uses the collected data.

Inventive Concept 74. The method according to Inventive Concept 72, wherein driving each one of the one or more cameras to capture images of the two-dimensional calibration object comprises driving each one of the one or more cameras to capture a plurality of images of the two-dimensional calibration object from a plurality of different viewpoints with respect to the two-dimensional calibration object.

Inventive Concept 75. A method for computing a three-dimensional structure of an intraoral three-dimensional surface, the method comprising:
  driving one or more structured light projectors to project a structured light pattern on the intraoral three-dimensional surface;
  driving one or more cameras to capture a plurality of structured light images, each structured light image including at least a portion of the structured light pattern;
  driving one or more unstructured light projectors to project unstructured light on the intraoral three-dimensional surface;
  driving the one or more cameras to capture a plurality of two-dimensional images of the intraoral three-dimensional surface using illumination from the unstructured light; and
  using a processor:
  computing respective three-dimensional positions of a plurality of points on the intraoral three-dimensional surface, as captured in the plurality of structured light images; and
  computing a three-dimensional structure of the intraoral three-dimensional surface, based on the plurality of two-dimensional images of the intraoral three-dimensional surface, constrained by some or all of the computed three-dimensional positions of the plurality of points.

Inventive Concept 76. The method according to Inventive Concept 75, wherein the unstructured light is non-coherent light, and wherein the plurality of two-dimensional images comprise a plurality of color two-dimensional images.

Inventive Concept 77. The method according to Inventive Concept 75, wherein the unstructured light is near infrared (NIR) light, and wherein the plurality of two-dimensional images comprise a plurality of monochromatic NIR images.

Inventive Concept 78. The method according to Inventive Concept 75, wherein the unstructured light is broad spectrum light, and wherein the plurality of two-dimensional images comprise a plurality of color two-dimensional images.

Inventive Concept 79. The method according to Inventive Concept 75, wherein driving the one or more structured light projectors comprises driving the one or more structured light projectors to each project a distribution of discrete unconnected spots of light.

Inventive Concept 80. The method according to any one of Inventive Concepts 75-79, wherein computing the three-dimensional structure comprises:
  inputting to a neural network the plurality of two-dimensional images of the intraoral three-dimensional surface; and
  determining, by the neural network, a respective estimated map of the intraoral three-dimensional surface as captured in each of the two-dimensional images.

Inventive Concept 81. The method according to Inventive Concept 80, wherein inputting to the neural network further comprises inputting to the neural network the computed respective three-dimensional positions of the plurality of points on the intraoral three-dimensional surface.

Inventive Concept 82. The method according to any one of Inventive Concepts 80-81, wherein the method further comprises regulating the capturing of the structured light images and the capturing of the two-dimensional images to produce an alternating sequence of one or more image frames of structured light interspersed with one or more image frames of unstructured light.

Inventive Concept 83. The method according to any one of Inventive Concepts 80-82, further comprising using the processor to stitch the respective estimated maps together to obtain the three-dimensional structure of the intraoral three-dimensional surface.

Inventive Concept 84. The method according to any one of Inventive Concepts 80-82, wherein determining comprises determining, by the neural network, a respective estimated depth map of the intraoral three-dimensional surface as captured in each of the two-dimensional images.

Inventive Concept 85. The method according to Inventive Concept 84, further comprising using the processor to stitch the respective estimated depth maps together to obtain the three-dimensional structure of the intraoral three-dimensional surface.

Inventive Concept 86. The method according to Inventive Concept 84:
  wherein the processor generates a respective point cloud corresponding to the computed respective three-dimensional positions of the plurality of points on the intraoral three-dimensional surface, as captured in each of the structured light images, and
  further comprising using the processor to stitch the respective estimated depth maps to the respective point clouds.

Inventive Concept 87. The method according to Inventive Concept 84, further comprising determining, by the neural network, a respective estimated normal map of the intraoral three-dimensional surface as captured in each of the two-dimensional images.

Inventive Concept 88. The method according to any one of Inventive Concepts 80-82, wherein determining comprises determining, by the neural network, a respective estimated normal map of the intraoral three-dimensional surface as captured in each of the two-dimensional images.

Inventive Concept 89. The method according to Inventive Concept 88, further comprising using the processor to stitch the respective estimated normal maps together to obtain the three-dimensional structure of the intraoral three-dimensional surface.

Inventive Concept 90. The method according to Inventive Concept 88, wherein using the processor further comprises, based on the respective estimated normal maps of the intraoral three-dimensional surface as captured in each of the two-dimensional images, interpolating three-dimensional positions on the intraoral three-dimensional surface between the computed respective three-dimensional positions of the plurality of points on the intraoral three-dimensional surface, as captured in the plurality of structured light images.

Inventive Concept 91. The method according to Inventive Concept 88, wherein the method further comprises regulating the capturing of the structured light images and the capturing of the two-dimensional images to produce an alternating sequence of one or more image frames of structured light interspersed with one or more image frames of unstructured light, and wherein using the processor further comprises:

generating a respective point cloud corresponding to the computed respective three-dimensional positions of the plurality of points on the intraoral three-dimensional surface, as captured in each image frame of structured light; and stitching the respective point clouds together using, as an input to the stitching, for a least a subset of the plurality of points for each point cloud, the normal to the surface at each point of the subset of points, wherein for a given point cloud the normal to the surface at at least one point of the subset of points is obtained from the respective estimated normal map of the intraoral three-dimensional surface as captured in an adjacent image frame of unstructured light.

Inventive Concept 92. The method according to Inventive Concept 91, wherein the method further comprises using the processor to compensate for motion of the intraoral scanner between an image frame of structured light and an adjacent image frame of unstructured light by estimating the motion of the intraoral scanner based on previous image frames.

Inventive Concept 93. The method according to any one of Inventive Concepts 80-82, wherein determining comprises determining, by the neural network, curvature of the intraoral three-dimensional surface as captured in each of the two-dimensional images.

Inventive Concept 94. The method according to Inventive Concept 93, wherein determining curvature comprises determining, by the neural network, a respective estimated curvature map of the intraoral three-dimensional surface as captured in each of the two-dimensional images.

Inventive Concept 95. The method according to Inventive Concept 93, wherein the method further comprises, using the processor:

assessing the curvature of the intraoral three-dimensional surface as captured in each of the two-dimensional images; and based on the assessed curvature of the intraoral three-dimensional surface as captured in each of the two-dimensional images, interpolating three-dimensional positions on the intraoral three-dimensional surface between the computed respective three-dimensional positions of the plurality of points on the intraoral three-dimensional surface, as captured in the plurality of structured light images.

Inventive Concept 96. The method according to any one of Inventive Concepts 80-82, wherein:

driving the one or more cameras to capture the plurality of structured light images comprises driving each one of two or more cameras to capture a respective plurality of structured light images; and driving the one or more cameras to capture the plurality of two-dimensional images comprises driving each one of the two or more cameras to capture a respective plurality of two-dimensional images.

Inventive Concept 97. The method according to Inventive Concept 96, wherein:

driving the two or more cameras comprises, in a given image frame, driving each one of the two or more cameras to simultaneously capture a respective two-dimensional image of a respective portion of the intraoral three-dimensional surface, inputting to the neural network comprises, for the given image frame, inputting all of the respective two-dimensional images to the neural network as a single input, wherein each one of the respective two-dimensional images has an overlapping field of view with at least one other of the respective two-dimensional images, and determining by the neural network comprises, for the given image frame, determining an estimated depth map of the intraoral three-dimensional surface that combines the respective portions of intraoral three-dimensional surface.

Inventive Concept 98. The method according to Inventive Concept 96, wherein:

driving the two or more cameras to capture the plurality of structured light images comprises driving each one of three or more cameras to capture a respective plurality of structured light images, driving the two or more cameras to capture the plurality of two-dimensional images comprises driving each one of the three or more cameras to capture a respective plurality of two-dimensional images, driving the three or more cameras comprises, in a given image frame, driving each one of the three or more cameras to simultaneously capture a respective two-dimensional image of a respective portion of the intraoral three-dimensional surface, inputting to the neural network comprises, for a given image frame, inputting a subset of the respective two-dimensional images to the neural network as a single input, wherein:

the subset comprises at least two of the respective two-dimensional images, and each image of the subset of respective two-dimensional images has an overlapping field of view with at least one other of the subset of respective two-dimensional images, and determining by the neural network comprises, for the given image frame, determining an estimated depth map of the intraoral three-dimensional surface that combines the respective portions of the intraoral three-dimensional surface as captured in the subset of the respective two-dimensional images.

Inventive Concept 99. The method according to Inventive Concept 96, wherein:

driving the two or more cameras comprises, in a given image frame, driving each one of the two or more cameras to simultaneously capture a respective two-dimensional image of a respective portion of the intraoral three-dimensional surface, inputting to the neural network comprises, for a given image frame, inputting each one of the respective two-dimensional images to the neural network as a separate input, determining by the neural network comprises, for the given image frame, determining a respective estimated depth map of each of the respective portions of the intraoral three-dimensional surface as captured in each of the respective two-dimensional images captured in the given image frame, and the method further comprises, using the processor, merging the respective estimated depth maps together to obtain a combined estimated depth map of the intraoral three-dimensional surface as captured in the given image frame.

Inventive Concept 100. The method according to Inventive Concept 99, wherein the method further comprises training the neural network, wherein each input to the neural network during the training comprises an image captured by only one camera.

Inventive Concept 101. The method according to Inventive Concept 99, wherein determining further comprises determining, by the neural network, a respective estimated confidence map corresponding to each estimated depth map, each confidence map indicating a confidence level per region of the respective estimated depth map.

Inventive Concept 102. The method according to Inventive Concept 101, wherein merging the respective estimated depth maps together comprises, using the processor:

in response to determining a contradiction between corresponding respective regions in at least two of the estimated depth maps, merging the at least two estimated depth maps based on the confidence level of each of the corresponding respective regions as indicated by the respective confidence maps for each of the at least two estimated depth maps.

Inventive Concept 103. The method according to any one of Inventive Concepts 80-82, wherein driving the one or more cameras comprises driving one or more cameras of an intraoral scanner, and wherein the method further comprises training the neural network using training-stage images as captured by a plurality of training-stage handheld wands, wherein:

each of the training-stage handheld wands comprises one or more reference cameras, and each of the one or more cameras of the intraoral scanner corresponds to a respective one of the one or more reference cameras on each of the training-stage handheld wands.

Inventive Concept 104. The method according to any one of Inventive Concepts 80-82, wherein:

driving the one or more structured light projectors comprises driving one or more structured light projectors of an intraoral scanner, driving the one or more unstructured light projectors comprises driving one or more unstructured light projectors of the intraoral scanner, driving the one or more cameras comprises driving one or more cameras of the intraoral scanner, and the method further comprises:

initially training the neural network using training-stage images as captured by one or more training-stage cameras of a training-stage handheld wand, each of the one or more cameras of the intraoral scanner corresponding to a respective one of the one or more training-stage cameras;

subsequently driving (i) the one or more structured light projectors of the intraoral scanner and (ii) the one or more unstructured light projectors of the intraoral scanner during a plurality of refining-stage scans;

driving the one or more cameras of the intraoral scanner to capture (a) a plurality of refining-stage structured light images and (b) a plurality of refining-stage two-dimensional images, during the refining-stage scans;

computing the three-dimensional structure of the intraoral three-dimensional surface based on the plurality of refining-stage structured light images; and refining the training of the neural network for the intraoral scanner using (a) the plurality of refining-stage two-dimensional images captured during the refining-stage scans and (b) the computed three-dimensional structure of the intraoral three-dimensional surface as computed based on the plurality of refining-stage structured light images.

Inventive Concept 105. The method according to Inventive Concept 104, wherein the neural network comprises a plurality of layers, and wherein refining the training of the neural network comprises constraining a subset of the layers.

Inventive Concept 106. The method according to Inventive Concept 104, wherein the method further comprises selecting, from a plurality of scans, which of the plurality of scans to use as the refining-stage scans based on a quality level of each scan.

Inventive Concept 107. The method according to Inventive Concept 104, wherein the method further comprises, during the refining-stage scans, using the computed three-dimensional structure of the intraoral three-dimensional surface as computed based on the plurality of refining-stage structured light images as an end-result three-dimensional structure of the intraoral three-dimensional surface for a user of the intraoral scanner.

Inventive Concept 108. The method according to any one of Inventive Concepts 80-82, wherein:

driving the one or more cameras comprises driving one or more cameras of an intraoral scanner, each one of the one or more cameras of the intraoral scanner corresponding to a respective one of one or more reference cameras, and the method further comprises, using the processor:

for each camera c of the one or more cameras of the intraoral scanner, cropping and morphing at least one of the two-dimensional images of the intraoral three-dimensional surface from camera c to obtain a plurality of cropped and morphed two-dimensional images, each cropped and morphed image corresponding to a cropped and morphed field of view of camera c, the cropped and morphed field of view of camera c matching a cropped field of view of the corresponding reference camera;

inputting to the neural network the plurality of two-dimensional images comprises inputting to the neural network the plurality of cropped and morphed two-dimensional images of the intraoral three-dimensional surface; and determining, by the neural network, comprises determining a respective estimated map of the intraoral three-dimensional surface as captured in each of the cropped and morphed two-dimensional images, the neural network having been trained using training-stage images corresponding to the cropped fields of view of each of the one or more reference cameras.

Inventive Concept 109. The method according to Inventive Concept 108, wherein the step of cropping and morphing comprises the processor using (a) stored calibration values indicating a camera ray corresponding to each pixel on the camera sensor of each one of the one or more cameras, and (b) reference calibration values indicating (i) a camera ray corresponding to each pixel on a reference camera sensor of each one of one or more reference cameras, and (ii) a cropped field of view for each one of the one or more reference cameras.

Inventive Concept 110. The method according to Inventive Concept 108, wherein the unstructured light is non-coherent light, and wherein the plurality of two-dimensional images comprise a plurality of two-dimensional color images.

Inventive Concept 111. The method according to Inventive Concept 108, wherein the unstructured light is near infrared (NIR) light, and wherein the plurality of two-dimensional images comprise a plurality of monochromatic NIR images.

Inventive Concept 112. The method according to Inventive Concept 108, wherein the cropped fields of view of each of the one or more reference cameras is 85-97% of a respective full field of view of each of the one or more reference cameras.

Inventive Concept 113. The method according to Inventive Concept 108, wherein using the processor further comprises, for each camera c, performing a reverse of the morphing for each of the respective estimated maps of the intraoral three-dimensional surface as captured in each of the cropped and morphed two-dimensional images to obtain a respective non-morphed estimated map of the intraoral surface as seen in each of the at least one two-dimensional images from camera c prior to the morphing.

Inventive Concept 114. The method according to any one of Inventive Concepts 108-113, wherein determining comprises determining, by the neural network, a respective estimated depth map of the intraoral three-dimensional surface as captured in each of the cropped and morphed two-dimensional images.

Inventive Concept 115. The method according to Inventive Concept 114, further comprising using the processor to stitch the respective estimated depth maps together to obtain the three-dimensional structure of the intraoral three-dimensional surface.

Inventive Concept 116. The method according to any one of Inventive Concepts 114-115:
  wherein the processor generates a respective point cloud corresponding to the respective three-dimensional positions of the plurality of points on the intraoral three-dimensional surface, as captured in each of the structured light images, and
  further comprising using the processor to stitch the respective estimated depth maps to the respective point clouds.

Inventive Concept 117. The method according to any one of Inventive Concepts 114-116, wherein determining comprises further determining, by the neural network, a respective estimated normal map of the intraoral three-dimensional surface as captured in each of the cropped and morphed two-dimensional images.

Inventive Concept 118. The method according to any one of Inventive Concepts 108-113, wherein determining comprises determining, by the neural network, a respective estimated normal map of the intraoral three-dimensional surface as captured in each of the cropped and morphed two-dimensional images.

Inventive Concept 119. The method according to Inventive Concept 118, further comprising using the processor to stitch the respective estimated normal maps together to obtain the three-dimensional structure of the intraoral three-dimensional surface.

Inventive Concept 120. The method according to any one of Inventive Concepts 118-119, wherein using the processor further comprises, based on the respective estimated normal maps of the intraoral three-dimensional surface as captured in each of the cropped and morphed two-dimensional images, interpolating three-dimensional positions on the intraoral three-dimensional surface between the computed respective three-dimensional positions of the plurality of points on the intraoral three-dimensional surface, as captured in the plurality of structured light images.

Inventive Concept 121. The method according to any one of Inventive Concepts 118-120, wherein the method further comprises regulating the capturing of the structured light images and the capturing of the two-dimensional images to produce an alternating sequence of one or more image frames of structured light interspersed with one or more image frames of unstructured light, and wherein
  using the processor further comprises:
  generating a respective point cloud corresponding to the respective three-dimensional positions of the plurality of points on the intraoral three-dimensional surface, as captured in each image frame of structured light; and
  stitching the respective point clouds together using, as an input to the stitching, for a least a subset of the plurality of points, the normal to the surface at each point of the subset of points, wherein the normal to the surface at at least one point of the subset of points is obtained from the respective estimated normal map of the intraoral three-dimensional surface as captured in an adjacent image frame of unstructured light.

Inventive Concept 122. The method according to Inventive Concept 121, wherein the method further comprises using the processor to compensate for motion of the intraoral scanner between an image frame of structured light and an adjacent image frame of unstructured light by estimating the motion of the intraoral scanner based on previous image frames.

Inventive Concept 123. The method according to any one of Inventive Concepts 108-113, wherein determining comprises determining, by the neural network, curvature of the intraoral three-dimensional surface as captured in each of the cropped and morphed two-dimensional images.

Inventive Concept 124. The method according to Inventive Concept 123, wherein determining curvature comprises determining, by the neural network, a respective estimated curvature map of the intraoral three-dimensional surface as captured in each of the cropped and morphed two-dimensional images.

Inventive Concept 125. The method according to any one of Inventive Concepts 123-124, wherein the method further comprises, using the processor:
  assessing the curvature of the intraoral three-dimensional surface as captured in each of the cropped and morphed two-dimensional images; and
  based on the assessed curvature of the intraoral three-dimensional surface as captured in each of the two-dimensional images, interpolating three-dimensional positions on the intraoral three-dimensional surface between the computed respective three-dimensional positions of the plurality of points on the intraoral three-dimensional surface, as captured in the plurality of structured light images.

Inventive Concept 126. The method according to any one of Inventive Concepts 108-113, wherein:
  driving the one or more structured light projectors comprises driving one or more structured light projectors of the intraoral scanner,
  driving the one or more unstructured light projectors comprises driving one or more unstructured light projectors of the intraoral scanner, and
  wherein the method further comprises, subsequently to the neural network having been trained using the training-stage images corresponding to the cropped fields of view of each of the one or more reference cameras:
  driving the one or more structured light projectors of the intraoral scanner and the one or more unstructured light projectors of the intraoral scanner during a plurality of refining-stage scans, driving the one or more cameras of the intraoral scanner to capture (a) a plurality of refining-stage structured light images and (b) a plurality of refining-stage two-dimensional images, during the plurality of refining-stage structured light scans, computing the three-dimensional structure of the intraoral three-dimensional surface based on the plurality of refining-stage structured light images, and refining the training of the neural network for the intraoral scanner using (a) the plurality of refining-stage two-dimensional images captured during the refining-stage scans and (b) the computed three-dimensional structure of the intraoral three-dimensional surface as computed based on the plurality of refining-stage structured light images.

Inventive Concept 127. The method according to Inventive Concept 126, wherein the neural network comprises a plurality of layers, and wherein refining the training of the neural network comprises constraining a subset of the layers.

Inventive Concept 128. The method according to any one of Inventive Concepts 108-113, wherein:
driving the one or more structured light projectors comprises driving one or more structured light projectors of the intraoral scanner,
driving the one or more unstructured light projectors comprises driving one or more unstructured light projectors of the intraoral scanner,
determining comprises determining, by the neural network, a respective estimated depth map of the intraoral three-dimensional surface as captured in each of the cropped and morphed two-dimensional images, and
the method further comprises, using the processor:
computing the three-dimensional structure of the intraoral three-dimensional surface based on the computed respective three-dimensional positions of the plurality of points on the intraoral three-dimensional surface, as captured in the plurality of structured light images;
computing the three-dimensional structure of the intraoral three-dimensional surface based on the respective predicted estimated depth maps of the intraoral three-dimensional surface, as captured in each of the cropped and morphed two-dimensional images;
comparing (i) the three-dimensional structure of the intraoral three-dimensional surface as computed based on the computed respective three-dimensional positions of the plurality of points on the intraoral three-dimensional surface and (ii) the three-dimensional structure of the intraoral three-dimensional surface as computed based on the respective estimated depth maps of the intraoral three-dimensional surface; and
in response to determining a discrepancy between (i) and (ii):
driving (A) the one or more structured light projectors of the intraoral scanner and (B) the one or more unstructured light projectors of the intraoral scanner, during a plurality of refining-stage scans,
driving the one or more cameras of the intraoral scanner to capture (a) a plurality of refining-stage structured light images and (b) a plurality of refining-stage two-dimensional images, during the plurality of refining-stage scans,
computing the three-dimensional structure of the intraoral three-dimensional surface based on the plurality of refining-stage structured light images, and
refining the training of the neural network for the intraoral scanner using (a) the plurality of two-dimensional images captured during the refining-stage scans and (b) the computed three-dimensional structure of the intraoral three-dimensional surface as computed based on the plurality of refining-stage structured light images.

Inventive Concept 129. The method according to Inventive Concept 128, wherein the neural network comprises a plurality of layers, and wherein refining the training of the neural network comprises constraining a subset of the layers.

Inventive Concept 130. The method according to any one of Inventive Concepts 80-82, further comprising training the neural network, the training comprising:
driving one or more training-stage structured light projectors to project a training-stage structured light pattern on a training-stage three-dimensional surface;
driving one or more training-stage cameras to capture a plurality of structured light images, each image including at least a portion of the training-stage structured light pattern;
driving one or more training-stage unstructured light projectors to project unstructured light onto the training-stage three-dimensional surface;
driving the one or more training-stage cameras to capture a plurality of two-dimensional images of the training-stage three-dimensional surface using illumination from the training-stage unstructured light projectors;
regulating the capturing of the structured light images and the capturing of the two-dimensional images to produce an alternating sequence of one or more image frames of structured light images interspersed with one or more image frames of two-dimensional images;
inputting to the neural network the plurality of two-dimensional images;
estimating, by the neural network, an estimated map of the training-stage three-dimensional surface as captured in each of the two-dimensional images;
inputting to the neural network a respective plurality of three-dimensional reconstructions of the training-stage three-dimensional surface, based on structured light images of the training-stage three-dimensional surface, the three-dimensional reconstructions including computed three-dimensional positions of a plurality of points on the training-stage three-dimensional surface;
interpolating a position of the one or more training-stage cameras with respect to the training-stage three-dimensional surface for each two-dimensional image frame based on the computed three-dimensional positions of the plurality of points on the training-stage three-dimensional surface as computed based on respective structured light image frames before and after each two-dimensional image frame;
projecting the three-dimensional reconstructions on respective fields of view of each of the one or more training-stage cameras and, based on the projections, calculating a true map of the training-stage three-dimensional surface as seen in each two-dimensional image, constrained by the computed three-dimensional positions of the plurality of points;
comparing each estimated map of the training-stage three-dimensional surface to a corresponding true map of the training-stage three-dimensional surface; and
based on differences between each estimated map and the corresponding true map, optimizing the neural network to better estimate a subsequent estimated map.

Inventive Concept 131. The method according to Inventive Concept 130, wherein driving the one or more structured light projectors to project the training-stage structured light pattern comprises driving the one or more structured light projectors to each project a distribution of discrete unconnected spots of light on the training-stage three-dimensional surface.

Inventive Concept 132. The method according to Inventive Concept 130, wherein driving one or more training-stage cameras comprises driving at least two training-stage cameras.

Inventive Concept 133. The method according to any one of Inventive Concepts 130-132, wherein:
the training comprises an initial training of the neural network,
driving the one or more structured light projectors comprises driving one or more structured light projectors of an intraoral scanner,
driving the one or more unstructured light projectors comprises driving one or more unstructured light projectors of the intraoral scanner,
driving the one or more cameras comprises driving one or more cameras of the intraoral scanner, and
wherein the method further comprises, subsequently to the initial training of the neural network:
driving (i) the one or more structured light projectors of the intraoral scanner and (ii) the one or more unstructured light projectors of the intraoral scanner during a plurality of refining-stage structured light scans;
driving the one or more cameras of the intraoral scanner to capture (a) a plurality of refining-stage structured light images and (b) a plurality of refining-stage two-dimensional images, during the refining-stage structured light scans;
computing the three-dimensional structure of the intraoral three-dimensional surface based on the plurality of refining-stage structured light images; and
refining the training of the neural network for the intraoral scanner using (a) the plurality of two-dimensional images captured during the refining-stage scans and (b) the computed three-dimensional structure of the intraoral three-dimensional surface as computed based on the plurality of refining-stage structured light images.

Inventive Concept 134. The method according to Inventive Concept 133, wherein the neural network comprises a plurality of layers, and wherein refining the training of the neural network comprises constraining a subset of the layers.

Inventive Concept 135. An apparatus for intraoral scanning, the apparatus comprising:
an elongate handheld wand comprising a probe at a distal end of the elongate handheld wand;
one or more illumination sources coupled to the probe;
one or more near infrared (NIR) light sources coupled to the probe;
one or more cameras coupled to the probe, and configured to (a) capture images using light from the one or more illumination sources, and (b) capture images using NIR light from the NIR light source; and
a processor configured to run a navigation algorithm to determine a location of the elongate handheld wand as the elongate handheld wand moves in space, inputs to the navigation algorithm being (a) the images captured using the light from the one or more illumination sources, and (b) the images captured using the NIR light.

Inventive Concept 136. The apparatus according to Inventive Concept 135, wherein the one or more illumination sources comprise one or more structured light sources.

Inventive Concept 137. The apparatus according to Inventive Concept 135, wherein the one or more illumination sources comprise one or more non-coherent light sources.

Inventive Concept 138. A method for tracking motion of an intraoral scanner, the method comprising:
using one or more illumination sources coupled to the intraoral scanner, illuminating an intraoral three-dimensional surface;
using one or more near infrared (NIR) light sources coupled to the intraoral scanner, driving each one of the one or more NIR light sources to emit NIR light onto the intraoral three-dimensional surface;
using one or more cameras coupled to the intraoral scanner, (a) capturing a first plurality of images using light from the one or more illumination sources, and (b) capturing a second plurality of images using the NIR light; and
using a processor:
running a navigation algorithm to track motion of the intraoral scanner with respect to the intraoral three-dimensional surface using (a) the first plurality of images captured using light from the one or more illumination sources, and (b) the second plurality of images captured using the NIR light.

Inventive Concept 139. The method according to Inventive Concept 138, wherein using the one or more illumination sources comprises illuminating the intraoral three-dimensional surface.

Inventive Concept 140. The method according to Inventive Concept 138, wherein using the one or more illumination sources comprises using one or more non-coherent light sources.

Inventive Concept 141. An apparatus for intraoral scanning, the apparatus comprising:
an elongate handheld wand comprising a probe at a distal end of the elongate handheld wand that is configured for being removably disposed in a sleeve;
at least one structured light projector coupled to the probe, the at least one structured light projector (a) comprising a laser configured to emit polarized laser light, and (b) comprising a pattern generating optical element configured to generate a pattern of light when the laser is activated to transmit light through the pattern generating optical element; and
a camera coupled to the probe, the camera comprising a camera sensor;
wherein the probe is configured such that light exits and enters the probe through the sleeve;
wherein the laser is positioned at a distance with respect to the camera, such that when the probe is disposed in the sleeve, a portion of the pattern of light is reflected off of the sleeve and reaches the camera sensor; and
wherein the laser is positioned at a rotational angle, with respect to its own optical axis, such that, due to polarization of the pattern of light, an extent of reflection by the sleeve of the portion of the pattern of light is less than a threshold reflection for all possible rotational angles of the laser with respect to its optical axis.

Inventive Concept 142. The apparatus according to Inventive Concept 141, wherein a distance between the structured light projector and the camera is 1-6 times a distance between the structured light projector and the sleeve, when the elongate handheld wand is disposed in the sleeve.

Inventive Concept 143. The apparatus according to Inventive Concept 141, wherein the at least one structured light projector has a field of illumination of at least 30 degrees, and wherein the camera has a field of view of at least 30 degrees.

Inventive Concept 144. The apparatus according to any one of Inventive Concepts 141-143, wherein the threshold is 70% of a maximum reflection for all the possible rotational angles of the laser with respect to its optical axis.

Inventive Concept 145. The apparatus according to Inventive Concept 144, wherein the laser is positioned at the rotational angle, with respect to its own optical axis, such that due to the polarization of the pattern of light, the extent of reflection by the sleeve of the portion of the pattern of light is less than 60% of the maximum reflection for all possible rotational angles of the laser with respect to its optical axis.

Inventive Concept 146. The apparatus according to Inventive Concept 145, wherein the laser is positioned at the rotational angle, with respect to its own optical axis, such that due to the polarization of the pattern of light, the extent of reflection by the sleeve of the portion of the pattern of light is 15%-60% of the maximum reflection for all possible rotational angles of the laser with respect to its optical axis.

Inventive Concept 147. A method for generating a three-dimensional image using an intraoral scanner, the method comprising:
  using at least two cameras that are rigidly connected to the intraoral scanner, such that respective fields of view of each of the cameras have non-overlapping portions, capturing a plurality of images of an intraoral three-dimensional surface; and
  using a processor, running a simultaneous localization and mapping (SLAM) algorithm using captured images from each of the cameras for the non-overlapping portions of the respective fields of view, the localization of each of the cameras being solved based on motion of each of the cameras being the same as motion of every other one of the cameras.

Inventive Concept 148. The method according to Inventive Concept 147, wherein:
  the respective fields of view of a first one of the cameras and a second one of the cameras also have overlapping portions;
  the capturing comprises capturing the plurality of images of the intraoral three-dimensional surface such that a feature of the intraoral three-dimensional surface that is in the overlapping portions of the respective fields of view appears in the images captured by the first and second cameras; and
  using the processor comprises running the SLAM algorithm using features of the intraoral three-dimensional surface that appear in the images of at least two of the cameras.

Inventive Concept 149. A method for generating a three-dimensional image using an intraoral scanner, the method comprising:
  driving one or more structured light projectors to project a pattern of structured light on an intraoral three-dimensional surface;
  driving one or more cameras to capture a plurality of structured light images, each structured light image including at least a portion of the structured light pattern;
  driving one or more unstructured light projectors to project unstructured light onto the intraoral three-dimensional surface;
  driving at least one camera to capture two-dimensional images of the intraoral three-dimensional surface using illumination from the unstructured light projectors;
  regulating capturing of the structured light and capturing of the unstructured light to produce an alternating sequence of one or more image frames of structured light interspersed with one or more image frames of unstructured light; and
  using a processor:
  computing respective three-dimensional positions of a plurality of points on the intraoral three-dimensional surface, as captured in the one or more image frames of structured light;
  interpolating motion of the at least one camera between a first image frame of unstructured light and a second image frame of unstructured light based on the computed three-dimensional positions of the plurality of points in respective structured light image frames before and after the image frames of unstructured light, and
  running a simultaneous localization and mapping (SLAM) algorithm (a) using features of the intraoral three-dimensional surface as captured by the at least one camera in the first and second image frames of unstructured light, and (b) constrained by the interpolated motion of the camera between the first image frame of unstructured light and the second image frame of unstructured light.

Inventive Concept 150. The method according to Inventive Concept 149, wherein driving the one or more structured light projectors to project the structured light pattern comprises driving the one or more structured light projectors to each project a distribution of discrete unconnected spots of light on the intraoral three-dimensional surface.

Inventive Concept 151. The method according to any one of Inventive Concepts 149-150, wherein the unstructured light comprises broad spectrum light, and wherein the two-dimensional images comprise two-dimensional color images.

Inventive Concept 152. The method according to any one of Inventive Concepts 149-150, wherein the unstructured light comprises near infrared (NIR) light, and wherein the two-dimensional images comprise two-dimensional monochromatic NIR images.

Inventive Concept 153. A method for generating a three-dimensional image using an intraoral scanner, the method comprising:
  driving one or more structured light projectors to project a pattern of structured light on an intraoral three-dimensional surface;
  driving one or more cameras to capture a plurality of structured light images, each structured light image including at least a portion of the structured light pattern;
  driving one or more unstructured light projectors to project unstructured light onto the intraoral three-dimensional surface;
  driving the one or more cameras to capture two-dimensional images of the intraoral three-dimensional surface using illumination from the unstructured light projectors;
  regulating capturing of the structured light and capturing of the unstructured light to produce an alternating sequence of one or more image frames of structured light interspersed with one or more image frames of unstructured light; and using a processor:
computing a three-dimensional position of a feature on the intraoral three-dimensional surface, based on the image frames of structured light, the feature also being captured in a first image frame of unstructured light and a second image frame of unstructured light,
calculating motion of the one or more cameras between the first image frame of unstructured light and the second image frame of unstructured light based on the computed three-dimensional position of the feature; and
running a simultaneous localization and mapping (SLAM) algorithm using (i) a feature of the intraoral three-dimensional surface for which the three-dimensional position was not computed based on the image frames of structured light, as captured by the one or more cameras in the first and second image frames of unstructured light, and (ii) the calculated motion of the camera between the first and second image frames of unstructured light.

Inventive Concept 154. The method according to Inventive Concept 153, wherein driving the one or more structured light projectors to project the structured light pattern comprises driving the one or more structured light projectors to each project a distribution of discrete unconnected spots of light on the intraoral three-dimensional surface.

Inventive Concept 155. The method according to any one of Inventive Concepts 153-154, wherein the unstructured light comprises broad spectrum light, and wherein the two-dimensional images comprise two-dimensional color images.

Inventive Concept 156. The method according to any one of Inventive Concepts 153-154, wherein the unstructured light comprises near infrared (NIR) light, and wherein the two-dimensional images comprise two-dimensional monochromatic NIR images.

Inventive Concept 157. A method for computing a three-dimensional structure of an intraoral three-dimensional surface within an intraoral cavity of a subject, the method comprising:
driving one or more structured light projectors to project a pattern of structured light on the intraoral three-dimensional surface, the pattern comprising a plurality of features;
driving one or more cameras to capture a plurality of structured light images, each structured light image including at least one of the features of the structured light pattern;
driving one or more unstructured light projectors to project unstructured light onto the intraoral three-dimensional surface;
driving at least one camera to capture two-dimensional images of the intraoral three-dimensional surface using illumination from the one or more unstructured light projectors;
regulating capturing of the structured light and capturing of the unstructured light to produce an alternating sequence of one or more image frames of structured light interspersed with one or more image frames of unstructured light; and
using a processor:
determining for one or more features of the plurality of features of the structured light pattern whether the feature is being projected on moving or stable tissue within the intraoral cavity, based on the two-dimensional images;
based on the determination, assigning a respective confidence grade for each of the one or more features, high confidence being for fixed tissue and low confidence being for moving tissue; and
based on the confidence grade for each of the one or more features, running a three-dimensional reconstruction algorithm using the one or more features.

Inventive Concept 158. The method according to Inventive Concept 157, wherein the plurality of features comprise a plurality of spots, and wherein driving the one or more structured light projectors to project the structured light pattern comprises driving the one or more structured light projectors to each project a distribution of discrete unconnected spots of light on the intraoral three-dimensional surface.

Inventive Concept 159. The method according to any one of Inventive Concepts 157-158, wherein the unstructured light comprises broad spectrum light, and wherein the two-dimensional images are two-dimensional color images.

Inventive Concept 160. The method according to any one of Inventive Concepts 157-158, wherein the unstructured light comprises near infrared (NIR) light, and wherein the two-dimensional images are two-dimensional monochromatic NIR images.

Inventive Concept 161. The method according to any one of Inventive Concepts 157-158, wherein running the three-dimensional reconstruction algorithm is performed using only a subset of the plurality of features, the subset consisting of features that were assigned a confidence grade above a fixed-tissue threshold value.

Inventive Concept 162. The method according to any one of Inventive Concepts 157-158, wherein running the three-dimensional reconstruction algorithm comprises, (a) for each feature, assigning a weight to that feature based on the respective confidence grade assigned to that feature, and (b) using the respective weights for each feature in the three-dimensional reconstruction algorithm.

Inventive Concept 163. A method for computing a three-dimensional structure of an intraoral three-dimensional surface, the method comprising:
driving one or more light sources of an intraoral scanner to project light on the intraoral three-dimensional surface;
driving two or more cameras of the intraoral scanner to each capture a plurality of two-dimensional images of the intraoral three-dimensional surface, each of the two or more cameras of the intraoral scanner corresponding to a respective one of two or more reference cameras; and
using a processor:
for each camera c of the two or more cameras of the intraoral scanner, modifying at least one of the two-dimensional images from camera c to obtain a plurality of modified two-dimensional images, each modified image corresponding to a modified field of view of camera c, the modified field of view of camera c matching a modified field of view of a corresponding one of the reference cameras; and
computing a three-dimensional structure of the intraoral three-dimensional surface, based on the plurality of modified two-dimensional images of the intraoral three-dimensional surface.

Inventive Concept 164. A method for computing a three-dimensional structure of an intraoral three-dimensional surface, the method comprising:

driving one or more light sources of an intraoral scanner to project light on the intraoral three-dimensional surface;

driving two or more cameras of the intraoral scanner to each capture a plurality of two-dimensional images of the intraoral three-dimensional surface, each of the one or more cameras of the intraoral scanner corresponding to a respective one of two or more reference cameras;

using a processor:

for each camera c of the two or more cameras of the intraoral scanner, cropping and morphing at least one of the two-dimensional images from camera c to obtain a plurality of cropped and morphed two-dimensional images, each cropped and morphed image corresponding to a cropped and morphed field of view of camera c, the cropped and morphed field of view of camera c matching a cropped field of view of a corresponding one of the reference cameras; and computing a three-dimensional structure of the intraoral three-dimensional surface, based on the plurality of cropped and morphed two-dimensional images of the intraoral three-dimensional surface by:

inputting to a neural network the plurality of cropped and morphed two-dimensional images of the intraoral three-dimensional surface, and determining, by the neural network, a respective estimated map of the intraoral three-dimensional surface as captured in each of the plurality of cropped and morphed two-dimensional images, the neural network having been trained using training-stage images corresponding to the cropped fields of view of each of the one or more reference cameras.

Inventive Concept 165. The method according to Inventive Concept 164, wherein the light is non-coherent light, and wherein the plurality of two-dimensional images comprise a plurality of two-dimensional color images.

Inventive Concept 166. The method according to Inventive Concept 164, wherein the light is near infrared (NIR) light, and wherein the plurality of two-dimensional images comprise a plurality of monochromatic NIR images.

Inventive Concept 167. The method according to Inventive Concept 164, wherein the light is broad spectrum light, and wherein the plurality of two-dimensional images comprise a plurality of two-dimensional color images.

Inventive Concept 168. The method according to Inventive Concept 164, wherein the step of cropping and morphing comprises the processor using (a) stored calibration values indicating a camera ray corresponding to each pixel on the camera sensor of each one of the one or more cameras c, and (b) reference calibration values indicating (i) a camera ray corresponding to each pixel on a reference camera sensor of each one of one or more reference cameras, and (ii) a cropped field of view for each one of the one or more reference cameras.

Inventive Concept 169. The method according to Inventive Concept 164, wherein the cropped fields of view of each of the one or more reference cameras is 85-97% of a respective full field of view of each of the one or more reference cameras.

Inventive Concept 170. The method according to Inventive Concept 164, wherein using the processor further comprises, for each camera c, performing a reverse of the morphing for each of the respective estimated maps of the intraoral three-dimensional surface as captured in each of the cropped and morphed two-dimensional images to obtain a respective non-morphed estimated map of the intraoral surface as seen in each of the at least one two-dimensional images from camera c prior to the morphing.

Inventive Concept 171. The method according to any one of Inventive Concepts 164-170, wherein determining comprises determining, by the neural network, a respective estimated depth map of the intraoral three-dimensional surface as captured in each of the cropped and morphed two-dimensional images.

Inventive Concept 172. The method according to Inventive Concept 171, further comprising using the processor to stitch the respective estimated depth maps together to obtain the three-dimensional structure of the intraoral three-dimensional surface.

Inventive Concept 173. The method according to Inventive Concept 171, wherein determining comprises further determining, by the neural network, a respective estimated normal map of the intraoral three-dimensional surface as captured in each of the cropped and morphed two-dimensional images.

Inventive Concept 174. The method according to any one of Inventive Concepts 164-170, wherein determining comprises determining, by the neural network, a respective estimated normal map of the intraoral three-dimensional surface as captured in each of the cropped and morphed two-dimensional images.

Inventive Concept 175. The method according to Inventive Concept 174, further comprising using the processor to stitch the respective estimated normal maps together to obtain the three-dimensional structure of the intraoral three-dimensional surface.

Inventive Concept 176. The method according to any one of Inventive Concepts 164-170, wherein determining comprises determining, by the neural network, curvature of the intraoral three-dimensional surface as captured in each of the cropped two-dimensional images.

Inventive Concept 177. The method according to Inventive Concept 176, wherein determining curvature comprises determining, by the neural network, a respective estimated curvature map of the intraoral three-dimensional surface as captured in each of the cropped and morphed two-dimensional images.

Inventive Concept 178. The method according to any one of Inventive Concepts 164-170, wherein driving the one or more light sources comprises driving one or more unstructured light projectors of the intraoral scanner to project unstructured light on the intraoral three-dimensional surface, and wherein the method further comprises, and the method further comprises:

driving one or more structured light projectors of the intraoral scanner to project a structured light pattern on the intraoral three-dimensional surface;

driving the one or more cameras of the intraoral scanner to capture a plurality of structured light images, each image including at least a portion of the structured light pattern; and using the processor:

computing respective three-dimensional positions of a plurality of points on the intraoral three-dimensional surface, as captured in the plurality of structured light images, and constraining (a) the computing of the three-dimensional structure of the intraoral three-dimensional surface, based on the plurality of cropped and morphed two-dimensional images, by (b) some or all of the computed three-dimensional positions of the plurality of points.

Inventive Concept 179. The method according to Inventive Concept 178, wherein determining comprises determining, by the neural network, a respective estimated depth map of the intraoral three-dimensional surface as captured in each of the cropped and morphed two-dimensional images.

Inventive Concept 180. The method according to Inventive Concept 179, further comprising using the processor to stitch the respective estimated depth maps together to obtain the three-dimensional structure of the intraoral three-dimensional surface.

Inventive Concept 181. The method according to any one of Inventive Concepts 179-180:
- wherein the processor generates a respective point cloud corresponding to the respective three-dimensional positions of the plurality of points on the intraoral three-dimensional surface, as captured in each of the structured light images, and
- further comprising using the processor to stitch the respective estimated depth maps to the respective point clouds.

Inventive Concept 182. The method according to any one of Inventive Concepts 179-181, wherein determining comprises further determining, by the neural network, a respective estimated normal map of the intraoral three-dimensional surface as captured in each of the cropped and morphed two-dimensional images.

Inventive Concept 183. The method according to Inventive Concept 178, wherein determining comprises determining, by the neural network, a respective estimated normal map of the intraoral three-dimensional surface as captured in each of the cropped and morphed two-dimensional images.

Inventive Concept 184. The method according to Inventive Concept 183, further comprising using the processor to stitch the respective estimated normal maps together to obtain the three-dimensional structure of the intraoral three-dimensional surface.

Inventive Concept 185. The method according to any one of Inventive Concepts 183-184, wherein using the processor further comprises, based on the respective estimated normal maps of the intraoral three-dimensional surface as captured in each of the cropped and morphed two-dimensional images, interpolating three-dimensional positions on the intraoral three-dimensional surface between the computed respective three-dimensional positions of the plurality of points on the intraoral three-dimensional surface, as captured in the plurality of structured light images.

Inventive Concept 186. The method according to any one of Inventive Concepts 183-185, wherein the method further comprises regulating the capturing of the structured light images and the capturing of the two-dimensional images to produce an alternating sequence of one or more image frames of structured light interspersed with one or more image frames of unstructured light, and wherein
using the processor further comprises:
- generating a respective point cloud corresponding to the respective three-dimensional positions of the plurality of points on the intraoral three-dimensional surface, as captured in each image frame of structured light;
- stitching the respective point clouds together using, as an input to the stitching, for a least a subset of the plurality of points for each point cloud, the normal to the surface at each point of the subset of points, wherein for a given point cloud the normal to the surface at at least one point of the subset of points is obtained from the respective estimated normal map of the intraoral three-dimensional surface as captured in an adjacent image frame of unstructured light.

Inventive Concept 187. The method according to Inventive Concept 186, wherein the method further comprises using the processor to compensate for motion of the intraoral scanner between an image frame of structured light and an adjacent image frame of unstructured light by estimating the motion of the intraoral scanner based on previous image frames.

Inventive Concept 188. The method according to Inventive Concept 178, wherein determining comprises determining, by the neural network, curvature of the intraoral three-dimensional surface as captured in each of the cropped and morphed two-dimensional images.

Inventive Concept 189. The method according to Inventive Concept 188, wherein determining curvature comprises determining, by the neural network, a respective estimated curvature map of the intraoral three-dimensional surface as captured in each of the cropped and morphed two-dimensional images.

Inventive Concept 190. The method according to any one of Inventive Concepts 188-189, wherein the method further comprises, using the processor:
- assessing the curvature of the intraoral three-dimensional surface as captured in each of the cropped and morphed two-dimensional images, and
- based on the assessed curvature of the intraoral three-dimensional surface as captured in each of the cropped and morphed two-dimensional images, interpolating three-dimensional positions on the intraoral three-dimensional surface based on between the computed respective three-dimensional positions of the plurality of points on the intraoral three-dimensional surface, as captured in the plurality of structured light images.

Inventive Concept 191. The method according to Inventive Concept 178, wherein the method further comprises, subsequently to the neural network having been trained using the training-stage images corresponding to the cropped fields of view of each of the one or more reference cameras:
- driving (i) the one or more structured light projectors of the intraoral scanner and (ii) the one or more unstructured light projectors of the intraoral scanner during a plurality of refining-stage scans;
- driving the one or more cameras of the intraoral scanner to capture (a) a plurality of refining-stage structured light images and (b) a plurality of refining-stage two-dimensional images, during the refining-stage structured light scans;
- computing the three-dimensional structure of the intraoral three-dimensional surface based on the plurality of refining-stage structured light images; and
- subsequently refining the training of the neural network for the intraoral scanner using (a) the plurality of refining-stage two-dimensional images captured during the refining-stage scans and (b) the computed three-dimensional structure of the intraoral three-dimensional surface as computed based on the plurality of refining-stage structured light images.

Inventive Concept 192. The method according to Inventive Concept 191, wherein the neural network comprises a plurality of layers, and wherein refining the training of the neural network comprises constraining a subset of the layers.

Inventive Concept 193. The method according to Inventive Concept 178, wherein determining comprises determining, by the neural network, a respective estimated depth map of the intraoral three-dimensional surface as captured in each of the cropped and morphed two-dimensional images, and the method further comprises, using the processor:
computing the three-dimensional structure of the intraoral three-dimensional surface based on the computed respective three-dimensional positions of the plurality of points on the intraoral three-dimensional surface, as captured in the plurality of structured light images;
computing the three-dimensional structure of the intraoral three-dimensional surface based on the respective estimated depth maps of the intraoral three-dimensional surface, as captured in each of the cropped and morphed two-dimensional color images;
comparing (i) the three-dimensional structure of the intraoral three-dimensional surface as computed based on the computed respective three-dimensional positions of the plurality of points on the intraoral three-dimensional surface and (ii) the three-dimensional structure of the intraoral three-dimensional surface as computed based on the respective estimated depth maps of the intraoral three-dimensional surface; and
in response to determining a discrepancy between (i) and (ii):
driving (i) the one or more structured light projectors of the intraoral scanner and (ii) the one or more unstructured light projectors of the intraoral scanner, during a plurality of refining-stage structured light scans,
driving the one or more cameras of the intraoral scanner to capture (a) a plurality of refining-stage structured light images and (b) a plurality of refining-stage two-dimensional images during the plurality of refining-stage structured light scans,
computing the three-dimensional structure of the intraoral three-dimensional surface based on the plurality of refining-stage structured light images, and
refining the training of the neural network for the intraoral scanner using (a) the plurality of two-dimensional images captured during the refining-stage scans and (b) the computed three-dimensional structure of the intraoral three-dimensional surface as computed based on the plurality of refining-stage structured light images.

Inventive Concept 194. A method for computing a three-dimensional structure of an intraoral three-dimensional surface, the method comprising:
driving one or more light projectors to project light on the intraoral three-dimensional surface;
driving one or more cameras to capture a plurality of two-dimensional images of the intraoral three-dimensional surface; and
using a processor:
inputting the plurality of two-dimensional images of the intraoral three-dimensional surface to a first neural network module and to a second neural network module;
determining, by the first neural network module, a respective estimated depth map of the intraoral three-dimensional surface as captured in each of the two-dimensional images; and
determining, by the second neural network module, a respective estimated confidence map corresponding to each estimated depth map, each confidence map indicating a confidence level per region of the respective estimated depth map.

Inventive Concept 195. The method according to Inventive Concept 194, wherein the first neural network module and the second neural network module are separate modules of a same neural network.

Inventive Concept 196. The method according to Inventive Concept 194, wherein each of the first and second neural network modules are not separate modules of a same neural network.

Inventive Concept 197. The method according to any one of Inventive Concepts 194-196, wherein the method further comprises training the second neural network module to determine the respective estimated confidence map corresponding to each estimated depth map as determined by the first neural network module, by initially training the first neural network module to determine the respective estimated depth maps using a plurality of depth-training-stage two-dimensional images, and
subsequently:
inputting to the first neural network module a plurality of confidence-training-stage two-dimensional images of a training-stage three-dimensional surface,
determining, by the first neural network module, a respective estimated depth map of the training-stage three-dimensional surface as captured in each of the confidence-training-stage two-dimensional images,
computing a difference between each estimated depth map and a corresponding respective true depth map to obtain a respective target confidence map corresponding to each estimated depth map as determined by the first neural network module,
inputting to the second neural network module the plurality of confidence-training-stage two-dimensional images,
estimating, by the second neural network module, a respective estimated confidence map indicating a confidence level per region of each respective estimated depth map, and
comparing each estimated confidence map to the corresponding target confidence map, and based on the comparison, optimizing the second neural network module to better estimate a subsequent estimated confidence map.

Inventive Concept 198. The method according to Inventive Concept 197, wherein the plurality of confidence-training-stage two-dimensional images are not the same as the plurality of depth-training-stage two-dimensional images.

Inventive Concept 199. The method according to Inventive Concept 197, wherein the plurality of confidence-training-stage two-dimensional images are the same as the plurality of depth-training-stage two-dimensional images.

Inventive Concept 200. The method according to any one of Inventive Concepts 194-196, wherein:
driving the one or more cameras to capture the plurality of two-dimensional images comprises driving each one of two or more cameras, in a given image frame, to simultaneously capture a respective two-dimensional image of a respective portion of the intraoral three-dimensional surface,
inputting the plurality of two-dimensional images of the intraoral three-dimensional surface to the first neural network module and to the second neural network module comprises, for a given image frame, inputting each one of the respective two-dimensional images as a separate input to the first neural network module and to the second neural network module,
determining by the first neural network module comprises, for the given image frame, determining a respective estimated depth map of each of the respective portions of the intraoral three-dimensional surface as captured in each of the respective two-dimensional images captured in the given image frame, determining by the second neural network module comprises, for the given image frame, determining a respective estimated confidence map corresponding to each respective estimated depth map of each of the respective portions of the intraoral three-dimensional surface as captured in each of the respective two-dimensional images captured in the given image frame, and the method further comprises, using the processor, merging the respective estimated depth maps together to obtain a combined estimated depth map of the intraoral three-dimensional surface as captured in the given image frame, wherein, in response to determining a contradiction between corresponding respective regions in at least two of the estimated depth maps, merging the at least two estimated depth maps based on the confidence level of each of the corresponding respective regions as indicated by the respective confidence maps for each of the at least two estimated depth maps.

Inventive Concept 201. A method for computing a three-dimensional structure of an intraoral three-dimensional surface using an intraoral scanner, the method comprising:

driving one or more light sources of the intraoral scanner to project light on the intraoral three-dimensional surface;

driving one or more cameras of the intraoral scanner to capture a plurality of two-dimensional images of the intraoral three-dimensional surface;

using a processor, determining, by a neural network, a respective estimated map of the intraoral three-dimensional surface as captured in each of the two-dimensional images; and using the processor, overcoming manufacturing deviations of the one or more cameras of the intraoral scanner, to reduce a difference between the estimated maps and a true structure of the intraoral three-dimensional surface.

Inventive Concept 202. The method according to Inventive Concept 201, wherein overcoming manufacturing deviations of the one or more cameras comprises overcoming manufacturing deviations of the one or more cameras from a reference set of one or more cameras.

Inventive Concept 203. The method according to Inventive Concept 201, wherein the intraoral scanner is one of a plurality of manufactured intraoral scanners, each manufactured intraoral scanner comprising a set of one or more cameras, and wherein overcoming manufacturing deviations of the one or more cameras of the intraoral scanner comprises overcoming manufacturing deviations of the one or more cameras from the set of one or more cameras of at least one other of the plurality of manufactured intraoral scanners.

Inventive Concept 204. The method according to any one of Inventive Concepts 201-203, wherein:

driving one or more cameras comprises driving two or more cameras of the intraoral scanner to each capture a plurality of two-dimensional images of the intraoral three-dimensional surface, each of the two or more cameras of the intraoral scanner corresponding to a respective one of two or more reference cameras, the neural network having been trained using training-stage images captured by the two or more reference cameras; and overcoming the manufacturing deviations comprises overcoming manufacturing deviations of the two or more cameras of the intraoral scanner by:

using the processor:

for each camera c of the two or more cameras of the intraoral scanner, modifying at least one of the two-dimensional images from camera c to obtain a plurality of modified two-dimensional images, each modified image corresponding to a modified field of view of camera c, the modified field of view of camera c matching a modified field of view of a corresponding one of the reference cameras; and determining by the neural network the respective estimated maps of the intraoral three-dimensional surface based on the plurality of modified two-dimensional images of the intraoral three-dimensional surface.

Inventive Concept 205. The method according to Inventive Concept 204, wherein the light is non-coherent light, and wherein the plurality of two-dimensional images comprise a plurality of two-dimensional color images.

Inventive Concept 206. The method according to Inventive Concept 204, wherein the light is near infrared (NIR) light, and wherein the plurality of two-dimensional images comprise a plurality of monochromatic NIR images.

Inventive Concept 207. The method according to Inventive Concept 204, wherein the light is broad spectrum light, and wherein the plurality of two-dimensional images comprise a plurality of two-dimensional color images.

Inventive Concept 208. The method according to any one of Inventive Concepts 204-207, wherein the step of modifying comprises cropping and morphing the at least one of the two-dimensional images from camera c to obtain a plurality of cropped and morphed two-dimensional images, each cropped and morphed image corresponding to a cropped and morphed field of view of camera c, the cropped and morphed field of view of camera c matching a cropped field of view of a corresponding one of the reference cameras.

Inventive Concept 209. The method according to Inventive Concept 208, wherein the step of cropping and morphing comprises the processor using (a) stored calibration values indicating a camera ray corresponding to each pixel on the camera sensor of each one of the one or more cameras c, and (b) reference calibration values indicating (i) a camera ray corresponding to each pixel on a reference camera sensor of each one of one or more reference cameras, and (ii) a cropped field of view for each one of the one or more reference cameras.

Inventive Concept 210. The method according to Inventive Concept 208, wherein the cropped fields of view of each of the one or more reference cameras is 85-97% of a respective full field of view of each of the one or more reference cameras.

Inventive Concept 211. The method according to any one of Inventive Concepts 208-210, wherein using the processor further comprises, for each camera c, performing a reverse of the morphing for each of the respective estimated maps of the intraoral three-dimensional surface as captured in each of the cropped and morphed two-dimensional images to obtain a respective non-morphed estimated map of the intraoral surface as seen in each of the at least one two-dimensional images from camera c prior to the morphing.

Inventive Concept 212. The method according to any one of Inventive Concepts 201-203, wherein overcoming the manufacturing deviations of the one or more cameras of the intraoral scanner comprises training the neural network using training-stage images as captured by a plurality of training-stage intraoral scanners, wherein:

each of the training-stage intraoral scanners comprises one or more reference cameras, each of the one or more cameras of the intraoral scanner corresponds to a respective one of the one or more reference cameras on each of the training-stage intraoral scanners, and the manufacturing deviations of the one or more cameras are manufacturing deviations of the one or more cameras from the corresponding one or more reference cameras.

Inventive Concept 213. The method according to any one of Inventive Concepts 201-203, wherein:

driving one or more cameras comprises driving two or more cameras of the intraoral scanner to each capture a plurality of two-dimensional images of the intraoral three-dimensional surface; and overcoming the manufacturing deviations comprises overcoming manufacturing deviations of the two or more cameras of the intraoral scanner by:

training the neural network using training-stage images that are each captured by only one camera;

driving the two or more cameras of the intraoral scanner to, in a given image frame, simultaneously capture a respective two-dimensional image of a respective portion of the intraoral three-dimensional surface;

inputting to the neural network, for a given image frame, each one of the respective two-dimensional images to the neural network as a separate input;

determining, by the neural network, a respective estimated depth map of each of the respective portions of the intraoral three-dimensional surface as captured in each of the respective two-dimensional images captured in the given image frame; and using the processor, merging the respective estimated depth maps together to obtain a combined estimated depth map of the intraoral three-dimensional surface as captured in the given image frame.

Inventive Concept 214. The method according to Inventive Concept 213, wherein determining further comprises determining, by the neural network, a respective estimated confidence map corresponding to each estimated depth map, each confidence map indicating a confidence level per region of the respective estimated depth map.

Inventive Concept 215. The method according to Inventive Concept 214, wherein merging the respective estimated depth maps together comprises, using the processor:

in response to determining a contradiction between corresponding respective regions in at least two of the estimated depth maps, merging the at least two estimated depth maps based on the confidence level of each of the corresponding respective regions as indicated by the respective confidence maps for each of the at least two estimated depth maps.

Inventive Concept 216. The method according to any one of Inventive Concepts 201-203, wherein overcoming the manufacturing deviations of the one or more cameras of the intraoral scanner comprises:

initially training the neural network using training-stage images as captured by one or more training-stage cameras of one or more training-stage handheld wands, each of the one or more cameras of the intraoral scanner corresponding to a respective one of the one or more training-stage cameras on each of the one or more training-stage handheld wands; and subsequently:

driving the intraoral scanner to perform a plurality of refining-stage scans of the intraoral three-dimensional surface, and refining the training of the neural network for the intraoral scanner using the refining-stage scans of the intraoral three-dimensional surface.

Inventive Concept 217. The method according to Inventive Concept 216, wherein the neural network comprises a plurality of layers, and wherein refining the training of the neural network comprises constraining a subset of the layers.

Inventive Concept 218. The method according to Inventive Concept 216, wherein the method further comprises selecting, from a plurality of scans, which of the plurality of scans to use as the refining-stage scans based on a quality level of each scan.

Inventive Concept 219. The method according to any one of Inventive Concepts 216-218, wherein driving the intraoral scanner to perform the plurality of refining-stage scans comprises:

during the plurality of refining-stage scans, driving (i) one or more structured light projectors of the intraoral scanner to project a pattern of structured light on the intraoral three-dimensional surface and (ii) one or more unstructured light projectors of the intraoral scanner to project unstructured light on the intraoral three-dimensional surface;

driving one or more cameras of the intraoral scanner to capture (a) a plurality of refining-stage structured light images using illumination from the structured light projectors and (b) a plurality of refining-stage two-dimensional images using illumination from the unstructured light projectors, during the refining-stage scans; and computing the three-dimensional structure of the intraoral three-dimensional surface based on the plurality of refining-stage structured light images.

Inventive Concept 220. The method according to Inventive Concept 219, wherein refining the training of the neural network comprises refining the training of the neural network for the intraoral scanner using (a) the plurality of refining-stage two-dimensional images captured during the refining-stage scans and (b) the computed three-dimensional structure of the intraoral three-dimensional surface as computed based on the plurality of refining-stage structured light images.

Inventive Concept 221. The method according to Inventive Concept 219, wherein the method further comprises, during the refining-stage scans, using the computed three-dimensional structure of the intraoral three-dimensional surface as computed based on the plurality of refining-stage structured light images as an end-result three-dimensional structure of the intraoral three-dimensional surface for a user of the intraoral scanner.

Inventive Concept 222. A method for training a neural network for use with intraoral scanner, the training comprising:

inputting to the neural network a plurality of two-dimensional images of an intraoral three-dimensional surface;

estimating, by the neural network, an estimated map of the intraoral three-dimensional surface as captured in each of the two-dimensional images;

based on a plurality of structured light images of the intraoral three-dimensional surface, computing a true map of the intraoral three-dimensional surface as seen in each of the two-dimensional images;

comparing each estimated map of the intraoral three-dimensional surface to a corresponding true map of the intraoral three-dimensional surface; and based on differences between each estimated map and the corresponding true map, optimizing the neural network to better estimate a subsequent estimated map, wherein, for a two-dimensional image in which moving tissue is identified, processing the image so as to exclude at least a portion of the moving tissue prior to inputting the two-dimensional image to the neural network.

Inventive Concept 223. The method according to Inventive Concept 222, wherein:

the method further comprises:

driving one or more structured light projectors to project a structured light pattern on the intraoral three-dimensional surface;

driving one or more cameras to capture the plurality of structured light images, each image including at least a portion of the structured light pattern;

driving one or more unstructured light projectors to project unstructured light onto the intraoral three-dimensional surface;

driving the one or more cameras to capture the plurality of two-dimensional images of the intraoral three-dimensional surface using illumination from the unstructured light projectors;

regulating the capturing of the structured light images and the capturing of the two-dimensional images to produce an alternating sequence of one or more image frames of structured light images interspersed with one or more image frames of two-dimensional images; and computing the true map of the intraoral three-dimensional surface as seen in each of the two-dimensional images comprises:

inputting to the neural network a respective plurality of three-dimensional reconstructions of the intraoral three-dimensional surface, based on structured light images of the intraoral three-dimensional surface, the three-dimensional reconstructions including computed three-dimensional positions of a plurality of points on the intraoral three-dimensional surface;

interpolating a position of the one or more cameras with respect to the intraoral three-dimensional surface for each two-dimensional image frame based on the computed three-dimensional positions of the plurality of points on the intraoral three-dimensional surface as computed based on respective structured light image frames before and after each two-dimensional image frame; and projecting the three-dimensional reconstructions on respective fields of view of each of the one or more cameras and, based on the projections, calculating a true map of the intraoral three-dimensional surface as seen in each two-dimensional image, constrained by the computed three-dimensional positions of the plurality of points.

Inventive Concept 224. A method comprising:

receiving, from an intraoral scanner, scan data of a patient's intraoral cavity;

assessing a calibration of the intraoral scanner based on at least some of the received scan data of the patient's intraoral cavity; and outputting an indication associated with the assessed calibration.

Inventive Concept 225. The method of Inventive Concept 224, wherein assessing the calibration comprises:

determining one or more calibration assessment values; and comparing the one or more calibration assessment values to a threshold; and determining that the one or more calibration assessment values exceed a threshold, wherein the indication is outputted in response to the one or more calibration assessment values exceeding the threshold.

Inventive Concept 226. The method of Inventive Concept 224, further comprising:

monitoring the calibration of the intraoral scanner based on the assessed calibration and previous assessments of the calibration of the intraoral scanner.

Inventive Concept 227. The method of Inventive Concept 224, wherein the indication comprises a notification to recalibrate the intraoral scanner.

Inventive Concept 228. The method of Inventive Concept 224, further comprising:

automatically recalibrating the intraoral scanner responsive to determining that the assessed calibration satisfies a recalibration criterion, wherein the indication comprises a notification that the intraoral scanner has been recalibrated.

Inventive Concept 229. A method comprising:

receiving, from an intraoral scanner, scan data of a patient's intraoral cavity;

assessing a calibration of the intraoral scanner based on at least some of the received scan data of the patient's intraoral cavity, wherein assessing the calibration comprises determining a calibration assessment value;

comparing the calibration assessment value to a threshold; and in response to the calibration assessment value exceeding the threshold, automatically recalibrating the intraoral scanner.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An intraoral scanning system, comprising:

an intraoral scanner comprising one or more cameras and one or more structured light projectors, the intraoral scanner to generate a series of images using the one or more cameras, each image including at least a portion of a pattern projected by the one or more structured light projectors onto an intraoral three-dimensional surface; and a processor to:

run a correspondence algorithm to compute respective three-dimensional positions of a plurality of features of the pattern on the intraoral three-dimensional surface, as captured in the series of images;

identify the computed three-dimensional position of a detected feature of the pattern as corresponding to a particular projector ray r, in at least a subset of the series of images; and track the particular projector ray r across the series of images.

2. The intraoral scanning system of claim 1, wherein the processor is further to:

based on the three-dimensional position of the detected feature corresponding to the particular projector ray r in the subset of images, assess a length corresponding to the projector ray r in each image of the subset of images.

3. The intraoral scanning system of claim 2, wherein the processor is further to:
compute an estimated length of the projector ray r in at least one of the series of images in which a three-dimensional position of the projected feature from the projector ray r was not identified.

4. The intraoral scanning system of claim 3, wherein the processor is further to:
based on the estimated length of projector ray r in the at least one of the series of images, determine a one-dimensional search space in the at least one of the series of images in which to search for a feature of the pattern from the projector ray r, the one-dimensional search space being along a path of pixels corresponding to the projector ray r.

5. The intraoral scanning system of claim 2, wherein each one of the one or more cameras comprises a camera sensor comprising an array of pixels, wherein computation of the respective three-dimensional positions of the plurality of features of the pattern on the intraoral three-dimensional surface and identification of the computed three-dimensional position of the detected feature of the pattern as corresponding to the particular projector ray r is performed based on stored calibration values indicating (i) a camera ray corresponding to each pixel on the camera sensor of each one of the one or more cameras, and (ii) a projector ray corresponding to each one of the features of the projected pattern of light from each one of the one or more structured light projectors, wherein each projector ray corresponds to a respective path of pixels on the camera sensor of at least one of the one or more cameras.

6. The intraoral scanning system of claim 5, wherein the processor is further to:
compute an estimated length of the projector ray r in at least one of the series of images in which a three-dimensional position of the projected feature from the projector ray r was not identified, and
based on the estimated length of the projector ray r in the at least one of the series of images, determine a one-dimensional search space in the at least one of the series of images in which to search for a projected feature from the projector ray r, the one-dimensional search space being along the respective path of pixels corresponding to the projector ray r.

7. The intraoral scanning system of claim 5, wherein the processor is further to:
compute an estimated length of the projector ray r in at least one of the series of images in which a three-dimensional position of the projected feature from the projector ray r was not identified, and
based on the estimated length of the projector ray r in the at least one of the series of images, determine a one-dimensional search space in respective pixel arrays of a plurality of the cameras in which to search for a projected spot from the projector ray r, for each of the respective pixel arrays, the one-dimensional search space being along the respective path of pixels corresponding to the projector ray r.

8. The intraoral scanning system of claim 7, wherein the processor is further to:
determine a one-dimensional search space in respective pixel arrays of all of the cameras, in which to search for a projected feature from the projector ray r.

9. The intraoral scanning system of claim 2, wherein the processor is further to:
based on the correspondence algorithm, in each of at least one of the series of images that is not in the subset of images, identify more than one candidate three-dimensional position of the projected feature from the projector ray r, and compute an estimated length of the projector ray r in the at least one of the series of images in which more than one candidate three-dimensional position of the projected feature from projector ray r was identified.

10. The intraoral scanning system of claim 9, wherein the processor is further to:
determine which of the more than one candidate three-dimensional positions is a correct three-dimensional position of the projected feature by determining which of the more than one candidate three-dimensional positions corresponds to the estimated length of the projector ray r in the at least one of the series of images.

11. The intraoral scanning system of claim 9, wherein the processor is further to perform the following based on the estimated length of the projector ray r in the at least one of the series of images:
determine a one-dimensional search space in the at least one of the series of images in which to search for a projected feature from the projector ray r; and
determine which of the more than one candidate three-dimensional positions of the projected feature is a correct three-dimensional position of the projected feature produced by the projector ray r by determining which of the more than one candidate three-dimensional positions corresponds to a feature produced by the projector ray r found within the one-dimensional search space.

12. The intraoral scanning system of claim 2, wherein the processor is further to:
define a curve based on the assessed length of the projector ray r in each image of the subset of images; and
remove from being considered as a point on the intraoral three-dimensional surface a detected feature which was identified as being from the projector ray r if the three-dimensional position of the projected feature corresponds to a length of the projector ray r that is at least a threshold distance away from the defined curve.

13. The intraoral scanning system of claim 1, wherein the pattern comprises a plurality of spots, and wherein each of the plurality of features of the pattern comprises a spot of the plurality of spots.

14. A non-transitory computer readable medium comprising instructions that, when executed by a processor, cause the processor to perform operations comprising:
receiving a series of images generated by one or more cameras of an intraoral scanner, each image including at least a portion of a pattern projected by one or more structured light projectors of the intraoral scanner onto an intraoral three-dimensional surface;
running a correspondence algorithm to compute respective three-dimensional positions of a plurality of features of the pattern on the intraoral three-dimensional surface, as captured in the series of images;
identifying the computed three-dimensional position of a detected feature of the pattern as corresponding to a particular projector ray r, in at least a subset of the series of images; and
tracking the particular projector ray r across the series of images.

15. The non-transitory computer readable medium of claim 14, the operations further comprising:
based on the three-dimensional position of the detected feature corresponding to the particular projector ray r in the subset of images, assessing a length corresponding to the projector ray r in each image of the subset of images.

16. The non-transitory computer readable medium of claim 15, the operations further comprising:
computing an estimated length of the projector ray r in at least one of the series of images in which a three-dimensional position of the projected feature from the projector ray r was not identified.

17. The non-transitory computer readable medium of claim 16, the operations further comprising:
based on the estimated length of projector ray r in the at least one of the series of images, determining a one-dimensional search space in the at least one of the series of images in which to search for a feature of the pattern from the projector ray r, the one-dimensional search space being along a path of pixels corresponding to the projector ray r.

18. The non-transitory computer readable medium of claim 15, wherein each one of the one or more cameras comprises a camera sensor comprising an array of pixels, wherein computation of the respective three-dimensional positions of the plurality of features of the pattern on the intraoral three-dimensional surface and identification of the computed three-dimensional position of the detected feature of the pattern as corresponding to the particular projector ray r is performed based on stored calibration values indicating (i) a camera ray corresponding to each pixel on the camera sensor of each one of the one or more cameras, and (ii) a projector ray corresponding to each one of the features of the projected pattern of light from each one of the one or more structured light projectors, wherein each projector ray corresponds to a respective path of pixels on the camera sensor of at least one of the one or more cameras.

19. The non-transitory computer readable medium of claim 18, the operations further comprising:
computing an estimated length of the projector ray r in at least one of the series of images in which a three-dimensional position of the projected feature from the projector ray r was not identified, and
based on the estimated length of the projector ray r in the at least one of the series of images, determining a one-dimensional search space in the at least one of the series of images in which to search for a projected feature from the projector ray r, the one-dimensional search space being along the respective path of pixels corresponding to the projector ray r.

20. The non-transitory computer readable medium of claim 18, the operations further comprising:
computing an estimated length of the projector ray r in at least one of the series of images in which a three-dimensional position of the projected feature from the projector ray r was not identified, and
based on the estimated length of the projector ray r in the at least one of the series of images, determining a one-dimensional search space in respective pixel arrays of a plurality of the cameras in which to search for a projected spot from the projector ray r, for each of the respective pixel arrays, the one-dimensional search space being along the respective path of pixels corresponding to the projector ray r.

21. The non-transitory computer readable medium of claim 20, the operations further comprising:
determining a one-dimensional search space in respective pixel arrays of all of the cameras, in which to search for a projected feature from the projector ray r.

22. The non-transitory computer readable medium of claim 15, the operations further comprising:
based on the correspondence algorithm, in each of at least one of the series of images that is not in the subset of images, identifying more than one candidate three-dimensional position of the projected feature from the projector ray r, and computing an estimated length of the projector ray r in the at least one of the series of images in which more than one candidate three-dimensional position of the projected feature from projector ray r was identified.

23. The non-transitory computer readable medium of claim 22, the operations further comprising:
determining which of the more than one candidate three-dimensional positions is a correct three-dimensional position of the projected feature by determining which of the more than one candidate three-dimensional positions corresponds to the estimated length of the projector ray r in the at least one of the series of images.

24. The non-transitory computer readable medium of claim 22, the operations further comprising performing the following based on the estimated length of the projector ray r in the at least one of the series of images:
determining a one-dimensional search space in the at least one of the series of images in which to search for a projected feature from the projector ray r; and
determining which of the more than one candidate three-dimensional positions of the projected feature is a correct three-dimensional position of the projected feature produced by the projector ray r by determining which of the more than one candidate three-dimensional positions corresponds to a feature produced by the projector ray r found within the one-dimensional search space.

25. The non-transitory computer readable medium of claim 15, the operations further comprising:
defining a curve based on the assessed length of the projector ray r in each image of the subset of images; and
removing from being considered as a point on the intraoral three-dimensional surface a detected feature which was identified as being from the projector ray r if the three-dimensional position of the projected feature corresponds to a length of the projector ray r that is at least a threshold distance away from the defined curve.

26. The non-transitory computer readable medium of claim 14, wherein the pattern comprises a plurality of spots, and wherein each of the plurality of features of the pattern comprises a spot of the plurality of spots.

27. A method comprising:
receiving a series of images generated by one or more cameras of an intraoral scanner, each image including at least a portion of a pattern projected by one or more structured light projectors of the intraoral scanner onto an intraoral three-dimensional surface;
running a correspondence algorithm to compute respective three-dimensional positions of a plurality of features of the pattern on the intraoral three-dimensional surface, as captured in the series of images;
identifying the computed three-dimensional position of a detected feature of the pattern as corresponding to a particular projector ray r, in at least a subset of the series of images; and tracking the particular projector ray r across the series of images to determine the three-dimensional position of the detected feature of the pattern in the series of images.

* * * * *